United States Patent
Davies et al.

(10) Patent No.: US 11,952,330 B2
(45) Date of Patent: Apr. 9, 2024

(54) ANTIBIOTIC AMMONIUM COMPOUNDS AND METHODS FOR THE TREATMENT OF BACTERIAL INFECTIONS

(71) Applicant: Board of Regents, The University of Texas System, Austin, TX (US)

(72) Inventors: Bryan Davies, Austin, TX (US); Stanton McHardy, San Antonio, TX (US); Ashley Cunningham, Austin, TX (US); Hua-Yu Wang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 99 days.

(21) Appl. No.: 17/428,584

(22) PCT Filed: Feb. 5, 2020

(86) PCT No.: PCT/US2020/016793
§ 371 (c)(1),
(2) Date: Aug. 4, 2021

(87) PCT Pub. No.: WO2020/163479
PCT Pub. Date: Aug. 13, 2020

(65) Prior Publication Data
US 2022/0098148 A1    Mar. 31, 2022

Related U.S. Application Data

(60) Provisional application No. 62/801,518, filed on Feb. 5, 2019.

(51) Int. Cl.
C07C 317/32    (2006.01)
C07C 311/41    (2006.01)
C07D 207/09    (2006.01)
C07D 211/52    (2006.01)
C07D 241/04    (2006.01)

(52) U.S. Cl.
CPC .......... *C07C 317/32* (2013.01); *C07C 311/41* (2013.01); *C07D 207/09* (2013.01); *C07D 211/52* (2013.01); *C07D 241/04* (2013.01)

(58) Field of Classification Search
None
See application file for complete search history.

(56) References Cited

U.S. PATENT DOCUMENTS 3,898,278 A    8/1975  Ghelardoni et al.
2016/0024004 A1    1/2016  Xu et al.

OTHER PUBLICATIONS

Ghelardoni, Mario. Quaternary Salts of Substituted 2-Aminoethyl N-Benzoylaminobenzoate. A New Class of Smooth Muscle Relaxant Agents. Journal of Medicinal Chemistry. 16(9), 1973.*
Database Registry Chemical Abstracts Service, Columbus, Ohio, Accession No. RN 26095-63-6. Entered STN Nov. 16, 1984.*
International Search Report and Written Opinion dated Jun. 10, 2020 in PCT Application No. PCT/US2020/016793, 41 pages.
PUBCHEM-CID: 3039969 Create Date: Aug. 9, 2005 (Aug. 9, 2005) pp. 1-13; p. 3, structure.
PUBCHEM-CID: 4942051 Create Date: Sep. 17, 2005 (Sep. 17, 2005) pp. 1-8; p. 2, structure.

* cited by examiner

*Primary Examiner* — Samantha L Shterengarts
(74) *Attorney, Agent, or Firm* — Kilpatrick Townsend & Stockton LLP

(57) ABSTRACT

The present disclosure provides ammonium compounds, e.g., compounds according to Formula I as set forth herein, which are useful as antimicrobial agents. Methods for the treatment of bacterial infections and associated conditions, e.g., gastrointestinal conditions, are also described, as well as methods for altering the microbiome of subjects such as humans.

17 Claims, 1 Drawing Sheet

ANTIBIOTIC AMMONIUM COMPOUNDS AND METHODS FOR THE TREATMENT OF BACTERIAL INFECTIONS

CROSS-REFERENCES TO RELATED APPLICATIONS

The present application is a national stage application, filed under 35 U.S.C. § 371, of International Pat. Appl. No. PCT/US2020/016793, filed Feb. 5, 2020, which claims the benefit of priority to U.S. Provisional Pat. Appl. No. 62/801,518, filed on Feb. 5, 2019, which is incorporated herein by reference in its entirety.

BACKGROUND OF THE INVENTION

Infectious diseases are currently the second leading cause of death worldwide and the third leading cause of death in economically advanced countries despite the development of antibiotics. [Nathan, Nature, 437:899-902, 2004.] Furthermore, the threatening emergence of bacterial resistance to many antibiotics presents a serious challenge for their clinical use. As our antibiotic options continue to shrink, prevention becomes increasingly important in elevating the burden of hospital-associated bacterial infections. [Otter, et al. *Infection Control and Hospital Epidemiology*, 32(7):687-699, 2011; Weber, et al. *Am. J. of Infection Control*, 38:S25-S33, 2010; Barsanti, et al. *Infect. Dis. Clin. N. Am.*, 23:703-725, 2009.] Surface decontamination relies heavily on the use of biocides, that is, chemical agents with antimicrobial properties. Among the biocide classes, quaternary amine compounds (QACs) such as benzalkonium chloride (BAC), are frequently used for disinfecting medical equipment, hospital surfaces, patient wounds, and healthcare workers' hands. QACs are recommended for use at concentrations many times their minimal inhibitory concentration (MIC) and effectively eradicate vegetative bacteria at these doses under laboratory conditions. Practical clinical conditions including high bacterial density, the presence of biofilm and organic matter, and high ion concentrations dramatically decrease the effectiveness of QAC biocides, which allows bacteria to escape death and persist in the hospital environment. [Klimek, et al. *Applied Microbiology*, 4(1):53-59, 1956; Otter, et al. *J. Hospital Infection*, 89:16-27, 2015.] Despite their wide use, the antimicrobial effects of QACs are unclear, especially at near inhibitory concentrations. Additionally, the incomplete understanding of QAC action has fueled concerns of cross-resistance between biocides and antibiotics. If this were to occur, resistant bacteria could be selected both during antibiotic treatment and clinical disinfection, promoting the propagation of resistant endemic strains.

BRIEF SUMMARY OF THE INVENTION

Provided herein are ammonium compounds, including compounds according to Formula I:

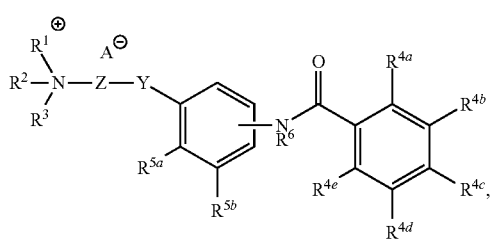

(I)

wherein
A is a pharmaceutically acceptable anion;
Y is selected from the group consisting of —OC(O)—, —NR$^7$C(O)—, and —NR$^7$SO$_2$—;
Z is C$_{1-4}$ alkylene;
R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;
L$^1$ is C$_{1-6}$ alkylene;
R$^{1a}$ is selected from the group consisting of C$_{3-8}$ cycloalkyl, C$_{6-10}$ aryl, 3- to 10-membered heterocyclyl, and 5- to 10-membered heteroaryl;
R$^2$ and R$^3$ are independently selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;
L$^2$ is C$_{1-6}$ alkylene;
R$^{2a}$ is selected from the group consisting of C$_{3-8}$ cycloalkyl, C$_{6-10}$ aryl, 3- to 10-membered heterocyclyl, and 5- to 10-membered heteroaryl;
R$^2$ and R$^3$ are optionally taken together with the nitrogen to which they are attached to form 3- to 10-membered heterocyclyl;
one of R$^2$ and R$^3$ is optionally taken together with the nitrogen to which it is attached and Y or Z to form 3- to 10-membered heterocyclyl;
R$^{4a}$, R$^{4b}$, R$^{4c}$, R$^{4d}$, and R$^{4e}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^4$-R$^{4x}$;
L$^4$ is selected from the group consisting of C$_{1-6}$ alkylene, 2- to 6-membered heteroalkylene, and —O—;
R$^{4x}$ is selected from the group consisting of C$_{3-8}$ cycloalkyl, C$_{6-10}$ aryl, 3- to 10-membered heterocyclyl, and 5- to 10-membered heteroaryl;
R$^{5a}$ and R$^{5b}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^5$-R$^{5x}$;
L$^5$ is selected from the group consisting of C$_{1-6}$ alkylene, 2- to 6-membered heteroalkylene, and —O—;
R$^{5x}$ is selected from the group consisting of C$_{3-8}$ cycloalkyl, C$_{6-10}$ aryl, 3- to 10-membered heterocyclyl, and 5- to 10-membered heteroaryl;
R$^6$ is selected from the group consisting of H, C$_{1-6}$ alkyl, and C$_{2-7}$ acyl;
R$^6$ is optionally taken together with R$^{4a}$ or R$^{4e}$ to form a 5- to 8-membered ring; each R$^7$ is independently selected from the group consisting of H, C$_{1-6}$ alkyl, and C$_{2-7}$ acyl;
each C$_{3-8}$ cycloalkyl, C$_{6-10}$ aryl, 3- to 10-membered heterocyclyl, and 5- to 10-membered heteroaryl is optionally and independently substituted with one or more substituents selected from the group consisting of C$_{1-18}$ alkyl, C$_{1-18}$ haloalkyl, C$_{1-18}$ alkenyl, C$_{1-18}$ alkoxy, halogen, —OH, —C(O)R$^8$, —C(O)N(R$^7$)$_2$, —N(R$^7$)$_2$, —NO$_2$, —SO$_3$, and —SO$_2$N(R$^7$)$_2$; and
each R$^8$ is independently selected from the group consisting of C$_{1-6}$ alkyl, C$_{1-6}$ alkoxy, and —OH,
provided that at least one of R$^{4a}$, R$^{4b}$, R$^{4c}$, R$^{4d}$, and R$^{4e}$ is C$_{4-18}$ alkoxy; and
provided that if Y is —OC(O)—, Z is ethylene, R$^1$ is methyl, R$^2$ and R$^3$ are ethyl, then at least two of R$^{4a}$, R$^{4b}$, R$^{4c}$, R$^{4d}$, and R$^{4e}$ are other than H; and provided that the compound is other than:
- an N,N-diethyl-N-methyl-2-(4-(2-(octyloxy)benzamido)benzamido)ethan-1-aminium species,
- an N,N,N-trimethyl-2-((4-(2-(octyloxy)benzamido)benzoyl)oxy)ethan-1-aminium species,
- an N,N,N-trimethyl-2-((4-(4-(isopentyloxy)benzamido)benzoyl)oxy)ethan-1-aminium species,
- an N,N,N-trimethyl-2-((4-(4-(isopentyloxy)benzamido)benzoyl)oxy)propan-1-aminium species,
- an 1-methyl-1-(2-((4-(2-(octyloxy)benzamido)benzoyl)oxy)ethyl)piperidin-1-ium species, or
- 4-methyl-4-(2-((4-(2-(octyloxy)benzamido)benzoyl)oxy)ethyl)morpholin-4-ium bromide.

Also provided herein are methods for treating bacterial infections in a subject and methods for altering the microbiome of a subject. The methods include administering to a subject an ammonium compound according to the present disclosure. In some embodiments, the methods can be used for treatment of infections caused by Gram-positive bacteria such as *C. difficile, S. aureus, Streptococcus* spp., *Enterococcus* spp., *C. diphtheriae*, and *L. monocytogenes*.

DETAILED DESCRIPTION OF THE INVENTION

Figure 1:
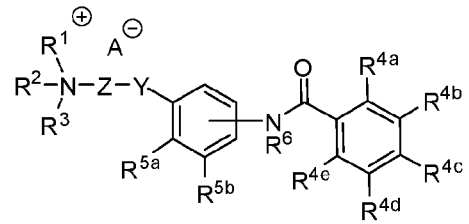
FIG. 1 shows the structure of antibiotic ammonium compounds according to the present disclosure.

New compounds exhibiting increased anti-bacterial action, decreased eukaryotic toxicity, and/or increased stability have been developed as described herein. These compounds may be used to treat *C. difficle* infections and other infections.

I. DEFINITIONS

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. In some embodiments, "substituted alkyl" groups can be substituted with one or more groups selected from halo, hydroxy, amino, alkylamino, amido, acyl, carboxy, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "alkoxy," by itself or as part of another substituent, refers to a moiety having the formula —OR, wherein R is an alkyl group as defined herein.

Examples of alkoxy groups include, but are not limited to, methoxy, ethoxy, and isopropyloxy.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. In some embodiments, "substituted cycloalkyl" groups are substituted with one or more groups selected from halo, hydroxy, amino, alkylamino, amido, acyl, carboxy, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio, or amino group. Alternatively, the heteroatom portion can be the connecting atom, or be inserted between two carbon atoms.

As used herein, the term "heteroalkylene" refers to a heteroalkyl group, as defined above, linking at least two other groups (i.e., a divalent heteroalkyl radical). The two moieties linked to the heteroalkylene group can be linked to the same atom or different atoms of the heteroalkylene group.

As used herein, the term "haloalkyl" refers to an alkyl moiety as defined above substituted with at least one halogen atom.

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclic groups can be saturated (e.g., azetidinyl, pyrrolidinyl, piperidinyl, morpholine, oxetanyl, tetrahydrofuranyl, or tetrahydropyranyl) or unsaturated (e.g., 2,3-dihydrofuranyl, 2,5-dihydrofuranyl, 3,4-dihydropyranyl, 3,6-dihydropyranyl, or 1,4-dihydropyridinyl). Heterocyclyl groups can be unsubstituted or substituted. In some embodiments, "substituted heterocyclyl" groups are substituted with one or more groups selected from halo, hydroxy, amino, oxo (=O), alkylamino, amido, acyl, carboxy, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "aryl," by itself or as part of another substituent, refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. In some embodiments, "substituted aryl" groups are substituted with one or more groups selected from halo, hydroxy, amino, alkylamino, amido, acyl, carboxy, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. In some embodiments, "substituted heteroaryl" groups are substituted with one or more groups selected from halo, hydroxy, amino, alkylamino, amido, acyl, carboxy, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the terms "halo" and "halogen," by themselves or as part of another substituent, refer to a fluorine, chlorine, bromine, or iodine atom.

As used herein, the term "cyano" refers to a carbon atom triple-bonded to a nitrogen atom (i.e., the moiety —C≡N).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —$NR_3$, wherein each R group is H or a carbon radical such as an alkyl group.

As used herein, the term "ammonium" refers to a cationic amine group —$(N^+)R_4$, wherein each R group is H or a carbon radical, e.g., an $R^1$ group, an $R^2$ group, an $R^3$ group, or a Z group as described herein. An "ammonium compound" refers to a compound having at least one ammonium group.

As used herein, the term "hydroxy" refers to the moiety —OH.

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or alkyl.

As used herein, the term "nitro" refers to the moiety —$NO_2$.

As used herein, the term "oxo" refers to an oxygen atom that is double-bonded to a compound (i.e., O=).

As used herein, the term "salt" refers to acid or base salts of the compounds set forth herein. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid, fumaric acid, and the like) salts, and quaternary ammonium (methyl iodide, ethyl iodide, and the like) salts. It is understood that the pharmaceutically acceptable salts are non-toxic.

Pharmaceutically acceptable salts of the acidic compounds of the present disclosure are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

As used herein, the term "excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present disclosure include, but are not limited to, binders, fillers, disintegrants, lubricants, glidants, coatings, sweeteners, flavors and colors.

As used herein, the terms "treat," "treatment," and "treating" refer to any indicia of success in the treatment or amelioration of an injury, pathology, condition, or symptom (e.g., inflammation), including any objective or subjective parameter such as abatement; remission; diminishing of symptoms or making the symptom, injury, pathology or condition more tolerable to the patient; reduction in the rate of symptom progression; decreasing the frequency or duration of the symptom or condition. In some situations, treating can including preventing the onset of the injury, pathology, condition, or symptom. The treatment or amelioration of symptoms can be based on any objective or subjective parameter; including, e.g., the result of a physical examination.

As used herein, the term "bacterial infection" refers to the growth of unwanted bacteria (e.g., disease-causing bacteria) in one or more cells, tissues, or organs of a subject such as a human or animal. Bacterial infections include, but are not limited to, oral infections, gastrointestinal infections, bloodstream infections, respiratory infections, and sexually transmitted infections.

As used herein, the term "microbiome" refers to the totality of microbes (bacteria, fungae, protists) in a defined environment. The microbiome of a subject such as a human or animal may represent a whole-body microbiome or a microbiome associated with any particular organ, organ system, or anatomical region, e.g., a gut microbiome, an oral microbiome, an intestinal microbiome, a bronchial microbiome, or a skin microbiome.

As used herein, the term "administering" refers to oral, topical, parenteral, intravenous, intraperitoneal, intramuscular, intralesional, intranasal, subcutaneous, or intrathecal administration to a subject, as well administration as a suppository or the implantation of a slow-release device, e.g., a mini-osmotic pump, in the subject.

As used herein, the term "subject" refers to a person or other animal to whom a compound or composition as described herein is administered. In some embodiments, the subject is human.

As used herein, the terms "effective amount" and "therapeutically effective amount" refer to a dose of a compound such as an ammonium compound that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, 11th Edition, 2006, Brunton, Ed., McGraw-Hill; and *Remington: The Science and Practice of Pharmacy*, 21st Edition, 2005, Hendrickson, Ed., Lippincott, Williams & Wilkins).

II. AMMONIUM COMPOUNDS

Provided herein are compounds according to Formula I:

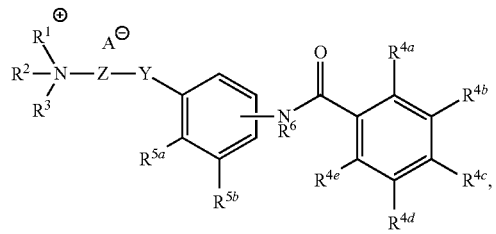

wherein

A is a pharmaceutically acceptable anion;

Y is selected from the group consisting of —OC(O)—, —NR$^7$C(O)—, and —NR$^7$SO$_2$—;

Z is C$_{1-6}$ alkylene;

R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;

L$^1$ is C$_{1-6}$ alkylene;

R$^{1a}$ is selected from the group consisting of C$_{3-8}$ cycloalkyl, C$_{6-10}$ aryl, 3- to 10-membered heterocyclyl, and 5- to 10-membered heteroaryl;

R$^2$ and R$^3$ are independently selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;

L$^2$ is C$_{1-6}$ alkylene;

R$^{2a}$ is selected from the group consisting of C$_{3-8}$ cycloalkyl, C$_{6-10}$ aryl, 3- to 10-membered heterocyclyl, and 5- to 10-membered heteroaryl;

R$^2$ and R$^3$ are optionally taken together with the nitrogen to which they are attached to form 3- to 10-membered heterocyclyl;

one of R$^2$ and R$^3$ is optionally taken together with the nitrogen to which it is attached and Y or Z to form 3- to 10-membered heterocyclyl;

R$^{4a}$, R$^{4b}$, R$^{4c}$, R$^{4d}$, and R$^{4e}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^4$-R$^{4x}$;

L$^4$ is selected from the group consisting of C$_{1-6}$ alkylene, 2- to 6-membered heteroalkylene, and —O—;

R$^{4x}$ is selected from the group consisting of C$_{3-8}$ cycloalkyl, C$_{6-10}$ aryl, 3- to 10-membered heterocyclyl, and 5- to 10-membered heteroaryl;

R$^5$ and R$^{5b}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^5$-R$^{5x}$;

L$^5$ is selected from the group consisting of C$_{1-6}$ alkylene, 2- to 6-membered heteroalkylene, and —O—;

R$^{5x}$ is selected from the group consisting of C$_{3-8}$ cycloalkyl, C$_{6-10}$ aryl, 3- to 10-membered heterocyclyl, and 5- to 10-membered heteroaryl;

R$^6$ is selected from the group consisting of H, C$_{1-6}$ alkyl, and C$_{2-7}$ acyl;

R$^6$ is optionally taken together with R$^{4a}$ or R$^{4e}$ to form a 5- to 8-membered ring; each R$^7$ is independently selected from the group consisting of H, C$_{1-6}$ alkyl, and C$_{2-7}$ acyl;

each C$_{3-8}$ cycloalkyl, C$_{6-10}$ aryl, 3- to 10-membered heterocyclyl, and 5- to 10-membered heteroaryl is optionally and independently substituted with one or more substituents selected from the group consisting of C$_{1-18}$ alkyl, C$_{1-18}$ haloalkyl, C$_{1-18}$ alkenyl, C$_{1-18}$ alkoxy, halogen, —OH, —C(O)R$^8$, —C(O)N(R$^7$)$_2$, —N(R$^7$)$_2$, —NO$_2$, —SO$_3$, and —SO$_2$N(R$^7$)$_2$; and each R$^8$ is independently selected from the group consisting of C$_{1-6}$ alkyl, C$_{1-6}$ alkoxy, and —OH, provided that at least one of R$^{4a}$, R$^{4b}$, R$^{4c}$, R$^{4d}$, and R$^{4e}$ is C$_{4-18}$ alkoxy; and provided that if Y is —OC(O)—, Z is ethylene, R$^1$ is methyl, R$^2$ and R$^3$ are ethyl, then at least two of R$^{4a}$, R$^{4b}$, R$^{4c}$, R$^{4d}$, and R$^{4e}$ is other than H; and provided that the compound is other than:

an N,N-diethyl-N-methyl-2-(4-(2-(octyloxy)benzamido)benzamido)ethan-1-aminium species, an N,N,N-trimethyl-2-((4-(2-(octyloxy)benzamido)benzoyl)oxy)ethan-1-aminium species, an N,N,N-trimethyl-2-((4-(4-(isopentyloxy)benzamido)benzoyl)oxy)ethan-1-aminium species, an N,N,N-trimethyl-2-((4-(4-(isopentyloxy)benzamido)benzoyl)oxy)propan-1-aminium species, an 1-methyl-1-(2-((4-(2-(octyloxy)benzamido)benzoyl)oxy)ethyl)piperidin-1-ium species, or 4-methyl-4-(2-((4-(2-(octyloxy)benzamido)benzoyl)oxy)ethyl)morpholin-4-ium bromide.

In some embodiments, the compound has a structure according to Formula I-i, Formula I-ii, or Formula I-iii as shown below.

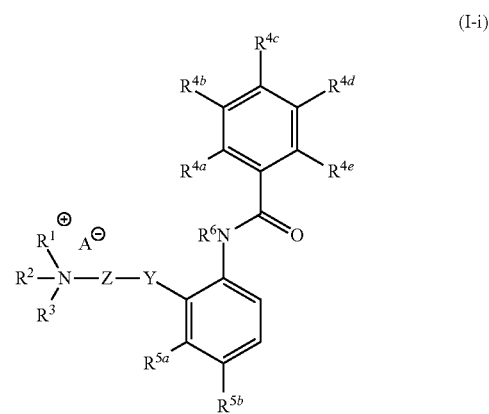

(I-i)

-continued

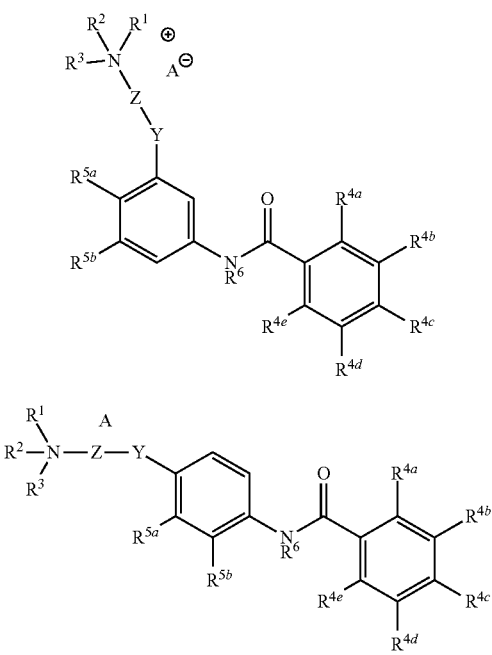

(I-ii)

(I-iii)

In some embodiments, at least one of $R^{4a}$, $R^{4b}$, $R^{4c}$, $R^{4d}$, and $R^{4e}$ in compounds according to Formula I, Formula I-i, Formula I-ii, or Formula I-iii is $C_{4-18}$ alkoxy. $R^{4a}$, $R^{4b}$, $R^{4c}$, $R^{4d}$, and $R^{4e}$ may be, for example, n-butyloxy, isobutyloxy, sec-butyloxy, tert-butyloxy, n-pentyloxy, branched pentyloxy, n-hexyloxy, branched hexyloxy (e.g., hexan-2-yloxy, hexan-3-yloxy, or (4-methylpentyl)oxy), n-heptyloxy, branched heptyloxy (e.g., heptan-2-yloxy, heptan-3-yloxy, heptan-4-yloxy, or (5-methylhexyl)oxy), n-octyloxy, branched octyloxy, n-nonyloxy, branched nonyloxy, n-decyloxy, branched decyloxy, n-undecyloxy, branched undecyloxy, n-dodecyloxy, branched dodecyloxy, n-tridecyloxy, branched tridecyloxy, n-tetradecyloxy, branched tetradecyloxy, n-pentadecyloxy, branched pentadecyloxy, n-hexadecyloxy, branched hexadecyloxy, n-heptadecyloxy, branched heptadecyloxy, n-octadecyloxy, or branched octadecyloxy. In some embodiments, at least one of $R^{4a}$ and $R^{4e}$ in compounds according to Formula I, Formula I-i, Formula I-ii, or Formula I-iii is $C_{4-18}$ alkoxy. In some embodiments, at least one of $R^{4a}$, $R^{4b}$, $R^{4c}$, $R^{4d}$, and $R^{4e}$ in compounds according to Formula I, Formula I-i, Formula I-ii, or Formula I-iii is halogen. $R^{4a}$, $R^{4b}$, $R^{4c}$, $R^{4d}$, and $R^{4e}$ can independently be, fluoro, chloro, bromo, or iodo.

In some embodiments, at least two of $R^{4a}$, $R^{4b}$, $R^{4c}$, $R^{4d}$, and $R^{4e}$ in compounds according to Formula I, Formula I-i, Formula I-ii, or Formula I-iii are $C_{4-18}$ alkoxy. For example, $R^{4a}$ and $R^{4b}$ can be $C_{4-18}$ alkoxy, or $R^{4a}$ and $R^{4c}$ can be $C_{4-18}$ alkoxy, or $R^{4a}$ and $R^{4d}$ can be $C_{4-18}$ alkoxy, or $R^{4a}$ and $R^{4e}$ can be $C_{4-18}$ alkoxy, or $R^{4b}$ and $R^{4c}$ can be $C_{4-18}$ alkoxy, or $R^{4b}$ and $R^{4d}$ can be $C_{4-18}$ alkoxy; each $C_{4-18}$ alkoxy may be the same or different. In some embodiments, $R^{4a}$ and $R^{4b}$ are independently $C_{4-18}$ alkoxy, and $R^{4c}$, $R^{4d}$, and $R^{4e}$ are independently H or halogen. In some embodiments, $R^{4a}$ and $R^{4c}$ are independently $C_{4-18}$ alkoxy, and $R^{4b}$, $R^{4d}$, and $R^{4e}$ are independently H or halogen. In some embodiments, $R^{4a}$ and $R^{4d}$ are independently $C_{4-18}$ alkoxy, and $R^{4b}$, $R^{4c}$, and $R^{4e}$ are independently H or halogen. In some embodiments, $R^{4a}$ and $R^{4e}$ are independently $C_{4-18}$ alkoxy, and $R^{4b}$, $R^{4c}$, and $R^{4d}$ are independently H or halogen. Each halogen may be the same or different. In some embodiments, at least three, four, or five of $R^{4a}$, $R^{4b}$, $R^{4c}$, $R^{4d}$, and $R^{4e}$ are $C_{4-18}$ alkoxy.

In some embodiments, at one of $R^{4a}$, $R^{4b}$, $R^{4c}$, $R^{4d}$, and $R^{4e}$ in compounds according to Formula I, Formula I-i, Formula I-ii, or Formula I-iii is $C_{4-18}$ alkoxy (e.g., $C_{4-12}$ alkoxy or $C_{4-8}$ alkoxy) and at least one of $R^{4a}$, $R^{4b}$, $R^{4c}$, $R^{4d}$, and $R^{4e}$ is halogen (e.g., fluoro, chloro, or bromo). For example, $R^{4a}$ can be $C_{4-18}$ alkoxy and $R^{4b}$ can be halogen; or $R^{4a}$ can be $C_{4-18}$ alkoxy and $R^{4c}$ can be halogen; or $R^{4a}$ can be $C_{4-18}$ alkoxy and $R^{4d}$ can be halogen; or $R^{4a}$ can be $C_{4-18}$ alkoxy and $R^{4e}$ can be halogen; or $R^{4b}$ can be $C_{4-18}$ alkoxy and $R^{4c}$ can be halogen; or $R^{4b}$ can be $C_{4-18}$ alkoxy and $R^{4d}$ can be halogen. In some embodiments, $R^{4a}$ is halogen and $R^{4b}$ is $C_{4-18}$ alkoxy; or $R^{4a}$ is halogen and $R^{4c}$ is $C_{4-18}$ alkoxy; or $R^{4a}$ is halogen and $R^{4d}$ is $C_{4-18}$ alkoxy; or $R^{4a}$ is halogen and $R^{4e}$ is $C_{4-18}$ alkoxy; or $R^{4b}$ is halogen and $R^{4c}$ is $C_{4-18}$ alkoxy; or $R^{4b}$ is halogen and $R^{4d}$ is $C_{4-18}$ s alkoxy.

In some embodiments, at least one or two of $R^{4a}$, $R^{4b}$, $R^{4c}$, $R^{4d}$, and $R^{4e}$ in compounds according to Formula I, Formula I-i, Formula I-ii, or Formula I-iii are independently selected from butoxy, pentyl, hexyloxy, heptyloxy, octyloxy, nonyloxy, decyloxy, undecyloxy, dodecyloxy, tridecyloxy, and tetradecyloxy. In some such embodiments, the remaining three or four of $R^{4a}$, $R^{4b}$, $R^{4c}$, $R^{4d}$, and $R^{4e}$ are independently selected from the group consisting of H and fluoro. In some embodiments, $R^{4a}$ is butoxy, pentyl, hexyloxy, heptyloxy, or octyloxy; $R^{4c}$ is fluoro or chloro; and $R^{4b}$, $R^{4d}$, and $R^{4e}$ are H.

In some embodiments, $R^{5a}$ and $R^{5b}$ in compounds of Formula I, Formula I-i, Formula I-ii, or Formula I-iii are independently selected from the group consisting of $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -L$^5$-R$^{5x}$.

In some embodiments, $R^{5a}$ and $R^{5b}$ are independently selected from the group consisting of H and halogen. In some embodiments, $R^{5a}$ and $R^{5b}$ in compounds of Formula I, Formula I-i, Formula I-ii, or Formula I-iii are H. In some embodiments, $R^{5a}$ and $R^{5b}$ in compounds of Formula I, Formula I-i, Formula I-ii, or Formula I-iii are independently selected halogen (e.g., fluoro or bromo). In some embodiments, $R^{5a}$ and $R^{5b}$ are independently selected from H and fluoro.

In some embodiments, the compound is a compound according to Formula Ia:

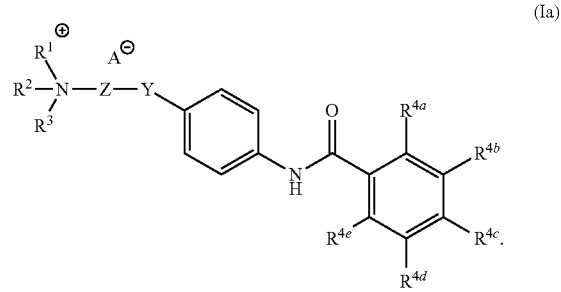

(Ia)

In some embodiments, $R^1$ is selected from the group consisting of $C_{3-18}$ alkyl and -L$^1$-R$^{1a}$.

In some embodiments, $R^1$ is $C_{3-18}$ alkyl in compounds of Formula I, Formula I-i, Formula I-ii, Formula I-iii, or Formula Ia. $R^1$ may be, for example, n-propyl, isopropyl, n-butyl, isobutyl, sec-butyl, tert-butyl, n-pentyl, branched pentyl, n-hexyl, branched hexyl, n-heptyl, branched heptyl, n-octyl, branched octyl, n-nonyl, branched nonyl, n-decyl, branched decyl, n-undecyl, branched undecyl, n-dodecyl, branched dodecyl, n-tridecyl, branched tridecyl, n-tetradecyl, branched tetradecyl, n-pentadecyl, branched pentadecyl, n-hexadecyl, branched hexadecyl, n-heptadecyl, branched heptadecyl, n-octadecyl, or branched octadecyl. In some embodiments, $R^1$ is $C_{3-18}$ alkyl and $R^2$ and $R^3$ are independently selected $C_{1-6}$ alkyl groups. For example, $R^2$ and $R^3$ can be independently selected from methyl, ethyl, n-propyl, isopropyl, n-butyl, isobutyl, sec-butyl, tert-butyl, n-pentyl, branched pentyl, n-hexyl, and branched hexyl. In some such embodiments, $R^2$ and $R^3$ are ethyl.

In some embodiments, $R^1$ in compounds of Formula I, Formula I-i, Formula I-ii, Formula I-iii, or Formula Ia is selected from the group consisting of n-propyl, isopropyl, n-butyl, isobutyl, sec-butyl, tert-butyl, n-pentyl, branched pentyl, n-hexyl, branched hexyl, n-heptyl, branched heptyl, n-octyl, branched octyl, n-nonyl, branched nonyl, n-decyl, branched decyl, n-undecyl, branched undecyl, n-dodecyl, and branched dodecyl. In some embodiments, $R^1$ is selected from the group consisting of n-propyl, n-butyl, n-pentyl, 3-methyl-butyl, n-hexyl, 3,3-dimethyl-butyl, n-heptyl, n-octyl, n-decyl, and n-undecyl. In some such embodiments, $R^2$ and $R^3$ are independently selected $C_{1-6}$ alkyl groups. In some embodiments, $R^2$ and $R^3$ are ethyl. In some such embodiments, Z is ethylene (e.g., —(CH$_2$)$_2$—), propylene (e.g., —(CH$_2$)$_3$—), or butylene (e.g., —(CH$_2$)$_4$—). In some embodiments, Z is —(CH$_2$)—.

In some embodiments, $R^1$ is -$L^1$-$R^{1a}$ in compounds of Formula I, Formula I-i, Formula I-ii, Formula I-iii, or Formula Ia. $L^1$ can be straight-chain alkylene or branched alkylene. $L^1$ may be, for example, methylene (—CH$_2$—), ethylene (e.g., —(CH$_2$)$_2$—), propylene (e.g., —(CH$_2$)$_3$—), butylene (e.g., —(CH$_2$)$_4$—), pentylene (e.g., —(CH$_2$)$_2$—), or hexylene (e.g., —(CH$_2$)$_6$—). In some embodiments, $L^1$ is $C_{1-4}$ alkylene. In some embodiments, $R^{1a}$ is $C_{3-8}$ cycloalkyl or $C_{6-10}$ aryl. $R^{1a}$ may be, for example, cyclopropyl, cyclobutyl, cyclopentyl, cyclohexyl, cycloheptyl, cyclooctyl, phenyl, or naphthyl, each of which may be optionally substituted with one or more groups independently selected from $C_{1-6}$ alkyl, $C_{1-4}$ haloalkyl, $C_{1-6}$ alkoxy, halogen, —C(O)$R^8$, and —NO$_2$. In some embodiments, $L^1$ is $C_{1-4}$ alkylene, and $R^1$ is selected from cyclopentyl, cyclohexyl, and phenyl, wherein phenyl is optionally substituted with one or two substituents which are independently selected from fluoro, trifluoromethyl, methoxy, and methoxycarbonyl. In some embodiments, $R^1$ is -$L^1$-$R^{1a}$ and $R^2$ and $R^3$ are independently selected $C_{1-6}$ alkyl groups. In some such embodiments, $R^2$ and $R^3$ are ethyl.

In some embodiments, $R^2$ and $R^3$ in compounds according to Formula I, Formula I-i, Formula I-ii, Formula I-iii, or Formula Ia are taken together with the nitrogen to which they are attached to form 3- to 10-membered heterocyclyl. For example, $R^2$ and $R^3$ may form pyrrolidine, piperidine, or piperazine. In some such embodiments, $R^1$ is $C_{1-6}$ alkyl. $R^1$ may be, for example, methyl, ethyl, n-propyl, isopropyl, n-butyl, isobutyl, sec-butyl, tert-butyl, n-pentyl, branched pentyl, n-hexyl, or branched hexyl. In some embodiments, $R^1$ is selected from the group consisting of methyl, ethyl, n-propyl, and n-butyl.

In some embodiments, $R^2$ is taken together with the nitrogen to which it is attached and Z to form 3- to 10-membered heterocyclyl, e.g., pyrrolidine or piperidine. In some such embodiments, $R^1$ and $R^3$ are independently selected $C_{1-6}$ alkyl groups. In some embodiments, $R^2$ and $R^3$ are independently selected from the group consisting of methyl, ethyl, n-propyl, and n-butyl.

In some embodiments, Y is —NR$^7$C(O)— or —NR$^7$SO$_2$—, and $R^2$ is taken together with the nitrogen to which it is attached and $R^7$ to form 3- to 10-membered heterocyclyl, e.g., imidazolidine or piperazine. In some such embodiments, $R^1$ and $R^3$ are independently selected $C_{1-6}$ alkyl groups. In some embodiments, $R^2$ and $R^3$ are independently selected from the group consisting of methyl, ethyl, n-propyl, and n-butyl.

In some embodiments, Y in compounds of Formula I, Formula I-i, Formula I-ii, Formula I-iii, or Formula Ia, including any of the specific embodiments set forth above, is selected from the group consisting of —OC(O)— and —NR$^7$C(O)—.

In some embodiments, Y in compounds of Formula I, Formula I-i, Formula I-ii, Formula I-iii, or Formula Ia, including any of the specific embodiments set forth above, is —NR$^7$SO$_2$—.

Ammonium compounds according to the present disclosure are generally provided as pharmaceutically acceptable salts, wherein A in Formula I, Formula I-i, Formula I-ii, Formula I-iii, and Formula Ia is a pharmaceutically acceptable anion. Examples of pharmaceutically acceptable anions include, but are not limited to, chloride, bromide, iodide, acetate, benzenesulfonate, benzoate, bicarbonate, bitartrate, carbonate, citrate, edetate, fumarate, gluconate, glutamate, lactate, maleate, mesylate, methylsulfate, nitrate, pantothenate, phosphate/diphosphate, salicylate, stearate, succinate, sulfate, and tartrate. In some embodiments, A in compounds of Formula I, Formula I-i, Formula I-ii, Formula I-iii, or Formula Ia is a halide. In some embodiments, A in compounds of Formula I, Formula I-i, Formula I-ii, Formula I-iii, or Formula Ia is bromide.

In some embodiments, compounds of Formula I, Formula I-i, Formula I-ii, Formula I-iii, or Formula Ia are provided, wherein $R^1$ is $C_{4-8}$ alkyl; $R^2$ and $R^3$ are each $C_{1-6}$ alkyl; $R^{4a}$ is $C_{4-8}$ alkoxy; $R^{4c}$ is selected from H and halogen; $R^{4e}$ is selected from H and $C_{4-8}$ alkoxy; and $R^{4b}$ and $R^{4d}$ are H. In some such embodiments, Y is —OC(O)—. In some such embodiments, Y is —NR$^7$SO$_2$—. In some such embodiments, Z is —(CH$_2$)$_2$—).

In some embodiments, the compound is selected from the group consisting of:

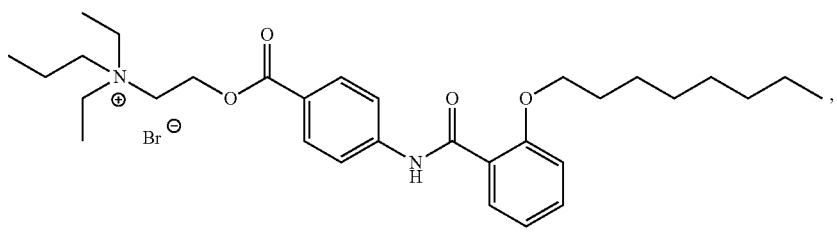

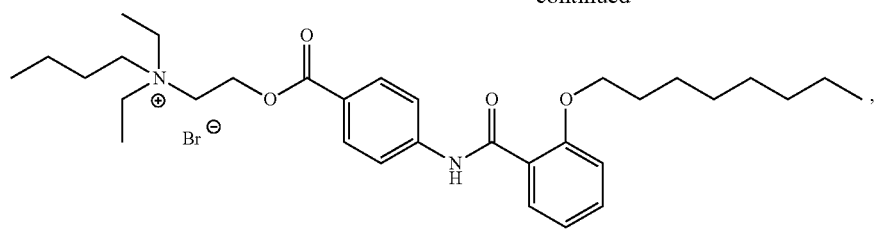,
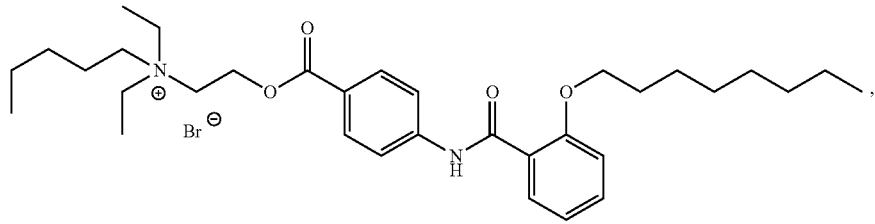,
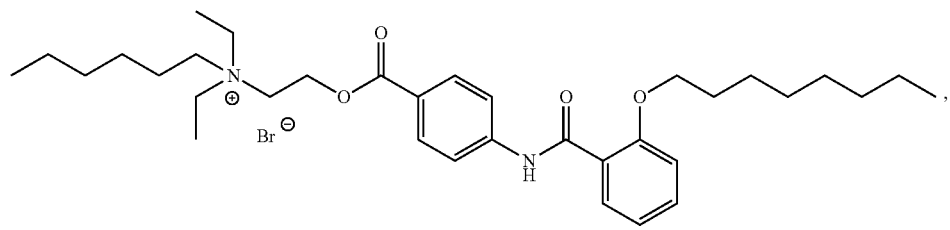,
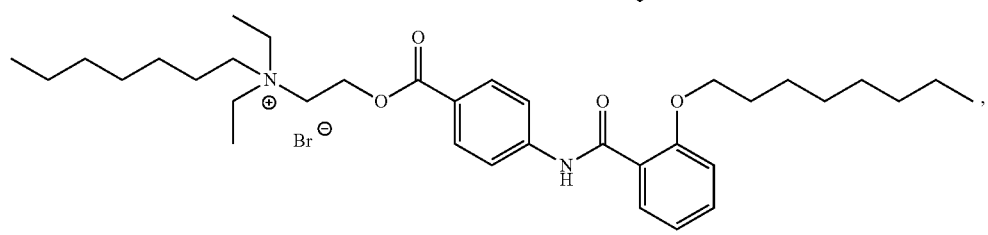,
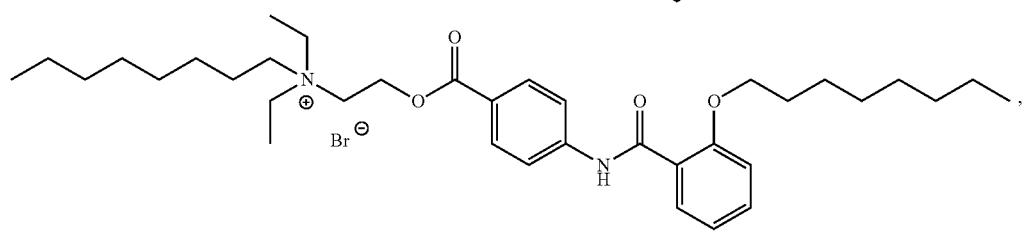,
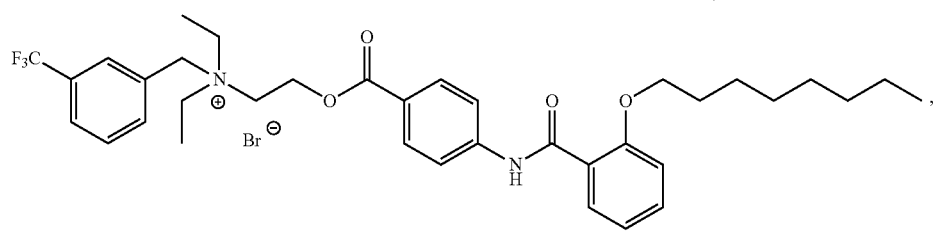,
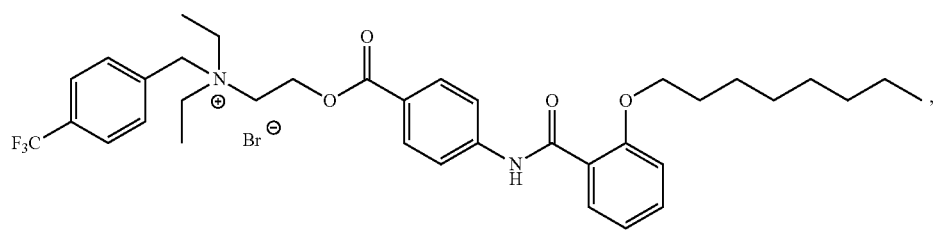, -continued
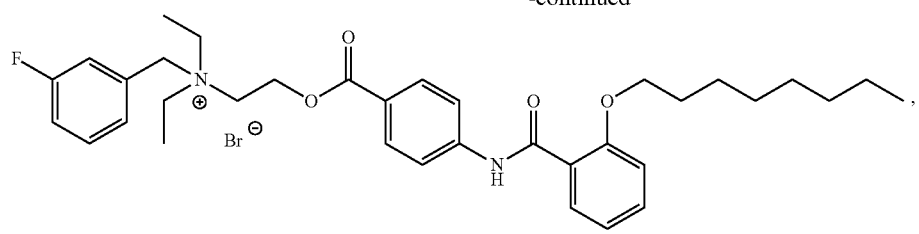
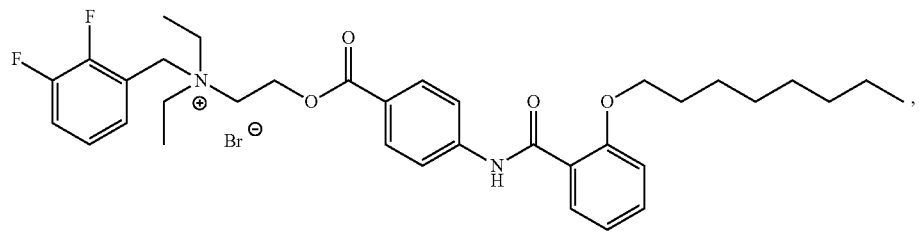
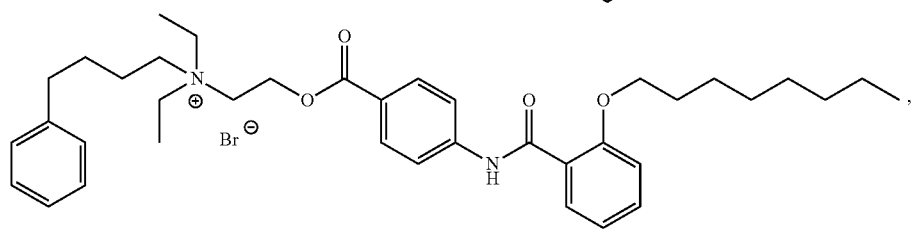
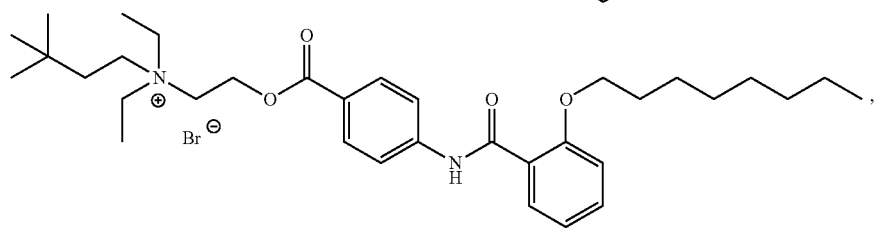
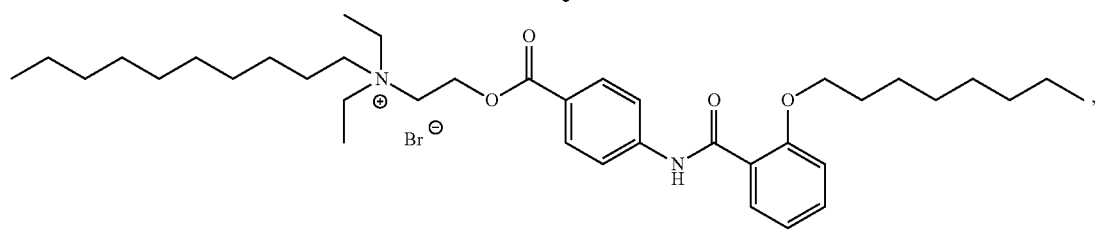
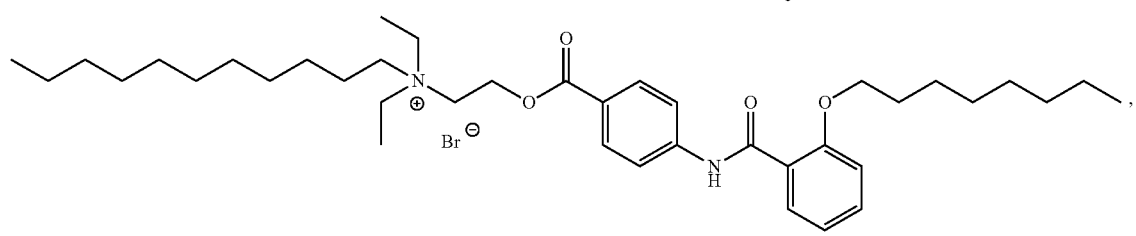
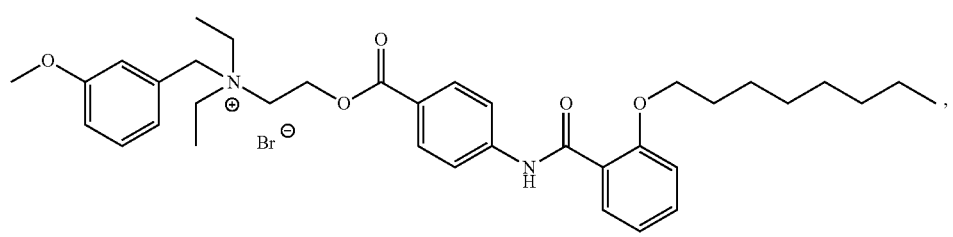

-continued
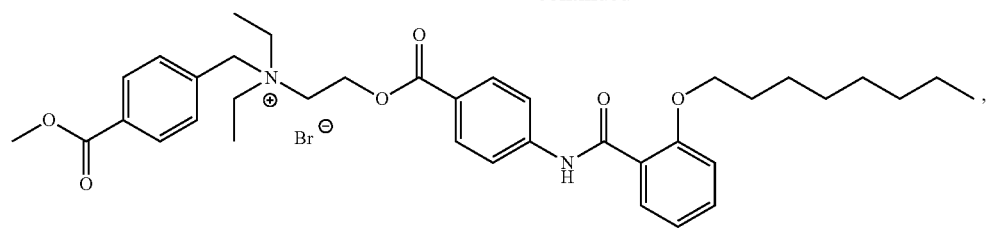
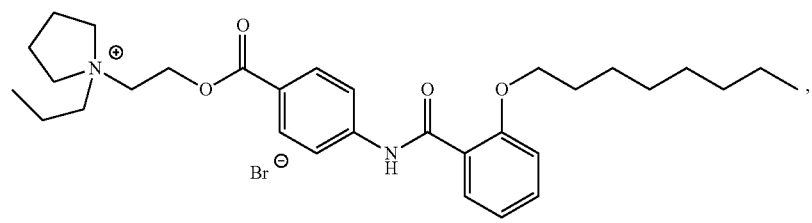
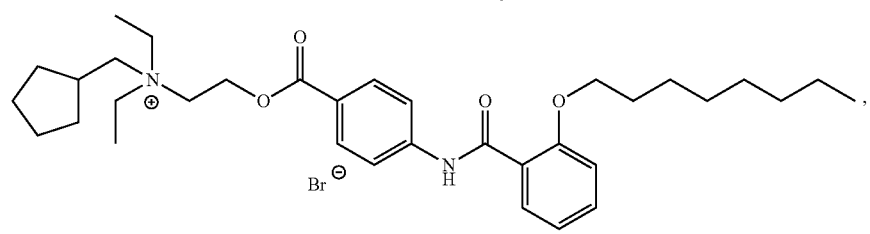
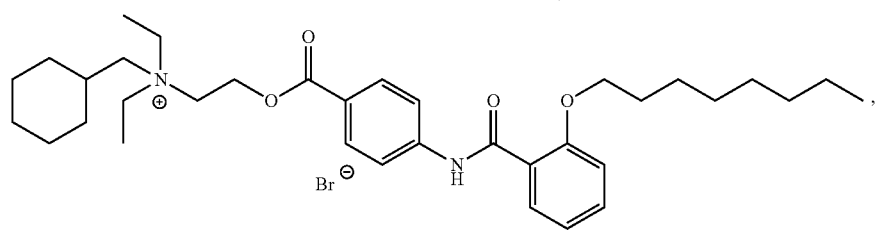
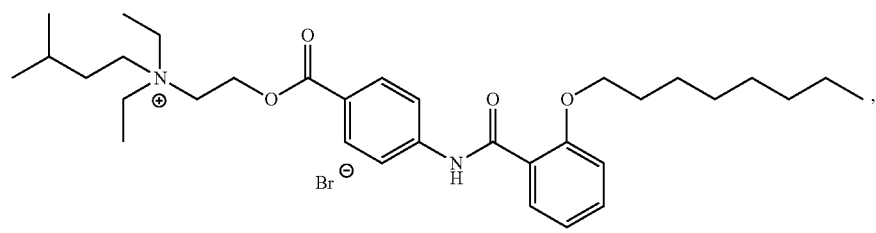
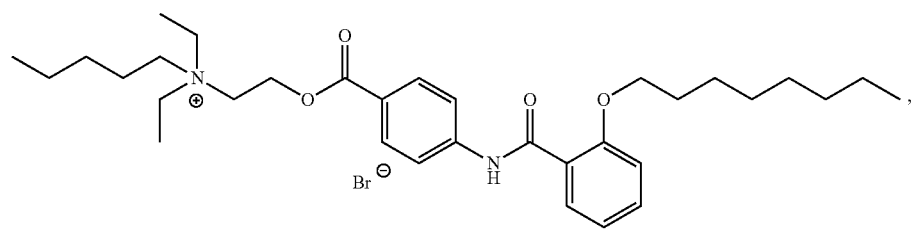
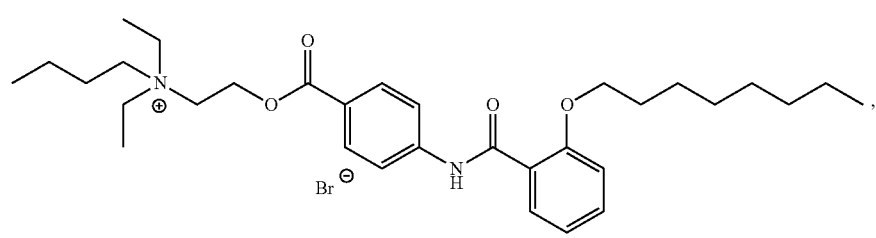

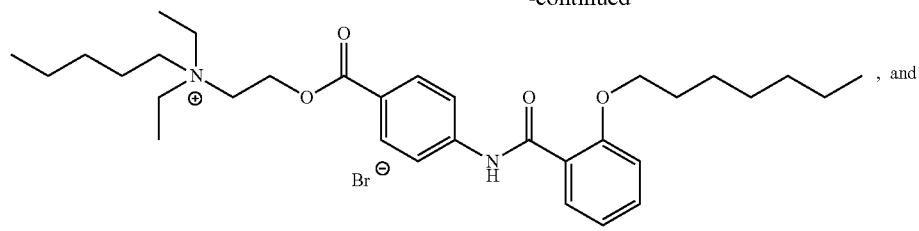, and
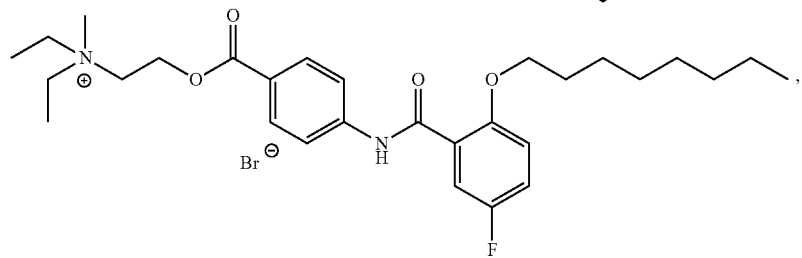
In some embodiments, the compound is selected from the group consisting of:
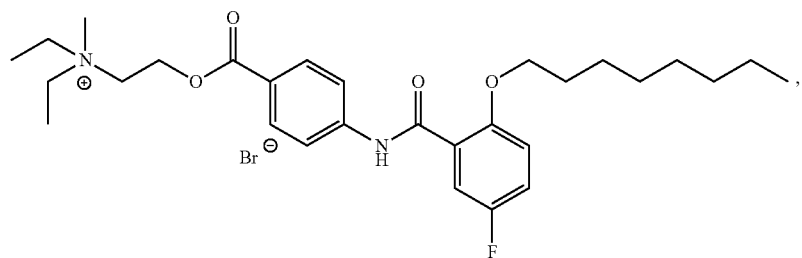
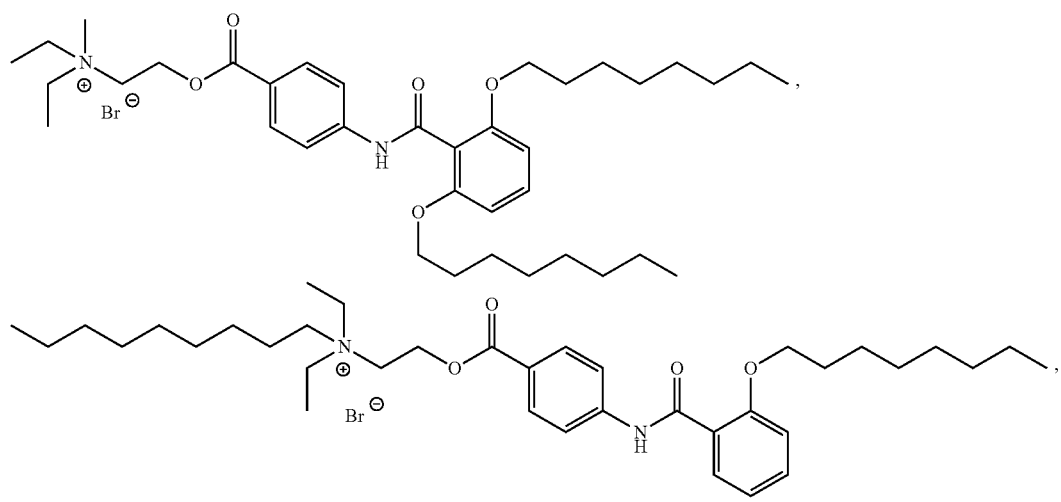
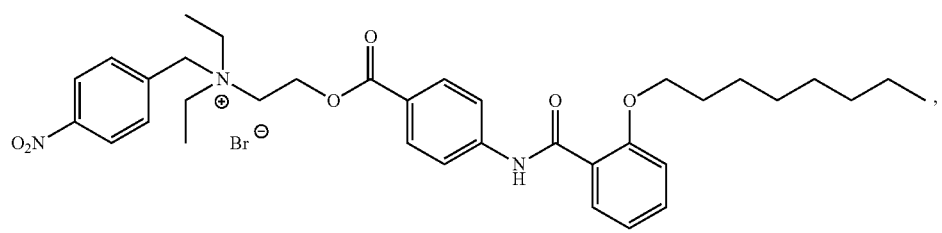

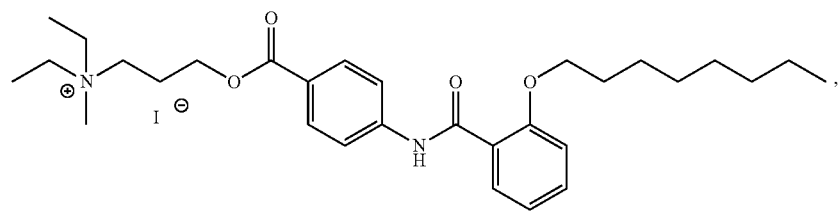
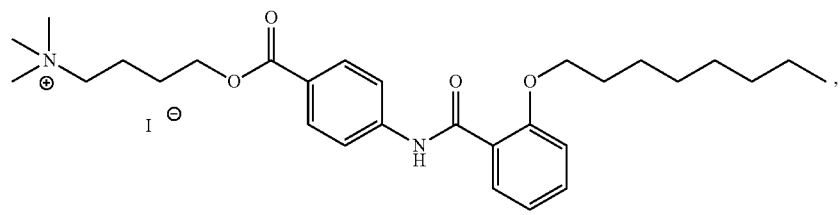
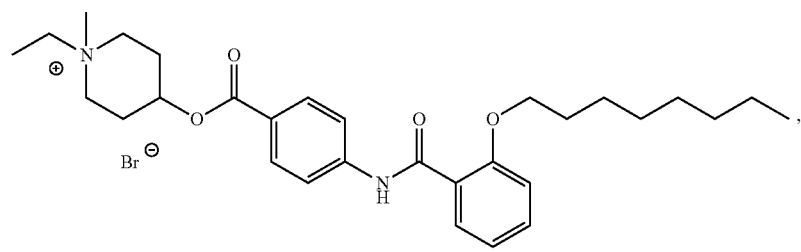
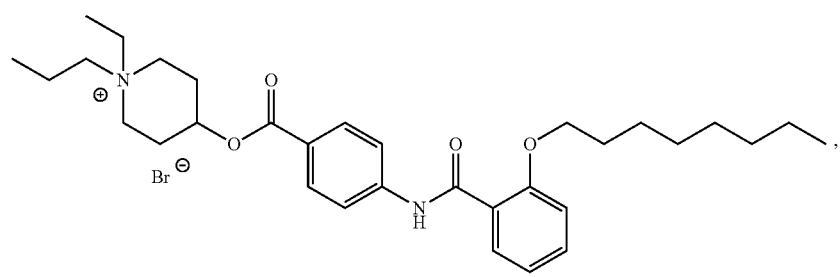
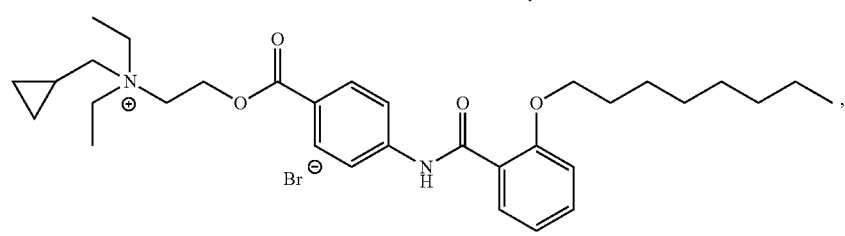
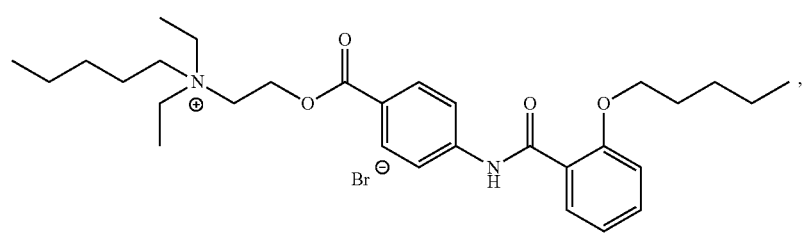
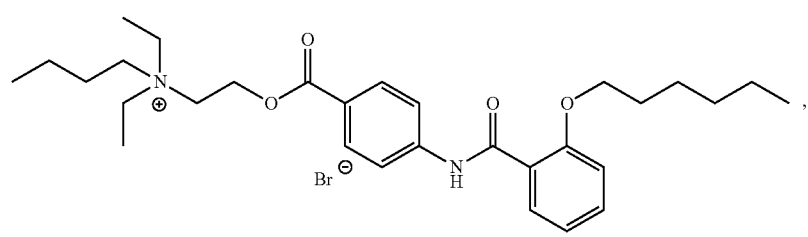

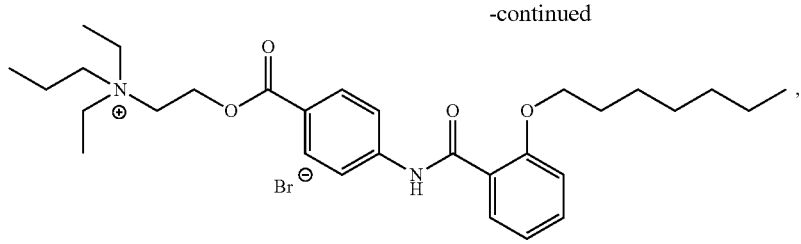
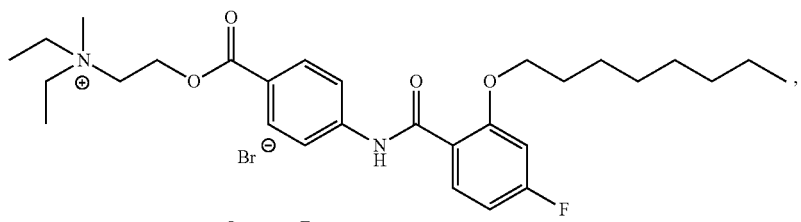
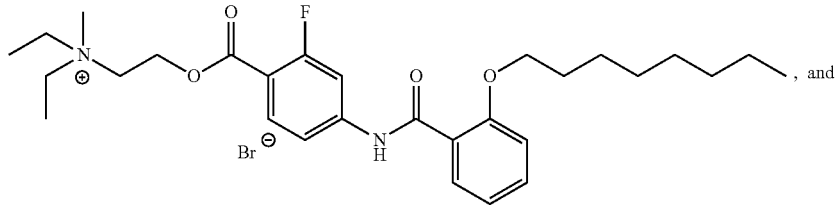, and
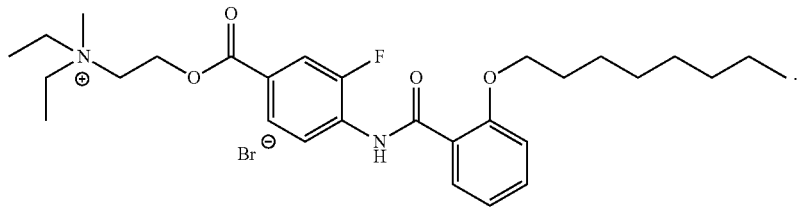
In some embodiments, the compound is selected from the group consisting of:
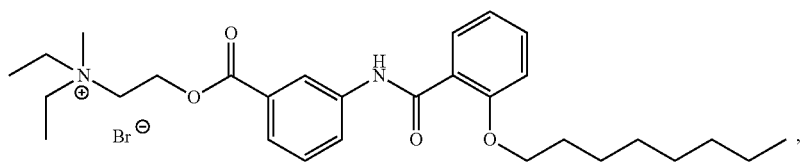
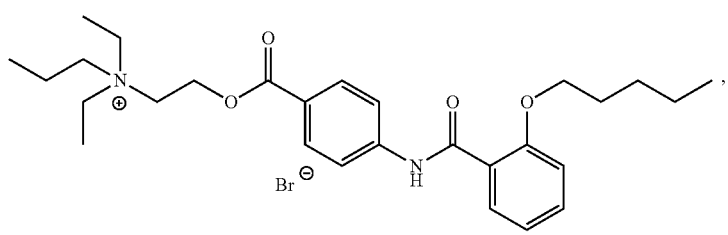
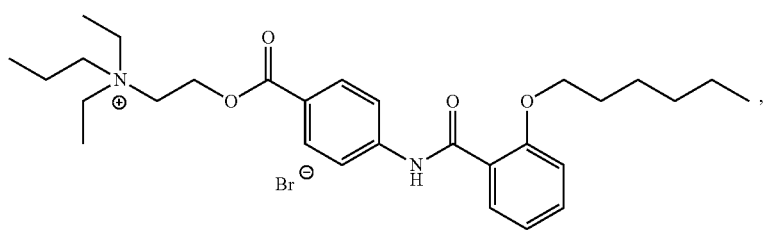

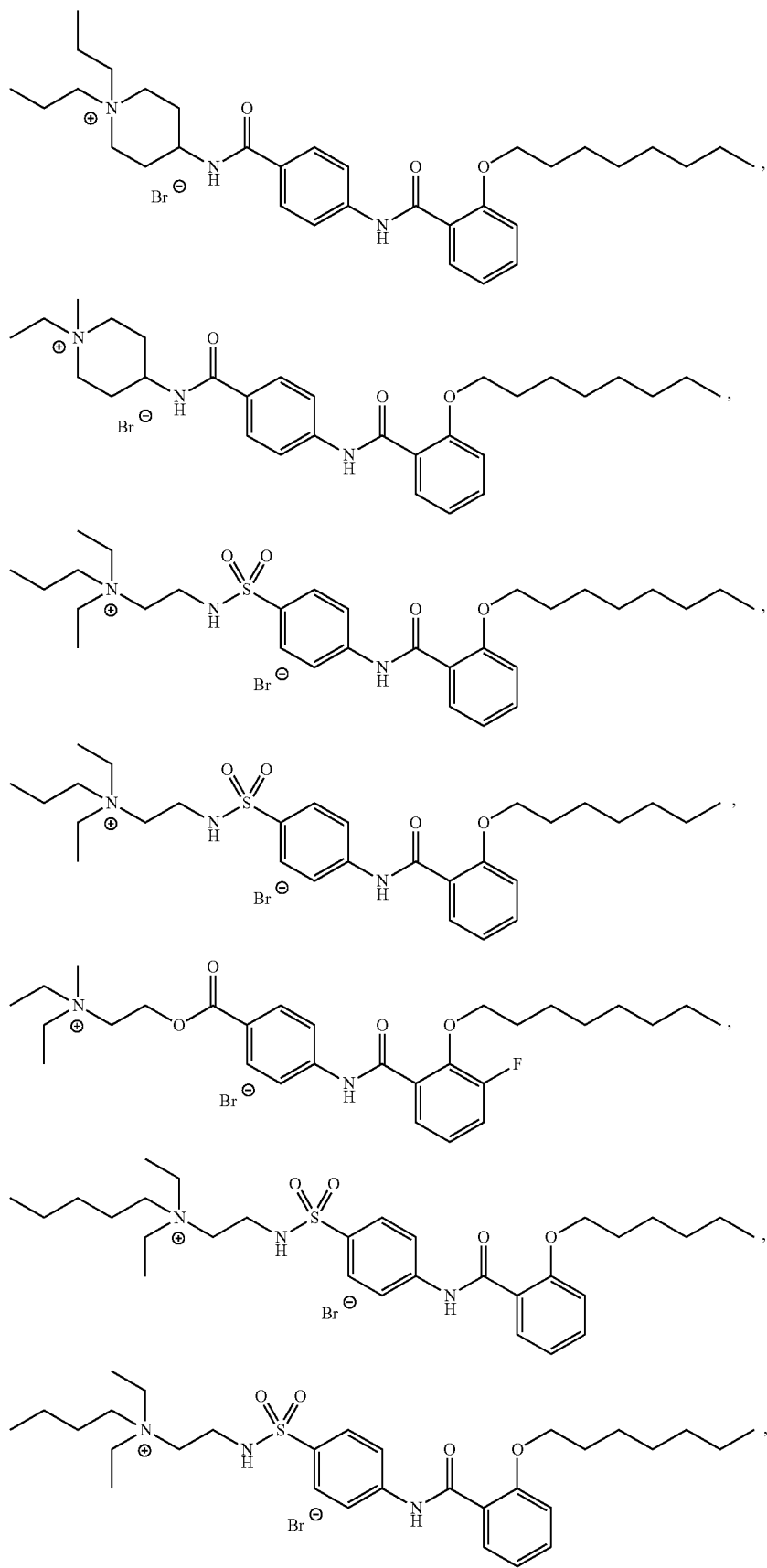

-continued
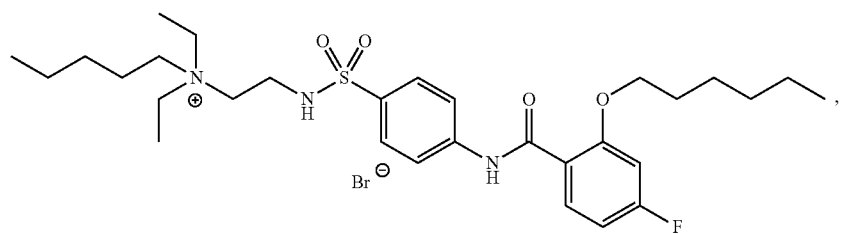
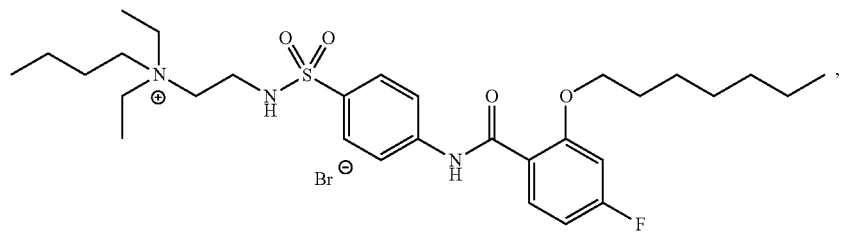
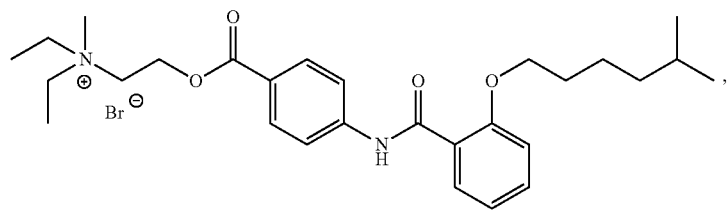
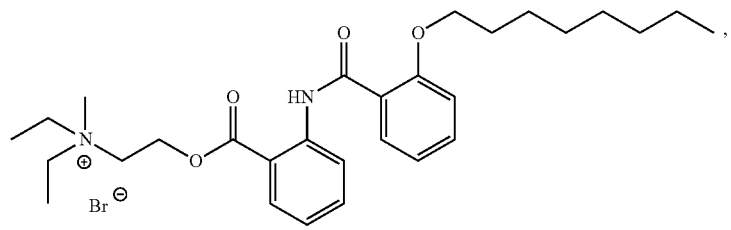
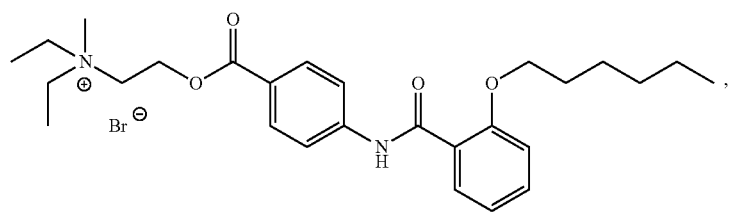
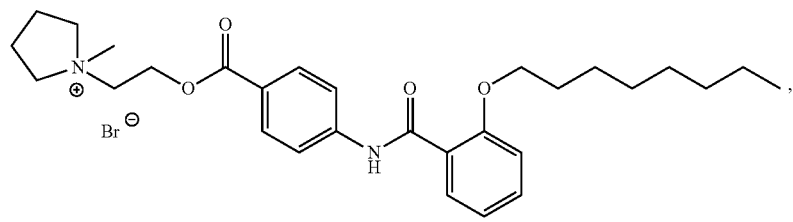
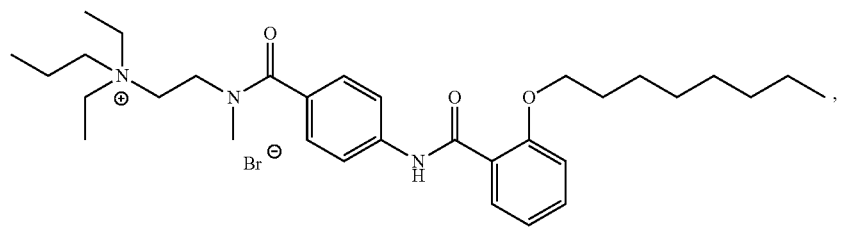

-continued
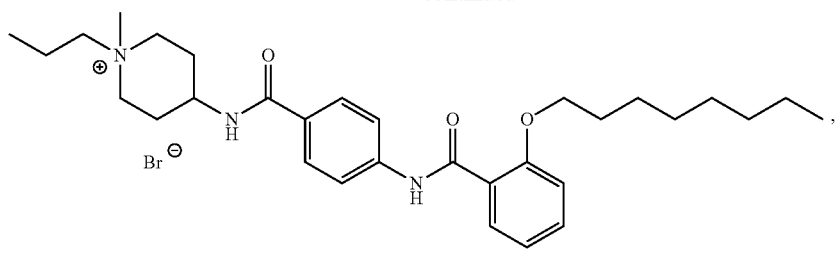
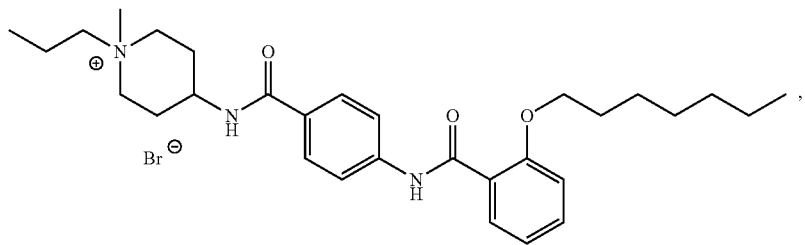
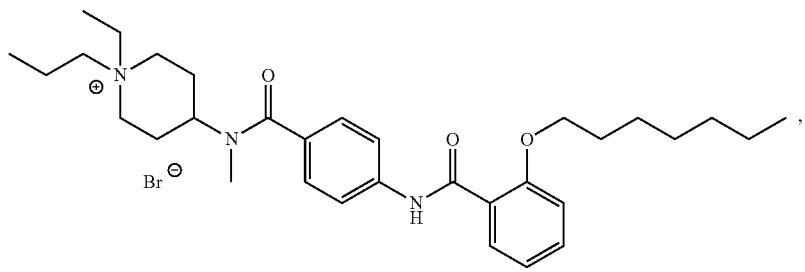
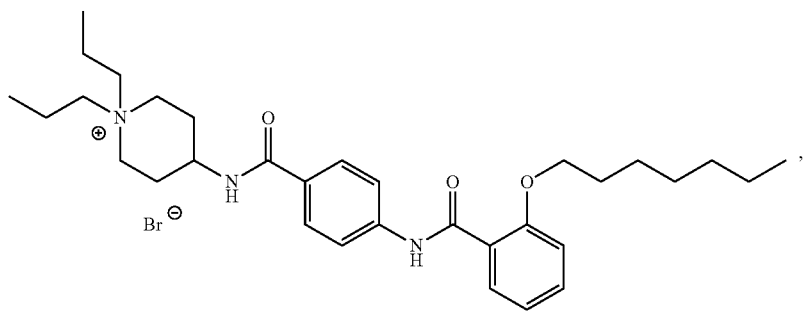
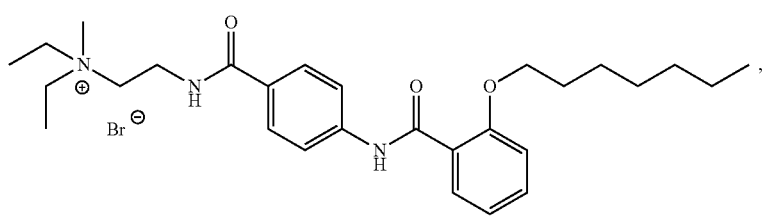
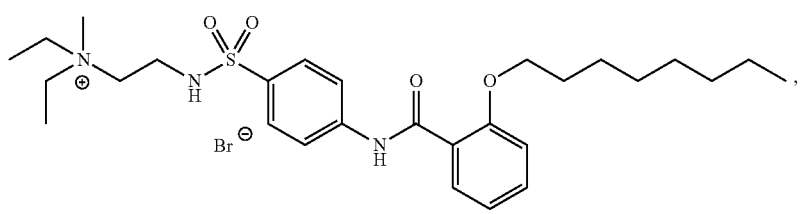
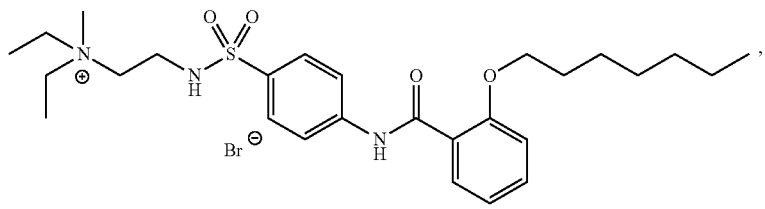

-continued
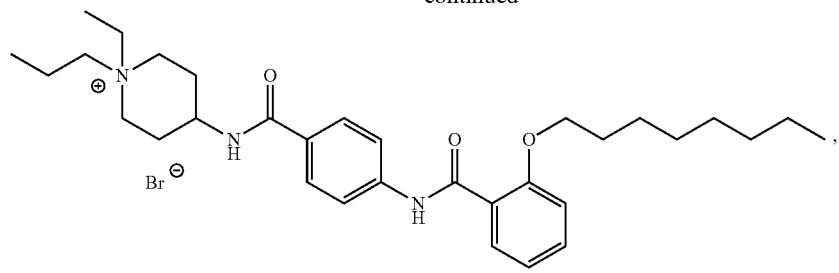
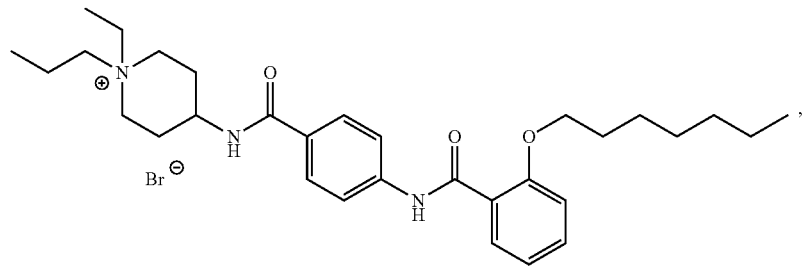
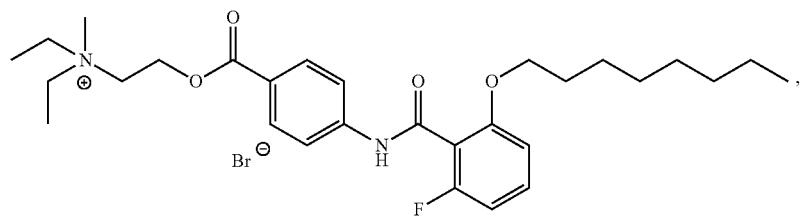
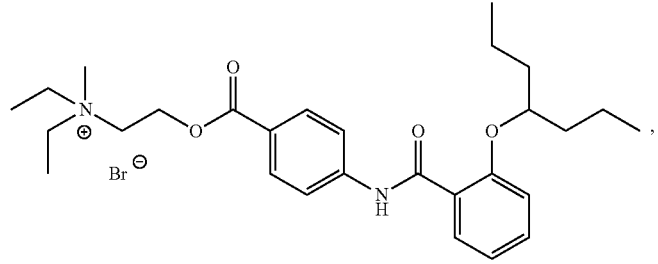
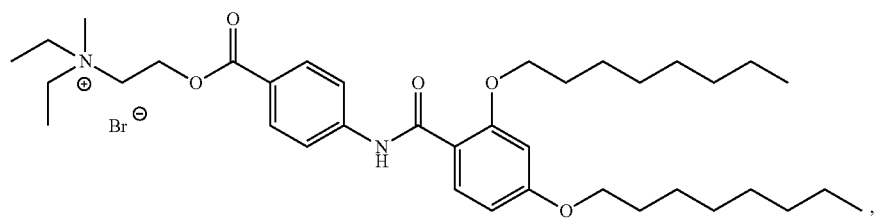
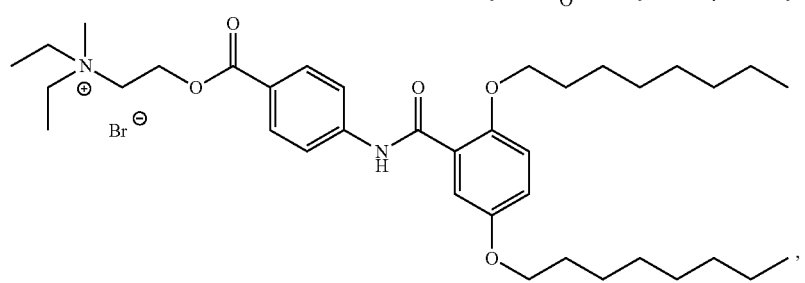
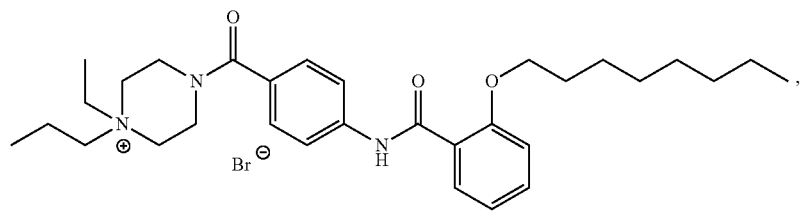

-continued
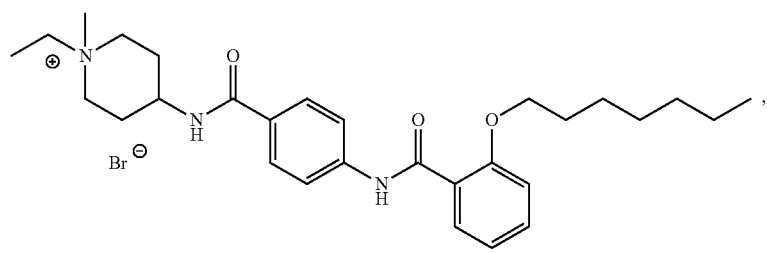
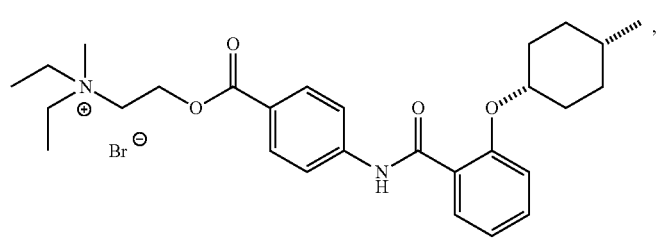
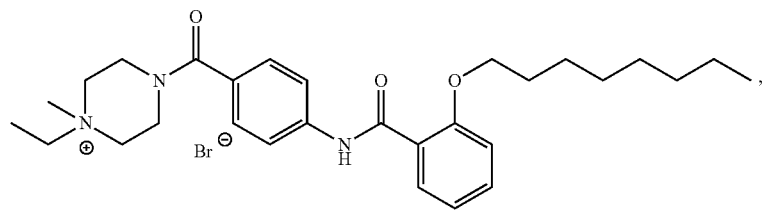
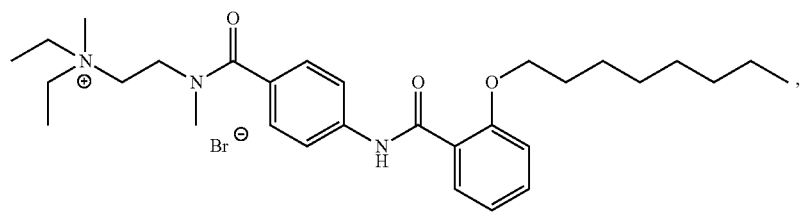
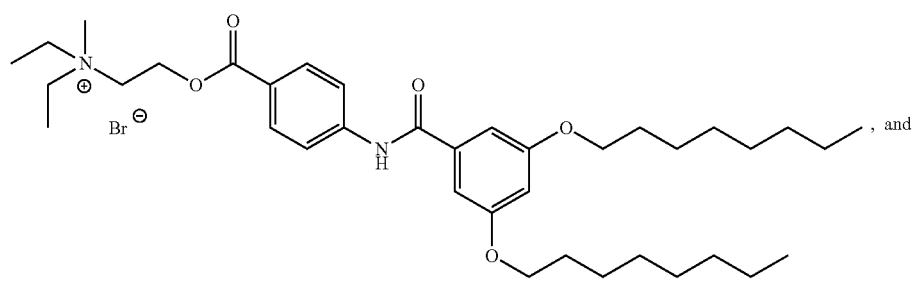, and
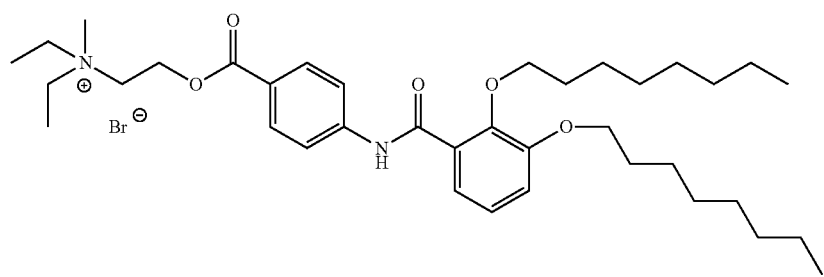

In some embodiments, the compound is selected from the group consisting of:

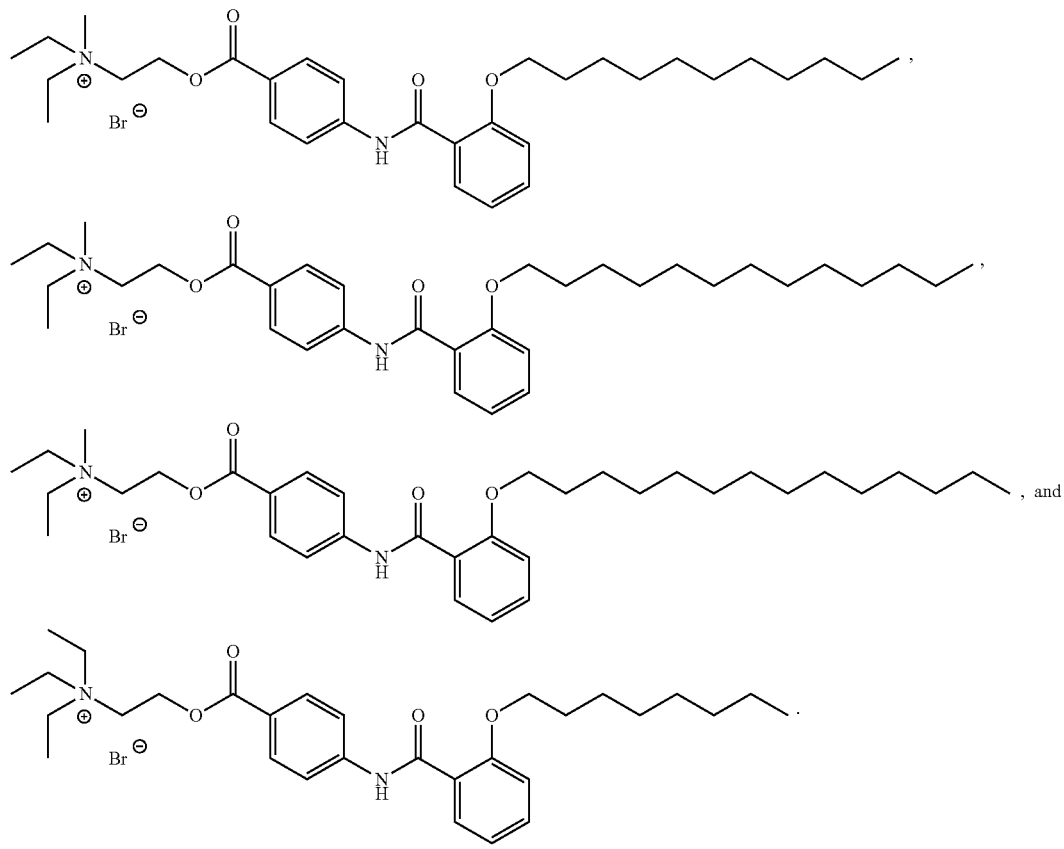

, and

.

Compounds according to Formula I, Formula I-i, Formula I-ii, Formula I-iii, and Formula Ia may be provided as solvates, tautomers, polymorphs, hydrates, or structural derivatives such as prodrugs. Compounds according to Formula I, Formula I-i, Formula I-ii, Formula I-iii, and Formula Ia can also be further substituted. Suitable monovalent substituents on a substitutable carbon atom of an "optionally substituted" group are independently halogen; —(CH$_2$)$_{0-4}$R$^\alpha$; —(CH$_2$)$_{0-4}$OR$^\alpha$; —O(CH$_2$)$_{0-4}$R$^\alpha$, —O—(CH$_2$)$_{0-4}$C(O)OR$^\alpha$; —(CH$_2$)$_{0-4}$CH(OR$^\alpha$)$_2$; —(CH$_2$)$_{0-4}$SR$^\alpha$; —(CH$_2$)$_{0-4}$Ph, wherein Ph is phenyl which may be substituted with R$^\alpha$; —(CH$_2$)$_{0-4}$O(CH$_2$)$_{0-1}$phenyl, which phenyl may be substituted with R$^\alpha$; —CH=CHPh, wherein Ph is phenyl which may be substituted with R$^\alpha$; —(CH$_2$)$_{0-4}$O(CH$_2$)$_{0-1}$-Py, wherein Py is pyridyl which may be substituted with R$^\alpha$; —NO$_2$; —CN; —N$_3$; —(CH$_2$)$_{0-4}$N(R$^\alpha$)$_2$; —(CH$_2$)$_{0-4}$N(R$^\alpha$)C(O)R$^\alpha$; —N(R$^\alpha$)C(S)R$^\alpha$; —(CH$_2$)$_{0-4}$N(R$^\alpha$)C(O)NR$^\alpha_2$; —N(R')C(S)NR$^\alpha_2$; —(CH$_2$)$_{0-4}$N(R$^\alpha$)C(O)OR$^\alpha$; —N(R$^\alpha$)N(R$^\alpha$)C(O)R$^\alpha$; —N(R$^\alpha$)N(R$^\alpha$)C(O)NR$^\alpha_2$; —N(R$^\alpha$)N(R$^\alpha$)C(O)OR$^\alpha$; —(CH$_2$)$_{0-4}$C(O)R$^\alpha$; —C(S)R$^\alpha$; —(CH$_2$)$_{0-4}$C(O)OR$^\alpha$; —(CH$_2$)$_{0-4}$C(O)SR$^\alpha$; —(CH$_2$)$_{0-4}$C(O)OSiR$^\alpha_3$; —(CH$_2$)$_{0-4}$OC(O)R$^\alpha$; —OC(O)(CH$_2$)$_{0-4}$SR—SC(S)SR$^\alpha$; —(CH$_2$)$_{0-4}$SC(O)R$^\alpha$; —(CH$_2$)$_{0-4}$C(O)NR$^\alpha_2$; —C(S)NR$^\alpha_2$, —C(S)SR$^\alpha$; —SC(S)SR$^\alpha$, —(CH$_2$)$_{0-4}$OC(O)NR$^\alpha_2$; —C(O)N(OR$^\alpha$)R$^\alpha$; —C(O)C(O)R$^\alpha$; —C(O)CH$_2$C(O)R$^\alpha$; —C(NOR$^\alpha$)R$^\alpha$; —(CH$_2$)$_{0-4}$SSR$^\alpha$; —(CH$_2$)$_{0-4}$S(O)$_2$R$^\alpha$; —(CH$_2$)$_{0-4}$S(O)$_2$OR$^\alpha$; —(CH$_2$)$_{0-4}$OS(O)$_2$R$^\alpha$; —S(O)$_2$NR$^\alpha_2$; —(CH$_2$)$_{0-4}$S(O)R$^\alpha$; —N(R$^\alpha$)S(O)$_2$NR$^\alpha$2; —N(R$^\alpha$)S(O)$_2$R$^\alpha$; —N(OR$^\alpha$)R$^\alpha$; —C(NH)NR$^\alpha_2$; —P(O)$_2$R$^\alpha$; —P(O)R$^\alpha_2$; —OP(O)R$^\alpha_2$; —OP(O)(OR$^\alpha$)$_2$; SiR$^\alpha_3$; —(C$_{1-4}$ straight or branched)alkylene)-O—N(R$^\alpha$)$_2$; or —(C$_{1-4}$ straight or branched)alkylene)-C(O)O—N(R$^\alpha$)$_2$. Each R$^\alpha$ is independently hydrogen; C$_{1-6}$ alkyl; —CH$_2$Ph, —O(CH$_2$)$_{0-1}$Ph; —CH$_2$-(5- to 6-membered heteroaryl); C$_{3-8}$ cycloalkyl; C$_{6-10}$ aryl; 4- to 10-membered heterocyclyl; or 6- to 10-membered heteroaryl; and each R$^\alpha$ may be further substituted as described below.

Suitable monovalent substituents on R$^\alpha$ are independently halogen, —(CH$_2$)$_{0-2}$R$^\beta$; —(CH$_2$)$_{0-2}$OH; —(CH$_2$)$_{0-2}$OR$^\beta$; —(CH$_2$)$_{0-2}$CH(OR$^\beta$)$_2$; —CN; —N$_3$; —(CH$_2$)$_{0-2}$C(O)R$^\beta$; —(CH$_2$)$_{0-2}$C(O)OH; —(CH$_2$)$_{0-2}$C(O)OR$^\beta$; —(CH$_2$)$_{0-2}$SR$^\beta$; —(CH$_2$)$_{0-2}$SH; —(CH$_2$)$_{0-2}$NH$_2$; —(CH$_2$)$_{0-2}$NHR$^\beta$; —(CH$_2$)$_{0-2}$NR$^\beta_2$; —NO$_2$; SiR$^\beta_3$; —OSiR$^\beta_3$; —C(O)SR$^\beta$; —(C$_{1-4}$ straight or branched alkylene)-C(O)OR$^\beta$; or —SSR$^\beta$; wherein each R$^\beta$ is independently selected from C$_{1-4}$ alkyl; —CH$_2$Ph; —O(CH$_2$)$_{0-1}$Ph; C$_{3-8}$ cycloalkyl; C$_{6-10}$ aryl; 4- to 10-membered heterocyclyl; or 6- to 10-membered heteroaryl. Suitable divalent substituents on a saturated carbon atom of R$^\alpha$ include =O and =S.

Suitable divalent substituents on a saturated carbon atom of an "optionally substituted" group include the following: =O; =S; =NNR$^\gamma_2$; =NNHC(O)R$^\gamma$; =NNHC(O)OR$^\gamma$; =NNHS(O)$_2$R$^\gamma$; =NR$^\gamma$; =NOR$^\gamma$; —O(C(R$^\gamma_2$))$_{2-3}$O—; or —S(C(R$^\gamma_2$))$_{2-3}$S—; wherein each independent occurrence of R$^\gamma$ is selected from hydrogen; C$_{1-6}$ alkyl, which may be substituted as defined below; C$_{3-8}$ cycloalkyl; C$_{6-10}$ aryl; 4- to 10-membered heterocyclyl; or 6- to 10-membered heteroaryl. Suitable divalent substituents that are bound to vicinal substitutable carbons of an "optionally substituted" group include: —O(CR$^\beta$$_2$)$_{2-3}$O—; wherein each independent occurrence of R$^\beta$ is selected from hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of R$^\gamma$ include halogen; —R$^\delta$; —OH; —OR$^\delta$; —CN; —C(O)OH; —C(O)OR$^\delta$; —NH$_2$; —NHR$^\delta$; —NR$^\delta$$_2$; or —NO$_2$; wherein each R$^\delta$ is independently C$_{1-4}$ alkyl; —CH$_2$Ph; —O(CH$_2$)$_{0-1}$Ph; 4- to 10-membered heterocyclyl; or 6- to 10-membered heteroaryl.

Suitable substituents on a substitutable nitrogen of an "optionally substituted" group include —R$^\varepsilon$; —NR$^\varepsilon$$_2$; —C(O)R$^\varepsilon$; —C(O)OR$^\varepsilon$; —C(O)C(O)R$^\varepsilon$—; —C(O)CH$_2$C(O)R$^\varepsilon$; —S(O)$_2$R$^\varepsilon$; —S(O)$_2$NR$^\varepsilon$$_2$; —C(S)NR$^\varepsilon$$_2$; —C(NH)NR$^\varepsilon$$_2$; or —N(R$^\varepsilon$)S(O)$_2$R$^\varepsilon$; wherein each R$^\varepsilon$ is independently hydrogen; C$_{1-6}$ alkyl which may be substituted as defined below; C$_{3-8}$ cycloalkyl; C$_{6-10}$ aryl; 4- to 10-membered heterocyclyl; or 6- to 10-membered heteroaryl.

Suitable substituents on the alkyl group of R$^\varepsilon$ are independently halogen; —R$^\delta$; —OH; —OR$^\delta$; —CN; —C(O)OH; —C(O)OR$^\delta$; —NH$_2$; —NHR$^\delta$; —NR$^\delta$$_2$; or —NO$_2$; wherein each R$^\delta$ is independently C$_{1-4}$ alkyl; —CH$_2$Ph; —O(CH$_2$)$_{0-1}$Ph; C$_{6-10}$ aryl; 4- to 10-membered heterocyclyl; or 6- to 10-membered heteroaryl.

Scheme 1

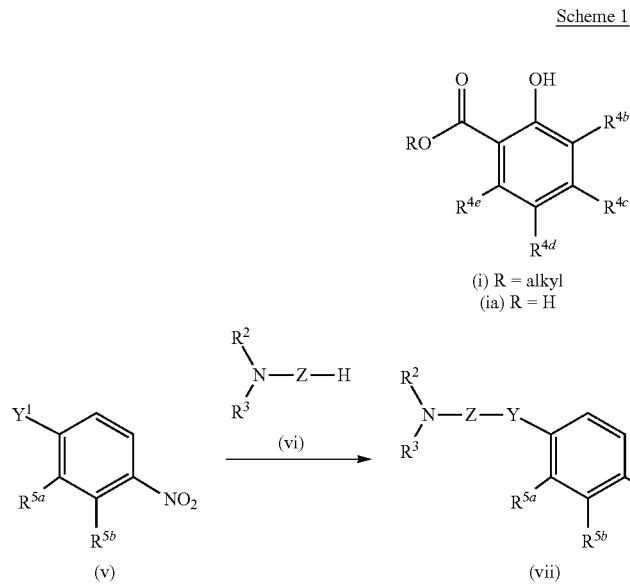

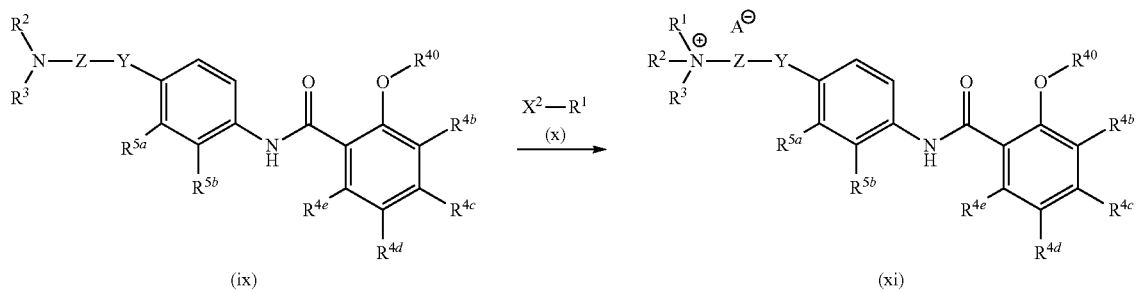

Compounds of the present disclosure can be prepared from readily available starting materials using synthetic routes such as the route depicted in Scheme 1. A hydroxybenzoate such as compound (i) can be treated with an alkylating agent (ii), wherein $R^{40}$ is alkyl, cycloalkyl, aryl, heterocyclyl, or heteroaryl and $X^1$ is a leaving group such as a halide, tosylate, triflate, or mesylate, in the presence of a suitable base, e.g., an inorganic base such as $K_2CO_3$, $Na_2CO_3$, or the like. The alkylation reaction can be carried out at temperatures ranging from room temperature to about the reflux temperature, in solvents such as MeCN, DMF, DMA, and the like, to produce aryl ether compound (iii). Hydroylsis of the ester moiety in aryl ether (iii) with a suitable base, e.g., a metal hydroxide such as NaOH, LiOH, KOH, or the like, in water/alcohol mixtures such as water/MeOH affords the corresponding carboxylic acid (iv). Alternatively, starting material (ia) can be alkylated to produce carboxylic acid (iv) directly.

Reaction of a nitro-substituted compound (v), wherein $Y^1$ is a halocarbonyl moiety or a halosulfonyl moiety, with a amine-functionalized moiety (vi), in the presence of a suitable base, e.g., a tertiary amine such as TEA, in solvents such as DCM or DCE affords the corresponding amino-ester (vii). Reduction of the nitro group in compound (vii) to the corresponding aniline (viii) can be accomplished by treatment of compound (vii) with hydrogen gas (atmospheric to 200 psi) and a suitable metal catalyst such as palladium on carbon, Raney nickel, platinum, rhenium, or the like, in alcohol solvents such as MeOH or EtOH, affording the desired aniline (viii).

The acyl chloride corresponding to carboxylic acid (vi) can be generated with a suitable chlorinating agent such as $SOCl_2$, $(COCl)_2$, or the like. The reaction can be carried out neat or in solvents such as DMF, DCM or DCE, at temperatures ranging from room temperature to reflux, to produce the corresponding acid chloride. Reaction of the resulting acid chloride with aniline (viii), in the presence of a suitable base, e.g., a tertiary amine base such as TEA or DIPEA, in solvents such as DCM, DCE, and the like, affords the desired amide compound (ix). Alternatively, the carboxylic acid (iv) and the aniline (viii) can be coupled directly by employing suitable coupling agents such as DCC (with or without a nucleophilic catalyst such as DMAP), HBTU, EDC, and the like, to produce the desired amide (ix). Finally, the tertiary amine in compounds of structure (ix) can be alkylated with a suitable alkylating agent (x), wherein $R^1$ is alkyl, cycloalkyl, aryl, heterocyclyl, heteroaryl, or -$L^1$-$R^{1a}$ and $X^2$ is a leaving group such as a halide, tosylate, triflate or mesylate, to afford the desired ammonium salts (xi). This reaction can be carried out at temperatures ranging from room temperature to reflux, in solvents such as MeCN, DMF, and the like.

III. PHARMACEUTICAL COMPOSITIONS

In a related aspect, the present disclosure provides pharmaceutical compositions comprising one or more ammonium compounds as described above and one or more pharmaceutically acceptable excipients. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing compounds as set forth herein can be formulated for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Compounds according to the present disclosure can also be administered topically as a solution, ointment, cream, gel, or suspension, as well as in mouth washes, eye-drops, and the like. Still further, transdermal delivery can be accomplished by means of iontophoretic patches and the like.

Pharmaceutical compositions containing compounds of the present disclosure can also be in the form of a sterile injectable aqueous or oleaginous solutions and suspensions. Sterile injectable preparations can be formulated using nontoxic parenterally-acceptable vehicles including water, Ringer's solution, and isotonic sodium chloride solution, and acceptable solvents such as 1,3-butane diol. In addition, sterile, fixed oils can be used as a solvent or suspending medium. For this purpose, any bland fixed oil can be employed including synthetic monoglycerides, diglycerides, or triglycerides.

Aqueous suspensions can contain one or more compound of the present disclosure in admixture with excipients including, but not limited to: suspending agents such as sodium carboxymethylcellulose, methylcellulose, oleaginopropylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Dispersible powders and granules (suitable for preparation of an aqueous suspension by the addition of water) can contain one or more compounds of the present disclosure in admixture with a dispersing agent, wetting agent, suspending agent, or combinations thereof. Oily suspensions can be formulated by suspending a compound of the present disclosure in a vegetable oil (e.g., arachis oil, olive oil, sesame oil or coconut oil), or in a mineral oil (e.g., liquid paraffin). Oily suspensions can contain one or more thickening agents, for example beeswax, hard paraffin, or cetyl alcohol. These compositions can be preserved by the addition of an antioxidant such as ascorbic acid.

The pharmaceutical compositions can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions can also include one or more additional active agents useful in the treatment of bacterial infections. For example, the pharmaceutical compositions can include one or more bacteriocidal or bacteriostatic compounds including, but not limited to: a quinolone (e.g., moxifloxacin, gemifloxacin, ciprofloxacin, oflaxacin, trovafloxacin, sitafloxacin, or the like), a β-lactam (e.g., a penicillin such as amoxicillin, amoxacilin-clavulanate, piperacillin-tazobactam, penicillin G, or the like; or a cephalosporin such as ceftriaxone or the like), a macrolide (e.g., erythromycin, azithromycin, clarithromycin, lipiarmycin, or the like), a carbapenem (e.g., doripenem, imipenem, meropinem, ertapenem, or the like), a thiazolide (e.g., tizoxanidine, nitazoxanidine, RM 4807, RM 4809, or the like), a tetracycline (e.g., tetracycline, minocycline, doxycycline, eravacycline, or the like), a polymyxin (e.g., polymyxin B, collistin, or the like), a rifamycin (e.g., rifampicin, rifabutin, rifaximin, or the like), a sulfonamide (e.g., sulfadiazine, sulfadoxine, or the like), or a lincosamide (e.g., lincomycin, clindamycin, or the like).

Other examples of bacteriostatic/bacteriocidal compounds contemplated for use in conjunction with the ammonium compounds provided herein include arsphenamine, aztreonam, bacitracin, capreomycin, chloramphenicol, chlorhexidines such as chlorhexidine digluconate, cycloserine, dalfopristin, daptomycin, ethionamide, fosfomycin, furazolidone, fusidic acid, kanamycin, linezolid, metronidazole, mupirocin, platensimycin, quinupristin, rifapentine, satranidazole, spiramycin, streptomycin, teicoplanin, telithromycin, thiamphenicol, tigecycline, tinidazole, trimethoprim, vancomycin, and zinc compounds such as zinc acetate. The pharmaceutical compositions can contain one or more ammonium compounds as set forth above with one or more (e.g., two, three, four, five, six, or more) bacteriocidal/bacteriostatic compounds.

IV. METHODS FOR BACTERIAL INFECTION TREATMENT AND MICROBIOME ALTERATION

While humans and other animal subjects contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy. The compounds and methods provided herein are useful for the treatment of such conditions.

Additionally, different bacteria have a wide range of interactions with the body and those interactions can modulate the ability of the bacteria to cause an infection. For example, bacteria can be conditionally pathogenic such that they only cause an infection under specific conditions. For example, *Staphylococcus* and *Streptococcus* bacteria exist in the normal human bacterial biome, but the bacteria can cause skin infections, pneumonia, or sepsis when they are allowed to colonize other parts of the body. Other bacteria are opportunistic pathogens that only cause diseases in patients with weakened immune systems or another diseases or disorders.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce; such bacteria include, but are not limited to, *Chlamydophila, Rickettsia*, and *Ehrlichia*, which are known to cause pneumonia, urinary tract infections, typhus, and Rocky Mountain spotted fever. Facultative intracellular parasites can reproduce either intracellularly or extracellularly. Examples of facultative intracellular parasites include, but are not limited to, *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis. Disordered microbiome fluctuations (e.g., overgrowth of pathogenic aerobes such as Enterobacteriaceae) can also contribute to complex conditions including, but not limited to, irritable bowel syndrome, hepatic encephalopathy, and small bowel overgrowth.

Provided herein are methods for treating a bacterial infection. The methods include administering to a subject in need thereof a therapeutically effective amount of a compound according to Formula II:

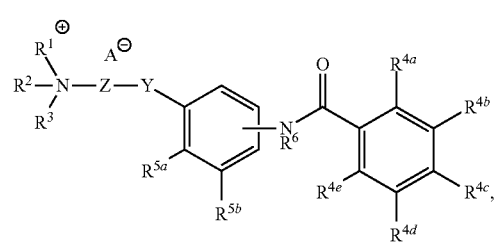

wherein

A is a pharmaceutically acceptable anion;

Y is selected from the group consisting of —OC(O)—, —NR$^7$C(O)—, and —NR$^7$SO$_2$—;

Z is C$_{1-6}$ alkylene;

R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;

L is C$_{1-6}$ alkylene;

R$^{1a}$ is selected from the group consisting of C$_{3-8}$ cycloalkyl, C$_{6-10}$ aryl, 3- to 10-membered heterocyclyl, and 5- to 10-membered heteroaryl;

R$^2$ and R$^3$ are independently selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;

$L^2$ is $C_{1-6}$ alkylene;

$R^{2a}$ is selected from the group consisting of $C_{3-8}$ cycloalkyl, $C_{6-10}$ aryl, 3- to 10-membered heterocyclyl, and 5- to 10-membered heteroaryl;

$R^2$ and $R^3$ are optionally taken together with the nitrogen to which they are attached to form 3- to 10-membered heterocyclyl;

one of $R^2$ and $R^3$ is optionally taken together with the nitrogen to which it is attached and Y or Z to form 3- to 10-membered heterocyclyl;

$R^{4a}$, $R^{4b}$, $R^{4c}$, $R^{4d}$, and $R^{4e}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -$L^4$-$R^{4x}$;

$L^4$ is selected from the group consisting of $C_{1-6}$ alkylene, 2- to 6-membered heteroalkylene, and —O—;

$R^{4x}$ is selected from the group consisting of $C_{3-8}$ cycloalkyl, $C_{6-10}$ aryl, 3- to 10-membered heterocyclyl, and 5- to 10-membered heteroaryl;

$R^{5a}$ and $R^{5b}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -$L^5$-$R^{5x}$;

$L^5$ is selected from the group consisting of $C_{1-6}$ alkylene, 2- to 6-membered heteroalkylene, and —O—;

$R^{5x}$ is selected from the group consisting of $C_{3-8}$ cycloalkyl, $C_{6-10}$ aryl, 3- to 10-membered heterocyclyl, and 5- to 10-membered heteroaryl;

$R^6$ is selected from the group consisting of H, $C_{1-6}$ alkyl, and $C_{2-7}$ acyl;

$R^6$ is optionally taken together with $R^{4a}$ or $R^{4e}$ to form a 5- to -8-membered ring;

each $R^7$ is independently selected from the group consisting of H, $C_{1-6}$ alkyl, and $C_{2-7}$ acyl;

each $C_{3-8}$ cycloalkyl, $C_{6-10}$ aryl, 3- to 10-membered heterocyclyl, and 5- to 10-membered heteroaryl is optionally and independently substituted with one or more substituents selected from the group consisting of $C_{1-18}$ alkyl, $C_{1-18}$ haloalkyl, $C_{1-18}$ alkenyl, $C_{1-18}$ alkoxy, halogen, —OH, —C(O)$R^8$, —C(O)N($R^7$)$_2$, —N($R^7$)$_2$, —NO$_2$, —SO$_3$, and —SO$_2$N($R^7$)$_2$; and each $R^8$ is independently selected from the group consisting of $C_{1-6}$ alkyl, $C_{1-6}$ alkoxy, and —OH, provided that the compound is other than otilonium bromide.

In some embodiments, the compounds of the present disclosure are used to treat a bacterial infection by a gram-positive bacteria. Gram-positive bacteria contain a thick peptidoglycan layer within the cell wall which prevents the bacteria from releasing the stain when dyed with crystal violet. Without being bound by theory, the gram-positive bacteria are often more susceptible to antibiotics. Generally, gram-positive bacteria, in addition to the thick peptidoglycan layer, also comprise a lipid monolayer and contain teichoic acids which react with lipids to form lipoteichoic acids that can act as a chelating agent. Additionally, in gram-positive bacteria, the peptidoglycan layer is present on the outer surface of the bacteria. Many gram-positive bacteria have been known to cause disease including, but are not limited to, *Streptococcus, Staphylococcus, Corynebacterium, Enterococcus, Listeria, Bacillus, Clostridium, Rathayibacter, Leifsonia,* and *Clavibacter.*

The compounds described herein may be used in the treatment of infections caused by *Staphyloccocus aureus. S. aureus* is a major human pathogen, causing a wide variety of illnesses ranging from mild skin and soft tissue infections and food poisoning to life-threatening illnesses such as deep post-surgical infections, septicemia, endocarditis, necrotizing pneumonia, and toxic shock syndrome. *S. aureus* has a remarkable ability to accumulate additional antibiotic resistance determinants, resulting in the formation of multiply-drug-resistant strains. Methicillin, being the first semi-synthetic penicillin to be developed, was introduced in 1959 to overcome the problem of penicillin-resistant *S. aureus* due to β-lactamase (penicillinase) production. [Livermore, *Int. J. Antimicrob. Agents,* 16(1):S3-10, 2000.] However, methicillin-resistant *S. aureus* (MRSA) strains were identified soon after the introduction of methicillin. [Barber, *J. Clin. Pathol.,* 14:385-393, 1961; Jevons, *British Med. J.,* 1:124-125, 1961.] The methods described herein may be used in the treatment of MRSA bacterial strains.

Additionally, the compounds of the present disclosure may be used to treat *Steptococcus pneumoniae* infections. *Streptococcus pneumoniae* is a gram-positive, alpha-hemolytic, bile soluble aerotolerant anaerobe. *S. pneumoniae* is part of the normal upper respiratory tract flora but as with many natural flora, it can become pathogenic under the right conditions (e.g., if the immune system of the host is suppressed). A significant human pathogenic bacterium, *S. pneumoniae* was recognized as a major cause of pneumonia in the late 19th century and is the subject of many humoral immunity studies. *S. pneumoniae,* despite its name, causes many types of pneumococcal infection other than pneumonia, including acute sinusitis, otitis media, meningitis, bacteremia, sepsis, osteomyelitis, septic arthritis, endocarditis, peritonitis, pericarditis, cellulitis, and brain abscess. *S. pneumoniae* is the most common cause of bacterial meningitis in adults and children, and is one of the top two isolates found in ear infection, otitis media. Pneumococcal pneumonia is more common in the very young and the very old. *S. pneumoniae* can be differentiated from *S. viridans,* some of which are also alpha hemolytic, using an optochin test, as *S. pneumoniae* is optochin sensitive. *S. pneumoniae* can also be distinguished based on its sensitivity to lysis by bile. The encapsulated, gram-positive coccoid bacteria have a distinctive morphology on gram stain, the so-called "lancet shape." It has a polysaccharide capsule that acts as a virulence factor for the organism; more than 90 different serotypes are known, and these types differ in virulence, prevalence, and extent of drug resistance.

In some embodiments, the bacterial infection is caused by Gram-positive bacteria. In some embodiments, the Gram-positive bacteria are selected from the group consisting of *C. difficile, S. aureus, Streptococcus* spp., *Enterococcus* spp., *C. diphtheriae, L. monocytogenes,* and combinations thereof.

In some embodiments, the compounds of the present disclosure are used to treat a bacterial infection by a gram-negative bacteria. Gram-negative bacteria do not retain the crystal violet stain after washing with alcohol. Gram-negative bacteria, on the other hand, have a thin peptidoglycan layer with an outer membrane of lipopolysaccharides and phospholipids as well as a space between the peptidoglycan and the outer cell membrane called the periplasmic space. Gram-negative bacterial generally do not have teichoic acids or lipoteichoic acids in their outer coating. Generally, gram-negative bacteria also release some endotoxin and contain prions which act as molecular transport units for specific compounds. Most bacteria are gram-negative. Some non-limiting examples of gram-negative bacteria include *Bordetella, Borrelia, Burcelia, Campylobacteria, Escherichia, Francisella, Haemophilus, Helicobacter, Legionella, Leptospira, Neisseria, Pseudomonas, Rickettsia, Salmonella, Shigella, Treponema, Vibrio,* and *Yersinia.*

In some embodiments, the compounds of the present disclosure are used to treat a bacterial infection by a gram-indeterminate bacteria. Gram-indeterminate bacteria do not full stain or partially stain when exposed to crystal violet. Without being bound by theory, a gram-indeterminate bacteria may exhibit some of the properties of the gram-positive and gram-negative bacteria. Non-limiting examples of a gram-indeterminate bacteria include *Mycobacterium tuberculosis* or *Mycobacterium leprae*.

Infections in human and non-human subjects can be treated using the methods of the present disclosure. In some embodiments, a compound or composition as described herein is administered to a subject (e.g., a mammal such as a rodent, a human, a non-human primate, a canine, a bovine, an equine, a feline) in an amount effective for producing a desirable result in the subject (e.g., killing pathogenic bacterial cells or inhibiting the growth of pathogenic bacterial cells in the subject).

Ammonium compounds as described herein can be administered at any suitable dose in the methods provided herein. In general, an ammonium compound is administered at a dose ranging from about 0.01 milligrams to about 1000 milligrams per kilogram of a subject's body weight (i.e., about 0.01-1000 mg/kg). The dose of ammonium compound can be, for example, about 0.1-1000 mg/kg, or about 1-500 mg/kg, or about 25-250 mg/kg, or about 50-100 mg/kg. The dose of ammonium compound can be about 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the infection being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the infection.

Ammonium compounds can be administered for periods of time which will vary depending upon the nature and/or severity of the infection, and the overall condition of the subject to whom the ammonium compound is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the infection. The dosage of the ammonium compound can either be increased in the event the subject does not respond significantly to a particular dosage level, or the dose can be decreased if an alleviation of the symptoms of the infection is observed, or if the infection has been remedied, or if unacceptable side effects are seen with a particular dosage. A therapeutically effective amount of an ammonium compound can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days).

Ammonium compounds can be administered alone or in combination with one or more additional therapeutically active agents. An ammonium compound can be administered in combination with bactericidal/bacteriostatic compounds, including those described above, or with another active agent such as an anti-inflammatory or an antispasmodic agent. Examples of suitable anti-inflammatories include, but are not limited to, NSAIDs such as apazone, diclofenac, ibuprofen, indomethacin, ketoprofen, nabumetone, naproxen, piroxicam, and sulindac, as well as pharmaceutically acceptable salts thereof. Examples of antispasmodic agents include, but are not limited to, dicylomine, hyoscyamine, carisoprodol, mebeverine, baclofen, cyclobenzaprine, metaxalone, methocarbamol, clonidine, and dantrolene.

A combination therapy may involve administering the active agents at the same time, e.g., by using a single pharmaceutical composition containing both active agents as described above, or by using separate pharmaceutical compositions containing individual active agents at the same time. Alternatively, administration of an ammonium compound according to the present disclosure may precede or follow administration of another active agent by intervals ranging from minutes to weeks, such that the active agents exert an advantageously combined effect. For example, two or more active agents may be administered within about 12-24 hours of each other, within about 6-12 hours of each other, or within less than 6 hours of each other (e.g., within 4 hours or less, or 2 hours or less, or 1 hour or less). Different numbers of doses may be alternated in various combinations, and that the total number of doses of the ammonium compound may differ from the total number of doses of additional active agent(s).

Also provided herein are methods for altering the microbiome of a subject. The methods include administering to a subject in need thereof a compound according to Formula I, as described above, in an amount sufficient to alter the microbiome of the subject. In some embodiments, altering the microbiome includes altering the growth of Gram-positive bacteria (e.g., slowing or stopping the growth of Gram-positive bacteria, or killing Gram-positive bacteria). In some embodiments, the Gram-positive bacteria are selected from the group consisting of *C. difficile, S. aureus, Streptococcus* spp., *Enterococcus* spp., *C. diphtheriae, L. monocytogenes*, and combinations thereof.

Administration of according to the methods disclosed herein typically results in the reduction of bacteria observed in a sample obtained from the subject. In certain embodiments, administration of an ammonium compound results in at least a 5% reduction of bacterial levels (e.g., pathogenic bacterial levels) observed in a sample obtained from the subject to whom the compound is administered, as compared to the pathogenic bacterial level observed in a sample obtained prior to treatment. For example, the level of pathogenic bacteria in the sample may be reduced by about 25% to 99%, or by about 35% to 95%, or by about 40% to 85%, or by about 40% to 80% as compared to the corresponding pathogenic bacterial level 24 hours prior to the first administration of the ammonium compound. In some embodiments, the level of pathogenic bacteria is undetectable in the subject following treatment according to the methods described herein. In some embodiments, the load of one or more pathogenic bacteria in a target tissue, organ, or organ system (e.g., the gastrointestinal system) of a subject may be reduced by 2-fold, 5-fold, 20-fold, 100-fold, or greater. In some embodiments, the total bacterial load in the gut of a subject may be reduced by 2-fold, 5-fold, 20-fold, 100-fold, or greater.

In some embodiments, the infection is an oral infection, a gastrointestinal infection, an eye infection, or an infection of the skin, hair, and/or nails. Treatment of the infection may lead to therapeutic outcomes in subjects having conditions including, but not limited to, pneumonia, urinary tract infections, typhus, Rocky Mountain spotted fever, food poisoning, typhoid fever, sepsis, meningitis, Legionnaire's disease, tuberculosis, leprosy, brucellosis, irritable bowel syndrome, hepatic encephalopathy, small bowel overgrowth, and combinations thereof.

In some embodiments, at least one of $R^{4a}$, $R^{4b}$, $R^{4c}$, $R^{4d}$, and $R^{4e}$ in the administered compound is $C_{4-18}$ alkoxy. In some embodiments, at least one of $R^{4a}$ and $R^{4e}$ in the administered compound is $C_{4-18}$ alkoxy. In some embodiments, $R^1$ is selected from the group consisting of $C_{3-18}$ alkyl and -$L^1$-$R^{1a}$. In some embodiments, $R^1$ is $C_{4-18}$ alkyl. In some embodiments, $R^2$ and $R^3$ are each $C_{1-6}$ alkyl. In some embodiments, Y is -OC(O)—.

In some embodiments, the compound is selected from the group consisting of:

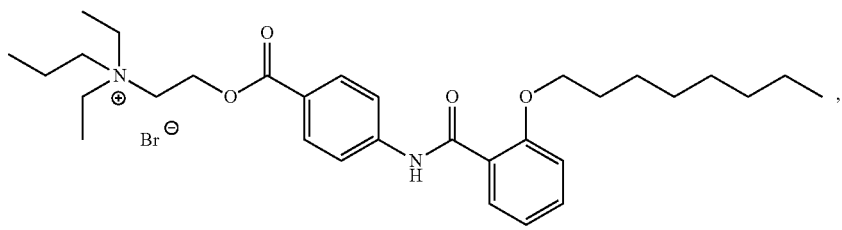

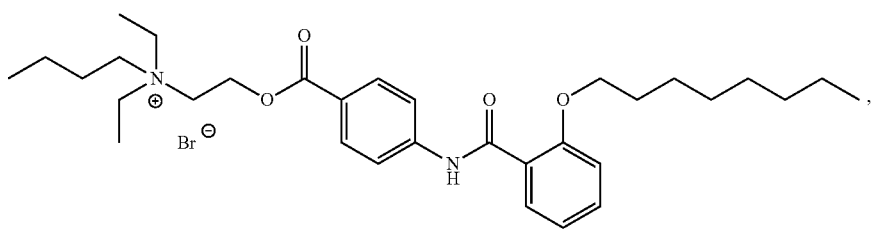

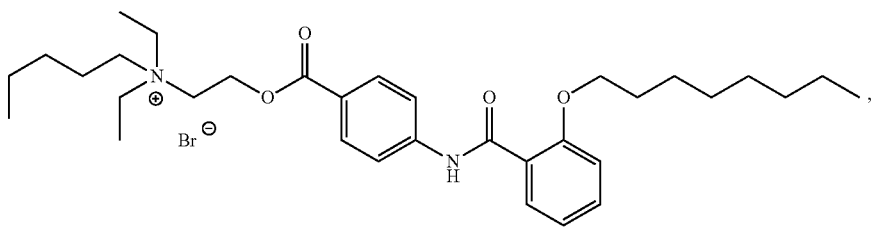

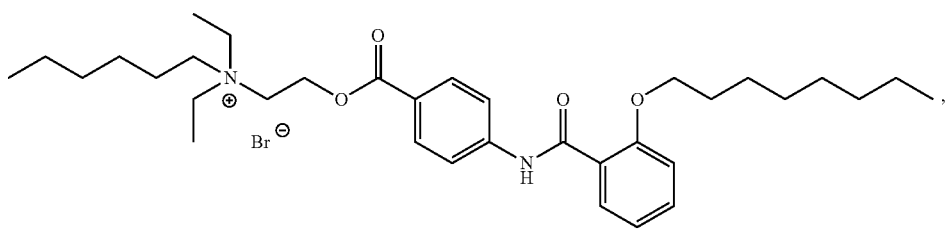

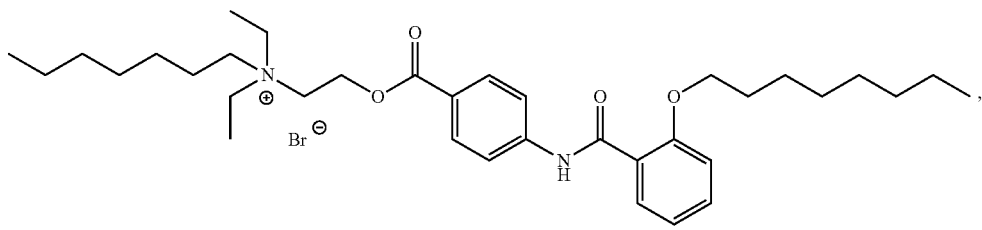

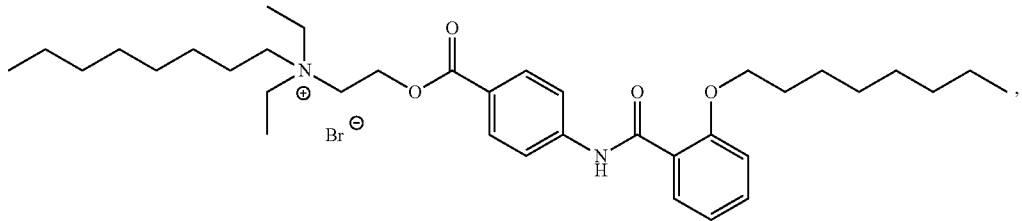

-continued
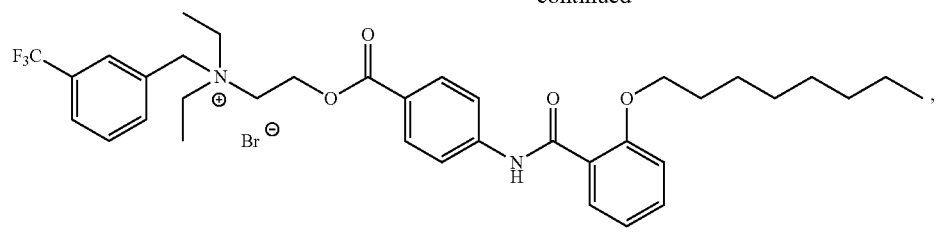
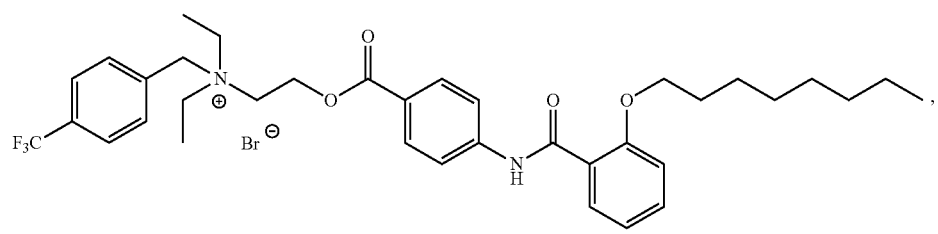
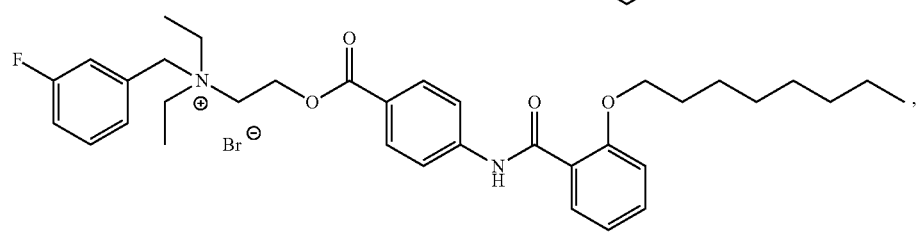
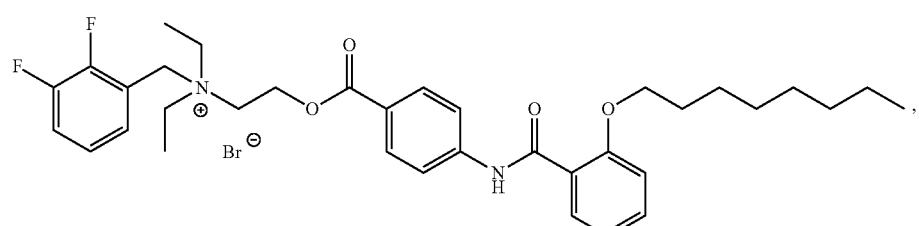
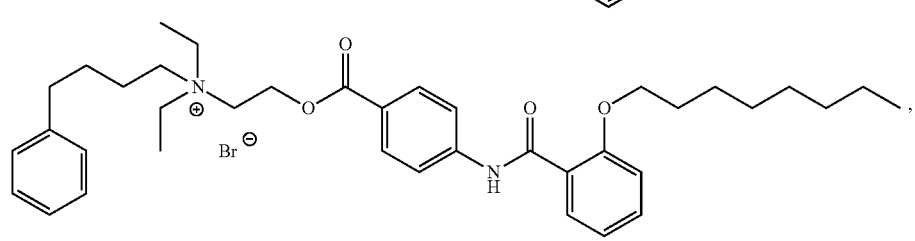
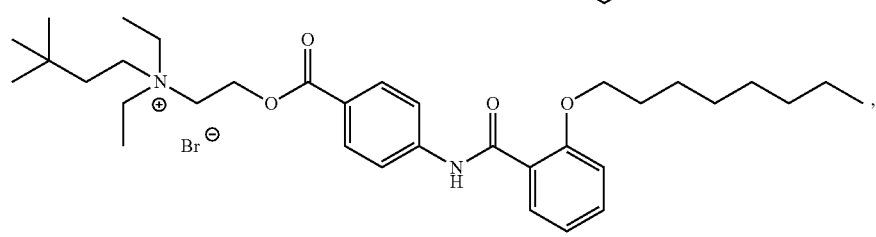
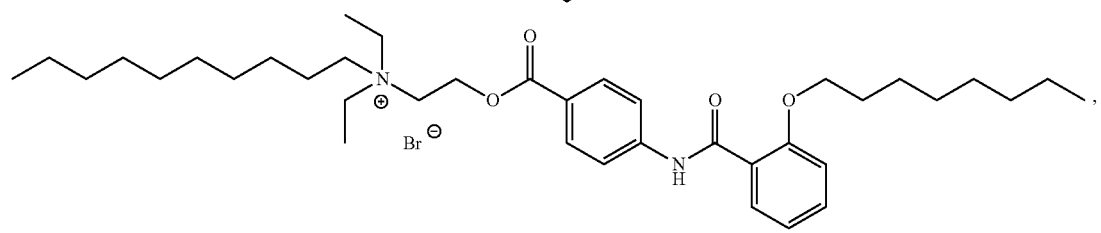

-continued
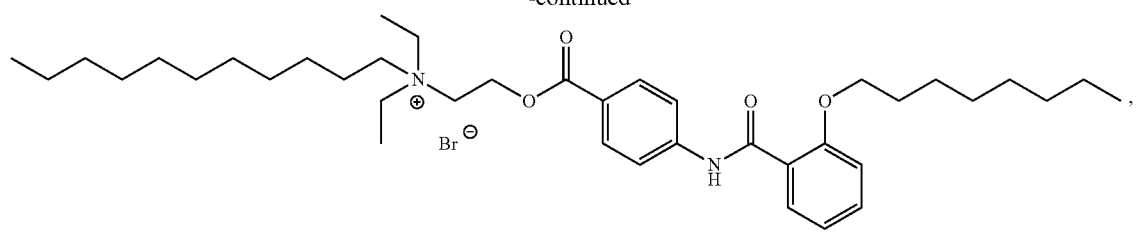
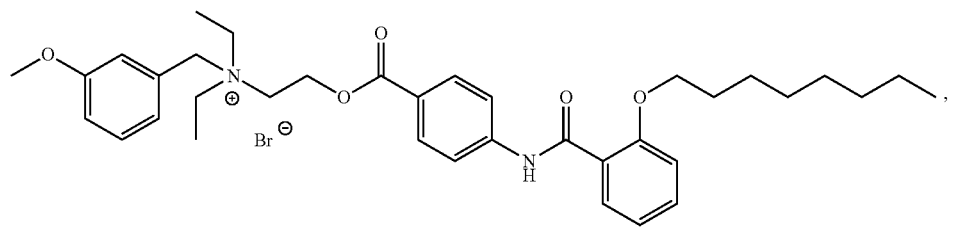
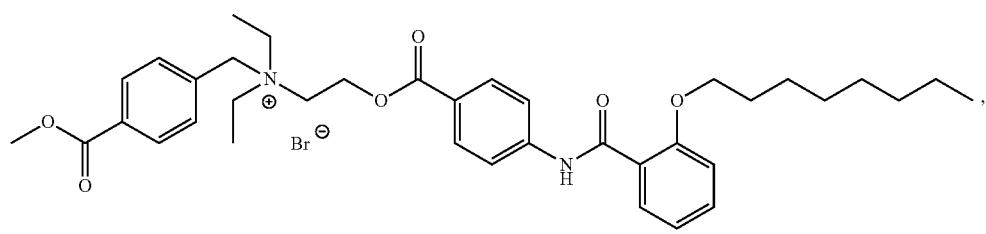
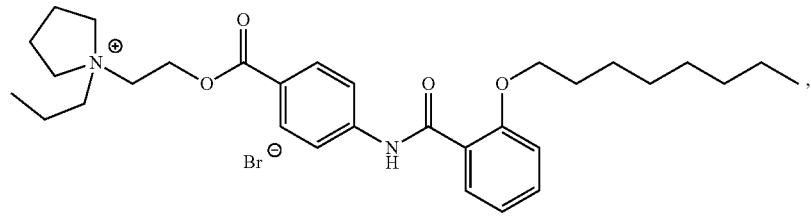
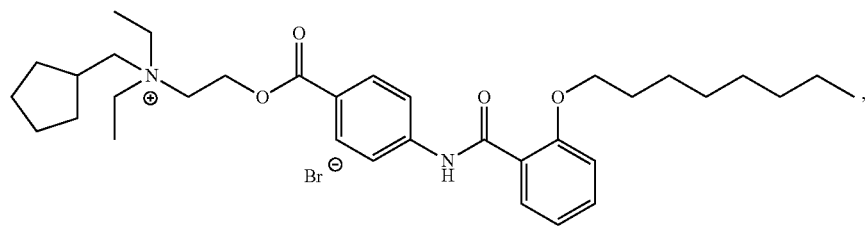
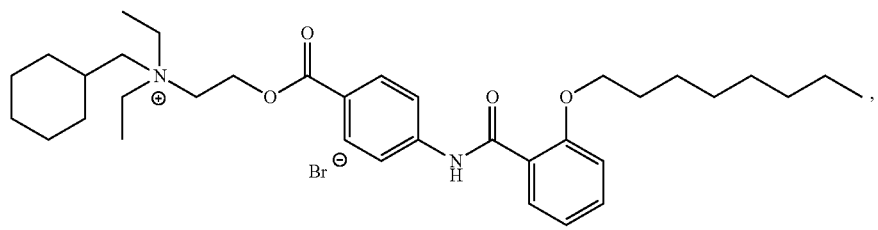
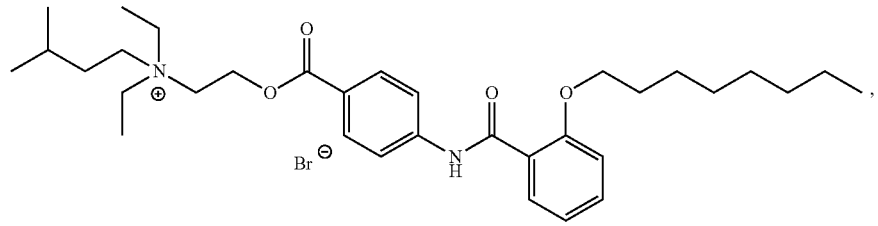

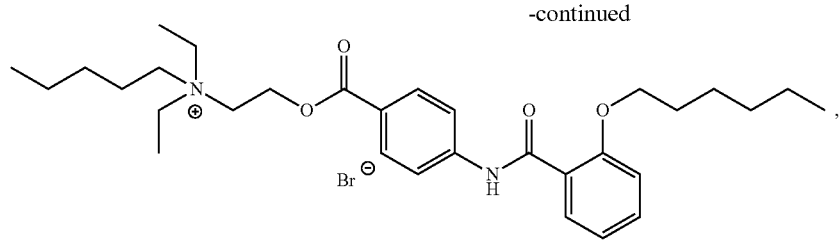
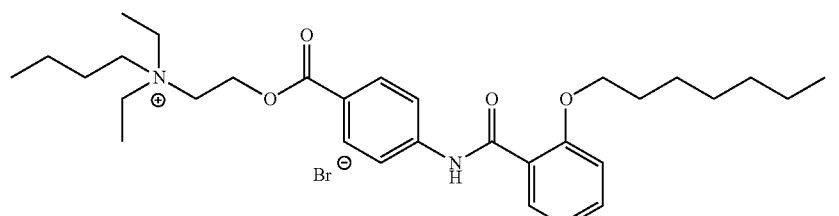
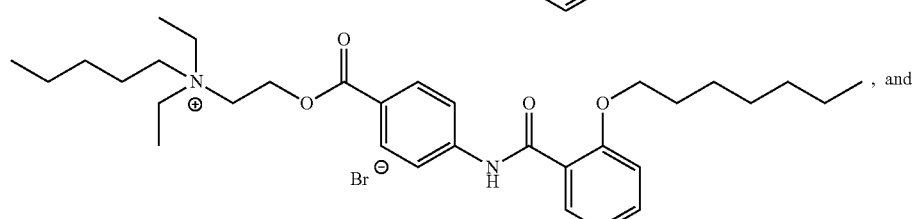
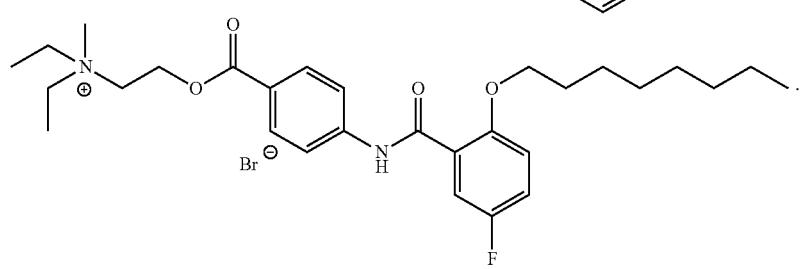
In some embodiments, the compound is selected from the group consisting of:
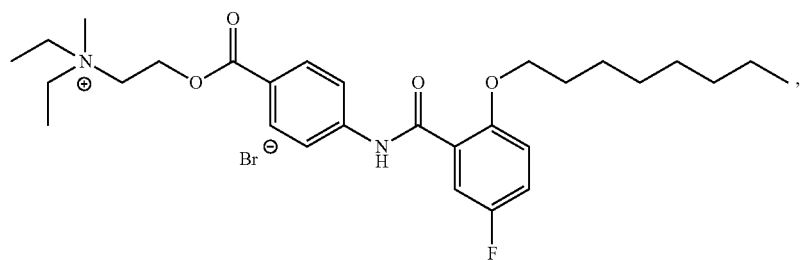
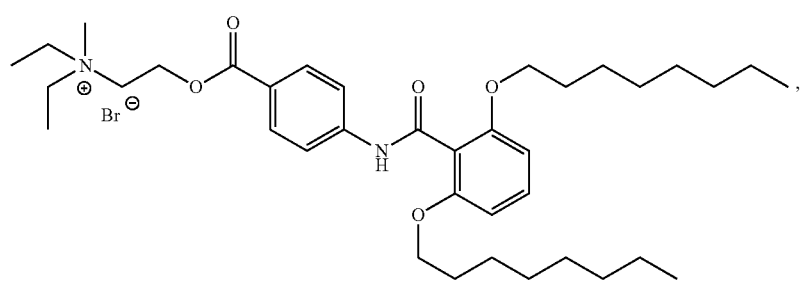

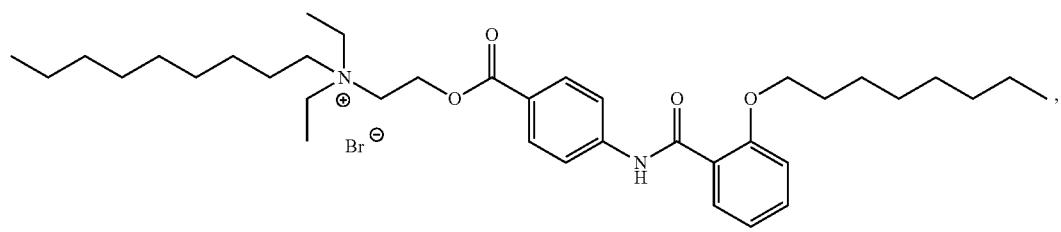
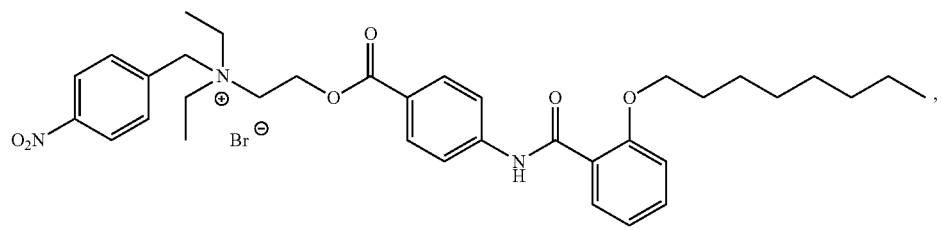
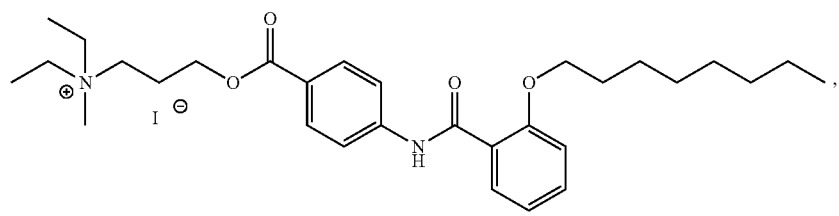
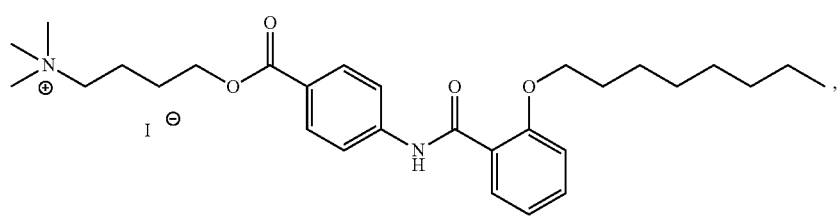
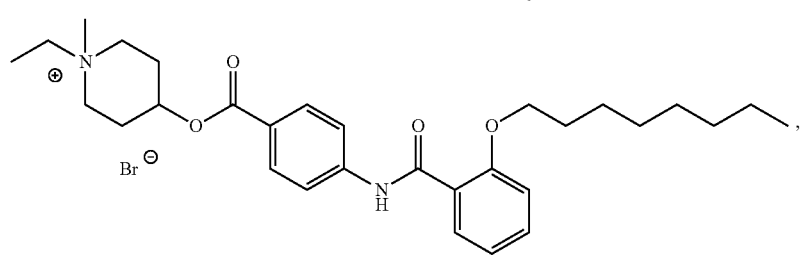
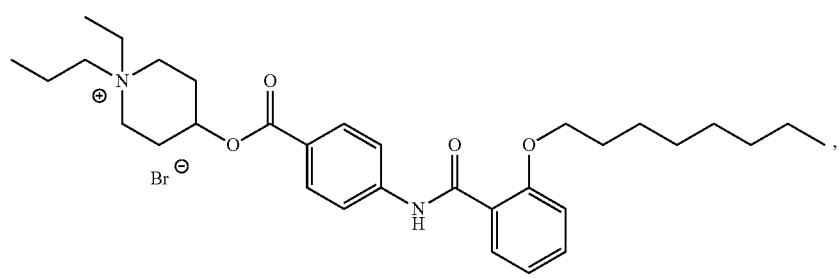
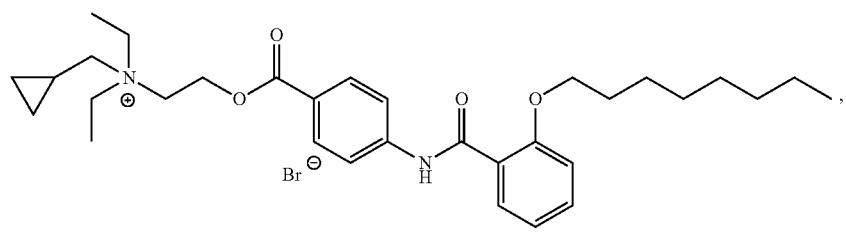

-continued
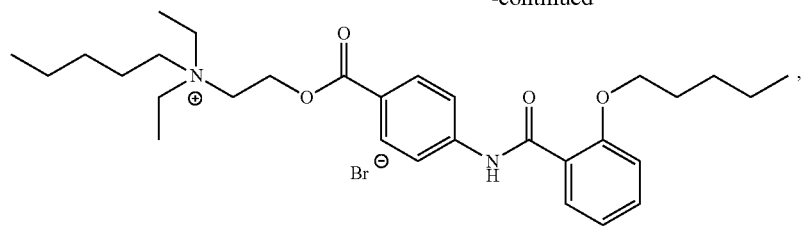
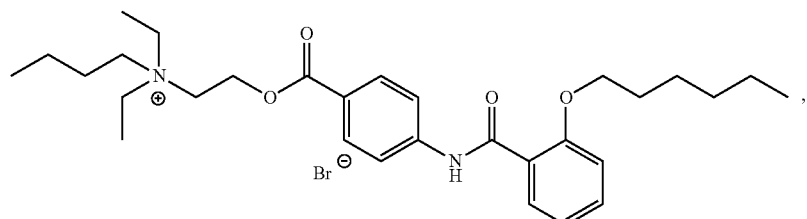
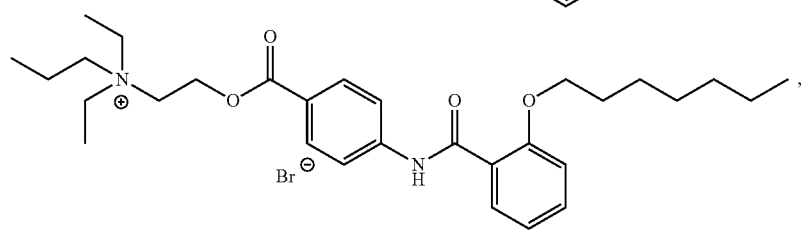
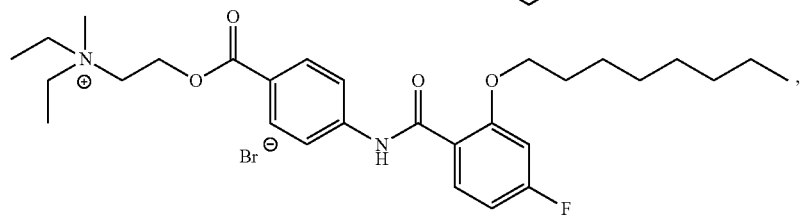
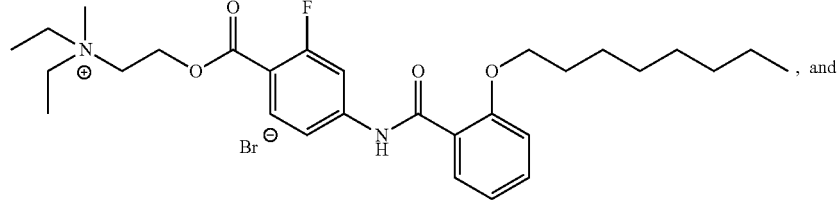, and
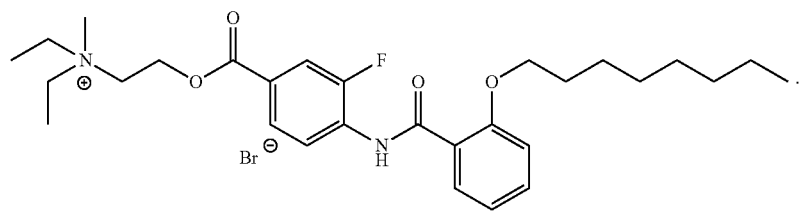.
In some embodiments, the compound is selected from the group consisting of:
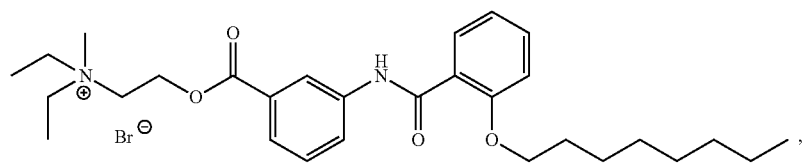,

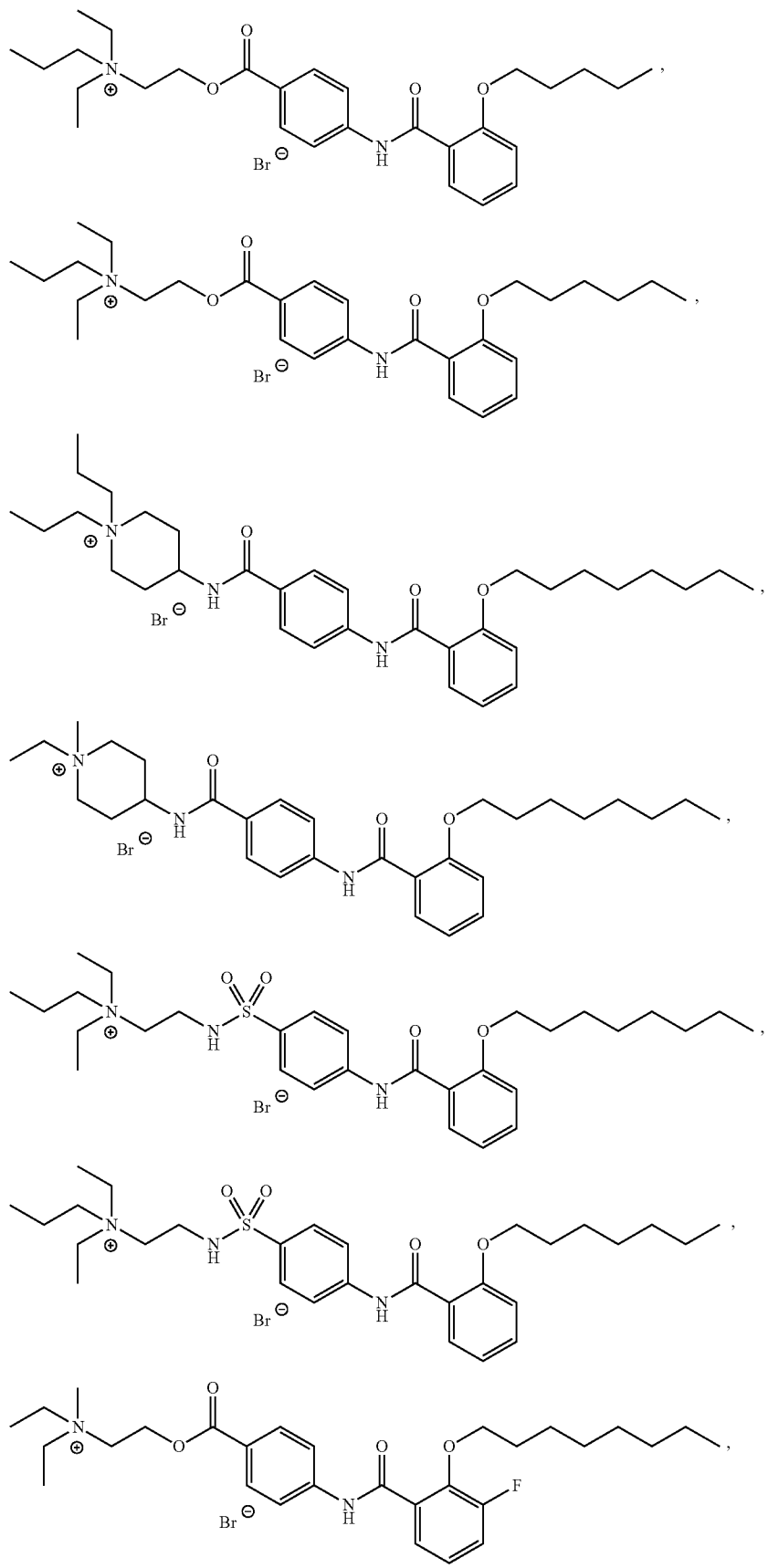

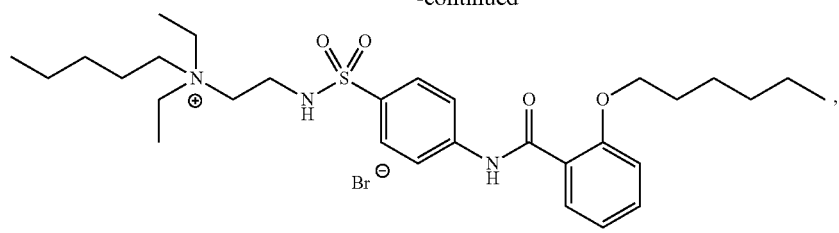
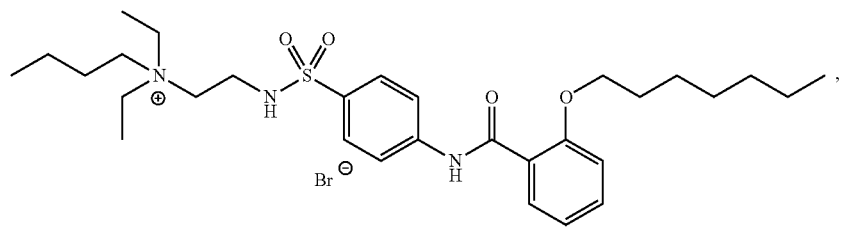
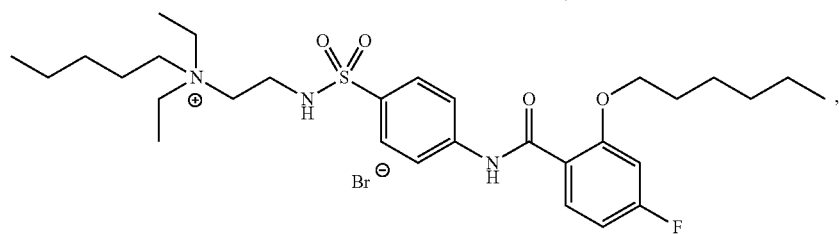
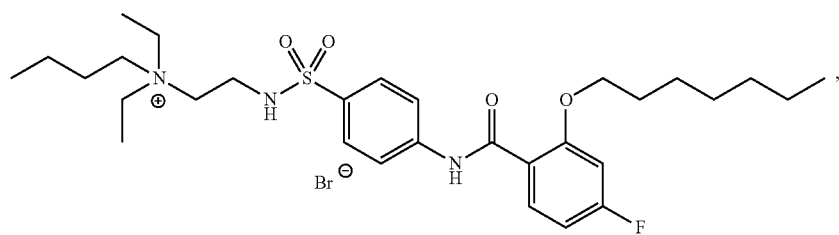
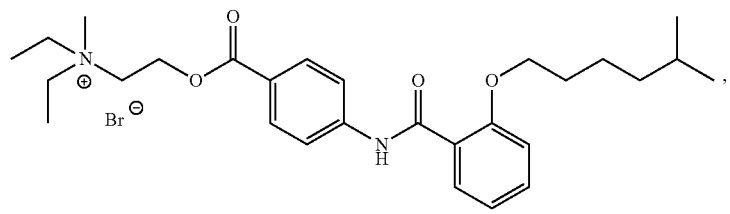
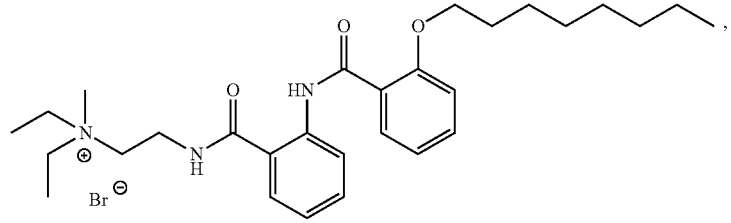
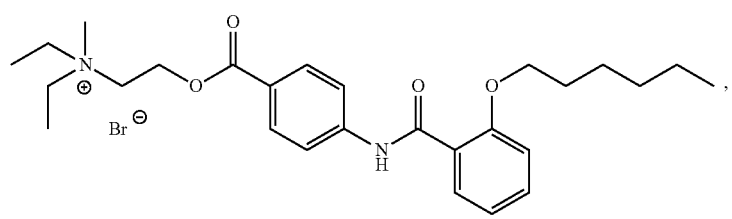

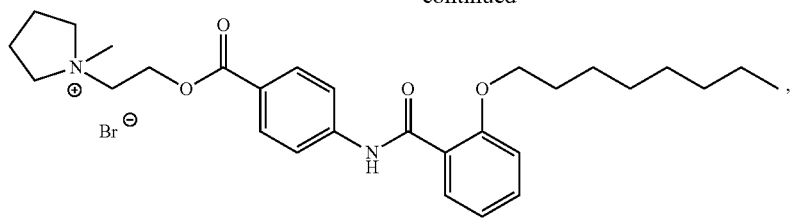,
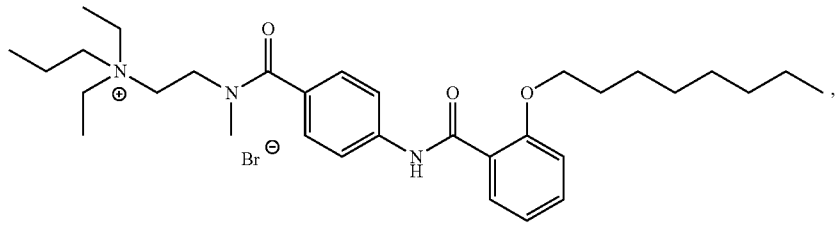,
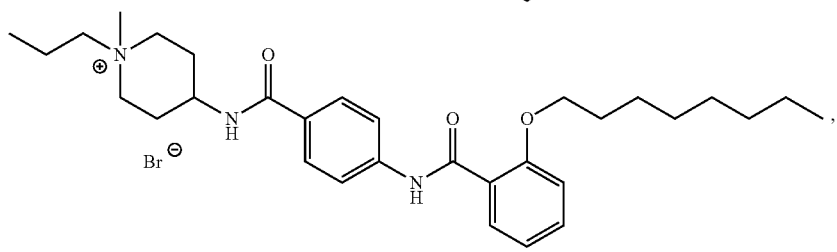,
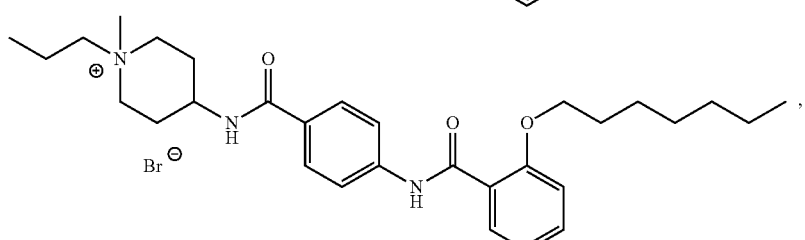,
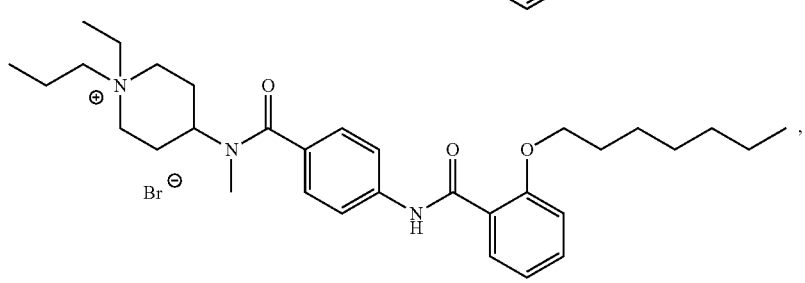,
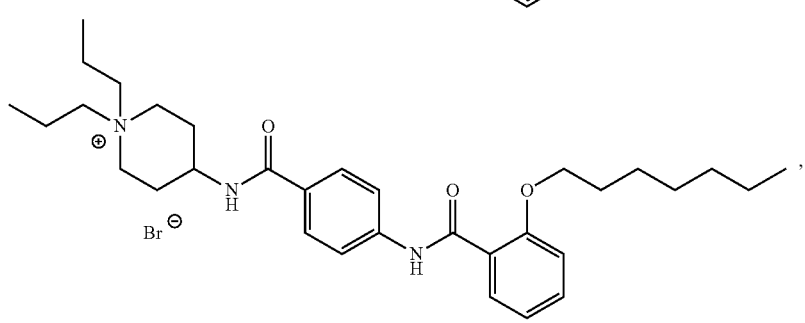,
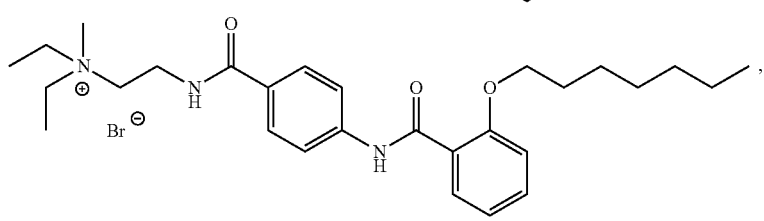,

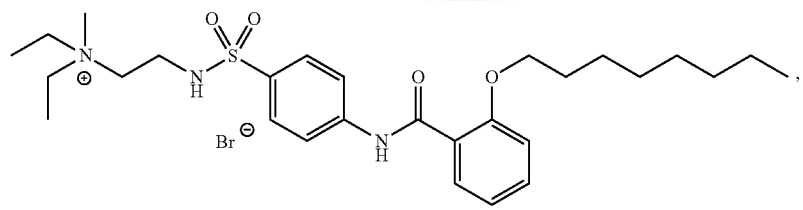
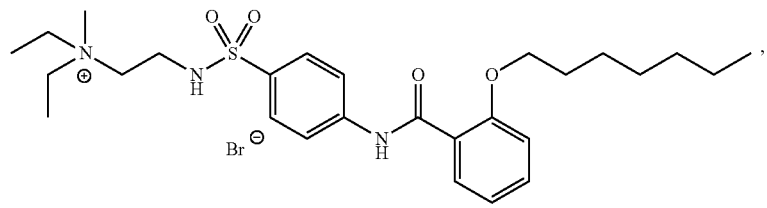
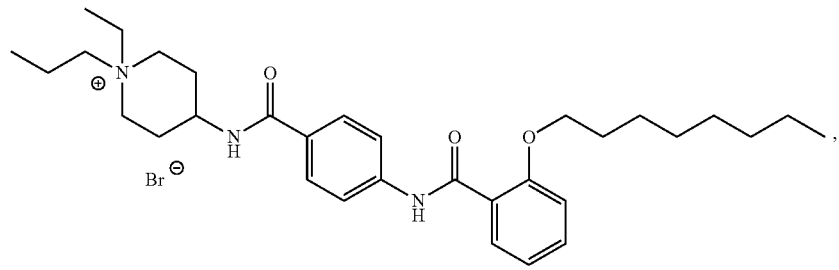
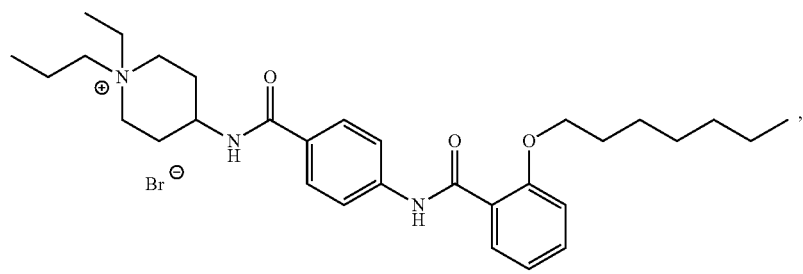
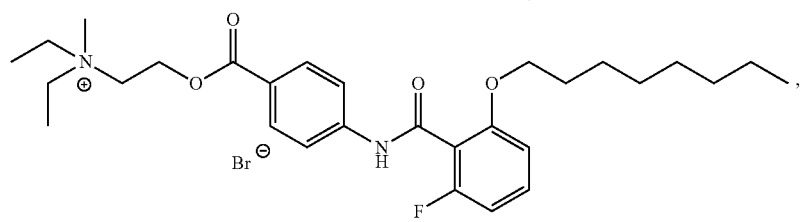
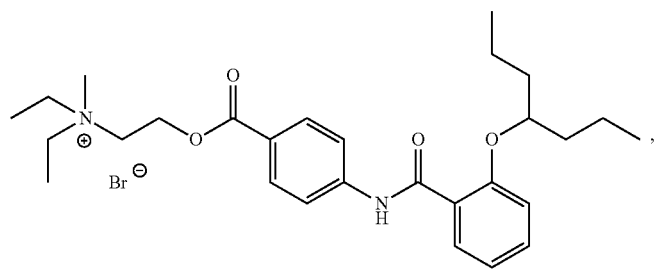
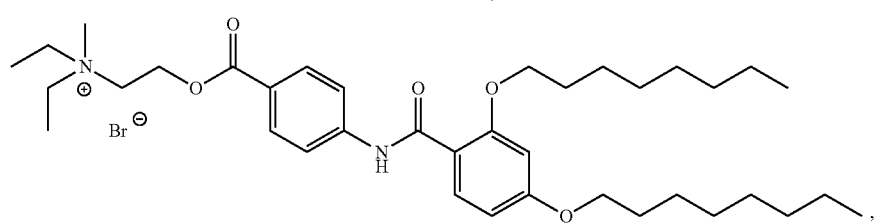

-continued
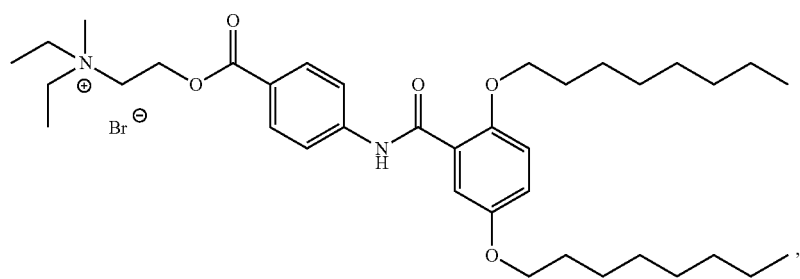
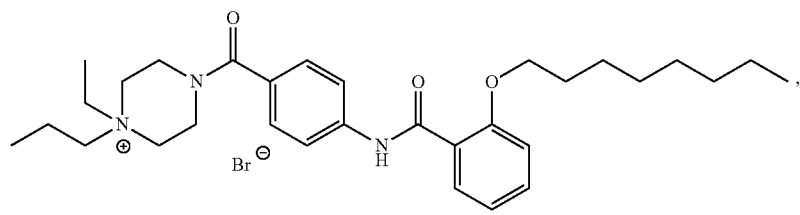
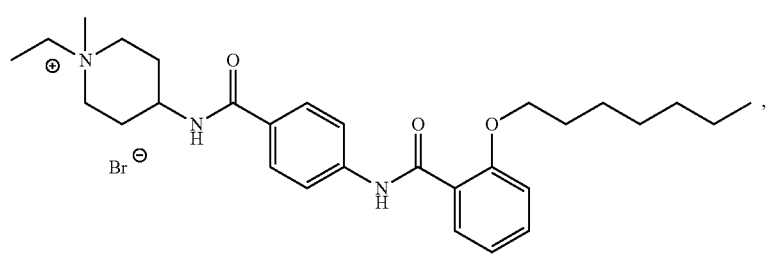
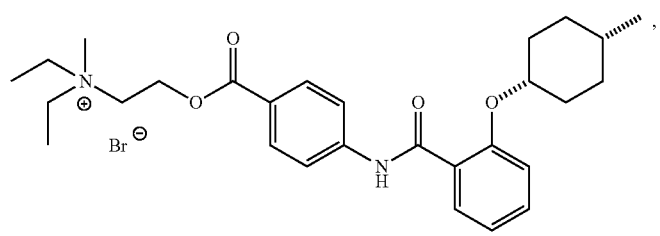
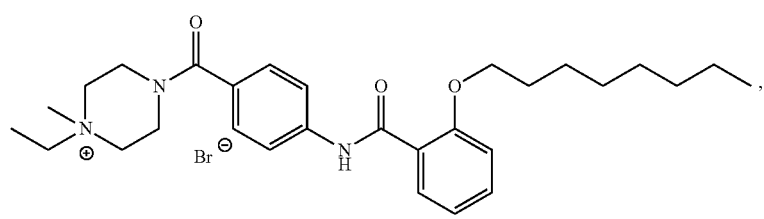
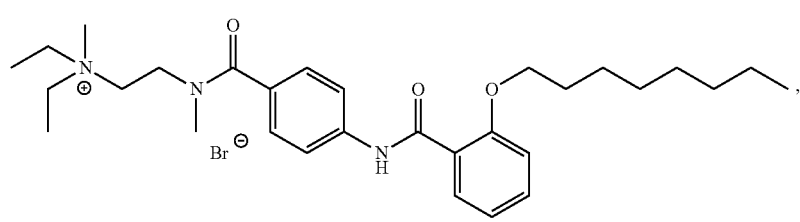
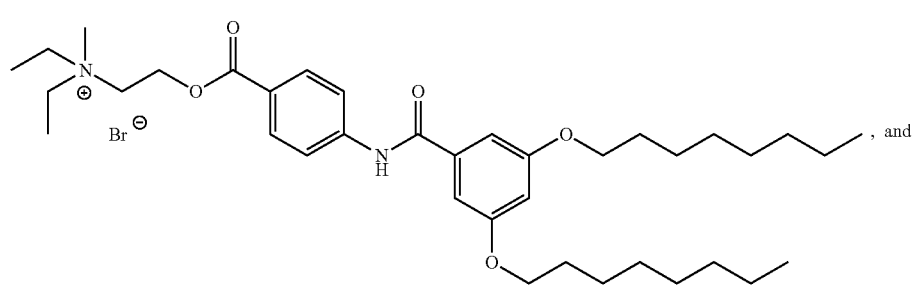

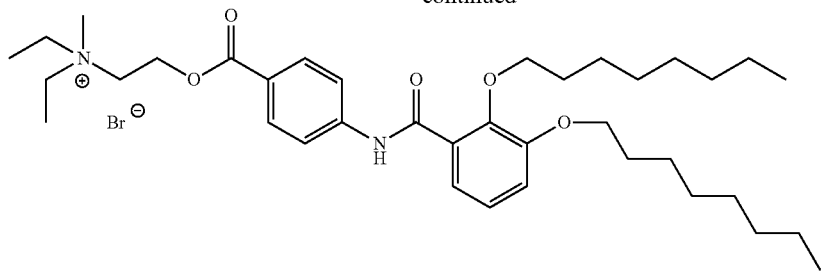

In some embodiments, the compound is selected from the group consisting of:

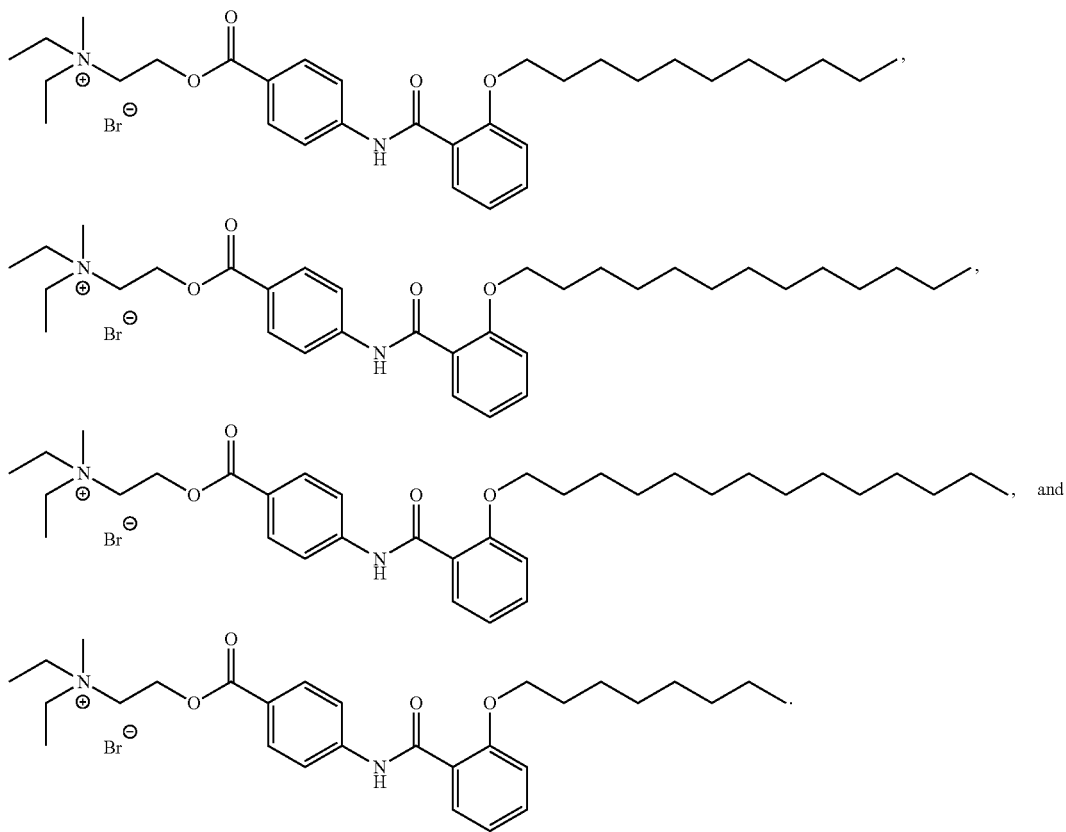

V. EXAMPLES

Unless otherwise indicated all reactions were conducted in standard commercially available glassware using standard synthetic chemistry methods and setup. All air- and moisture-sensitive reactions were performed under nitrogen atmosphere with dried solvents and glassware under anhydrous conditions. Starting materials and reagents were commercial compounds of the highest purity available and were used without purification. Solvents used for reactions were indicated as of commercial dry or extra-dry or analytical grade. Analytical thin layer chromatography was performed on aluminum plates coated with Merck Kieselgel 60F254 and visualized by UV irradiation (254 nm) or by staining with a solution of potassium permanganate. Flash column chromatography was performed on Biotage Isolera One 2.2 using commercial columns that were pre-packed with Merck Kieselgel 60 (230-400 mesh) silica gel. Final compounds for biological testing are all ≥95% purity as determined by HPLC-MS and $^1$H NMR.

NMR experiments were recorded on Agilent DD2 400 MHz spectrometers at ambient temperature. Samples were dissolved and prepared in deuterated solvents (CDCl$_3$, CD$_3$OD and DMSOd$_6$) with residual solvents being used as the internal standard in all cases. All deuterated solvent peaks were corrected to the standard chemical shifts (CDCl$_3$, d$_H$=7.26 ppm; CD$_3$OD, d$_H$=3.31 ppm; DMSO-d$_6$ d$_H$=2.50 ppm). Spectra were all manually integrated after automatic baseline correction. Chemical shifts (d) are given in parts per million (ppm), and coupling constants (J) are given in Hertz (Hz). The proton spectra are reported as follows: d (multiplicity, coupling constant J, number of protons), using the abbreviations app=apparent, b=broad, d=doublet, dd=doublet of doublets, ddd=doublet of doublet of doublets, dddd=doublet of doublet of doublet of doublets, m=multiplet, s=singlet, t=triplet.

Low-resolution mass spectral data (EI) were obtained on platform 1: a Agilent 1290 series HPLC system (Method 1) comprised of binary pumps, degasser and UV detector, equipped with an auto-sampler that is coupled with Agilent 6150 mass spectrometer; platform 2: a Thermo Scientific Vanquish UHPLC system. The general Liquid Chromatography parameters were as follows using solvent A (0.10% formic acid in water) and solvent B (100% acetonitrile): Method 1: analysis was performed on a Zorbax Eclipse Plus C18 column with dimension of 2.1×50 mm. The flow rate was 0.7 ml/minute running a gradient of 5% to 95% solvent B in 5 minutes and hold at 95% solvent B for 2 minutes. Method 2: analysis was performed on a Hypersil GOLD C18 column with dimension of 2.1×100 mm. The flow rate was 1.0 ml/minute running a gradient of 5% to 95% solvent B in 0.8 minutes and hold at 95% solvent B for 0.4 minutes. The ionization type for the mass detector of the Mass Spectrophotometer was atmospheric pressure electrospray in the positive ion mode with a fragmentation voltage of 50 volts.

The following abbreviations are used: $K_2CO_3$: potassium carbonate; MeCN: acetonitrile; NaOH: sodium hydroxide; LiOH: lithium hydroxide; KOH: potassium hydroxide; MeOH: methanol; $SOCl_2$: thionyl chloride; DMF: dimethylformamide; DMA: dimethylacetamide; $CH_2Cl_2$: dichloromethane; DCM: dichloromethane; DCE: 1,2-dichloroethane; THF: tetrahydrofuran; $Et_3N$: triethylamine; TEA: triethylamine; DIPEA: diisopropylethylamine; Pd/C: palladium on activated carbon; EtOH: ethanol; $NaHCO_3$: sodium bicarbonate; HCl: hydrogen chloride; EtOAc: ethyl acetate; $Na_2SO_4$: sodium sulfate; DCC: dicyclohexylcarbodiimide; DMAP: Dimethylaminopyridine; EDC: 1-ethyl-3-(3-dimethylaminopropyl)carbodiimide; HBTU: N,N,N',N'-yetramethyl-O-(1H-benzotriazol-1-yl)uronium hexafluorophosphate.

Example 1

Scheme 2. Representative example for the synthesis of otilonium bromide

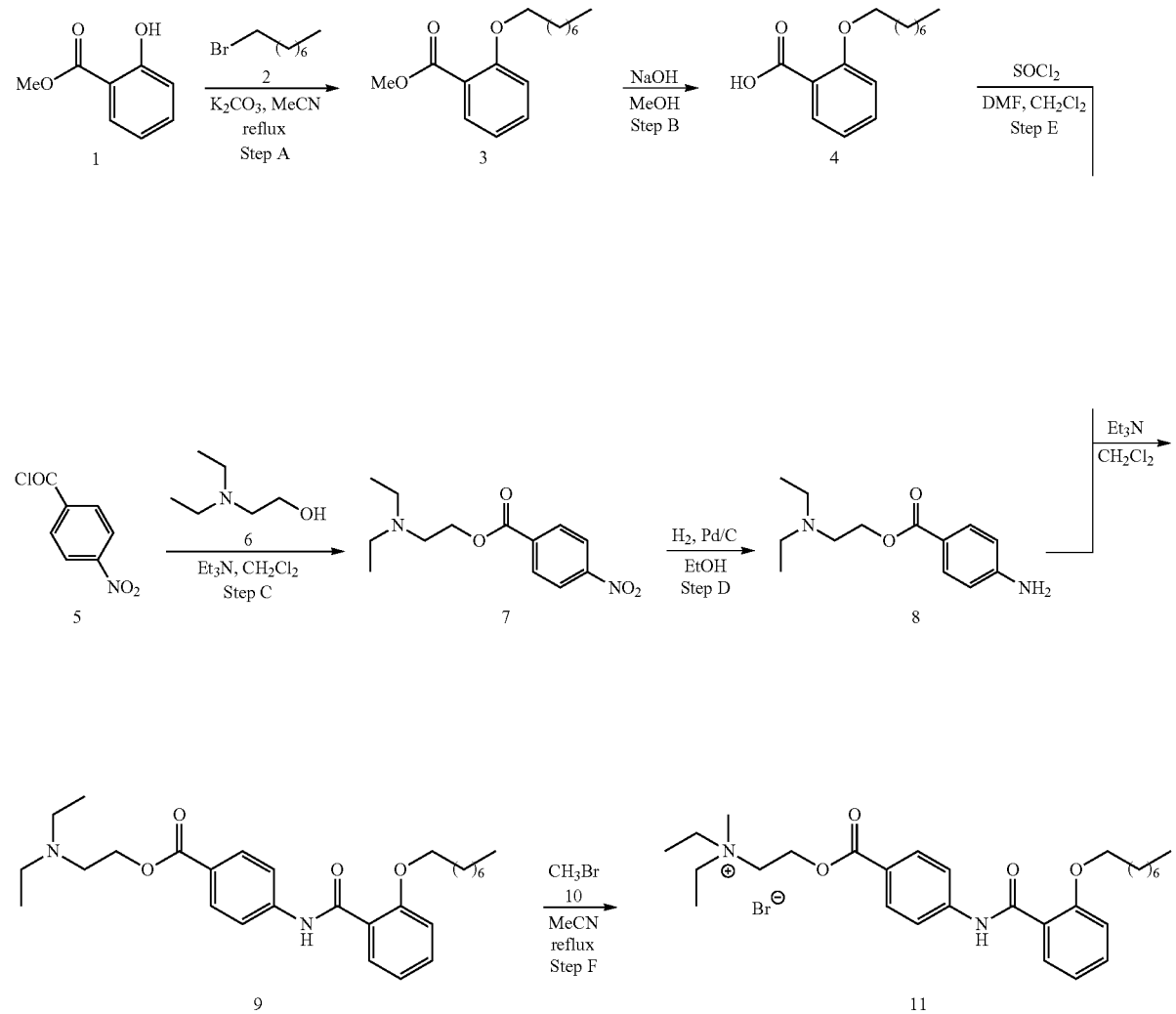

General Procedure—Step A: alkylation of methyl 2-hydroxybenzoate (3). A solution of the methyl salicylate (5.0 g, 32.8 mmol, 1 equiv) in dry MeCN (65 ml) at room temperature was added 1-bromooctane (1.25 equiv, 7.92 g, 41.1 mmol) and $K_2CO_3$ (2 equiv, 9.08 g, 65.7 mmol), and the resulting slurry was sealed in a pressure vessel and heated to 85° C. for overnight. The reaction mixture was cooled to ambient temperature and filtered to remove any insoluble salts and washed the residue with hexanes. The filtrate was concentrated to give the title ester product 3 (8.6 g, 100%) as viscous oil, which was subjected to the next step as is.

General Procedure—Step B: hydrolysis of methyl 2-(octyloxy)benzoate (4). A slurry of the methyl 2-(octyloxy)benzoate (8.6 g, 32.8 mmol) in MeOH/THF (v:v=1:1, 40 ml) at room temperature was treated with NaOH (1M solution in $H_2O$, 100 ml, 100 mmol). The reaction mixture was heated to 85° C. for overnight. Removal of the solvent in vacuo followed by dissolving the residue solids with $H_2O$ and acidified with 1N HCl, and extracted with EtOAc (3×100 mL). The combined organic extracts were dried over $Na_2SO_4$, filtered and concentrated under reduced pressure. The crude material was purified by Biotage flash chromatography (gradient elution, 0 to 30% EtOAc in hexanes) to obtain the title compound 4 (8.0 g, 97%) as colorless oil. $^1H$ NMR (400 MHz, DMSO-$d_6$) δ 12.31 (s, 1H), 7.59 (dd, J=7.6, 1.8 Hz, 1H), 7.46 (ddd, J=7.8, 7.8, 1.8 Hz, 1H), 7.09 (d, J=8.2 Hz, 1H), 6.96 (dd, J=7.6, 7.6 Hz, 1H), 4.01 (t, J=6.4 Hz, 1H), 1.70 (m, 2H), 1.43 (m, 2H), 1.35-1.22 (m, 8H), 0.86 (t, J=6.8 Hz, 3H). LCMS (m/z) 251.2 (M+H); RT (Method B, std LCMS method), 1.34 min General Procedure—Step C: acylation of 4-nitrobenzoyl chloride (7). A solution of the 2-(diethylamino)ethan-1-ol (6) (3.47 g, 29.6 mmol, 1.1 equiv) and $Et_3N$ (4.08 g, 40.35 mmol, 1.5 equiv) in dry DCM (67 ml) under nitrogen was added 4-nitrobenzoyl chloride (5) (5 g, 26.9 mmol, 1 equiv) and catalytic amount of 4-dimethylaminopyridine (656 mg, 5.38 mmol). After 30 minutes the reaction was added water (50 ml) and extracted with DCM until full recovery of the desired product based on TLC analysis (10% 1M $NH_3$/MeOH in DCM). The combined organic layers were dried over $Na_2SO_4$, filtered and concentrated under reduced pressure. The crude material was purified by Biotage flash chromatography (gradient elution, 0 to 15% 3M $NH_3$/MeOH in DCM) to obtain the title compound 7 (7.1 g, 90% yield) as yellow oil.

General Procedure—Step D: hydrogenation of 2-(diethylamino)ethyl 4-nitrobenzoate (8). A solution of 7 (7.1 g, 26.7 mmol, 1 equiv) in EtOH (90 ml) was added 10% activated Pd/C (1.43 g, 1.34 mmol, 0.05 equiv) and the resulting reaction suspension was degassed and re-purged with hydrogen, and this process was repeated three times before allowing the reaction stirred at ambient temperature under $H_2$ (1 atm) for overnight. The reaction mixture was filtered through Celite and washed with MeOH until full recovery of the desired product based on TLC analysis (10% 3M $NH_3$/MeOH in DCM). The filtrate was concentrated under reduced pressure and was purified by Biotage flash chromatography (gradient elution, 0 to 20% 3M $NH_3$/MeOH in DCM) to obtain the title compound 8 (5.7 g, 90% yield) as yellow oil. $^1H$ NMR (400 MHz, DMSO-d6) δ 7.62 (d, J=8.6 Hz, 2H), 6.55 (d, J=8.6 Hz, 2H), 5.95 (br, 2H), 4.18 (t, J=6.2 Hz, 2H), 2.70 (t, J=6.2 Hz, 2H), 2.54 (q, J=7.2 Hz, 4H), 0.96 (t, J=7.2 Hz, 3H). LCMS (m/z) 237.2 (M+H); RT (Method B, std LCMS method), 0.70 min.

General Procedure—Step E: amidation coupling of 2-(diethylamino)ethyl 4-aminobenzoate (9). A solution of 4 (500 mg, 2 mmol, 1 equiv) in anhydrous DCM (10 ml) was added thionyl chloride (713 mg, 6 mmol, 3 equiv) and catalytic amount of DMF (2-3 syringe drops). The resulting reaction mixture was stirred at ambient temperature for 1-2 hours. A small reaction fraction was extracted and quenched with methanol and monitored the reaction progress by HPLC/MS (the m/z of the corresponding methyl ester). The reaction mixture was concentrated to remove residual amount of HCl generated from the reaction, and the reaction was dried under high-vac for 30 minutes before it was added in a solution of dry DCM (5 ml) to a separate reaction flask containing a solution of 8 (315 mg, 1.33 mmol, 0.67 equiv) in anhydrous DCM (5 ml) and $Et_3N$ (404 mg, 4 mmol). The reaction was diluted with saturated $NaHCO_3$ solution (20 ml) and extracted with 2-propanol/chloroform (v:v=1:4) until full recovery of the desired product based on TLC analysis (10% 1M $NH_3$/MeOH in DCM). The combined extracts were dried over $Na_2SO_4$, filtered and concentrated under reduced pressure. The crude material was purified by Biotage flash chromatography (gradient elution, 0 to 10% MeOH in DCM) to obtain the title compound 9 (500 mg, 80% yield) as yellow oil. $^1H$ NMR (400 MHz, DMSO-d6) δ 10.41 (s, 1H), 7.93 (d, J=8.6 Hz, 2H), 7.84 (d, J=8.6 Hz, 2H), 7.63 (dd, J=7.6, 1.8 Hz, 1H), 7.50 (ddd, J=8.2, 8.2, 1.8 Hz, 1H), 7.17 (d, J=8.4 Hz, 1H), 7.06 (dd, J=7.4, 7.4 Hz, 1H), 4.28 (t, J=6.2 Hz, 2H), 4.09 (t, J=6.2 Hz, 2H), 2.75 (t, J=6.0 Hz, 2H), 2.55 (q, J=7.2 Hz, 4H), 1.74 (m, 2H), 1.38 (m, 2H), 1.31-1.09 (m, 8H), 0.97 (t, J=7.2 Hz, 6H), 0.79 (t, J=6.8 Hz, 3H). LCMS (m/z) 469.4 (M+H); RT (Method B, std LCMS method), 1.10 min.

General Procedure—Step F: alkylation to make quaternary amine salt (10). A solution of 9 (100 mg, 0.21 mmol, 1 equiv) in acetone (2.5 ml) was added bromomethane (60 mg, 0.64 mmol, 3 equiv) and the resulting reaction was sealed and heated to reflux at 60° C. for 2 days. The reaction was cooled to ambient temperature and the white precipitates were collected through filtration and washed with cold acetone to obtain the title compound 10 (40 mg, 33% yield) as white powder. $^1H$ NMR (400 MHz, DMSO-d6) δ 10.45 (s, 1H), 7.97 (d, J=8.0 Hz, 2H), 7.88 (d, J=8.0 Hz, 2H), 7.62 (d, J=7.6 Hz, 1H), 7.50 (dd, J=8.0, 6.8 Hz, 1H), 7.18 (d, J=8.4 Hz, 1H), 7.06 (dd, J=7.6, 7.6 Hz, 1H), 4.66 (m, 2H), 4.10 (t, J=6.4 Hz, 2H), 3.75 (m, 2H), 3.45 (q, J=7.2 Hz, 4H), 3.07 (s, 3H), 1.74 (m, 2H), 1.38 (m, 2H), 1.28-1.15 (m, 14H), 0.80 (t, J=7.2 Hz, 3H). LCMS (m/z) 483.4 (M); RT (Method A, std LCMS method), 3.83 min.

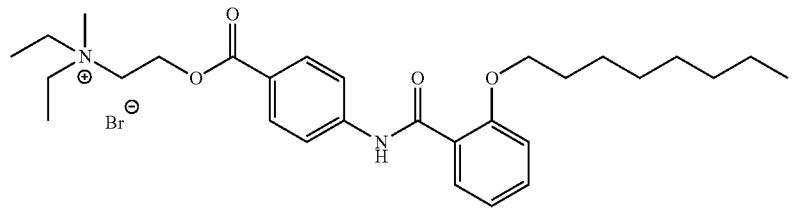 [SMILES: CCCCCCCCOc1ccccc1C(=O)Nc1ccc(C(=O)OCC[N+](C)(CC)CC)cc1 ; [Br-]]

N,N-diethyl-N-methyl-2-((4-(2-(octyloxy)benzamido)benzoyl)oxy)ethan-1-aminium bromide (otilonium bromide). According to general procedure step F; the title compound was obtained as white powder through filtration (33% yield). $^1$H NMR (400 MHz, DMSO-d6) δ 10.45 (s, 1H), 7.97 (d, J=8.0 Hz, 2H), 7.88 (d, J=8.0 Hz, 2H), 7.62 (d, J=7.6 Hz, 1H), 7.50 (dd, J=8.0, 6.8 Hz, 1H), 7.18 (d, J=8.4 Hz, 1H), 7.06 (dd, J=7.6, 7.6 Hz, 1H), 4.66 (m, 2H), 4.10 (t, J=6.4 Hz, 2H), 3.75 (m, 2H), 3.45 (q, J=7.2 Hz, 4H), 3.07 (s, 3H), 1.74 (m, 2H), 1.38 (m, 2H), 1.28-1.15 (m, 14H), 0.80 (t, J=7.2 Hz, 3H); LCMS (m/z) 483.4 (M); RT (Method A, std LCMS method), 3.83 min.

Example 2

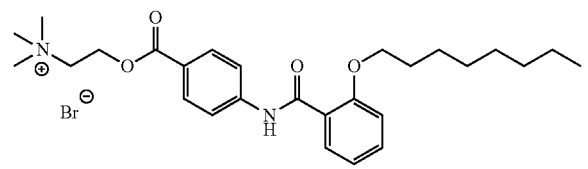 [SMILES: CCCCCCCCOc1ccccc1C(=O)Nc1ccc(C(=O)OCC[N+](C)(C)C)cc1 ; [Br-]]

N,N,N-Trimethyl-2-((4-(2-(octyloxy)benzamido)benzoyl)oxy)ethan-1-aminium bromide (11). According to general procedure step F; the title compound was obtained as white powder through filtration (20% yield). $^1$H NMR (400 MHz, DMSO-d6) δ 10.45 (s, 1H), 7.98 (d, J=8.7 Hz, 2H), 7.88 (d, J=8.7 Hz, 2H), 7.63 (dd, J=7.6, 1.7 Hz, 1H), 7.51 (ddd, J=7.8, 7.8, 1.7 Hz, 1H), 7.18 (d, J=8.2 Hz, 1H), 7.07 (t, J=7.6, 7.6 Hz, 1H), 4.69 (m, 2H), 4.10 (m, 2H), 3.81 (m, 2H), 3.20 (s, 9H), 1.74 (m, 2H), 1.39 (m, 2H), 1.30-1.11 (m, 8H), 0.80 (t, J=7.2 Hz, 3H); LCMS (m/z) 455.3 (M); RT (Method A, std LCMS method), 3.81 min.

Example 3

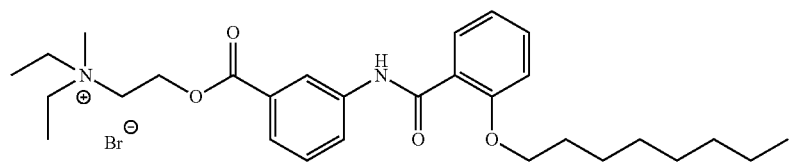 [SMILES: CCCCCCCCOc1ccccc1C(=O)Nc1cccc(C(=O)OCC[N+](C)(CC)CC)c1 ; [Br-]]

N,N-Diethyl-N-methyl-2-((3-(2-(octyloxy)benzamido)benzoyl)oxy)ethan-1-aminium bromide (12). According to general procedure step F; the crude material was purified by Biotage flash chromatography (gradient elution, 0 to 15% 3M NH$_3$/MeOH in DCM) to obtain the title compound as white powder (64% yield). $^1$H NMR (400 MHz, DMSO-d6) δ 10.33-10.29 (s, 1H), 8.60-8.42 (m, 1H), 7.93-7.79 (d, J=7.9 Hz, 1H), 7.71-7.61 (m, 2H), 7.54-7.46 (m, 2H), 7.19-7.16 (d, J=8.1 Hz, 1H), 7.06 (dd, J=8.0, 8.0 Hz, 1H), 5.26-4.68 (m, 2H), 4.10 (t, J=6.2 Hz, 2H), 3.82-3.75 (m, 2H), 3.50-3.33 (q, J=7.2 Hz, 4H), 3.08-2.96 (s, 3H), 1.79-1.70 (m, 2H), 1.43-1.35 (m, 2H), 1.30-1.07 (m, 14H), 0.79 (t, J=7.2 Hz, 3H); LCMS (m/z) 483.4 (M); RT (Method A, std LCMS method), 5.83 min.

Example 4

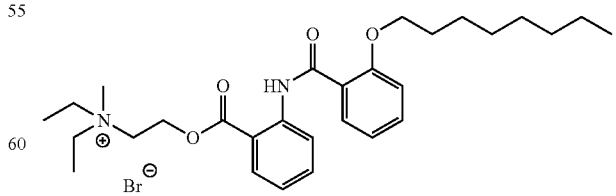

N,N-Diethyl-N-methyl-2-((2-(2-(octyloxy)benzamido)benzoyl)oxy)ethan-1-aminium bromide (13). According to general procedure step F; the crude material was purified by Biotage flash chromatography (gradient elution, 0 to 15%

3M NH₃/MeOH in DCM) to obtain the title compound as white powder (60% yield). ¹H NMR (400 MHz, DMSO-d6) δ 11.68-11.64 (s, 1H), 8.68-8.60 (d, J=9.0 Hz, 1H), 8.01 (dd, J=7.8, 1.4 Hz, 1H), 7.90-7.86 (dd, J=7.8, 1.7 Hz, 1H), 7.72-7.64 (m, 1H), 7.68-7.53 (m, 1H), 7.28-7.20 (m, 2H), 7.09 (dd, J=7.8, 7.0 Hz, 1H), 5.25 (t, J=5.0 Hz, 1H), 4.67 (m, 1H), 4.26-4.21 (m, 2H), 3.83-3.73 (m, 2H), 3.46-3.33 (q, J=7.2 Hz, 4H), 3.04-2.96 (s, 3H), 1.81-1.73 (m, 2H), 1.39-1.29 (m, 2H), 1.26-1.05 (m, 14H), 0.79-0.75 (t, J=7.2 Hz, 3H); LCMS (m/z) 483.4 (M); RT (Method A, std LCMS method), 6.09 min.

Example 5

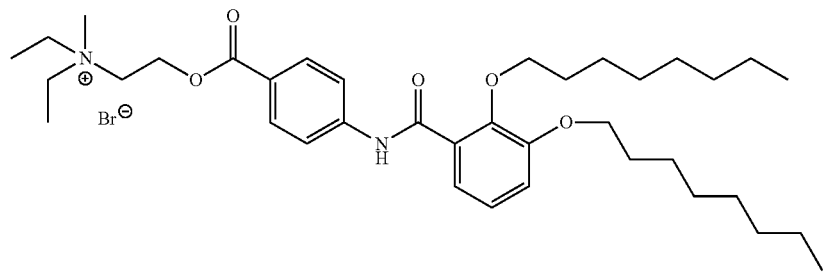 [SMILES: CCCCCCCCOc1cccc(C(=O)Nc2ccc(C(=O)OCC[N+](C)(CC)CC)cc2)c1OCCCCCCCC ; [Br-]]

2-((4-(2,3-Bis(octyloxy)benzamido)benzoyl)oxy)-N,N-diethyl-N-methylethan-1-aminium bromide (14). According to general procedure step F; the crude material was purified by Biotage flash chromatography (gradient elution, 0 to 15% 3M NH₃/MeOH in DCM) to obtain the title compound as white powder (80% yield). ¹H NMR (400 MHz, DMSO-d6) δ 10.53 (s, 1H), 7.94 (d, J=8.8 Hz, 2H), 7.86 (d, J=8.8 Hz, 2H), 7.18 (dd, J=8.0, 1.9 Hz, 1H), 7.13 (t, J=7.6 Hz, 1H), 7.08 (dd, J=7.4, 1.8 Hz, 1H), 4.02 (t, J=6.2 Hz, 2H), 3.98 (t, J=6.2 Hz, 2H), 3.83 (s, 2H), 3.80 (m, 2H), 3.35 (q, J=7.2 Hz, 4H), 2.96 (s, 3H), 1.75 (m, 2H), 1.57 (m, 2H), 1.46 (m, 2H), 1.37-1.02 (m, 24H), 0.86 (t, J=7.2 Hz, 3H), 0.79 (t, J=7.2 Hz, 3H); LCMS (m/z) 611.5 (M); RT (Method A, std LCMS method), 6.84 min.

Example 6

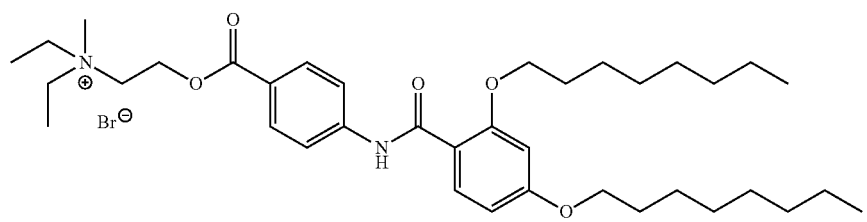 [SMILES: CCCCCCCCOc1ccc(C(=O)Nc2ccc(C(=O)OCC[N+](C)(CC)CC)cc2)c(OCCCCCCCC)c1 ; [Br-]]

2-((4-(2,4-Bis(octyloxy)benzamido)benzoyl)oxy)-N,N-diethyl-N-methylethan-1-aminium bromide (15). According to general procedure step F; the title compound was obtained as white powder through filtration (21% yield). $^1$H NMR (400 MHz, DMSO-d6) δ 10.25 (s, 1H), 7.96 (d, J=8.8 Hz, 2H), 7.86 (d, J=8.8 Hz, 2H), 7.72 (d, J=8.6 Hz, 1H), 6.69 (m, 1H), 6.66 (dd, J=8.5, 2.0 Hz, 1H), 4.66 (m, 2H), 4.15 (t, J=6.4 Hz, 2H), 4.05 (t, J=6.4 Hz, 2H), 3.74 (m, 2H), 3.45 (q, J=7.2 Hz, 4H), 3.06 (s, 3H), 1.80 (m, 2H), 1.73 (m, 2H), 1.42 (m, 4H), 1.35-1.14 (m, 22H), 0.86 (t, J=7.2 Hz, 3H), 0.80 (t, J=7.2 Hz, 3H); LCMS (m/z) 611.5 (M); RT (Method A, std LCMS method), 5.34 min.

Example 7

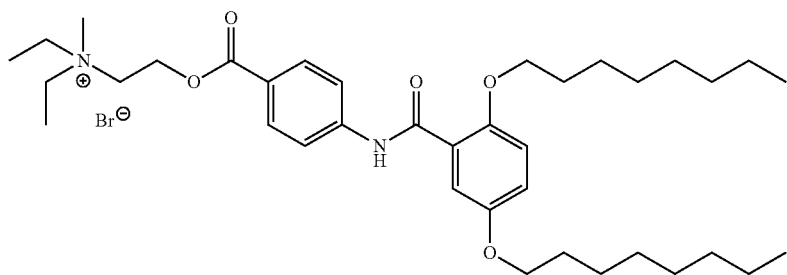 [SMILES: CCCCCCCCOc1ccc(OCCCCCCCC)c(C(=O)Nc2ccc(C(=O)OCC[N+](C)(CC)CC)cc2)c1 ; [Br-]]

2-((4-(2,5-Bis(octyloxy)benzamido)benzoyl)oxy)-N,N-diethyl-N-methylethan-1-aminium bromide (16). According to general procedure step F; the crude material was purified by Biotage flash chromatography (gradient elution, 0 to 15% 3M NH$_3$/MeOH in DCM) to obtain the title compound as white powder (84% yield). $^1$H NMR (400 MHz, DMSO-d6) δ 10.47-10.43 (s, 1H), 7.95 (m, 2H), 7.86 (m, 2H), 7.19 (m, 1H), 7.13-7.04 (m, 2H), 5.25 (t, J=5.0 Hz, 1H), 4.67 (m, 1H), 4.04 (m, 2H), 3.94 (d, J=6.7 Hz, 2H), 3.81-3.73 (m, 2H), 3.48-3.33 (q, J=7.2 Hz, 4H), 3.07-2.97 (s, 3H), 1.70 (m, 4H), 1.38 (m, 4H), 1.32-1.08 (m, 22H), 0.86 (t, J=7.2 Hz, 3H), 0.79 (t, J=7.2 Hz, 3H); LCMS (m/z) 611.5 (M); RT (Method A, std LCMS method), 5.20 min.

Example 8

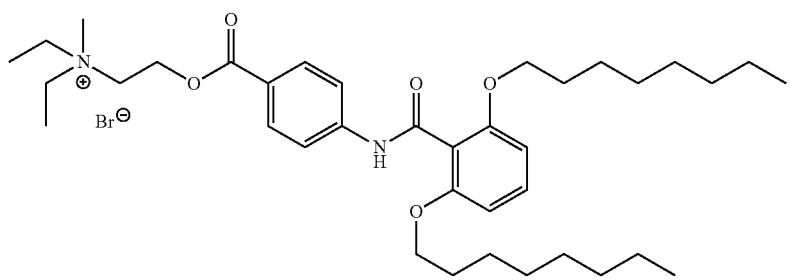 [SMILES: CCCCCCCCOc1cccc(OCCCCCCCC)c1C(=O)Nc1ccc(C(=O)OCC[N+](C)(CC)CC)cc1 ; [Br-]]

2-((4-(2,6-Bis(octyloxy)benzamido)benzoyl)oxy)-N,N-diethyl-N-methylethan-1-aminium bromide (17). According to general procedure step F; the crude material was purified by Biotage flash chromatography (gradient elution, 0 to 15% 3M NH$_3$/MeOH in DCM) to obtain the title compound as white powder (66% yield). $^1$H NMR (400 MHz, DMSO-d6) δ 10.52-10.47 (s, 1H), 7.91 (m, 2H), 7.83 (m, 2H), 7.31 (ddd, J=8.6, 8.4, 4.2 Hz, 1H), 6.70 (dd, J=8.4, 3.4 Hz, 2H), 5.25 (t, J=5.0 Hz, 1H), 4.67 (m, 1H), 3.97 (m, 4H), 3.80-3.72 (m, 2H), 3.48-3.32 (q, J=7.2 Hz, 4H), 3.06-2.96 (s, 3H), 1.59 (m, 4H), 1.33-1.04 (m, 26H), 0.79 (m, 6H); LCMS (m/z) 611.5 (M); RT (Method A, std LCMS method), 3.45 min.

Example 9

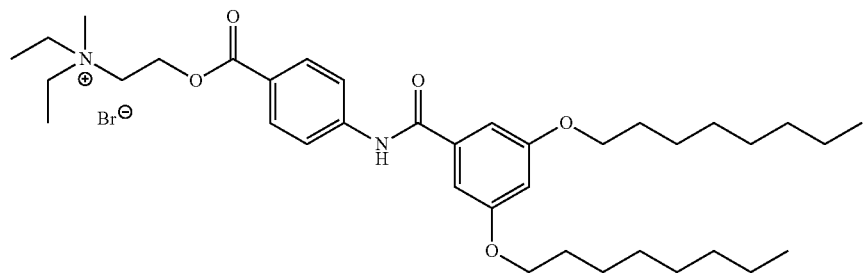 [SMILES: CCCCCCCCOc1cc(OCCCCCCCC)cc(C(=O)Nc2ccc(C(=O)OCC[N+](C)(CC)CC)cc2)c1 ; [Br-]]

2-((4-(3,5-Bis(octyloxy)benzamido)benzoyl)oxy)-N,N-diethyl-N-methylethan-1-aminium bromide (18). According to general procedure step F; the crude material was purified by Biotage flash chromatography (gradient elution, 0 to 15% 3M NH$_3$/MeOH in DCM) to obtain the title compound as white powder (64% yield). $^1$H NMR (400 MHz, DMSO-d6) δ 10.48-10.43 (s, 1H), 8.00-7.94 (m, 4H), 7.08 (d, J=2.0 Hz, 2H), 6.70 (m, 1H), 4.67 (m, 2H), 4.02 (t, J=6.6 Hz, 4H), 3.82-3.73 (m, 2H), 3.48-3.32 (q, J=7.2 Hz, 4H), 3.07-2.96 (s, 3H), 1.72 (m, 4H), 1.42 (m, 4H), 1.37-1.19 (m, 22H), 0.86 (m, 6H); LCMS (m/z) 611.5 (M); RT (Method A, std LCMS method), 5.83 min.

Example 10

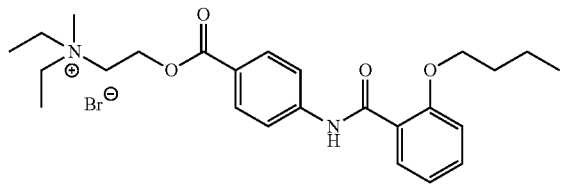 [SMILES: CCCCOc1ccccc1C(=O)Nc1ccc(C(=O)OCC[N+](C)(CC)CC)cc1 ; [Br-]]

2-((4-(2-Butoxybenzamido)benzoyl)oxy)-N,N-diethyl-N-methylethan-1-aminium bromide (19). According to general procedure step F; the title compound was obtained as white powder through filtration (62% yield). $^1$H NMR (400 MHz, DMSO-d6) δ 10.46 (s, 1H), 7.98 (d, J=8.6 Hz, 2H), 7.88 (d, J=8.6 Hz, 2H), 7.63 (dd, J=7.4, 1.2 Hz, 1H), 7.51 (ddd, J=8.6, 8.6, 1.8 Hz, 1H), 7.19 (d, J=8.4 Hz, 1H), 7.07 (dd, J=7.6, 7.4 Hz, 1H), 4.67 (m, 2H), 4.11 (t, J=6.2 Hz, 2H), 3.74 (m, 2H), 3.45 (q, J=7.4 Hz, 4H), 3.07 (s, 3H), 1.74 (m, 2H), 1.42 (m, 2H), 1.27 (t, J=7.2 Hz, 6H), 0.87 (t, J=7.4 Hz, 3H); LCMS (m/z) 427.3 (M); RT (Method A, std LCMS method), 2.85 min.

Example 11

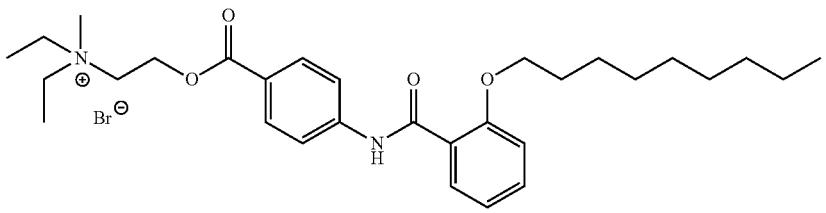 [SMILES: CCCCCCCCCOc1ccccc1C(=O)Nc1ccc(C(=O)OCC[N+](C)(CC)CC)cc1 ; [Br-]]

N,N-Diethyl-N-methyl-2-((4-(2-(nonyloxy)benzamido)benzoyl)oxy)ethan-1-aminium bromide (23). According to general procedure step F; the crude material was purified by Biotage flash chromatography (gradient elution, 0 to 15% 3M $NH_3$/MeOH in DCM) to obtain the title compound as white powder (64% yield). $^1$H NMR (400 MHz, DMSO-d6) δ 10.46-10.41 (s, 1H), 7.98-7.93 (d, J=8.8 Hz, 2H), 7.90-7.84 (d, J=8.8 Hz, 2H), 7.63 (dd, J=7.6, 1.7 Hz, 1H), 7.51 (m, 1H), 7.18 (d, J=8.4 Hz, 1H), 7.07 (dd, J=7.6, 7.4 Hz, 1H), 4.67 (m, 2H), 4.10 (t, J=6.2 Hz, 2H), 3.74 (m, 2H), 3.45 (q, J=7.4 Hz, 4H), 3.17-3.06 (s, 3H), 1.74 (m, 2H), 1.39 (m, 2H), 1.30-1.10 (m, 16H), 0.82 (t, J=7.4 Hz, 3H); LCMS (m/z) 497.4 (M); RT (Method A, std LCMS method), 4.22 min.

Example 12

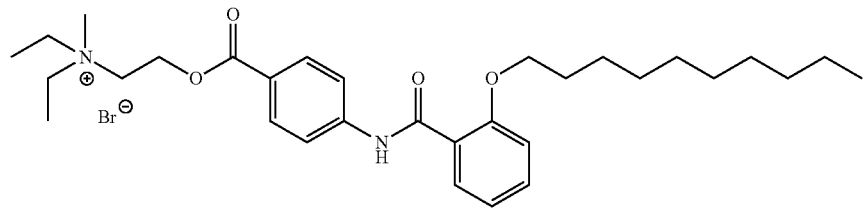 [SMILES: CCCCCCCCCCOc1ccccc1C(=O)Nc1ccc(C(=O)OCC[N+](C)(CC)CC)cc1 ; [Br-]]

2-((4-(2-(Decyloxy)benzamido)benzoyl)oxy)-N,N-diethyl-N-methylethan-1-aminium bromide (24). According to general procedure step F; the crude material was purified by Biotage flash chromatography (gradient elution, 0 to 15% 3M $NH_3$/MeOH in DCM) to obtain the title compound as white powder (76% yield). $^1$H NMR (400 MHz, DMSO-d6) δ 10.45-10.41 (s, 1H), 7.98-7.93 (d, J=8.8 Hz, 2H), 7.90-7.84 (d, J=8.8 Hz, 2H), 7.63 (dd, J=7.6, 1.6 Hz, 1H), 7.50 (m, 1H), 7.18 (m, 1H), 7.06 (m, 1H), 5.26 (m, 1H), 4.66 (m, 1H), 4.10 (t, J=6.2 Hz, 1H), 3.80 (m, 1H), 3.74 (m, 1H), 3.48-3.33 (q, J=7.4 Hz, 4H), 3.06-2.96 (s, 3H), 1.74 (m, 2H), 1.38 (m, 2H), 1.30-1.10 (m, 18H), 0.82 (t, J=7.4 Hz, 3H); LCMS (m/z) 511.4 (M); RT (Method A, std LCMS method), 4.23 min.

Example 13

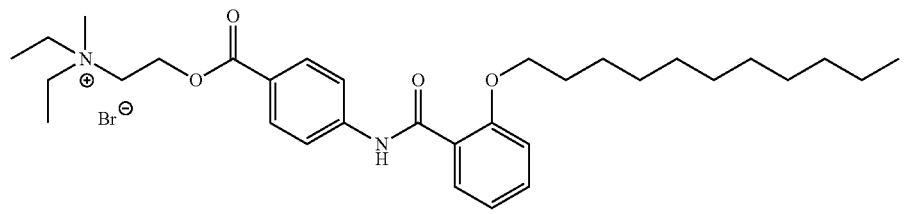 [SMILES: CCCCCCCCCCCOc1ccccc1C(=O)Nc1ccc(C(=O)OCC[N+](C)(CC)CC)cc1 ; [Br-]]

N,N-Diethyl-N-methyl-2-((4-(2-(undecyloxy)benzamido)benzoyl)oxy)ethan-1-aminium bromide (25). According to general procedure step F; the crude material was purified by Biotage flash chromatography (gradient elution, 0 to 15% 3M NH$_3$/MeOH in DCM) to obtain the title compound as white powder (81% yield). $^1$H NMR (400 MHz, DMSO-d6) δ 10.45-10.41 (s, 1H), 7.98-7.93 (d, J=8.8 Hz, 2H), 7.89-7.84 (d, J=8.8 Hz, 2H), 7.63 (dd, J=7.4, 1.6 Hz, 1H), 7.50 (m, 1H), 7.18 (d, J=8.8, 4.8 Hz, 1H), 7.06 (ddd, J=8.0, 7.2, 1.8 Hz, 1H), 5.25 (m, 1H), 4.67 (m, 1H), 4.10 (m, 2H), 3.80 (m, 1H), 3.74 (m, 1H), 3.48-3.33 (q, J=7.4 Hz, 4H), 3.07-2.96 (s, 3H), 1.74 (m, 2H), 1.38 (m, 2H), 1.30-1.10 (m, 20H), 0.84 (t, J=7.4 Hz, 3H); LCMS (m/z) 525.4 (M); RT (Method A, std LCMS method), 4.52 min.

Example 14

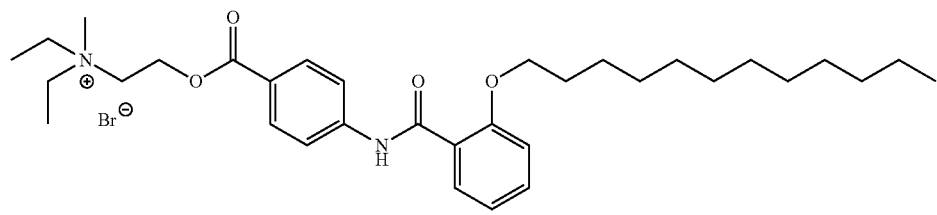 [SMILES: CCCCCCCCCCCCOc1ccccc1C(=O)Nc1ccc(C(=O)OCC[N+](C)(CC)CC)cc1 ; [Br-]]

2-((4-(2-(Dodecyloxy)benzamido)benzoyl)oxy)-N,N-diethyl-N-methylethan-1-aminium bromide (26). According to general procedure step F; the crude material was purified by Biotage flash chromatography (gradient elution, 0 to 15% 3M NH$_3$/MeOH in DCM) to obtain the title compound as white powder (69% yield). $^1$H NMR (400 MHz, DMSO-d6) δ 10.45-10.41 (s, 1H), 7.98-7.93 (d, J=8.8 Hz, 2H), 7.89-7.84 (d, J=8.8 Hz, 2H), 7.63 (dd, J=7.6, 1.6 Hz, 1H), 7.50 (m, 1H), 7.18 (d, J=8.6, 4.5 Hz, 1H), 7.06 (ddd, J=7.8, 7.4, 2.2 Hz, 1H), 5.26 (m, 1H), 4.66 (m, 1H), 4.10 (t, J=7.6 Hz, 2H), 3.80 (m, 1H), 3.74 (m, 1H), 3.48-3.33 (q, J=7.4 Hz, 4H), 3.07-2.97 (s, 3H), 1.74 (m, 2H), 1.38 (m, 2H), 1.30-1.10 (m, 22H), 0.84 (t, J=7.4 Hz, 3H); LCMS (m/z) 539.4 (M); RT (Method A, std LCMS method), 5.64 min.

Example 15

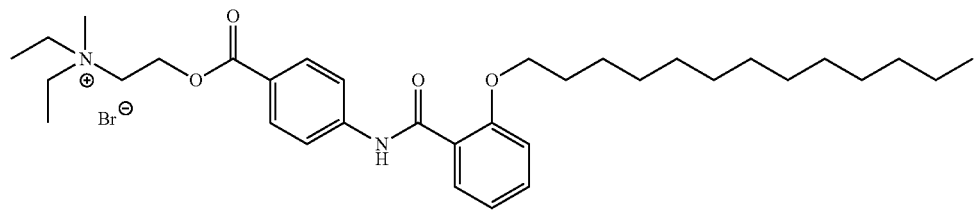 [SMILES: CCCCCCCCCCCCCOc1ccccc1C(=O)Nc1ccc(C(=O)OCC[N+](C)(CC)CC)cc1 ; [Br-]]

N,N-Diethyl-N-methyl-2-((4-(2-(tridecyloxy)benzamido)benzoyl)oxy)ethan-1-aminium bromide (27). According to general procedure step F; the crude material was purified by Biotage flash chromatography (gradient elution, 0 to 15% 3M NH$_3$/MeOH in DCM) to obtain the title compound as white powder (71% yield). $^1$H NMR (400 MHz, DMSO-d6) δ 10.45-10.41 (s, 1H), 7.98-7.92 (d, J=8.8 Hz, 2H), 7.89-7.83 (d, J=8.8 Hz, 2H), 7.63 (dd, J=7.6, 1.6 Hz, 1H), 7.50 (m, 1H), 7.18 (d, J=8.2, 4.6 Hz, 1H), 7.07 (ddd, J=7.8, 7.4, 2.2 Hz, 1H), 5.26 (m, 1H), 4.67 (m, 1H), 4.10 (t, J=7.6 Hz, 2H), 3.82-3.72 (m, 2H), 3.48-3.33 (q, J=7.4 Hz, 4H), 3.07-2.96 (s, 3H), 1.74 (m, 2H), 1.38 (m, 2H), 1.30-1.10 (m, 24H), 0.85 (t, J=7.4 Hz, 3H); LCMS (m/z) 553.5 (M); RT (Method A, std LCMS method), 4.33 min.

Example 16

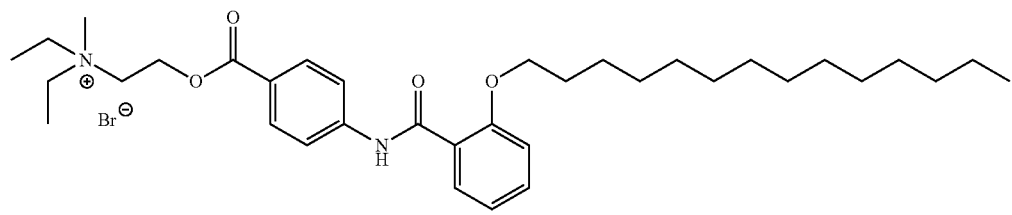 [SMILES: CCCCCCCCCCCCCCOc1ccccc1C(=O)Nc1ccc(C(=O)OCC[N+](C)(CC)CC)cc1 ; [Br-]]

N,N-Diethyl-N-methyl-2-((4-(2-(tetradecyloxy)benzamido)benzoyl)oxy)ethan-1-aminium bromide (28). According to general procedure step F; the crude material was purified by Biotage flash chromatography (gradient elution, 0 to 15% 3M NH$_3$/MeOH in DCM) to obtain the title compound as white powder (62% yield). $^1$H NMR (400 MHz, DMSO-d6) δ 10.45-10.41 (s, 1H), 7.98-7.92 (d, J=8.8 Hz, 2H), 7.89-7.83 (d, J=8.8 Hz, 2H), 7.63 (dd, J=7.6, 1.6 Hz, 1H), 7.50 (m, 1H), 7.18 (d, J=8.6, 4.6 Hz, 1H), 7.07 (m, 1H), 5.25 (m, 1H), 4.66 (m, 1H), 4.10 (t, J=6.6 Hz, 2H), 3.81-3.72 (m, 2H), 3.47-3.33 (q, J=7.4 Hz, 4H), 3.06-2.96 (s, 3H), 1.74 (m, 2H), 1.38 (m, 2H), 1.30-1.10 (m, 26H), 0.85 (t, J=7.2 Hz, 3H); LCMS (m/z) 567.5 (M); RT (Method A, std LCMS method), 5.77 min.

Example 17

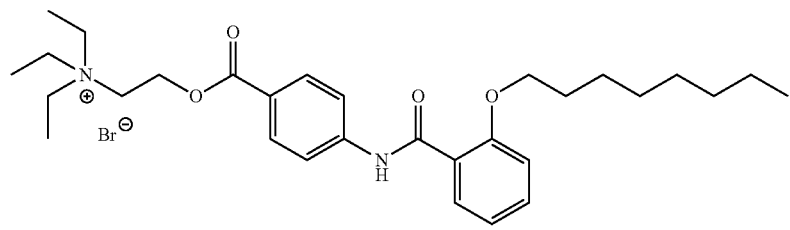 [SMILES: CCCCCCCCOc1ccccc1C(=O)Nc1ccc(C(=O)OCC[N+](CC)(CC)CC)cc1 ; [Br-]]

N,N,N-Triethyl-2-((4-(2-(octyloxy)benzamido)benzoyl)oxy)ethan-1-aminium bromide (29). According to general procedure step F; the crude material was purified by Biotage flash chromatography (gradient elution, 0 to 15% 3M NH$_3$/MeOH in DCM) to obtain the title compound as white powder (26% yield). $^1$H NMR (400 MHz, DMSO-d6) δ 10.32-10.26 (s, 1H), 8.27 (m, 1H), 8.05-7.97 (d, J=8.6 Hz, 2H), 7.76-7.72 (d, J=8.6 Hz, 2H), 7.49 (ddd, J=8.6, 8.6, 1.4 Hz, 1H), 7.12 (dd, J=7.6, 7.4 Hz, 1H), 7.02 (d, J=8.24 Hz, 1H), 4.84 (m, 2H), 4.22 (t, J=6.6 Hz, 2H), 4.12-4.02 (m, 2H), 3.68-3.53 (q, J=7.2 Hz, 4H), 2.00 (m, 2H), 1.55 (m, 2H), 1.48-1.22 (m, 17H), 0.86 (m, 3H); LCMS (m/z) 497.5 (M); RT (Method B, std LCMS method), 1.12 min.

Example 18

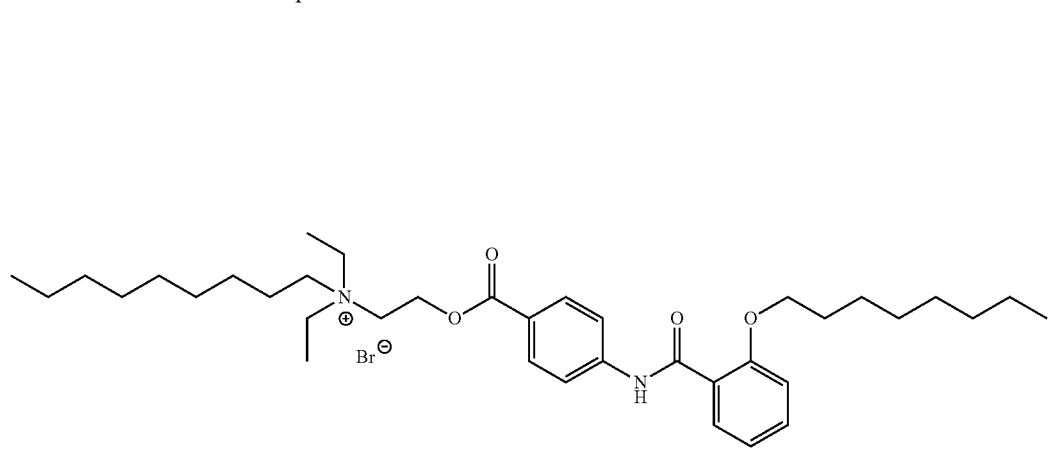

N,N-Diethyl-N-(2-((4-(2-(octyloxy)benzamido)benzoyl)oxy)ethyl)nonan-1-aminium bromide (30). According to general procedure step F; the title compound was obtained as white powder through filtration (88% yield). $^1$H NMR (400 MHz, DMSO-d6) δ 10.45 (s, 1H), 7.95 (d, J=8.6 Hz, 2H), 7.89 (d, J=8.6 Hz, 2H), 7.63 (dd, J=7.0, 1.6 Hz, 1H), 7.51 (ddd, J=8.4, 8.4, 1.6 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.73 (m, 2H), 3.41 (q, J=7.2 Hz, 4H), 3.28 (m, 2H), 1.74 (m, 2H), 1.62 (m, 2H), 1.39 (m, 2H), 1.30-1.12 (m, 26H), 0.81 (m, 6H); LCMS (m/z) 595.5 (M); RT (Method B, std LCMS method), 1.25 min.

Example 19

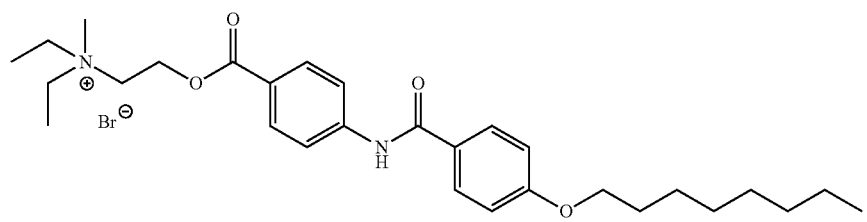 [SMILES: CCCCCCCCOc1ccc(C(=O)Nc2ccc(C(=O)OCC[N+](C)(CC)CC)cc2)cc1 ; [Br-]]

N,N-Diethyl-N-methyl-2-((4-(4-(octyloxy)benzamido)benzoyl)oxy)ethan-1-aminium bromide (31). According to general procedure step F; the crude material was purified by Biotage flash chromatography (gradient elution, 0 to 15% 3M NH$_3$/MeOH in DCM) to obtain the title compound as white powder (41% yield). $^1$H NMR (400 MHz, DMSO-d6) δ 10.52-10.42 (s, 1H), 8.00-7.94 (m, 4H), 7.81 (d, J=8.6 Hz, 2H), 7.06 (d, J=8.8 Hz, 1H), 6.87 (d, J=8.6 Hz, 1H), 5.02-4.65 (m, 2H), 4.05 (t, J=6.4 Hz, 1H), 3.98 (t, J=6.4 Hz, 1H), 3.82-3.72 (m, 2H), 3.46 (q, J=7.2 Hz, 4H), 3.06-2.96 (s, 3H), 1.72 (m, 2H), 1.62 (m, 2H), 1.39 (m, 2H), 1.30-1.12 (m, 16H), 0.86 (m, 3H); LCMS (m/z) 483.4 (M); RT (Method B, std LCMS method), 1.10 min.

Example 20

N,N-Diethyl-N-methyl-2-((4-(3-(octyloxy)benzamido)benzoyl)oxy)ethan-1-aminium bromide (32). According to general procedure step F; the crude material was purified by Biotage flash chromatography (gradient elution, 0 to 15% 3M NH$_3$/MeOH in DCM) to obtain the title compound as white powder (63% yield). $^1$H NMR (400 MHz, DMSO-d6) δ 10.54-10.50 (s, 1H), 8.02-7.92 (m, 4H), 7.66-7.42 (br, 3H), 7.17 (m, 1H), 5.26-4.67 (m, 2H), 4.04 (t, J=6.4 Hz, 2H), 3.82-3.73 (m, 2H), 3.48-3.33 (q, J=7.2 Hz, 4H), 3.07-2.96 (s, 3H), 1.74 (m, 2H), 1.43 (m, 2H), 1.33-1.17 (m, 14H), 0.86 (m, 3H); LCMS (m/z) 483.4 (M); RT (Method B, std LCMS method), 1.10 min.

Example 21

N,N-Diethyl-N-(2-((4-(2-(octyloxy)benzamido)benzoyl)oxy)ethyl)propan-1-aminium bromide (33). According to general procedure step F; the crude material was purified by Biotage flash chromatography (gradient elution, 0 to 15% 3M NH$_3$/MeOH in DCM) to obtain the title compound as white powder (79% yield). $^1$H NMR (400 MHz, DMSO-d6) δ 10.46 (s, 1H), 7.95 (d, J=8.8 Hz, 2H), 7.89 (d, J=8.8 Hz, 2H), 7.62 (dd, J=7.6, 1.8 Hz, 1H), 7.51 (ddd, J=8.8, 7.6, 1.8 Hz, 1H), 7.18 (d, J=8.2 Hz, 1H), 7.07 (dd, J=7.4, 7.4 Hz, 1H), 4.65 (m, 2H), 4.10 (t, J=6.2 Hz, 2H), 3.72 (m, 2H), 3.42 (q, J=7.0 Hz, 4H), 3.26 (m, 2H), 1.74 (m, 2H), 1.67 (m, 2H), 1.38 (m, 2H), 1.29-1.12 (m, 14H), 0.91 (t, J=7.2 Hz, 3H), 0.80 (t, J=7.2 Hz, 3H); LCMS (m/z) 511.4 (M); RT (Method B, std LCMS method), 1.13 min.

Example 22

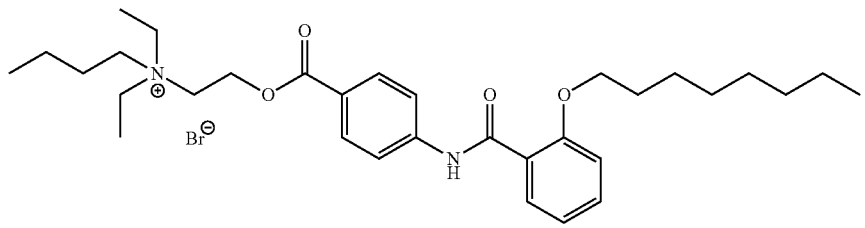 [SMILES: CCCCCCCCOc1ccccc1C(=O)Nc1ccc(C(=O)OCC[N+](CC)(CC)CCCC)cc1 ; [Br-]]

N,N-Diethyl-N-(2-((4-(2-(octyloxy)benzamido)benzoyl)oxy)ethyl)butan-1-aminium bromide (34). According to general procedure step F; the crude material was purified by Biotage flash chromatography (gradient elution, 0 to 15% 3M NH$_3$/MeOH in DCM) to obtain the title compound as white powder (78% yield). $^1$H NMR (400 MHz, DMSO-d6) δ 10.46 (s, 1H), 7.95 (d, J=8.8 Hz, 2H), 7.88 (d, J=8.8 Hz, 2H), 7.62 (dd, J=7.6, 1.8 Hz, 1H), 7.51 (ddd, J=8.6, 8.6, 1.8 Hz, 1H), 7.18 (d, J=8.8 Hz, 1H), 7.07 (dd, J=7.6, 7.6 Hz, 1H), 4.65 (m, 2H), 4.10 (t, J=6.2 Hz, 2H), 3.72 (m, 2H), 3.42 (q, J=7.2 Hz, 4H), 3.28 (m, 2H), 1.74 (m, 2H), 1.63 (m, 2H), 1.38 (m, 2H), 1.30 (m, 2H), 1.27-1.12 (m, 14H), 0.92 (t, J=7.2 Hz, 3H), 0.80 (t, J=7.2 Hz, 3H); LCMS (m/z) 525.4 (M); RT (Method B, std LCMS method), 1.14 min.

Example 23

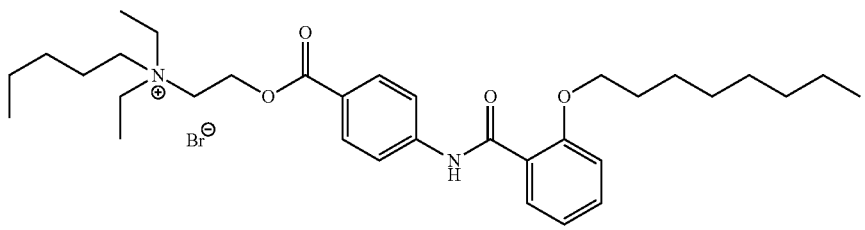 [SMILES: CCCCCCCCOc1ccccc1C(=O)Nc1ccc(C(=O)OCC[N+](CC)(CC)CCCCC)cc1 ; [Br-]]

N,N-Diethyl-N-(2-((4-(2-(octyloxy)benzamido)benzoyl)oxy)ethyl)pentan-1-aminium bromide (35). According to general procedure step F; the crude material was purified by Biotage flash chromatography (gradient elution, 0 to 15% 3M NH$_3$/MeOH in DCM) to obtain the title compound as white powder (50% yield). $^1$H NMR (400 MHz, DMSO-d6) δ 10.46 (s, 1H), 7.95 (d, J=8.8 Hz, 2H), 7.88 (d, J=8.8 Hz, 2H), 7.62 (d, J=8.2 Hz, 1H), 7.50 (t, J=7.8 Hz, 1H), 7.18 (d, J=8.6 Hz, 1H), 7.06 (t, J=7.6, 7.6 Hz, 1H), 4.65 (m, 2H), 4.10 (t, J=6.6 Hz, 2H), 3.72 (m, 2H), 3.41 (q, J=7.4 Hz, 4H), 3.27 (m, 2H), 1.74 (m, 2H), 1.64 (m, 2H), 1.38 (m, 2H), 1.30 (m, 2H), 1.28-1.11 (m, 16H), 0.86 (t, J=7.2 Hz, 3H), 0.80 (t, J=7.2 Hz, 3H); LCMS (m/z) 539.4 (M); RT (Method B, std LCMS method), 1.16 min.

Example 24

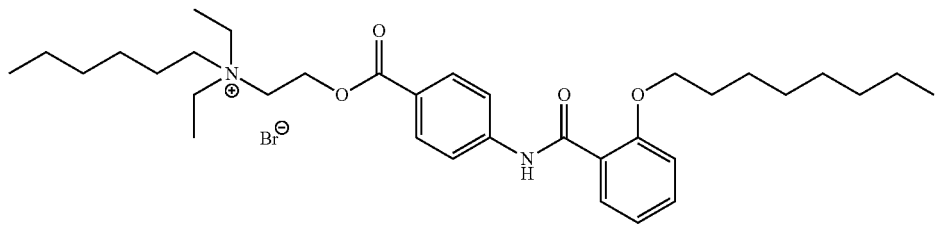 [SMILES: CCCCCCCCOc1ccccc1C(=O)Nc1ccc(C(=O)OCC[N+](CC)(CC)CCCCCC)cc1 ; [Br-]]

N,N-Diethyl-N-(2-((4-(2-(octyloxy)benzamido)benzoyl)oxy)ethyl)hexan-1-aminium bromide (36). According to general procedure step F; the crude material was purified by Biotage flash chromatography (gradient elution, 0 to 15% 3M NH$_3$/MeOH in DCM) to obtain the title compound as white powder (47% yield). $^1$H NMR (400 MHz, DMSO-d6) δ 10.46 (s, 1H), 7.95 (d, J=8.8 Hz, 2H), 7.89 (d, J=8.8 Hz, 2H), 7.61 (dd, J=7.8, 1.6 Hz, 1H), 7.51 (ddd, J=7.8, 7.8, 1.8 Hz, 1H), 7.18 (d, J=8.4 Hz, 1H), 7.07 (dd, J=7.4, 7.4 Hz, 1H), 4.65 (m, 2H), 4.10 (t, J=6.2 Hz, 2H), 3.72 (m, 2H), 3.41 (q, J=7.2 Hz, 4H), 3.28 (m, 2H), 1.73 (m, 2H), 1.63 (m, 2H), 1.38 (m, 2H), 1.30-1.12 (m, 20H), 0.85 (t, J=7.2 Hz, 3H), 0.80 (t, J=7.2 Hz, 3H); LCMS (m/z) 553.5 (M); RT (Method B, std LCMS method), 1.18 min.

Example 25

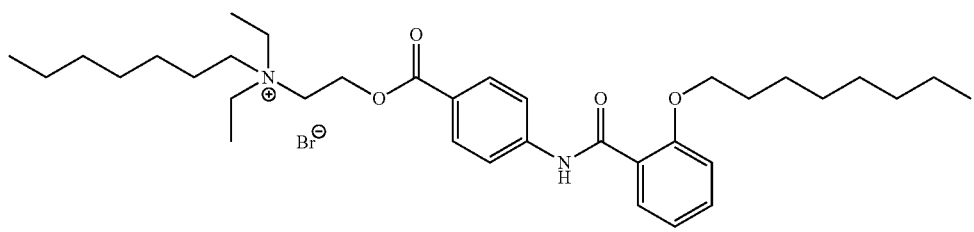 [SMILES: CCCCCCCCOc1ccccc1C(=O)Nc1ccc(C(=O)OCC[N+](CC)(CC)CCCCCCC)cc1 ; [Br-]]

N,N-Diethyl-N-(2-((4-(2-(octyloxy)benzamido)benzoyl)oxy)ethyl)heptan-1-aminium bromide (37). According to general procedure step F; the crude material was purified by Biotage flash chromatography (gradient elution, 0 to 15% 3M $NH_3$/MeOH in DCM) to obtain the title compound as white powder (45% yield). $^1$H NMR (400 MHz, DMSO-d6) δ 10.46 (s, 1H), 7.95 (d, J=8.8 Hz, 2H), 7.89 (d, J=8.8 Hz, 2H), 7.62 (d, J=8.0 Hz, 1H), 7.51 (ddd, J=7.8, 7.8, 1.8 Hz, 1H), 7.18 (d, J=8.4 Hz, 1H), 7.07 (dd, J=7.4, 7.4 Hz, 1H), 4.65 (m, 2H), 4.10 (t, J=6.2 Hz, 2H), 3.72 (m, 2H), 3.41 (q, J=7.2 Hz, 4H), 3.26 (m, 2H), 1.73 (m, 2H), 1.62 (m, 2H), 1.38 (m, 2H), 1.31-1.11 (m, 22H), 0.84 (t, J=7.2 Hz, 3H), 0.80 (t, J=7.2 Hz, 3H); LCMS (m/z) 567.5 (M); RT (Method B, std LCMS method), 1.20 min.

Example 26

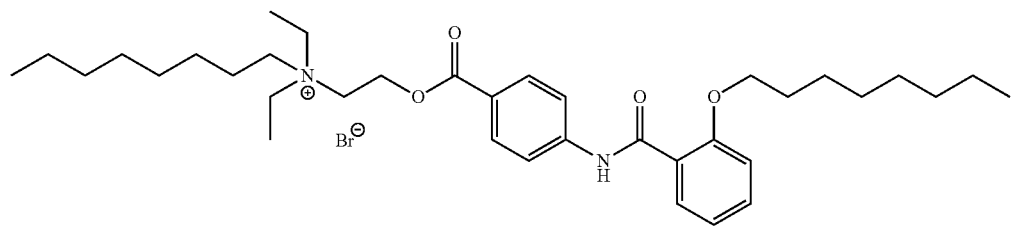 [SMILES: CCCCCCCCOc1ccccc1C(=O)Nc1ccc(C(=O)OCC[N+](CC)(CC)CCCCCCCC)cc1 ; [Br-]]

N,N-Diethyl-N-(2-((4-(2-(octyloxy)benzamido)benzoyl)oxy)ethyl)octan-1-aminium bromide (38). According to general procedure step F; the crude material was purified by Biotage flash chromatography (gradient elution, 0 to 15% 3M $NH_3$/MeOH in DCM) to obtain the title compound as white powder (54% yield). $^1$H NMR (400 MHz, DMSO-d6) δ 10.45 (s, 1H), 7.95 (d, J=8.8 Hz, 2H), 7.89 (d, J=8.8 Hz, 2H), 7.62 (dd, J=7.6, 1.8 Hz, 1H), 7.51 (ddd, J=8.6, 8.6, 1.8 Hz, 1H), 7.18 (d, J=8.2 Hz, 1H), 7.07 (dd, J=7.6, 7.6 Hz, 1H), 4.65 (m, 2H), 4.10 (t, J=6.2 Hz, 2H), 3.72 (m, 2H), 3.41 (q, J=7.2 Hz, 4H), 3.27 (m, 2H), 1.74 (m, 2H), 1.63 (m, 2H), 1.39 (m, 2H), 1.30-1.12 (m, 24H), 0.83 (t, J=7.2 Hz, 3H), 0.80 (t, J=7.2 Hz, 3H); LCMS (m/z) 581.5 (M); RT (Method B, std LCMS method), 1.22 min.

Example 27

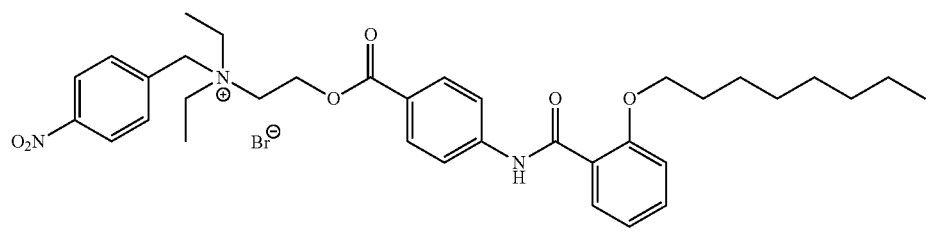 [SMILES: CCCCCCCCOc1ccccc1C(=O)Nc1ccc(C(=O)OCC[N+](CC)(CC)Cc2ccc([N+](=O)[O-])cc2)cc1 ; [Br-]]

N,N-Diethyl-N-(4-nitrobenzyl)-2-((4-(2-(octyloxy)benzamido)benzoyl)oxy)ethan-1-aminium bromide (39). According to general procedure step F; the title compound was obtained as white powder through filtration (47% yield). $^1$H NMR (400 MHz, DMSO-d6) δ 10.45 (s, 1H), 8.36 (d, J=8.6 Hz, 2H), 7.98 (d, J=8.8 Hz, 2H), 7.88 (m, 4H), 7.62 (d, J=7.2 Hz, 1H), 7.50 (ddd, J=7.2, 7.2, 1.8 Hz, 1H), 7.18 (d, J=8.5 Hz, 1H), 7.07 (dd, J=7.6, 7.6 Hz, 1H), 4.83 (m, 2H), 4.79 (m, 2H), 4.10 (t, J=6.4 Hz, 2H), 3.71 (m, 2H), 3.41 (q, J=7.2 Hz, 4H), 1.73 (m, 2H), 1.39 (t, J=7.2 Hz, 6H), 1.28-1.07 (m, 10H), 0.79 (t, J=6.8 Hz, 3H); LCMS (m/z) 604.4 (M); RT (Method B, std LCMS method), 1.14 min.

Example 28

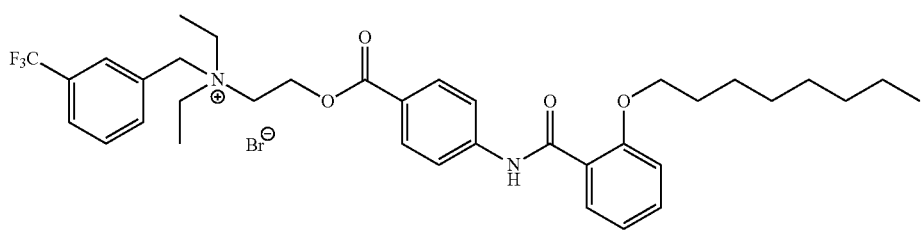 [SMILES: CCCCCCCCOc1ccccc1C(=O)Nc1ccc(C(=O)OCC[N+](CC)(CC)Cc2cccc(C(F)(F)F)c2)cc1 ; [Br-]]

N,N-Diethyl-2-((4-(2-(octyloxy)benzamido)benzoyl)oxy)-N-(3-(trifluoromethyl)-benzyl)ethan-1-aminium bromide (40). According to general procedure step F; the title compound was obtained as white powder through filtration (57% yield). $^1$H NMR (400 MHz, DMSO-d6) δ 10.45 (s, 1H), 7.98 (m, 3H), 7.94 (d, J=8.0 Hz, 1H), 7.90-7.80 (m, 3H), 7.78 (dd, J=7.6, 7.6 Hz, 1H), 7.62 (dd, J=7.8, 1.4 Hz, 1H), 7.51 (ddd, J=8.4, 8.4, 1.8 Hz, 1H), 7.18 (d, J=8.4 Hz, 1H), 7.07 (dd, J=7.6, 7.6 Hz, 1H), 4.78 (m, 4H), 4.10 (t, J=6.2 Hz, 2H), 3.71 (m, 2H), 3.41 (q, J=7.2 Hz, 4H), 1.73 (m, 2H), 1.38 (t, J=7.2 Hz, 6H), 1.28-1.07 (m, 10H), 0.78 (t, J=6.8 Hz, 3H); LCMS (m/z) 627.4 (M); RT (Method B, std LCMS method), 1.17 min.

Example 29

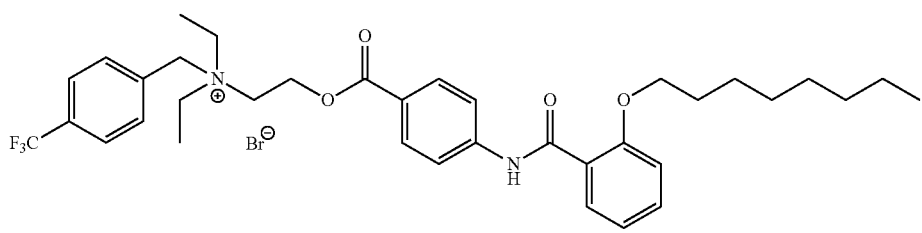 [SMILES: CCCCCCCCOc1ccccc1C(=O)Nc1ccc(C(=O)OCC[N+](CC)(CC)Cc2ccc(C(F)(F)F)cc2)cc1 ; [Br-]]

N,N-Diethyl-2-((4-(2-(octyloxy)benzamido)benzoyl)oxy)-N-(4-(trifluoromethyl)-benzyl)ethan-1-aminium bromide (41). According to general procedure step F; the title compound was obtained as white powder through filtration (43% yield). $^1$H NMR (400 MHz, DMSO-d6) δ 10.45 (s, 1H), 7.98 (d, J=8.8 Hz, 2H), 7.91 (d, J=8.2 Hz, 2H), 7.88 (d, J=8.8 Hz, 2H), 7.81 (d, J=8.2 Hz, 2H), 7.62 (dd, J=7.6, 1.8 Hz, 1H), 7.51 (ddd, J=8.4, 8.4, 1.6 Hz, 1H), 7.18 (d, J=8.4 Hz, 1H), 7.07 (dd, J=7.6, 7.6 Hz, 1H), 4.78 (m, 4H), 4.10 (t, J=6.2 Hz, 2H), 3.70 (m, 2H), 3.40 (q, J=7.2 Hz, 4H), 1.74 (m, 2H), 1.39 (t, J=7.2 Hz, 6H), 1.28-1.11 (m, 10H), 0.78 (t, J=6.8 Hz, 3H); LCMS (m/z) 627.4 (M); RT (Method B, std LCMS method), 1.18 min.

Example 30

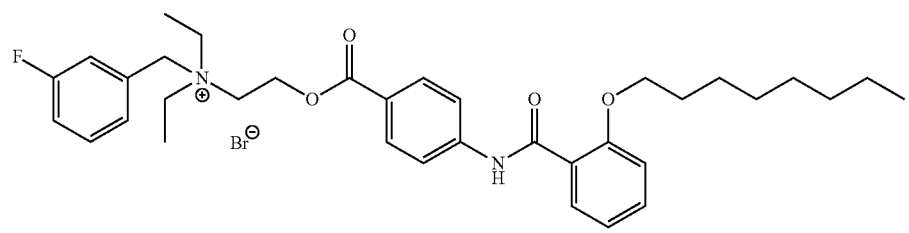 [SMILES: CCCCCCCCOc1ccccc1C(=O)Nc1ccc(C(=O)OCC[N+](CC)(CC)Cc2cccc(F)c2)cc1 ; [Br-]]

N,N-Diethyl-N-(3-fluorobenzyl)-2-((4-(2-(octyloxy)benzamido)benzoyl)oxy)ethan-1-aminium bromide (42). According to general procedure step F; the title compound was obtained as white powder through filtration (58% yield). $^1$H NMR (400 MHz, DMSO-d6) δ 10.45 (s, 1H), 7.98 (d, J=8.8 Hz, 2H), 7.88 (d, J=8.8 Hz, 2H), 7.62 (dd, J=7.4, 1.8 Hz, 1H), 7.58 (ddd, J=7.2, 7.2, 1.2 Hz, 1H), 7.51 (ddd, J=8.2, 8.2, 1.8 Hz, 1H), 7.47-7.40 (m, 3H), 7.18 (d, J=8.2 Hz, 1H), 7.07 (dd, J=8.0, 8.0 Hz, 1H), 4.77 (m, 2H), 4.68 (s, 2H), 4.10 (t, J=6.2 Hz, 2H), 3.70 (m, 2H), 3.40 (q, J=7.2 Hz, 4H), 1.74 (m, 2H), 1.38 (t, J=7.2 Hz, 6H), 1.28-1.10 (m, 10H), 0.78 (t, J=6.8 Hz, 3H); LCMS (m/z) 577.4 (M); RT (Method B, std LCMS method), 1.15 min.

Example 31

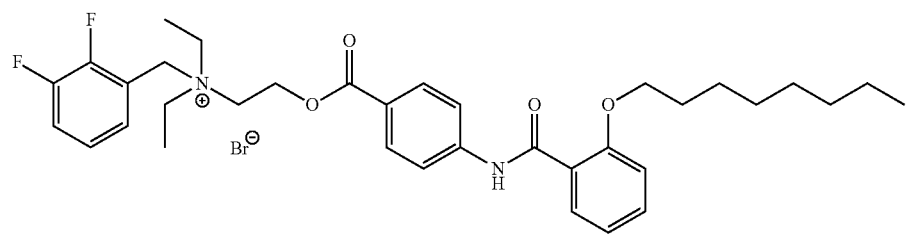 [SMILES: CCCCCCCCOc1ccccc1C(=O)Nc1ccc(C(=O)OCC[N+](CC)(CC)Cc2cccc(F)c2F)cc1 ; [Br-]]

N,N-Diethyl-N-(2,3-difluorobenzyl)-2-((4-(2-(octyloxy)benzamido)benzoyl)oxy)-ethan-1-aminium bromide (43). According to general procedure step F; the title compound was obtained as white powder through filtration (58% yield). $^1$H NMR (400 MHz, DMSO-d6) δ 10.45 (s, 1H), 7.98 (d, J=8.8 Hz, 2H), 7.88 (d, J=8.8 Hz, 2H), 7.68 (m, 1H), 7.62 (dd, J=7.8, 1.8 Hz, 1H), 7.51 (ddd, J=7.8, 7.8, 1.8 Hz, 1H), 7.47 (d, J=6.8 Hz, 1H), 7.40 (m, 1H), 7.18 (d, J=8.4 Hz, 1H), 7.07 (dd, J=7.4, 7.4 Hz, 1H), 4.79 (s, 4H), 4.10 (t, J=6.2 Hz, 2H), 3.73 (m, 2H), 3.44 (q, J=7.2 Hz, 4H), 1.73 (m, 2H), 1.38 (t, J=7.2 Hz, 6H), 1.28-1.10 (m, 10H), 0.79 (t, J=6.8 Hz, 3H); LCMS (m/z) 595.4 (M); RT (Method B, std LCMS method), 1.15 min.

Example 32

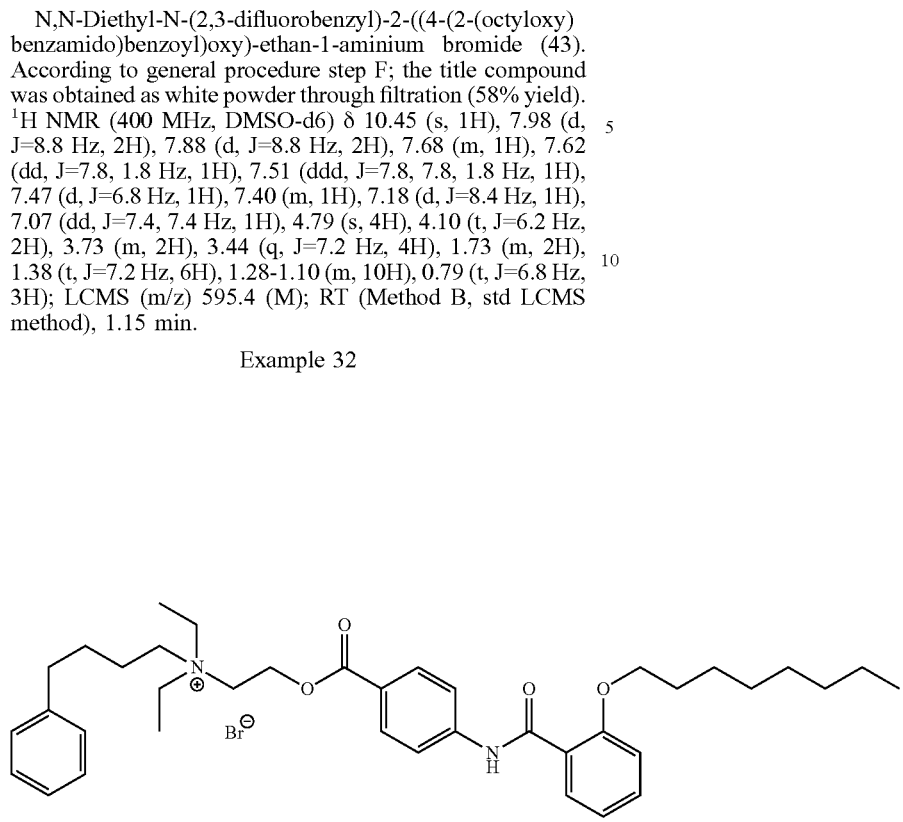

N,N-Diethyl-N-(2-((4-(2-(octyloxy)benzamido)benzoyl)oxy)ethyl)-4-phenylbutan-1-aminium bromide (44). According to general procedure step F; the title compound was obtained as white powder through filtration (81% yield). $^1$H NMR (400 MHz, DMSO-d6) δ 10.47 (s, 1H), 7.96 (d, J=8.8 Hz, 2H), 7.90 (d, J=8.8 Hz, 2H), 7.63 (dd, J=7.4, 1.6 Hz, 1H), 7.51 (ddd, J=8.2, 8.2, 1.6 Hz, 1H), 7.27 (m, 2H), 7.20-7.15 (m, 4H), 7.07 (dd, J=7.4, 7.4 Hz, 1H), 4.66 (m, 2H), 4.10 (t, J=6.2 Hz, 2H), 3.72 (m, 2H), 3.41 (q, J=7.2 Hz, 4H), 3.34 (m, 2H), 2.58 (t, J=8.0 Hz, 2H), 1.76-1.65 (br, 4H), 1.57 (m, 2H), 1.37 (m, 2H), 1.27-1.10 (m, 14H), 0.79 (t, J=6.8 Hz, 3H); LCMS (m/z) 601.5 (M); RT (Method B, std LCMS method), 1.18 min.

Example 33

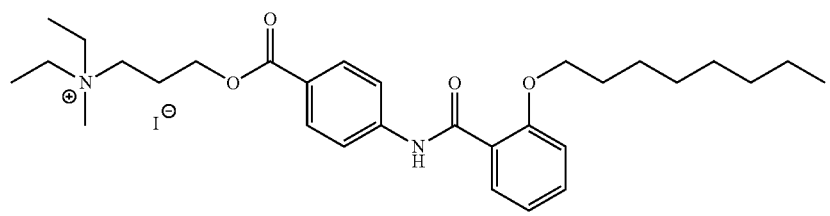 [SMILES: CCCCCCCCOc1ccccc1C(=O)Nc1ccc(C(=O)OCCC[N+](C)(CC)CC)cc1 ; [I-]]

N,N-Diethyl-N-methyl-3-((4-(2-(octyloxy)benzamido)benzoyl)oxy)propan-1-aminium iodide (45). According to general procedure step F; the title compound was obtained as white powder through filtration (34% yield). $^1$H NMR (400 MHz, DMSO-d6) δ 10.43 (s, 1H), 7.98 (d, J=8.8 Hz, 2H), 7.87 (d, J=8.8 Hz, 2H), 7.62 (dd, J=7.6, 1.8 Hz, 1H), 7.50 (ddd, J=8.2, 8.2, 1.8 Hz, 1H), 7.18 (d, J=8.4 Hz, 1H), 7.07 (dd, J=7.8, 7.8 Hz, 1H), 4.33 (t, J=5.6 Hz, 2H), 4.10 (t, J=6.0 Hz, 2H), 3.41-3.33 (m, 6H), 2.97 (s, 3H), 2.11 (m, 2H), 1.74 (m, 2H), 1.38 (m, 2H), 1.29-1.10 (m, 14H), 0.80 (t, J=7.2 Hz, 3H); LCMS (m/z) 497.4 (M); RT (Method B, std LCMS method), 1.12 min.

Example 34

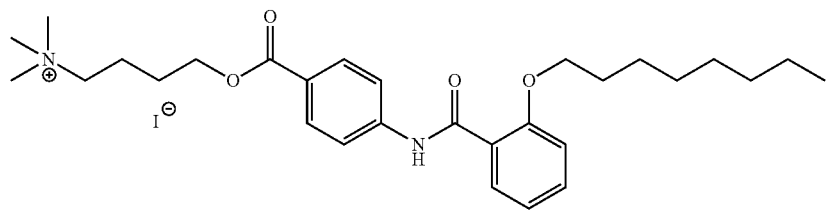 [SMILES: CCCCCCCCOc1ccccc1C(=O)Nc1ccc(C(=O)OCCCC[N+](C)(C)C)cc1 ; [I-]]

N,N,N-Trimethyl-4-((4-(2-(octyloxy)benzamido)benzoyl)oxy)butan-1-aminium iodide (46). According to general procedure step F; the title compound was obtained as white powder through filtration (22% yield). $^1$H NMR (400 MHz, DMSO-d6) δ 10.42 (s, 1H), 7.97 (d, J=8.8 Hz, 2H), 7.86 (d, J=8.8 Hz, 2H), 7.62 (dd, J=7.6, 1.8 Hz, 1H), 7.50 (ddd, J=8.2, 8.2, 1.8 Hz, 1H), 7.18 (d, J=8.4 Hz, 1H), 7.07 (dd, J=7.2, 7.2 Hz, 1H), 4.29 (t, J=6.2 Hz, 2H), 4.10 (t, J=6.2 Hz, 2H), 3.37 (m, 2H), 3.06 (s, 9H), 1.86 (m, 2H), 1.78-1.70 (m, 4H), 1.38 (m, 2H), 1.28-1.10 (m, 8H), 0.79 (t, J=7.2 Hz, 3H); LCMS (m/z) 483.4 (M); RT (Method B, std LCMS method), 1.11 min.

Example 35

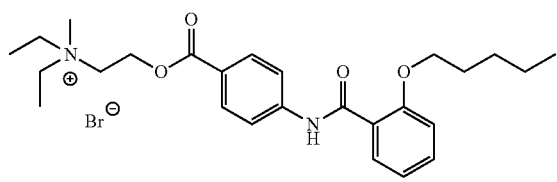 [SMILES: CCCCCOc1ccccc1C(=O)Nc1ccc(C(=O)OCC[N+](C)(CC)CC)cc1 ; [Br-]]

N,N-Diethyl-N-methyl-2-((4-(2-(pentyloxy)benzamido)benzoyl)oxy)ethan-1-aminium bromide (20). According to general procedure step F; the title compound was obtained as white powder through filtration (62% yield). $^1$H NMR (400 MHz, DMSO-d6) δ 10.46 (s, 1H), 7.98 (d, J=8.8 Hz, 2H), 7.88 (d, J=8.8 Hz, 2H), 7.62 (dd, J=7.6, 1.8 Hz, 1H), 7.51 (ddd, J=8.2, 8.2, 1.8 Hz, 1H), 7.19 (d, J=8.4 Hz, 1H), 7.08 (dd, J=7.6, 7.6 Hz, 1H), 4.67 (m, 2H), 4.10 (t, J=6.2 Hz, 2H), 3.74 (m, 2H), 3.45 (q, J=7.2 Hz, 4H), 3.06 (s, 3H), 1.75 (m, 2H), 1.38 (m, 2H), 1.31-1.23 (m, J=7.2 Hz, 8H), 0.78 (t, J=7.2 Hz, 3H); LCMS (m/z) 441.3 (M); RT (Method B, std LCMS method), 1.03 min.

Example 36

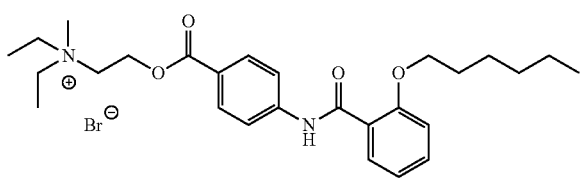 [SMILES: CCCCCCOc1ccccc1C(=O)Nc1ccc(C(=O)OCC[N+](C)(CC)CC)cc1 ; [Br-]]

N,N-Diethyl-2-((4-(2-(hexyloxy)benzamido)benzoyl)oxy)-N-methylethan-1-aminium bromide (21). According to general procedure step F; the title compound was obtained as white powder through filtration (58% yield). 1H NMR (400 MHz, DMSO-d6) δ 10.46 (s, 1H), 7.97 (d, J=8.8 Hz, 2H), 7.88 (d, J=8.8 Hz, 2H), 7.62 (dd, J=7.6, 1.8 Hz, 1H), 7.51 (ddd, J=8.2, 8.2, 1.8 Hz, 1H), 7.18 (d, J=8.4 Hz, 1H), 7.07 (dd, J=7.4, 7.4 Hz, 1H), 4.67 (m, 2H), 4.10 (t, J=6.2 Hz, 2H), 3.74 (m, 2H), 3.45 (q, J=7.2 Hz, 4H), 3.06 (s, 3H), 1.74 (m, 2H), 1.39 (m, 2H), 1.30-1.15 (m, 10H), 0.77 (t, J=7.2 Hz, 3H); LCMS (m/z) 455.4 (M); RT (Method B, std LCMS method), 1.06 min.

Example 37

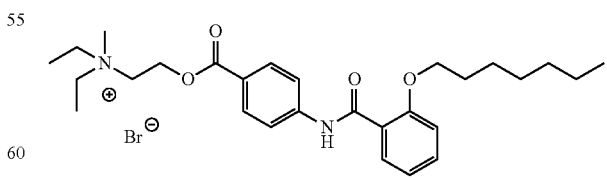

N,N-Diethyl-2-((4-(2-(heptyloxy)benzamido)benzoyl)oxy)-N-methylethan-1-aminium bromide (22). According to general procedure step F; the title compound was obtained as white powder through filtration (60% yield). 1H NMR (400 MHz, DMSO-d6) δ 10.46 (s, 1H), 7.97 (d, J=8.8 Hz, 2H), 7.89 (d, J=8.8 Hz, 2H), 7.62 (d, J=7.8 Hz, 1H), 7.51 (dd, J=7.8, 7.8 Hz, 1H), 7.19 (d, J=8.2 Hz, 1H), 7.07 (dd, J=8.2, 8.2 Hz, 1H), 4.67 (m, 2H), 4.10 (t, J=7.2, 7.2 Hz, 2H), 3.74 (m, 2H), 3.45 (q, J=7.2 Hz, 4H), 3.06 (s, 3H), 1.74 (m, 2H), 1.37 (m, 2H), 1.30-1.10 (m, 12H), 0.78 (t, J=7.2 Hz, 3H); LCMS (m/z) 469.4 (M); RT (Method B, std LCMS method), 1.08 min.

Example 38

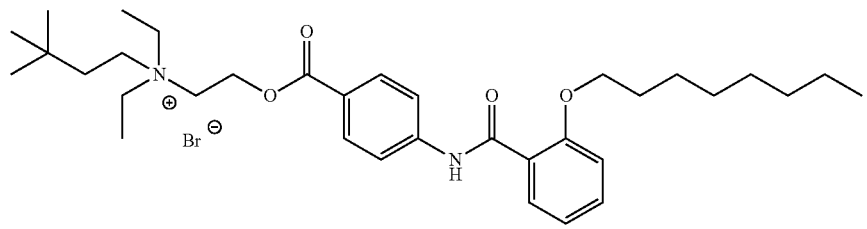

N,N-Diethyl-3,3-dimethyl-N-(2-((4-(2-(octyloxy)benzamido)benzoyl)oxy)ethyl)-butan-1-aminium bromide (47). According to general procedure step F; the crude material was purified by Biotage flash chromatography (gradient elution, 0 to 15% 3M NH$_3$/MeOH in DCM) to obtain the title compound as white powder (44% yield). $^1$H NMR (400 MHz, DMSO-d6) δ 10.46 (s, 1H), 7.96 (d, J=8.8 Hz, 2H), 7.89 (d, J=8.8 Hz, 2H), 7.62 (d, J=7.6 Hz, 1H), 7.50 (dd, J=7.6, 7.6 Hz, 1H), 7.18 (d, J=8.4 Hz, 1H), 7.07 (dd, J=7.4, 7.4 Hz, 1H), 4.65 (m, 2H), 4.10 (t, J=6.2 Hz, 2H), 3.73 (m, 2H), 3.44 (q, J=7.2 Hz, 4H), 3.29 (m, 2H), 1.74 (m, 2H), 1.57 (m, 2H), 1.38 (m, 2H), 1.28-1.11 (m, 14H), 0.94 (s, 9H), 0.80 (t, J=7.2 Hz, 3H); LCMS (m/z) 553.4 (M); RT (Method B, std LCMS method), 1.18 min.

Example 39

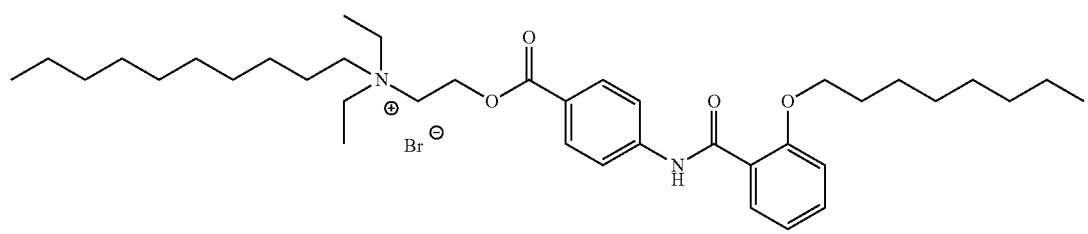

N,N-Diethyl-N-(2-((4-(2-(octyloxy)benzamido)benzoyl) oxy)ethyl)decan-1-aminium bromide (48). According to general procedure step F; the crude material was purified by Biotage flash chromatography (gradient elution, 0 to 15% 3M NH₃/MeOH in DCM) to obtain the title compound as white powder (30% yield). $^1$H NMR (400 MHz, DMSO-d6) δ 10.46 (s, 1H), 7.95 (d, J=8.8 Hz, 2H), 7.89 (d, J=8.8 Hz, 2H), 7.63 (dd, J=7.6, 1.8 Hz, 1H), 7.50 (ddd, J=8.4, 8.4, 1.8 Hz, 1H), 7.18 (d, J=8.4 Hz, 1H), 7.07 (dd, J=7.6 Hz, 1H), 4.65 (m, 2H), 4.10 (t, J=6.2 Hz, 2H), 3.73 (m, 2H), 3.41 (q, J=7.2 Hz, 4H), 3.28 (m, 2H), 1.75 (m, 2H), 1.62 (br, 2H), 1.39 (m, 2H), 1.30-1.12 (m, 28H), 0.81 (m, 6H); LCMS (m/z) 609.6 (M); RT (Method B, std LCMS method), 1.28 min.

Example 40

N,N-Diethyl-N-(2-((4-(2-(octyloxy)benzamido)benzoyl) oxy)ethyl)undecan-1-aminium bromide (49). According to general procedure step F; the crude material was purified by Biotage flash chromatography (gradient elution, 0 to 15% 3M NH₃/MeOH in DCM) to obtain the title compound as white powder (12% yield). $^1$H NMR (400 MHz, DMSO-d6) δ 10.45 (s, 1H), 7.95 (d, J=8.8 Hz, 2H), 7.88 (d, J=8.8 Hz, 2H), 7.64 (dd, J=7.6, 1.8 Hz, 1H), 7.51 (ddd, J=7.6, 7.6, 1.8 Hz, 1H), 7.19 (d, J=8.4 Hz, 1H), 7.07 (dd, J=7.6, 7.6 Hz, 1H), 4.65 (m, 2H), 4.10 (t, J=6.2 Hz, 2H), 3.73 (m, 2H), 3.41 (q, J=7.2 Hz, 4H), 3.28 (m, 2H), 1.75 (m, 2H), 1.62 (br, 2H), 1.39 (m, 2H), 1.30-1.12 (m, 30H), 0.80 (m, 6H); LCMS (m/z) 623.6 (M); RT (Method B, std LCMS method), 1.23 min.

Example 41

N,N-Diethyl-N-(3-methoxybenzyl)-2-((4-(2-(octyloxy)benzamido)benzoyl)oxy)-ethan-1-aminium bromide (50). According to general procedure step F; the crude material was purified by Biotage flash chromatography (gradient elution, 0 to 15% 3M NH$_3$/MeOH in DCM) to obtain the title compound as white powder (32% yield). $^1$H NMR (400 MHz, DMSO-d6) δ 10.45 (s, 1H), 7.98 (d, J=8.8 Hz, 2H), 7.88 (d, J=8.8 Hz, 2H), 7.62 (dd, J=7.6, 1.8 Hz, 1H), 7.50 (ddd, J=7.6, 7.6, 1.8 Hz, 1H), 7.45 (dd, J=8.4, 8.4 Hz, 1H), 7.18 (d, J=8.2 Hz, 1H), 7.13 (d, J=6.2 Hz, 3H), 7.07 (dd, J=7.6, 7.6 Hz, 1H), 4.77 (m, 2H), 4.63 (s, 2H), 4.10 (t, J=6.2 Hz, 2H), 3.80 (s, 3H), 3.68 (m, 2H), 3.39 (q, J=7.2 Hz, 4H), 1.73 (m, J=6.5 Hz, 2H), 1.38 (t, J=7.2 Hz, 6H), 1.29-1.11 (m, 10H), 0.79 (t, J=6.8 Hz, 3H); LCMS (m/z) 589.4 (M); RT (Method B, std LCMS method), 1.15 min.

Example 42

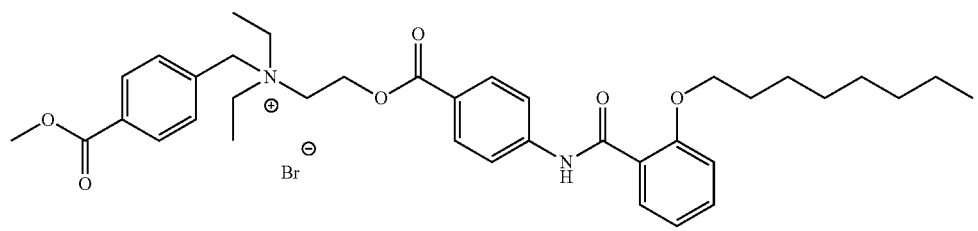

N,N-Diethyl-N-(4-(methoxycarbonyl)benzyl)-2-((4-(2-(octyloxy)benzamido)-benzoyl)oxy)ethan-1-aminium bromide (51). According to general procedure step F; the crude material was purified by Biotage flash chromatography (gradient elution, 0 to 15% 3M NH$_3$/MeOH in DCM) to obtain the title compound as white powder (35% yield). $^1$H NMR (400 MHz, DMSO-d6) δ 10.45 (s, 1H), 8.08 (d, J=8.4 Hz, 2H), 7.98 (d, J=8.8 Hz, 2H), 7.88 (d, J=8.8 Hz, 2H), 7.73 (d, J=8.2 Hz, 2H), 7.62 (dd, J=7.6, 1.8 Hz, 1H), 7.50 (ddd, J=8.0, 8.0, 1.8 Hz, 1H), 7.18 (d, J=8.4 Hz, 1H), 7.07 (dd, J=7.6, 7.6 Hz, 1H), 4.78 (m, 2H), 4.76 (s, 2H), 4.10 (t, J=6.2 Hz, 2H), 3.89 (s, 3H), 3.69 (m, 2H), 3.39 (q, J=7.2 Hz, 4H), 1.74 (m, 2H), 1.38 (t, J=7.2 Hz, 6H), 1.28-1.11 (m, 10H), 0.78 (t, J=6.8 Hz, 3H); LCMS (m/z) 617.5 (M); RT (Method B, std LCMS method), 1.14 min.

Example 43

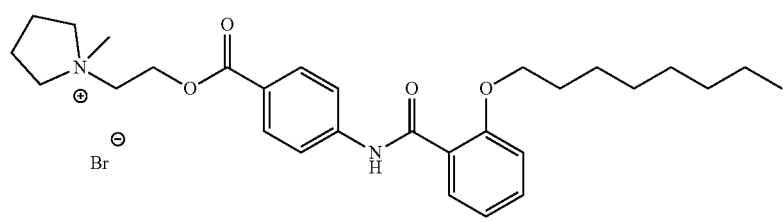

1-Methyl-1-(2-((4-(2-(octyloxy)benzamido)benzoyl)oxy)ethyl)pyrrolidin-1-ium bromide (52). According to general procedure step F; the crude material was purified by Biotage flash chromatography (gradient elution, 0 to 25% 1M NH$_3$/MeOH in DCM) to obtain the title compound as white foam (44% yield). $^1$H NMR (400 MHz, DMSO-d6) δ 10.44 (s, 1H), 7.98 (d, J=8.8 Hz, 2H), 7.88 (d, J=8.8 Hz, 2H), 7.63 (dd, J=7.6, 1.8 Hz, 1H), 7.50 (ddd, J=8.0, 8.0, 1.8 Hz, 1H), 7.18 (d, J=8.4 Hz, 1H), 7.07 (dd, J=7.6, 7.6 Hz, 1H), 4.70 (m, 2H), 4.10 (t, J=6.2 Hz, 2H), 3.84 (m, 2H), 3.60 (m, 4H), 3.13 (s, 3H), 2.13 (m, 2H), 1.74 (m, 2H), 1.43-1.11 (m, 12H), 0.80 (t, J=6.8 Hz, 3H); LCMS (m/z) 481.4 (M); RT (Method A, std LCMS method), 3.61 min.

Example 44

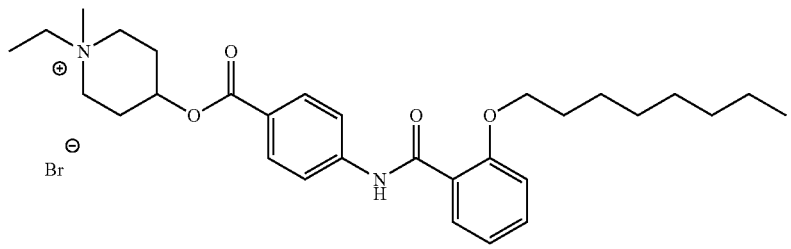 [SMILES: CCCCCCCCOc1ccccc1C(=O)Nc1ccc(C(=O)OC2CC[N+](C)(CC)CC2)cc1 ; [Br-]]

1-Ethyl-1-methyl-4-((4-(2-(octyloxy)benzamido)benzoyl)oxy)piperidin-1-ium bromide (53). According to general procedure step F; the crude material was purified by Biotage flash chromatography (gradient elution, 0 to 20% 1M NH$_3$/MeOH in DCM) to obtain the title compound as white foam (40% yield). 1H NMR (400 MHz, DMSO-d6) δ 10.43 (s, 1H), 8.05 (dd, J=8.8, 1.6 Hz, 2H), 7.87 (d, J=8.0 Hz, 2H), 7.63 (dd, J=7.6, 1.8 Hz, 1H), 7.50 (ddd, J=8.6, 8.6, 1.8 Hz, 1H), 7.18 (d, J=8.4 Hz, 1H), 7.07 (dd, J=7.2, 7.2 Hz, 1H), 5.15 (m, 1H), 4.10 (t, J=6.2 Hz, 2H), 3.58-3.44 (m, 6H), 3.11-3.04 (s, 3H), 2.28 (m, 2H), 2.05 (m, 2H), 1.74 (m, 2H), 1.42-1.10 (m, 10H), 0.79 (t, J=7.2 Hz, 3H); LCMS (m/z) 495.4 (M); RT (Method A, std LCMS method), 3.49 min.

Example 45

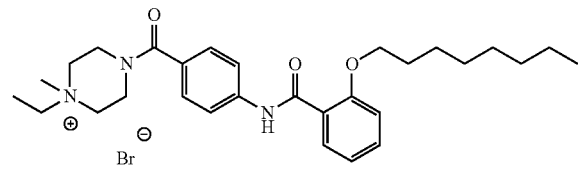 [SMILES: CCCCCCCCOc1ccccc1C(=O)Nc1ccc(C(=O)N2CC[N+](C)(CC)CC2)cc1 ; [Br-]]

1-Ethyl-1-methyl-4-(4-(2-(octyloxy)benzamido)benzoyl)piperazin-1-ium bromide (54). According to general procedure step F; the crude material was purified by Biotage flash chromatography (gradient elution, 0 to 20% 1M NH$_3$/MeOH in DCM) to obtain the title compound as white foam (38% yield). $^1$H NMR (400 MHz, DMSO-d6) δ 10.28 (s, 1H), 7.79 (d, J=8.6 Hz, 2H), 7.65 (dd, J=7.6, 1.8 Hz, 1H), 7.50 (ddd, J=7.6, 7.6, 1.8 Hz, 1H), 7.45 (d, J=8.4 Hz, 2H), 7.18 (d, J=8.6 Hz, 1H), 7.07 (dd, J=7.2, 7.2 Hz, 1H), 4.10 (m, 2H), 3.80 (m, 2H), 3.46 (m, 2H), 3.39 (m, 2H), 3.30 (m, 2H), 3.17 (d, J=5.2 Hz, 2H), 3.03 (s, 3H), 1.76 (m, 2H), 1.40 (m, 2H), 1.30-1.10 (m, 11H), 0.81 (t, J=7.2 Hz, 3H); LCMS (m/z) 480.4 (M); RT (Method A, std LCMS method), 3.24 min.

Example 46

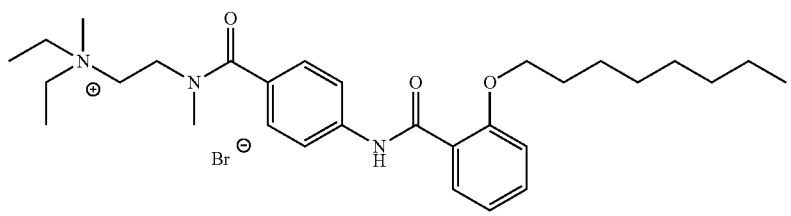

N,N-Diethyl-N-methyl-2-(N-methyl-4-(2-(octyloxy)benzamido)benzamido)ethan-1-aminium bromide (55). According to general procedure step F; the crude material was purified by Biotage flash chromatography (gradient elution, 0 to 20% 1M NH$_3$/MeOH in DCM) to obtain the title compound as white foam (42% yield). $^1$H NMR (400 MHz, DMSO-d6) δ 10.30 (s, 1H), 7.81 (d, J=8.6 Hz, 2H), 7.64 (dd, J=7.6, 1.8 Hz, 1H), 7.50 (ddd, J=7.8, 7.8, 1.8 Hz, 1H), (d, J=8.6 Hz, 2H), 7.18 (m, 1H), 7.06 (dd, J=7.6 Hz, 1H), 4.11 (t, J=6.2 Hz, 2H), 3.93 (m, 2H), 3.78 (m, 2H), 3.54 (m, 2H), 3.47 (s, 3H), 3.33 (m, 2H), 3.11 (s, 3H), 1.76 (m, 2H), 1.41 (m, 2H), 1.32-1.14 (m, 14H), 0.82 (t, J=6.8 Hz, 3H); LCMS (m/z) 496.4 (M); RT (Method A, std LCMS method), 3.57 min.

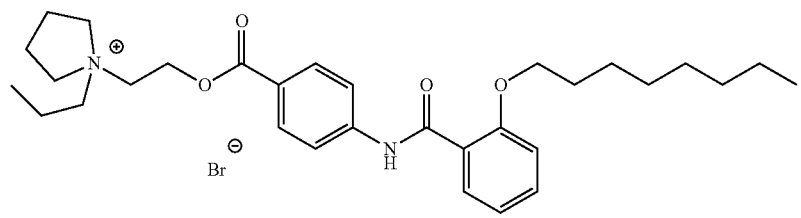 [SMILES: CCCCCCCCOc1ccccc1C(=O)Nc1ccc(C(=O)OCC[N+]2(CCC)CCCC2)cc1 ; [Br-]]

Example 47

1-(2-((4-(2-(Octyloxy)benzamido)benzoyl)oxy)ethyl)-1-propylpyrrolidin-1-ium bromide (56). According to general procedure step F; the crude material was purified by Biotage flash chromatography (gradient elution, 0 to 20% 1M NH$_3$/MeOH in DCM) to obtain the title compound as white foam (48% yield). $^1$H NMR (400 MHz, DMSO-d6) δ 10.45 (s, 1H), 7.96 (d, J=8.6 Hz, 2H), 7.88 (d, J=8.4 Hz, 2H), 7.63 (dd, J=7.4, 1.8 Hz, 1H), 7.51 (dd, J=7.5, 7.5 Hz, 1H), 7.18 (d, J=8.2 Hz, 1H), 7.07 (dd, J=7.6, 7.6 Hz, 1H), 4.66 (m, 2H), 4.10 (t, J=6.2 Hz, 2H), 3.78 (m, 2H), 3.61 (m, 4H), 3.34 (m, 2H), 2.10 (m, 4H), 1.74 (m, 4H), 1.38 (m, 2H), 1.30-1.11 (m, 8H), 0.89 (t, J=7.2 Hz, 3H), 0.80 (t, J=6.8 Hz, 3H); LCMS (m/z) 510.4 (M+H); RT (Method A, std LCMS method), 3.76 min.

Example 48

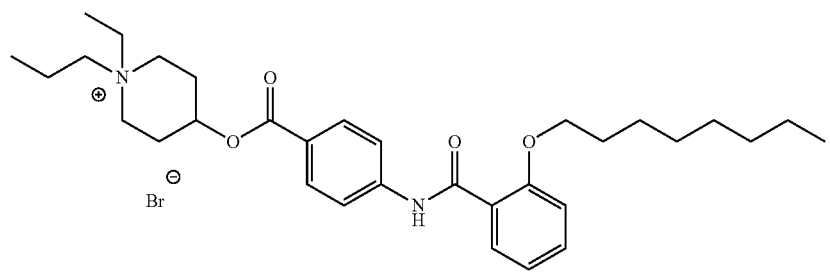 [SMILES: CCCCCCCCOc1ccccc1C(=O)Nc1ccc(C(=O)OC2CC[N+](CC)(CCC)CC2)cc1 ; [Br-]]

1-Ethyl-4-((4-(2-(octyloxy)benzamido)benzoyl)oxy)-1-propylpiperidin-1-ium bromide (57). According to general procedure step F; the crude material was purified by Biotage flash chromatography (gradient elution, 0 to 20% 1M $NH_3$/MeOH in DCM) to obtain the title compound as white foam (30% yield). $^1$H NMR (400 MHz, DMSO-d6) δ 10.43 (s, 1H), 8.05 (d, J=8.6 Hz, 2H), 7.87 (d, J=8.6 Hz, 2H), 7.63 (dd, J=7.6, 1.8 Hz, 1H), 7.50 (d, J=8.2, 8.2 Hz, 1H), 7.18 (d, J=8.4 Hz, 1H), 7.07 (dd, J=7.6, 7.6 Hz, 1H), 5.16 (m, 1H), 4.10 (t, J=6.2 Hz, 2H), 3.49 (m, 4H), 3.42 (m, 2H), 3.28 (m, 2H), 2.30 (m, 2H), 2.04 (m, 2H), 1.74 (m, 2H), 1.66 (m, 2H), 1.38 (m, 2H), 1.30-1.08 (m, 11H), 0.95 (t, J=6.8 Hz, 3H), 0.79 (t, J=6.8 Hz, 3H); LCMS (m/z) 523.4 (M); RT (Method A, std LCMS method), 3.57 min.

Example 49

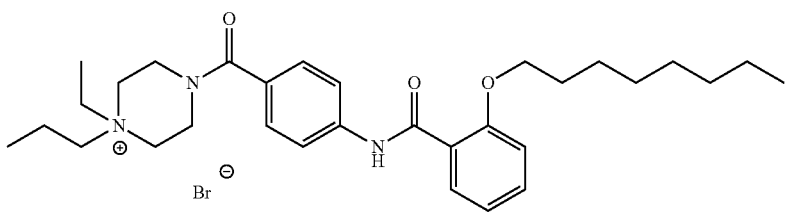 [SMILES: CCCCCCCCOc1ccccc1C(=O)Nc1ccc(C(=O)N2CC[N+](CC)(CCC)CC2)cc1 ; [Br-]]

1,1-Diethyl-4-(4-(2-(octyloxy)benzamido)benzoyl)piperazin-1-ium bromide (58). According to general procedure step F; the title compound was obtained as white powder through filtration (28% yield). $^1$H NMR (400 MHz, DMSO-d6) δ 10.28 (s, 1H), 7.79 (d, J=8.4 Hz, 2H), 7.64 (dd, J=7.4, 1.8 Hz, 1H), 7.50 (ddd, J=8.4, 8.4, 1.8 Hz, 1H), 7.44 (d, J=8.4 Hz, 2H), 7.18 (d, J=8.4 Hz, 1H), 7.06 (dd, J=7.5, 7.5 Hz, 1H), 4.11 (t, J=6.2 Hz, 2H), 3.77 (m, 2H), 3.42 (m, 2H), 3.22 (m, 2H), 3.09 (q, J=7.4 Hz, 4H), 3.04 (s, 2H), 1.75 (m, 2H), 1.41 (m, 2H), 1.32-1.14 (m, 14H), 0.94 (m, 2H), 0.81 (t, J=6.8 Hz, 3H); LCMS (m/z) 508.4 (M); RT (Method A, std LCMS method), 3.27 min.

Example 50

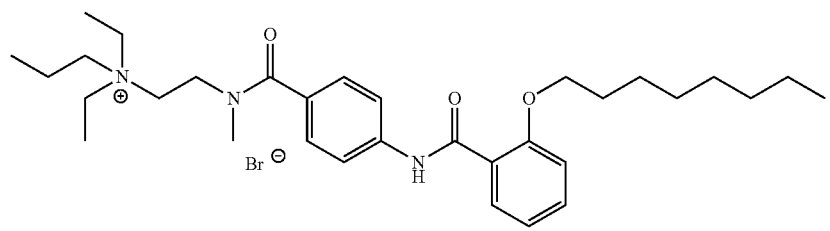 [SMILES: CCCCCCCCOc1ccccc1C(=O)Nc1ccc(C(=O)N(C)CC[N+](CC)(CC)CCC)cc1 ; [Br-]]

N,N-Diethyl-N-(2-(N-methyl-4-(2-(octyloxy)benzamido)benzamido)ethyl)propan-1-aminium bromide (59). According to general procedure step F; the crude material was purified by Biotage flash chromatography (gradient elution, 0 to 20% 1M NH$_3$/MeOH in DCM) to obtain the title compound as white foam (33% yield). $^1$H NMR (400 MHz, DMSO-d6) δ 10.30 (s, 1H), 7.82 (d, J=8.6 Hz, 2H), 7.65 (dd, J=7.6, 1.8 Hz, 1H), 7.50 (ddd, J=8.0, 8.0, 1.8 Hz, 1H), 7.46 (d, J=8.6 Hz, 2H), 7.19 (d, J=8.4 Hz, 1H), 7.07 (dd, J=7.4, 7.4 Hz, 1H), 4.11 (t, J=6.2 Hz, 2H), 3.85 (m, 4H), 3.48 (m, 7H), 3.35 (m, 2H), 1.77 (m, 2H), 1.65 (m, 2H), 1.41 (m, 2H), 1.31-1.15 (m, 14H), 0.94 (t, J=7.2 Hz, 3H), 0.82 (t, J=6.8 Hz, 3H); LCMS (m/z) 524.4 (M); RT (Method A, std LCMS method), 3.47 min.

Example 51

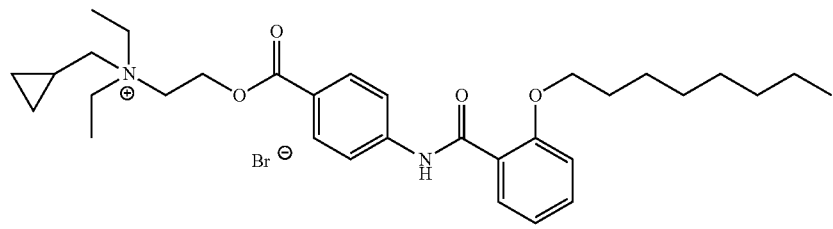 [SMILES: CCCCCCCCOc1ccccc1C(=O)Nc1ccc(C(=O)OCC[N+](CC)(CC)CC2CC2)cc1 ; [Br-]]

N-(Cyclopropylmethyl)-N,N-diethyl-2-((4-(2-(octyloxy)benzamido)benzoyl)oxy)-ethan-1-aminium bromide (60). According to general procedure step F; the crude material was purified by Biotage flash chromatography (gradient elution, 0 to 20% 1M NH$_3$/MeOH in DCM) to obtain the title compound as pale yellow solid (37% yield). $^1$H NMR (400 MHz, DMSO-d6) δ 10.45 (s, 1H), 7.96 (d, J=8.6 Hz, 2H), 7.88 (d, J=8.6 Hz, 2H), 7.63 (d, J=7.8 Hz, 1H), 7.51 (dd, J=7.8, 7.8 Hz, 1H), 7.18 (d, J=8.4 Hz, 1H), 7.07 (dd, J=7.4, 7.4 Hz, 1H), 4.68 (m, 2H), 4.10 (t, J=6.2 Hz, 2H), 3.79 (m, 2H), 3.49 (q, J=7.2 Hz, 4H), 3.17 (d, J=4.8 Hz, 2H), 1.74 (m, 2H), 1.39 (m, 2H), 1.30-1.10 (m, 15H), 0.80 (t, J=6.8 Hz, 3H), 0.70 (d, J=7.8 Hz, 2H), 0.44 (d, J=5.6 Hz, 2H); LCMS (m/z) 523.4 (M); RT (Method A, std LCMS method), 3.76 min.

Example 52

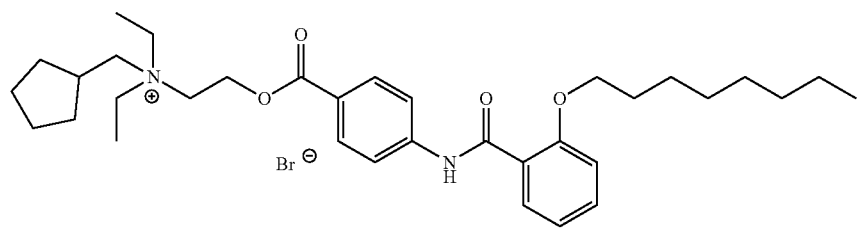 [SMILES: CCCCCCCCOc1ccccc1C(=O)Nc1ccc(C(=O)OCC[N+](CC)(CC)CC2CCCC2)cc1 ; [Br-]]

N-(Cyclopentylmethyl)-N,N-diethyl-2-((4-(2-(octyloxy) benzamido)benzoyl)oxy)-ethan-1-aminium bromide (61). According to general procedure step F; the crude material was purified by Biotage flash chromatography (gradient elution, 0 to 20% 1M NH$_3$/MeOH in DCM) to obtain the title compound as tan solid (37% yield). $^1$H NMR (400 MHz, DMSO-d6) δ 10.45 (s, 1H), 7.96 (d, J=8.6 Hz, 2H), 7.88 (d, J=8.6 Hz, 2H), 7.63 (dd, J=7.6, 1.8 Hz, 1H), 7.50 (dd, J=7.6, 7.6 Hz, 1H), 7.19 (d, J=8.4 Hz, 1H), 7.07 (d, J=7.6, 7.6 Hz, 1H), 4.66 (m, 2H), 4.10 (t, J=6.2 Hz, 2H), 3.75 (m, 2H), 3.48-3.43 (m, 6H), 2.25 (m, 1H), 1.93 (m, 2H), 1.74 (m, 2H), 1.64 (m, 2H), 1.52 (m, 2H), 1.39 (m, 2H), 1.30-1.10 (m, 16H), 0.80 (t, J=6.8 Hz, 3H); LCMS (m/z) 551.4 (M); RT (Method A, std LCMS method), 4.14 min.

Example 53

N-(Cyclohexylmethyl)-N,N-diethyl-2-((4-(2-(octyloxy) benzamido)benzoyl)oxy)-ethan-1-aminium bromide (62). According to general procedure step F; the crude material was purified by Biotage flash chromatography (gradient elution, 0 to 20% 1M NH$_3$/MeOH in DCM) to obtain the title compound as tan solid (20% yield). 1H NMR (400 MHz, DMSO-d6) δ 10.45 (s, 1H), 7.96 (d, J=8.8 Hz, 2H), 7.88 (d, J=8.8 Hz, 2H), 7.63 (dd, J=7.6, 1.8 Hz, 1H), 7.51 (ddd, J=8.0, 8.0, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.76 (m, 2H), 3.46 (q, J=7.2 Hz, 4H), 3.17 (d, J=5.2 Hz, 2H), 1.93 (m, 1H), 1.80-1.71 (m, 4H), 1.68-1.57 (m, 4H), 1.42-1.07 (m, 20H), 0.80 (t, J=6.8 Hz, 3H); LCMS (m/z) 565.5 (M); RT (Method A, std LCMS method), 4.04 min.

Example 54

N,N-Diethyl-3-methyl-N-(2-((4-(2-(octyloxy)benzamido)benzoyl)oxy)ethyl)butan-1-aminium bromide (63). According to general procedure step F; the crude material was purified by Biotage flash chromatography (gradient elution, 0 to 20% 1M $NH_3$/MeOH in DCM) to obtain the title compound as tan solid (36% yield). $^1$H NMR (400 MHz, DMSO-d6) δ 10.45 (s, 1H), 7.96 (d, J=8.6 Hz, 2H), 7.88 (d, J=8.6 Hz, 2H), 7.62 (dd, J=7.4, 1.8 Hz, 1H), 7.50 (dd, J=7.5, 7.5 Hz, 1H), 7.18 (d, J=8.4 Hz, 1H), 7.07 (dd, J=7.5, 7.5 Hz, 1H), 4.65 (m, 2H), 4.10 (t, J=6.2 Hz, 2H), 3.72 (m, 2H), 3.42 (q, J=7.2 Hz, 4H), 1.74 (m, 2H), 1.62-1.52 (m, 3H), 1.37 (m, 2H), 1.28-1.12 (m, 14H), 0.92 (d, J=6.0 Hz, 6H), 0.80 (t, J=6.8 Hz, 3H); LCMS (m/z) 539.4 (M); RT (Method A, std LCMS method), 3.68 min.

Example 55

N,N-Diethyl-N-(2-((4-(2-(pentyloxy)benzamido)benzoyl)oxy)ethyl)propan-1-aminium bromide (64). According to general procedure step F; the crude material was purified by Biotage flash chromatography (gradient elution, 0 to 20% 1M $NH_3$/MeOH in DCM) to obtain the title compound as white solid (30% yield). $^1$H NMR (400 MHz, DMSO-d6) δ 10.46 (s, 1H), 7.96 (d, J=8.8 Hz, 2H), 7.89 (d, J=8.8 Hz, 2H), 7.62 (dd, J=7.6, 1.8 Hz, 1H), 7.51 (ddd, J=7.6, 7.6, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.73 (m, 2H), 3.41 (q, J=7.2 Hz, 4H), 3.26 (m, 2H), 1.75 (m, 2H), 1.68 (m, 2H), 1.37 (m, 2H), 1.32-1.22 (m, 8H), 0.90 (t, J=7.2 Hz, 3H), 0.78 (t, J=7.2 Hz, 3H); LCMS (m/z) 469.4 (M); RT (Method A, std LCMS method), 3.27 min.

Example 56

N,N-Diethyl-N-(2-((4-(2-(pentyloxy)benzamido)benzoyl)oxy)ethyl)pentan-1-aminium bromide (65). According to general procedure step F; the crude material was purified by Biotage flash chromatography (gradient elution, 0 to 20% 1M $NH_3$/MeOH in DCM) to obtain the title compound as white solid (28% yield). $^1$H NMR (400 MHz, DMSO-d6) δ 10.47 (s, 1H), 7.96 (d, J=8.8 Hz, 2H), 7.89 (d, J=8.8 Hz, 2H), 7.62 (dd, J=7.6, 1.8 Hz, 1H), 7.51 (ddd, J=7.8, 7.8, 1.8 Hz, 1H), 7.18 (d, J=8.4 Hz, 1H), 7.07 (dd, J=7.2, 7.2 Hz, 1H), 4.65 (m, 2H), 4.10 (t, J=6.2 Hz, 2H), 3.72 (m, 2H), 3.41 (q, J=7.2 Hz, 4H), 3.28 (m, 2H), 1.75 (m, 2H), 1.64 (m, 2H), 1.42-1.21 (m, 14H), 0.86 (t, J=7.2 Hz, 3H), 0.78 (t, J=7.2 Hz, 3H); LCMS (m/z) 497.4 (M); RT (Method A, std LCMS method), 3.47 min.

Example 57

N,N-Diethyl-N-(2-((4-(2-(hexyloxy)benzamido)benzoyl)oxy)ethyl)propan-1-aminium bromide (66). According to general procedure step F; the crude material was purified by Biotage flash chromatography (gradient elution, 0 to 20%

1M NH₃/MeOH in DCM) to obtain the title compound as white solid (33% yield). ¹H NMR (400 MHz, DMSO-d6) δ 10.46 (s, 1H), 7.96 (d, J=8.8 Hz, 2H), 7.88 (d, J=8.8 Hz, 2H), 7.62 (dd, J=7.6, 1.8 Hz, 1H), 7.51 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.72 (m, 2H), 3.41 (q, J=7.2 Hz, 4H), 3.26 (m, 2H), 1.75 (m, 2H), 1.66 (m, 2H), 1.39 (m, 2H), 1.28-1.16 (m, 10H), 0.90 (t, J=7.2 Hz, 3H), 0.77 (t, J=7.2 Hz, 3H); LCMS (m/z) 483.4 (M); RT (Method A, std LCMS method), 3.55 min.

Example 58

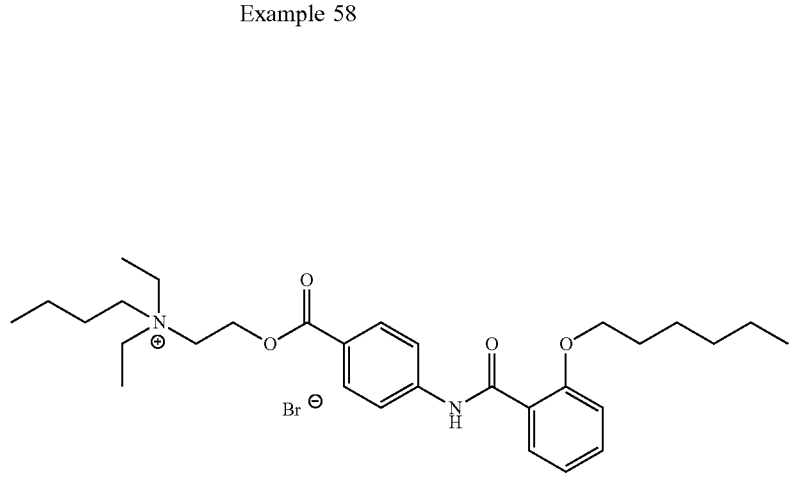

N,N-Diethyl-N-(2-((4-(2-(hexyloxy)benzamido)benzoyl)oxy)ethyl)butan-1-aminium bromide (67). According to general procedure step F; the crude material was purified by Biotage flash chromatography (gradient elution, 0 to 20% 1M NH₃/MeOH in DCM) to obtain the title compound as white solid (30% yield). ¹H NMR (400 MHz, DMSO-d6) δ 10.46 (s, 1H), 7.95 (d, J=8.8 Hz, 2H), 7.88 (d, J=8.8 Hz, 2H), 7.63 (dd, J=7.6, 1.8 Hz, 1H), 7.51 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.73 (m, 2H), 3.42 (q, J=7.2 Hz, 4H), 3.29 (m, 2H), 1.74 (m, 2H), 1.63 (m, 2H), 1.39 (m, 2H), 1.34-1.15 (m, 12H), 0.92 (t, J=7.2 Hz, 3H), 0.77 (t, J=7.2 Hz, 3H); LCMS (m/z) 498.4 (M+H); RT (Method A, std LCMS method), 3.57 min.

Example 59

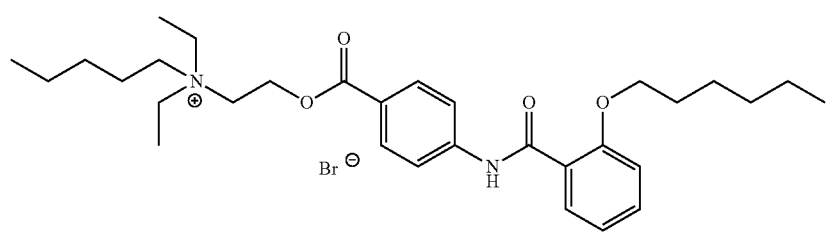 [SMILES: CCCCCCOc1ccccc1C(=O)Nc1ccc(C(=O)OCC[N+](CC)(CC)CCCCC)cc1 ; [Br-]]

N,N-Diethyl-N-(2-((4-(2-(hexyloxy)benzamido)benzoyl)oxy)ethyl)pentan-1-aminium bromide (68). According to general procedure step F; the crude material was purified by Biotage flash chromatography (gradient elution, 0 to 20% 1M NH$_3$/MeOH in DCM) to obtain the title compound as white solid (28% yield). $^1$H NMR (400 MHz, DMSO-d6) δ 10.46 (s, 1H), 7.95 (d, J=8.8 Hz, 2H), 7.88 (d, J=8.8 Hz, 2H), 7.62 (dd, J=7.6, 1.8 Hz, 1H), 7.51 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.73 (m, 2H), 3.42 (q, J=7.2 Hz, 4H), 3.28 (m, 2H), 1.74 (m, 2H), 1.64 (m, 2H), 1.39 (m, 2H), 1.35-1.16 (m, 14H), 0.87 (t, J=7.2 Hz, 3H), 0.77 (t, J=7.2 Hz, 3H); LCMS (m/z) 511.4 (M); RT (Method A, std LCMS method), 3.61 min.

Example 60

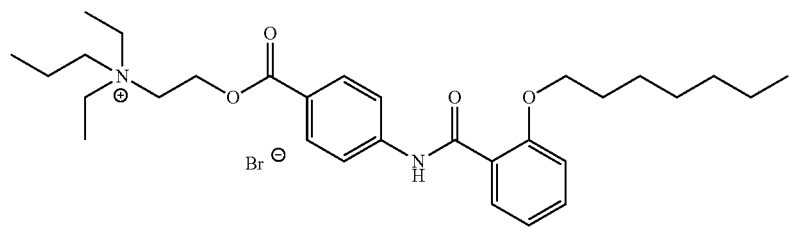 [SMILES: CCCCCCCOc1ccccc1C(=O)Nc1ccc(C(=O)OCC[N+](CC)(CC)CCC)cc1 ; [Br-]]

N,N-Diethyl-N-(2-((4-(2-(heptyloxy)benzamido)benzoyl)oxy)ethyl)propan-1-aminium bromide (69). According to general procedure step F; the crude material was purified by Biotage flash chromatography (gradient elution, 0 to 20% 1M NH$_3$/MeOH in DCM) to obtain the title compound as white solid (30% yield). $^1$H NMR (400 MHz, DMSO-d6) δ 10.46 (s, 1H), 7.96 (d, J=8.8 Hz, 2H), 7.88 (d, J=8.8 Hz, 2H), 7.62 (dd, J=7.8, 1.8 Hz, 1H), 7.51 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.72 (m, 2H), 3.41 (q, J=7.2 Hz, 4H), 3.27 (m, 2H), 1.73 (m, 2H), 1.67 (m, 2H), 1.38 (m, 2H), 1.29-1.12 (m, 12H), 0.90 (t, J=7.2 Hz, 3H), 0.78 (t, J=6.8 Hz, 3H); LCMS (m/z) 497.4 (M); RT (Method A, std LCMS method), 3.72 min.

Example 61

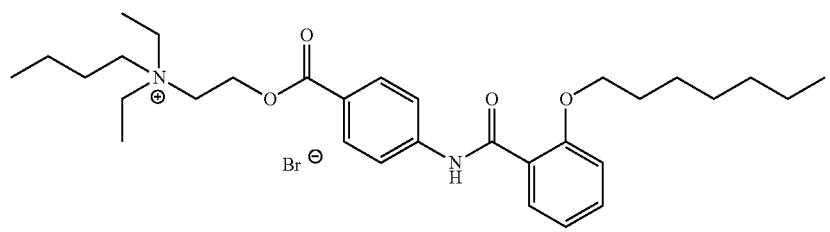 [SMILES: CCCCCCCOc1ccccc1C(=O)Nc1ccc(C(=O)OCC[N+](CC)(CC)CCCC)cc1 ; [Br-]]

N,N-Diethyl-N-(2-((4-(2-(heptyloxy)benzamido)benzoyl)oxy)ethyl)butan-1-aminium bromide (70). According to general procedure step F; the crude material was purified by Biotage flash chromatography (gradient elution, 0 to 20% 1M NH$_3$/MeOH in DCM) to obtain the title compound as white solid (30% yield). $^1$H NMR (400 MHz, DMSO-d6) δ 10.45 (s, 1H), 7.95 (d, J=8.8 Hz, 2H), 7.88 (d, J=8.8 Hz, 2H), 7.62 (dd, J=7.8, 1.8 Hz, 1H), 7.50 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.72 (m, 2H), 3.42 (q, J=7.2 Hz, 3H), 3.27 (m, 2H), 1.74 (m, 2H), 1.63 (m, 2H), 1.38 (m, 2H), 1.34-1.12 (m, 14H), 0.92 (t, J=7.2 Hz, 3H), 0.78 (t, J=6.8 Hz, 3H); LCMS (m/z) 512.4 (M+H); RT (Method A, std LCMS method), 3.68 min.

Example 62

N,N-Diethyl-N-(2-((4-(2-(heptyloxy)benzamido)benzoyl)oxy)ethyl)pentan-1-aminium bromide (71). According to general procedure step F; the crude material was purified by Biotage flash chromatography (gradient elution, 0 to 20% 1M NH$_3$/MeOH in DCM) to obtain the title compound as white solid (40% yield). $^1$H NMR (400 MHz, DMSO-d6) δ 10.46 (s, 1H), 7.95 (d, J=8.8 Hz, 2H), 7.88 (d, J=8.8 Hz, 2H), 7.62 (dd, J=7.8, 1.8 Hz, 1H), 7.50 (ddd, J=7.4, 7.4, 1.8 Hz, 1H), 7.18 (d, J=8.4 Hz, 1H), 7.07 (dd, J=7.6, 7.6 Hz, 1H), 4.65 (m, 2H), 4.10 (t, J=6.2 Hz, 2H), 3.72 (m, 2H), 3.41 (q, J=7.2 Hz, 4H), 3.27 (m, 2H), 1.74 (m, 2H), 1.64 (m, 2H), 1.42-1.10 (m, 18H), 0.86 (t, J=7.2 Hz, 3H), 0.78 (t, J=7.2 Hz, 3H); LCMS (m/z) 526.4 (M+H); RT (Method A, std LCMS method), 3.80 min.

Example 63

1-Methyl-4-(4-(2-(octyloxy)benzamido)benzamido)-1-propylpiperidin-1-ium bromide (72). According to general procedure step F; the crude material was purified by Biotage flash chromatography (gradient elution, 0 to 25% 3M NH$_3$/MeOH in DCM) to obtain the title compound as white solid (20% yield). $^1$H NMR (400 MHz, DMSO-d6) δ 10.31 (s, 1H), 8.28 (m, 1H), 7.86 (d, J=8.8 Hz, 2H), 7.80 (d, J=8.8 Hz, 2H), 7.65 (dd, J=7.6, 1.8 Hz, 1H), 7.50 (ddd, J=7.4, 7.4, 1.8 Hz, 1H), 7.18 (d, J=8.4 Hz, 1H), 7.07 (dd, J=7.6, 7.6 Hz, 1H), 4.11 (t, J=6.2 Hz, 2H), 4.10 (m, 1H), 3.50 (m, 2H), 3.44 (m, 2H), 3.30 (m, 2H), 3.04 (s, 3H), 2.01 (m, 4H), 1.76 (m, 4H), 1.39 (m, 2H), 1.30-1.12 (m, 8H), 0.93 (t, J=7.2 Hz, 3H), 0.80 (t, J=6.8 Hz, 3H); LCMS (m/z) 508.4 (M); RT (Method A, std LCMS method), 3.51 min.

Example 64

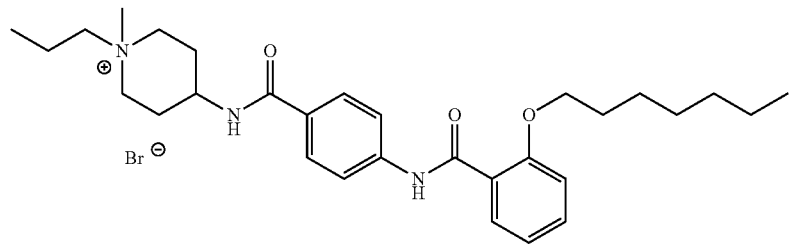 [SMILES: CCCCCCCOc1ccccc1C(=O)Nc1ccc(C(=O)NC2CC[N+](C)(CCC)CC2)cc1 ; [Br-]]

4-(4-(2-(Heptyloxy)benzamido)benzamido)-1-methyl-1-propylpiperidin-1-ium bromide (73). According to general procedure step F; the crude material was purified by Biotage flash chromatography (gradient elution, 0 to 25% 3M NH$_3$/MeOH in DCM) to obtain the title compound as white solid (56% yield). $^1$H NMR (400 MHz, DMSO-d6) δ 10.31 (s, 1H), 8.29 (d, J=8.2 Hz, 1H), 7.86 (d, J=8.8 Hz, 2H), 7.80 (d, J=8.8 Hz, 2H), 7.65 (dd, J=7.6, 1.8 Hz, 1H), 7.50 (ddd, J=7.6, 7.6, 1.8 Hz, 1H), 7.18 (d, J=8.4 Hz, 1H), 7.07 (dd, J=7.6, 7.6 Hz, 1H), 4.11 (t, J=6.2 Hz, 2H), 4.10 (m, 1H), 3.50 (m, 2H), 3.44 (m, 2H), 3.30 (m, 2H), 3.03 (s, 3H), 2.02 (m, 4H), 1.76 (m, 4H), 1.39 (m, 2H), 1.26 (m, 2H), 1.22-1.10 (m, 4H), 0.93 (t, J=7.2 Hz, 3H), 0.79 (t, J=6.8 Hz, 3H); LCMS (m/z) 494.4 (M); RT (Method A, std LCMS method), 3.17 min.

Example 65

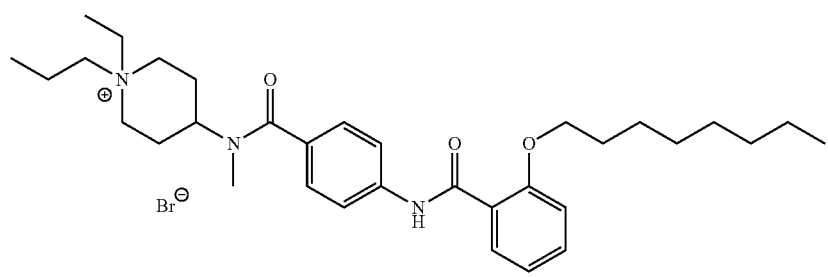 [SMILES: CCCCCCCCOc1ccccc1C(=O)Nc1ccc(C(=O)N(C)C2CC[N+](CC)(CCC)CC2)cc1 ; [Br-]]

1-Ethyl-4-(N-methyl-4-(2-(octyloxy)benzamido)benzamido)-1-propylpiperidin-1-ium bromide (74). According to general procedure step F; the crude material was purified by Biotage flash chromatography (gradient elution, 0 to 25% 3M $NH_3$/MeOH in DCM) to obtain the title compound as white solid (44% yield). $^1$H NMR (400 MHz, DMSO-d6) δ 10.27 (s, 1H), 7.78 (d, J=8.4 Hz, 2H), 7.64 (dd, J=8.4, 1.8 Hz, 1H), 7.50 (ddd, J=7.6, 7.6, 1.8 Hz, 1H), 7.41 (d, J=8.4 Hz, 2H), 7.18 (d, J=8.4 Hz, 1H), 7.06 (dd, J=7.6, 7.6 Hz, 1H), 4.11 (t, J=6.2 Hz, 2H), 4.10 (m, 1H), 3.62-3.45 (m, 4H), 3.40 (m, 2H), 3.16 (m, 2H), 2.93 (d, J=7.4 Hz, 3H), 2.22 (m, 2H), 1.85-1.73 (m, 4H), 1.61 (m, 2H), 1.41 (m, 2H), 1.32-1.13 (m, 11H), 0.97 (t, J=7.2 Hz, 1H), 0.90 (m, 2H), 0.82 (t, J=6.8 Hz, 3H); LCMS (m/z) 536.4 (M); RT (Method A, std LCMS method), 3.55 min.

Example 66

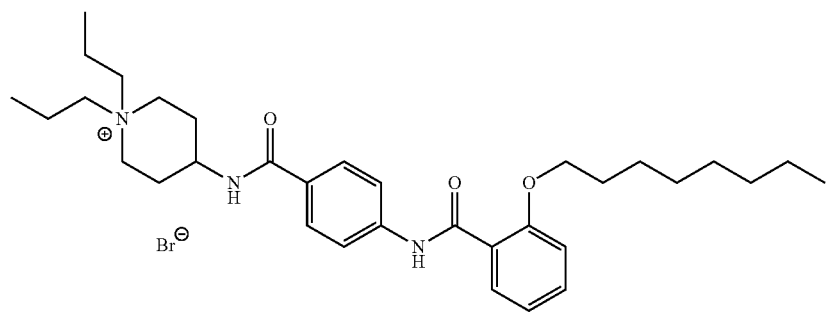 [SMILES: CCCCCCCCOc1ccccc1C(=O)Nc1ccc(C(=O)NC2CC[N+](CCC)(CCC)CC2)cc1 ; [Br-]]

4-(4-(2-(Octyloxy)benzamido)benzamido)-1,1-dipropylpiperidin-1-ium bromide (75). According to general procedure step F; the crude material was purified by Biotage flash chromatography (gradient elution, 0 to 25% 3M $NH_3$/MeOH in DCM) to obtain the title compound as white solid (44% yield). $^1$H NMR (400 MHz, DMSO-d6) δ 10.31 (s, 1H), 8.21 (m, 1H), 7.85 (d, J=8.8 Hz, 2H), 7.81 (d, J=8.8 Hz, 2H), 7.65 (dd, J=7.6, 1.8 Hz, 1H), 7.50 (ddd, J=7.6, 7.6, 1.8 Hz, 1H), 7.18 (d, J=8.4 Hz, 1H), 7.07 (dd, J=7.6, 7.6 Hz, 1H), 4.14 (m, 1H), 4.11 (t, J=6.2 Hz, 2H), 3.55 (m, 2H), 3.40 (m, 2H), 3.28 (m, 2H), 3.22 (m, 2H), 1.99 (m, 4H), 1.76 (m, 2H), 1.66 (m, 4H), 1.40 (m, 2H), 1.30-1.12 (m, 8H), 0.97 (t, J=7.2 Hz, 3H), 0.92 (t, J=7.2 Hz, 3H), 0.80 (t, J=6.8 Hz, 3H); LCMS (m/z) 536.4 (M); RT (Method A, std LCMS method), 3.58 min.

Example 67

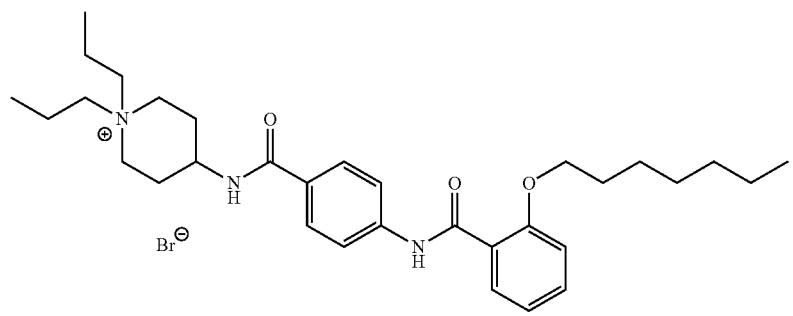 [SMILES: CCCCCCCOc1ccccc1C(=O)Nc1ccc(C(=O)NC2CC[N+](CCC)(CCC)CC2)cc1 ; [Br-]]

4-(4-(2-(Heptyloxy)benzamido)benzamido)-1,1-dipropylpiperidin-1-ium bromide (76). According to general procedure step F; the crude material was purified by Biotage flash chromatography (gradient elution, 0 to 25% 3M NH$_3$/MeOH in DCM) to obtain the title compound as white solid (36% yield). $^1$H NMR (400 MHz, DMSO-d6) δ 10.32 (s, 1H), 8.20 (d, J=8.0 Hz, 1H), 7.85 (d, J=8.8 Hz, 2H), 7.81 (d, J=8.8 Hz, 2H), 7.65 (dd, J=7.6, 1.8 Hz, 11H), 7.50 (ddd, J=7.6, 7.6, 1.8 Hz, 1H), 7.18 (d, J=8.4 Hz, 1H), 7.07 (dd, J=7.6, 7.6 Hz, 1H), 4.11 (m, 1H), 4.11 (t, J=6.2 Hz, 2H), 3.55 (m, 2H), 3.40 (m, 2H), 3.28 (m, 2H), 3.22 (m, 2H), 1.99 (m, 4H), 1.76 (m, 2H), 1.66 (m, 4H), 1.39 (m, 2H), 1.27 (m, 2H), 1.15 (m, 4H), 0.97 (t, J=7.2 Hz, 3H), 0.92 (d, J=7.2 Hz, 3H), 0.79 (t, J=6.8 Hz, 3H); LCMS (m/z) 522.4 (M); RT (Method A, std LCMS method), 3.66 min.

Example 68

N,N-Diethyl-2-(4-(2-(heptyloxy)benzamido)benzamido)-N-methylethan-1-aminium bromide (77). According to general procedure step F; the crude material was purified by Biotage flash chromatography (gradient elution, 0 to 25% 3M NH$_3$/MeOH in DCM) to obtain the title compound as white solid (18% yield). $^1$H NMR (400 MHz, DMSO-d6) δ 10.33 (s, 1H), 8.86 (t, J=5.7 Hz, 1H), 7.88 (d, J=8.6 Hz, 2H), 7.81 (d, J=8.6 Hz, 2H), 7.64 (dd, J=7.6, 1.8 Hz, 1H), 7.50 (ddd, J=7.6, 7.6, 1.8 Hz, 1H), 7.18 (d, J=8.4 Hz, 1H), 7.07 (dd, J=7.6, 7.6 Hz, 1H), 4.11 (t, J=6.2 Hz, 2H), 3.63 (m, 2H), 3.40 (q, J=7.2 Hz, 4H), 3.37 (m, 2H), 3.01 (s, 3H), 1.75 (m, 2H), 1.39 (m, 2H), 1.26 (t, J=7.2 Hz, 8H), 1.17 (m, 4H), 0.79 (t, J=6.8 Hz, 3H); LCMS (m/z) 468.4 (M); RT (Method A, std LCMS method), 2.95 min.

Example 69

N,N-Diethyl-N-methyl-2-((4-(2-(octyloxy)benzamido)phenyl)sulfonamido)ethan-1-aminium bromide (78). According to general procedure step F; the title compound was obtained as white powder through filtration (80% yield). $^1$H NMR (400 MHz, DMSO-d6) δ 10.47 (s, 1H), 7.96 (m, 1H), 7.94 (d, J=8.8 Hz, 2H), 7.81 (d, J=8.5 Hz, 2H), 7.62 (dd, J=7.6, 1.8 Hz, 1H), 7.51 (dd, J=7.8, 7.8 Hz, 1H), 7.19 (d, J=8.4 Hz, 1H), 7.07 (dd, J=7.6, 7.6 Hz, 1H), 4.10 (t, J=6.2 Hz, 2H), 3.35-3.30 (m, 6H), 3.15 (m, 2H), 2.95 (s, 3H), 1.75 (m, 2H), 1.39 (m, 2H), 1.29-1.15 (m, 14H), 0.82 (t, J=6.8 Hz, 3H); LCMS (m/z) 518.5 (M); RT (Method B, std LCMS method), 0.76 min.

Example 70

N,N-Diethyl-2-((4-(2-(heptyloxy)benzamido)phenyl)sulfonamido)-N-methylethan-1-aminium bromide (79). According to general procedure step F; the crude material was purified by Biotage flash chromatography (gradient elution, 0 to 25% 3M NH$_3$/MeOH in DCM) to obtain the title compound as white solid (42% yield). ¹H NMR (400 MHz, DMSO-d6) δ 10.48 (s, 1H), 7.94 (m, 1H), 7.93 (d, J=8.8 Hz, 2H), 7.81 (d, J=8.8 Hz, 2H), 7.62 (dd, J=7.6, 1.8 Hz, 1H), 7.51 (dd, J=7.8, 7.8 Hz, 1H), 7.19 (d, J=8.4 Hz, 1H), 7.07 (dd, J=7.6, 7.6 Hz, 1H), 4.10 (t, J=6.2 Hz, 2H), 3.32 (br, 6H), 3.15 (m, 2H), 2.95 (s, 3H), 1.74 (m, 2H), 1.38 (m, 2H), 1.32-1.13 (m, 12H), 0.80 (t, J=6.8 Hz, 3H); LCMS (m/z) 504.3 (M); RT (Method A, std LCMS method), 3.21 min.

Example 71

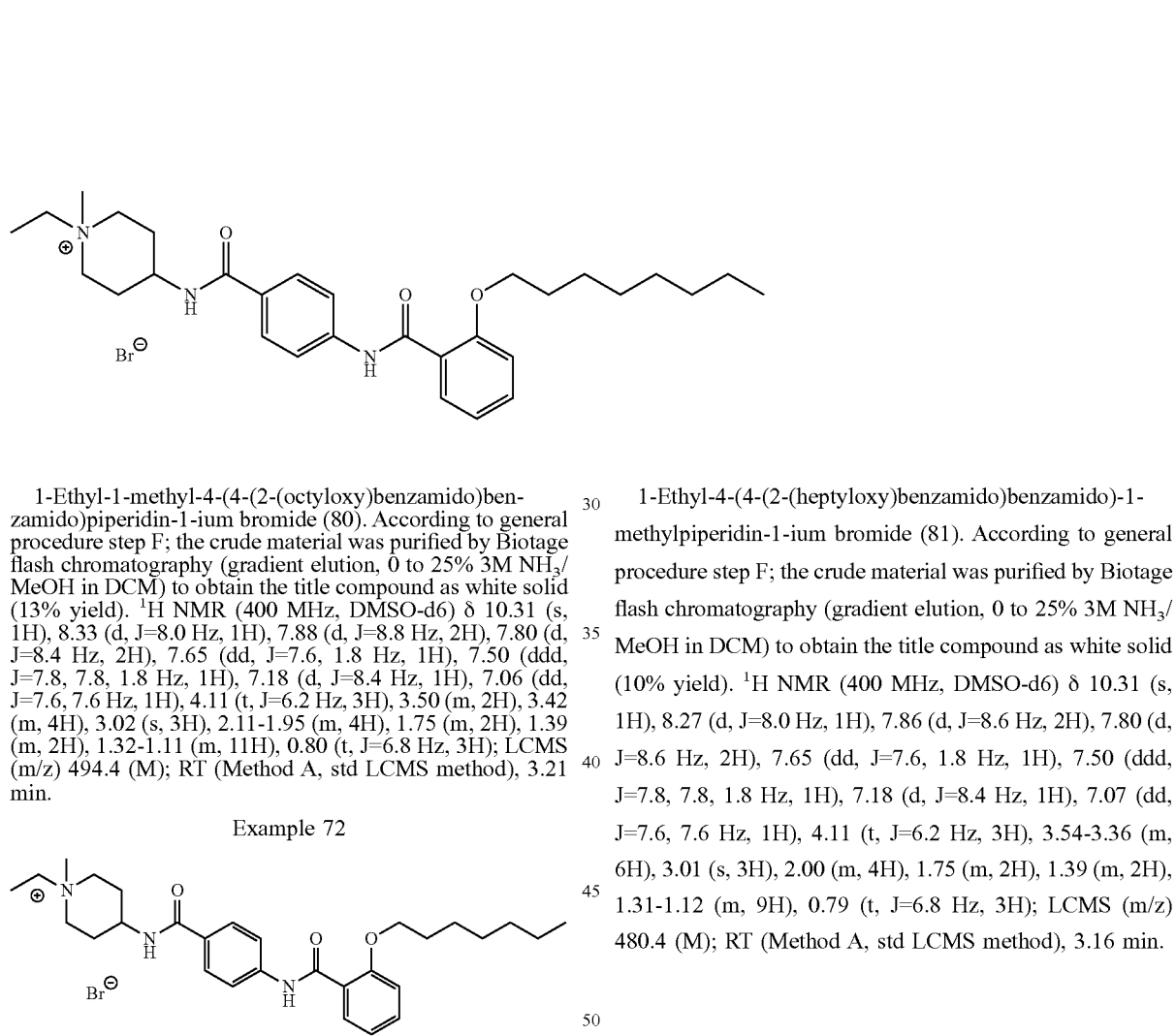

1-Ethyl-1-methyl-4-(4-(2-(octyloxy)benzamido)benzamido)piperidin-1-ium bromide (80). According to general procedure step F; the crude material was purified by Biotage flash chromatography (gradient elution, 0 to 25% 3M NH₃/MeOH in DCM) to obtain the title compound as white solid (13% yield). ¹H NMR (400 MHz, DMSO-d6) δ 10.31 (s, 1H), 8.33 (d, J=8.0 Hz, 1H), 7.88 (d, J=8.8 Hz, 2H), 7.80 (d, J=8.4 Hz, 2H), 7.65 (dd, J=7.6, 1.8 Hz, 1H), 7.50 (ddd, J=7.8, 7.8, 1.8 Hz, 1H), 7.18 (d, J=8.4 Hz, 1H), 7.06 (dd, J=7.6, 7.6 Hz, 1H), 4.11 (t, J=6.2 Hz, 3H), 3.50 (m, 2H), 3.42 (m, 4H), 3.02 (s, 3H), 2.11-1.95 (m, 4H), 1.75 (m, 2H), 1.39 (m, 2H), 1.32-1.11 (m, 11H), 0.80 (t, J=6.8 Hz, 3H); LCMS (m/z) 494.4 (M); RT (Method A, std LCMS method), 3.21 min.

Example 72

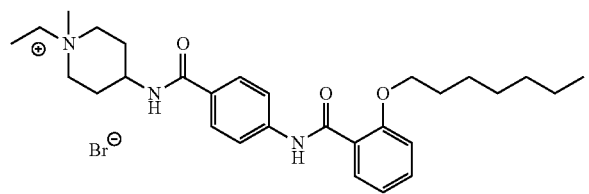

1-Ethyl-4-(4-(2-(heptyloxy)benzamido)benzamido)-1-methylpiperidin-1-ium bromide (81). According to general procedure step F; the crude material was purified by Biotage flash chromatography (gradient elution, 0 to 25% 3M NH₃/MeOH in DCM) to obtain the title compound as white solid (10% yield). ¹H NMR (400 MHz, DMSO-d6) δ 10.31 (s, 1H), 8.27 (d, J=8.0 Hz, 1H), 7.86 (d, J=8.6 Hz, 2H), 7.80 (d, J=8.6 Hz, 2H), 7.65 (dd, J=7.6, 1.8 Hz, 1H), 7.50 (ddd, J=7.8, 7.8, 1.8 Hz, 1H), 7.18 (d, J=8.4 Hz, 1H), 7.07 (dd, J=7.6, 7.6 Hz, 1H), 4.11 (t, J=6.2 Hz, 3H), 3.54-3.36 (m, 6H), 3.01 (s, 3H), 2.00 (m, 4H), 1.75 (m, 2H), 1.39 (m, 2H), 1.31-1.12 (m, 9H), 0.79 (t, J=6.8 Hz, 3H); LCMS (m/z) 480.4 (M); RT (Method A, std LCMS method), 3.16 min.

Example 73

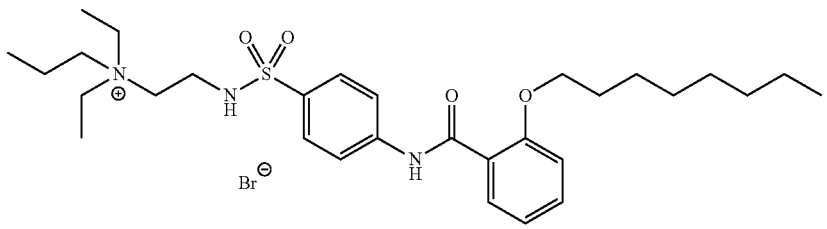 [SMILES: CCCCCCCCOc1ccccc1C(=O)Nc1ccc(S(=O)(=O)NCC[N+](CC)(CC)CCC)cc1 ; [Br-]]

N,N-Diethyl-N-(2-((4-(2-(octyloxy)benzamido)phenyl)sulfonamido)ethyl)propan-1-aminium bromide (82). According to general procedure step F; the crude material was purified by Biotage flash chromatography (gradient elution, 0 to 25% 3M NH₃/MeOH in DCM) to obtain the title compound as white solid (35% yield). ¹H NMR (400 MHz, DMSO-d6) δ 10.47 (s, 1H), 7.97 (m, 1H), 7.94 (d, J=8.8 Hz, 2H), 7.81 (d, J=8.6 Hz, 2H), 7.62 (dd, J=7.6, 1.8 Hz, 1H), 7.51 (ddd, J=7.8, 7.8, 1.8 Hz, 1H), 7.19 (d, J=8.4 Hz, 1H), 7.07 (dd, J=7.6, 7.6 Hz, 1H), 4.10 (t, J=6.4 Hz, 2H), 3.31-3.26 (br, 6H), 3.14 (m, 4H), 1.75 (m, 2H), 1.60 (m, 2H), 1.39 (m, 2H), 1.30-1.14 (m, 14H), 0.90 (t, J=7.2 Hz, 3H), 0.82 (t, J=6.8 Hz, 3H); LCMS (m/z) 546.3 (M); RT (Method A, std LCMS method), 3.70 min.

Example 74

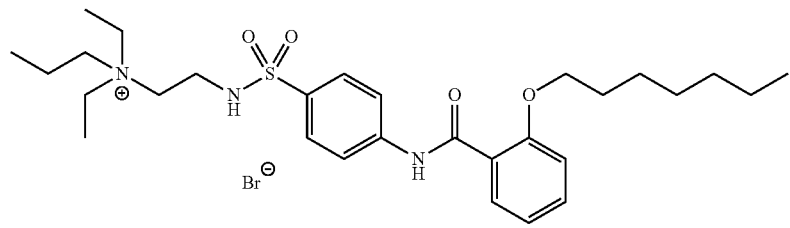 [SMILES: CCCCCCCOc1ccccc1C(=O)Nc1ccc(S(=O)(=O)NCC[N+](CC)(CC)CCC)cc1 ; [Br-]]

N,N-Diethyl-N-(2-((4-(2-(heptyloxy)benzamido)phenyl)sulfonamido)ethyl)propan-1-aminium bromide (83). According to general procedure step F; the title compound was obtained as white powder through filtration (82% yield). ¹H NMR (400 MHz, DMSO-d6) δ 10.48 (s, 1H), 7.94 (d, J=8.8 Hz, 2H), 7.81 (d, J=8.8 Hz, 2H), 7.62 (dd, J=7.6, 1.8 Hz, 1H), 7.51 (ddd, J=7.8, 7.8, 1.8 Hz, 1H), 7.26 (d, J=7.6 Hz, 1H), 7.18 (d, J=8.4 Hz, 1H), 7.07 (dd, J=7.6, 7.6 Hz, 1H), 4.10 (t, J=6.2 Hz, 2H), 3.31-3.24 (br, 6H), 3.14 (m, 4H), 1.74 (m, 2H), 1.60 (m, 2H), 1.39 (m, 2H), 1.30-1.14 (m, 12H), 0.90 (t, J=7.2 Hz, 3H), 0.80 (t, J=6.8 Hz, 3H); LCMS (m/z) 532.3 (M); RT (Method A, std LCMS method), 3.46 min.

Example 75

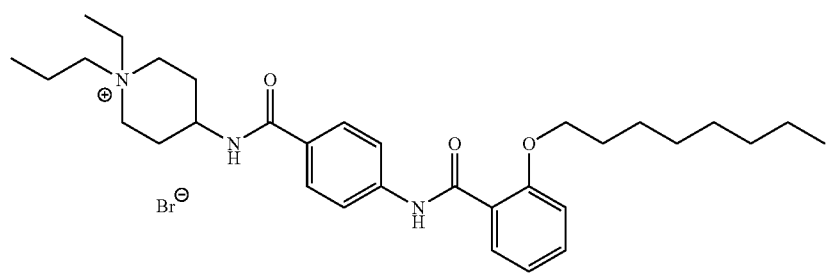 [SMILES: CCCCCCCCOc1ccccc1C(=O)Nc1ccc(C(=O)NC2CC[N+](CC)(CCC)CC2)cc1 ; [Br-]]

1-Ethyl-4-(4-(2-(octyloxy)benzamido)benzamido)-1-propylpiperidin-1-ium bromide (84). According to general procedure step F; the crude material was purified by Biotage flash chromatography (gradient elution, 0 to 25% 3M NH$_3$/MeOH in DCM) to obtain the title compound as white solid (35% yield). $^1$H NMR (400 MHz, DMSO-d6) δ 10.31 (s, 1H), 8.25 (m, 1H), 7.85 (d, J=8.8 Hz, 2H), 7.80 (d, J=8.8 Hz, 2H), 7.65 (dd, J=7.8, 1.8 Hz, 1H), 7.50 (ddd, J=7.8, 7.8, 1.8 Hz, 1H), 7.26 (d, J=7.6 Hz, 1H), 7.18 (d, J=8.4 Hz, 1H), 7.07 (dd, J=7.6, 7.6 Hz, 1H), 4.11 (t, J=6.2 Hz, 3H), 3.54 (m, 2H), 3.40 (m, 2H), 3.22 (m, 2H), 3.10 (m, 2H), 1.99 (m, 4H), 1.75 (m, 2H), 1.63 (m, 1H), 1.40 (m, 2H), 1.28-1.14 (m, 10H), 0.97 (t, J=7.2 Hz, 3H), 0.92 (q, J=7.2 Hz, 2H), 0.80 (t, J=6.8 Hz, 3H); LCMS (m/z) 522.4 (M); RT (Method A, std LCMS method), 3.44 min.

Example 76

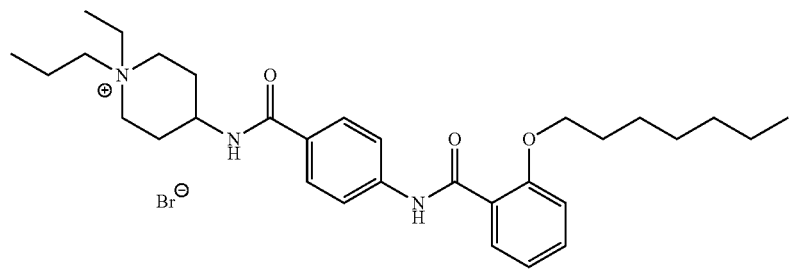 [SMILES: CCCCCCCOc1ccccc1C(=O)Nc1ccc(C(=O)NC2CC[N+](CC)(CCC)CC2)cc1 ; [Br-]]

1-Ethyl-4-(4-(2-(heptyloxy)benzamido)benzamido)-1-propylpiperidin-1-ium bromide (85). According to general procedure step F; the crude material was purified by Biotage flash chromatography (gradient elution, 0 to 25% 3M NH$_3$/MeOH in DCM) to obtain the title compound as white solid (13% yield). $^1$H NMR (400 MHz, DMSO-d6) δ 10.31 (s, 1H), 8.24 (m, 1H), 7.85 (dd, J=8.8, 2.8 Hz, 2H), 7.81 (d, J=7.8 Hz, 2H), 7.65 (dd, J=7.8, 1.8 Hz, 1H), 7.50 (ddd, J=7.8, 7.8, 1.8 Hz, 1H), 7.18 (d, J=8.4 Hz, 1H), 7.07 (dd, J=7.6, 7.6 Hz, 1H), 4.11 (t, J=6.2 Hz, 3H), 3.54 (m, 2H), 3.41 (m, 2H), 3.21 (m, 2H), 2.93 (m, 2H), 1.99 (m, 4H), 1.76 (m, 2H), 1.65 (m, 1H), 1.39 (m, 2H), 1.30-1.10 (m, 9H), 0.95 (m, 4H), 0.79 (t, J=6.8 Hz, 3H); LCMS (m/z) 508.4 (M); RT (Method A, std LCMS method), 3.31 min.

Example 77

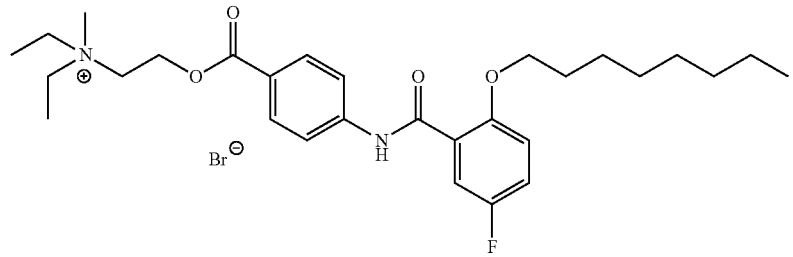 [SMILES: CCCCCCCCOc1ccc(F)cc1C(=O)Nc1ccc(C(=O)OCC[N+](C)(CC)CC)cc1 ; [Br-]]

N,N-Diethyl-2-((4-(5-fluoro-2-(octyloxy)benzamido)benzoyl)oxy)-N-methylethan-1-aminium bromide (86). According to general procedure step F; the crude material was purified by Biotage flash chromatography (gradient elution, 0 to 25% 3M NH$_3$/MeOH in DCM) to obtain the title compound as white solid (29% yield). $^1$H NMR (400 MHz, DMSO-d6) δ 10.53 (s, 1H), 7.97 (dd, J=8.8, 2.4 Hz, 2H), 7.88 (d, J=8.2 Hz, 2H), 7.43 (m, 1H), 7.36 (m, 1H), 7.21 (m, 1H), 4.67 (m, 2H), 4.07 (t, J=6.2 Hz, 2H), 3.73 (m, 2H), 3.44 (q, J=8.0 Hz, 4H), 3.06 (s, 3H), 1.71 (m, 2H), 1.36 (m, 2H), 1.28-1.14 (m, 14H), 0.80 (t, J=7.2 Hz, 3H); LCMS (m/z) 501.4 (M); RT (Method B, std LCMS method), 1.11 min.

Example 78

N,N-Diethyl-2-((4-(4-fluoro-2-(octyloxy)benzamido)benzoyl)oxy)-N-methylethan-1-aminium bromide (87). According to general procedure step F; the title compound was obtained as white powder through filtration (90% yield). $^1$H NMR (400 MHz, DMSO-d6) δ 10.40 (s, 1H), 7.97 (d, J=8.8 Hz, 2H), 7.87 (d, J=8.8 Hz, 2H), 7.68 (dd, J=8.6, 7.0 Hz, 1H), 7.11 (dd, J=11.5, 2.4 Hz, 1H), 6.90 (ddd, J=8.4, 8.4, 2.4 Hz, 1H), 4.67 (m, 2H), 4.11 (t, J=6.2 Hz, 2H), 3.74 (m, 2H), 3.45 (q, J=7.2 Hz, 4H), 3.06 (s, 3H), 1.74 (m, 2H), 1.38 (m, 2H), 1.30-1.08 (m, 14H), 0.80 (t, J=6.8 Hz, 3H); LCMS (m/z) 501.4 (M); RT (Method B, std LCMS method), 1.11 min.

Example 79

N,N-Diethyl-2-((4-(2-fluoro-6-(octyloxy)benzamido) benzoyl)oxy)-N-methylethan-1-aminium bromide (88). According to general procedure step F; the crude material was purified by Biotage flash chromatography (gradient elution, 0 to 25% 3M $NH_3$/MeOH in DCM) to obtain the title compound as white solid (29% yield). $^1$H NMR (400 MHz, DMSO-d6) δ 10.84 (s, 1H), 7.97 (d, J=8.8 Hz, 2H), 7.86 (d, J=8.8 Hz, 2H), 7.45 (q, J=8.0 Hz, 1H), 6.99 (d, J=8.4 Hz, 1H), 6.90 (dd, J=8.6, 8.6 Hz, 1H), 4.67 (m, 2H), 4.04 (t, J=6.2 Hz, 2H), 3.75 (m, 2H), 3.45 (q, J=7.2 Hz, 4H), 3.07 (s, 3H), 1.62 (m, 2H), 1.26 (q, J=7.2 Hz, 6H), 1.21-1.07 (m, 10H), 0.79 (t, J=7.2 Hz, 3H); LCMS (m/z) 501.4 (M); RT (Method B, std LCMS method), 1.06 min.

Example 80

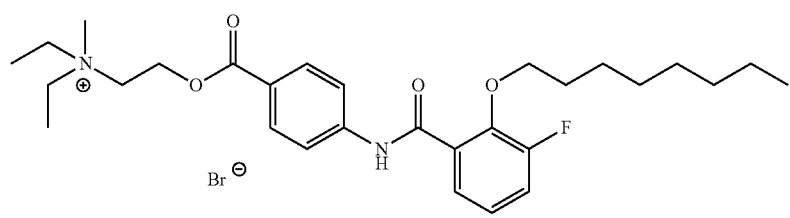 [SMILES: CCCCCCCCOc1c(F)cccc1C(=O)Nc1ccc(C(=O)OCC[N+](C)(CC)CC)cc1 ; [Br-]]

N,N-Diethyl-2-((4-(3-fluoro-2-(octyloxy)benzamido) benzoyl)oxy)-N-methylethan-1-aminium bromide (89). According to general procedure step F; the title compound was obtained as white powder through filtration (90% yield). $^1$H NMR (400 MHz, DMSO-d6) δ 10.69 (s, 1H), 7.98 (d, J=8.8 Hz, 2H), 7.89 (d, J=8.8 Hz, 2H), 7.44 (m, 1H), 7.35 (d, J=7.6 Hz, 1H), 7.22 (m, 1H), 4.66 (m, 2H), 4.07 (t, J=6.2 Hz, 2H), 3.74 (m, 2H), 3.45 (q, J=7.2 Hz, 4H), 3.06 (s, 3H), 1.60 (m, 2H), 1.27 (q, J=7.2 Hz, 6H), 1.19-1.05 (m, 10H), 0.79 (t, J=7.2 Hz, 3H); LCMS (m/z) 501.4 (M); RT (Method B, std LCMS method), 1.10 min.

Example 81

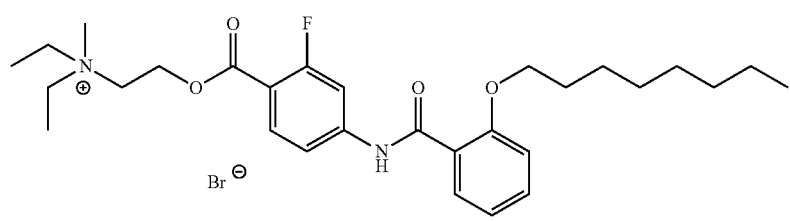 [SMILES: CCCCCCCCOc1ccccc1C(=O)Nc1ccc(C(=O)OCC[N+](C)(CC)CC)c(F)c1 ; [Br-]]

N,N-Diethyl-2-((2-fluoro-4-(2-(octyloxy)benzamido)benzoyl)oxy)-N-methylethan-1-aminium bromide (90). According to general procedure step F; the title compound was obtained as white powder through filtration (76% yield). $^1$H NMR (400 MHz, DMSO-d6) δ 10.61 (s, 1H), 7.93 (dd, J=8.6, 8.6 Hz, 1H), 7.81 (dd, J=13.8, 1.8 Hz, 1H), 7.60 (m, 2H), 7.51 (ddd, J=8.2, 8.2, 1.8 Hz, 1H), 7.18 (d, J=8.2 Hz, 1H), 7.07 (dd, J=7.4, 7.4 Hz, 1H), 4.68 (m, 2H), 4.09 (t, J=6.2 Hz, 2H), 3.73 (m, 2H), 3.44 (q, J=7.2 Hz, 4H), 3.05 (s, 3H), 1.72 (m, 2H), 1.37 (m, 2H), 1.28-1.12 (m, 14H), 0.80 (t, J=7.2 Hz, 3H); LCMS (m/z) 501.4 (M); RT (Method B, std LCMS method), 1.12 min.

Example 82

N,N-Diethyl-2-((3-fluoro-4-(2-(octyloxy)benzamido)benzoyl)oxy)-N-methylethan-1-aminium bromide (91). According to general procedure step F; the title compound was obtained as white powder through filtration (80% yield). $^1$H NMR (400 MHz, DMSO-d6) δ 10.53 (s, 1H), 8.62 (m, 1H), 8.02 (d, J=7.6 Hz, 1H), 7.86 (m, 2H), 7.60 (m, 1H), 7.30 (d, J=8.2 Hz, 1H), 7.15 (m, 1H), 4.69 (m, 2H), 4.24 (m, 2H), 3.75 (m, 2H), 3.45 (m, 4H), 3.07 (s, 3H), 1.89 (m, 2H), 1.42 (m, 2H), 1.34-1.14 (m, 14H), 0.81 (m, 3H); LCMS (m/z) 501.4 (M); RT (Method A, std LCMS method), 1.15 min.

Example 83

N,N-Diethyl-N-(2-((4-(2-(hexyloxy)benzamido)phenyl) sulfonamido)ethyl)pentan-1-aminium bromide (92). According to general procedure step F; the crude material was purified by Biotage flash chromatography (gradient elution, 0 to 25% 3M NH$_3$/MeOH in DCM) to obtain the title compound as white solid (20% yield). $^1$H NMR (400 MHz, DMSO-d6) δ 10.48 (s, 1H), 7.94 (d, J=8.6 Hz, 2H), 7.81 (d, J=8.6 Hz, 2H), 7.62 (d, J=8.0 Hz, 1H), 7.51 (dd, J=7.6, 7.6 Hz, 1H), 7.19 (d, J=8.4 Hz, 1H), 7.07 (dd, J=7.6, 7.6 Hz, 1H), 4.10 (t, J=6.0 Hz, 2H), 4.08 (m, 1H), 3.29 (m, 6H), 3.17 (m, 2H), 3.11 (m, 2H), 1.75 (m, 2H), 1.58 (m, 2H), 1.44-1.15 (m, 16H), 0.89 (t, J=7.2 Hz, 3H), 0.79 (t, J=6.8 Hz, 3H); LCMS (m/z) 546.5 (M); RT (Method B, std LCMS method), 0.76 min.

Example 84

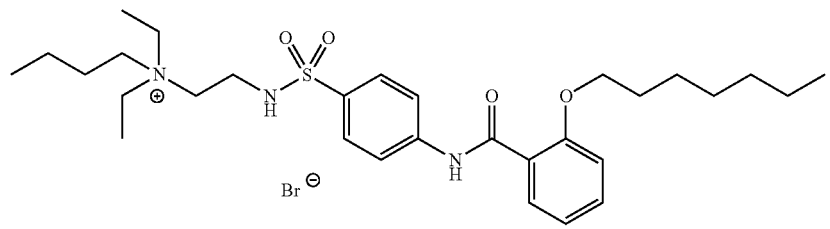 [SMILES: CCCCCCCOc1ccccc1C(=O)Nc1ccc(S(=O)(=O)NCC[N+](CC)(CC)CCCC)cc1 ; [Br-]]

N,N-Diethyl-N-(2-((4-(2-(heptyloxy)benzamido)phenyl) sulfonamido)ethyl)butan-1-aminium bromide (93). According to general procedure step F; the crude material was purified by Biotage flash chromatography (gradient elution, 0 to 20% 3M NH$_3$/MeOH in DCM) to obtain the title compound as white solid (33% yield). $^1$H NMR (400 MHz, DMSO-d6) δ 10.47 (s, 1H), 7.98 (br, 1H), 7.94 (d, J=8.8 Hz, 2H), 7.81 (d, J=8.8 Hz, 2H), 7.62 (dd, J=7.6, 1.8 Hz, 1H), 7.51 (ddd, J=7.6, 7.6, 1.8 Hz, 1H), 7.19 (d, J=8.4 Hz, 1H), 7.07 (dd, J=7.5, 7.5 Hz, 1H), 4.10 (t, J=6.2 Hz, 2H), 3.30-3.26 (m, 6H), 3.18 (m, 2H), 3.13 (m, 2H), 1.74 (m, 2H), 1.57 (m, 2H), 1.42-1.23 (m, 6H), 1.18 (m, 10H), 0.93 (t, J=7.2 Hz, 3H), 0.80 (t, J=6.8 Hz, 3H); LCMS (m/z) 546.5 (M); RT (Method B, std LCMS method), 0.77 min.

Example 85

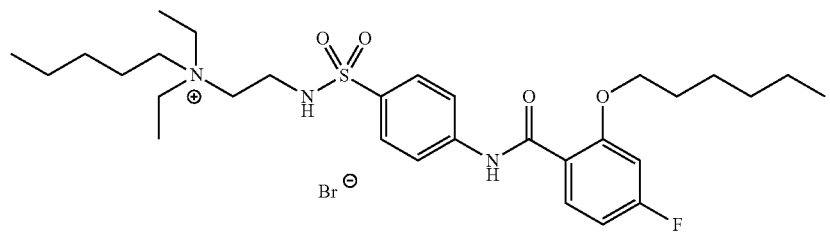 [SMILES: CCCCCCOc1cc(F)ccc1C(=O)Nc1ccc(S(=O)(=O)NCC[N+](CC)(CC)CCCCC)cc1 ; [Br-]]

N,N-Diethyl-N-(2-((4-(4-fluoro-2-(hexyloxy)benzamido)phenyl)sulfonamido)-ethyl)pentan-1-aminium bromide (94). According to general procedure step F; the crude material was purified by Biotage flash chromatography (gradient elution, 0 to 20% 3M NH₃/MeOH in DCM) to obtain the title compound as white solid (71% yield). ¹H NMR (400 MHz, DMSO-d6) δ 10.42 (s, 1H), 7.96 (m, 1H), 7.92 (d, J=8.8 Hz, 2H), 7.81 (d, J=8.8 Hz, 2H), 7.68 (dd, J=7.4, 7.4 Hz, 1H), 7.12 (dd, J=11.6, 2.4 Hz, 1H), 6.91 (ddd, J=8.2, 8.2, 2.6 Hz, 1H), 4.11 (t, J=6.2 Hz, 2H), 3.30-3.24 (m, 6H), 3.17 (m, 2H), 3.11 (m, 2H), 1.75 (m, 2H), 1.58 (m, 2H), 1.47-1.22 (m, 10H), 1.17 (m, 6H), 0.89 (t, J=7.2 Hz, 3H), 0.79 (t, J=6.8 Hz, 3H); LCMS (m/z) 564.5 (M); RT (Method B, std LCMS method), 0.78 min.

Example 86

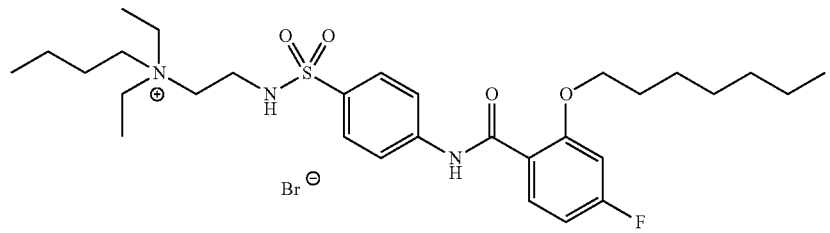 [SMILES: CCCCCCCOc1cc(F)ccc1C(=O)Nc1ccc(S(=O)(=O)NCC[N+](CC)(CC)CCCC)cc1 ; [Br-]]

N,N-Diethyl-N-(2-((4-(4-fluoro-2-(heptyloxy)benzamido)phenyl)sulfonamido)-ethyl)butan-1-aminium bromide (95). According to general procedure step F; the crude material was purified by Biotage flash chromatography (gradient elution, 0 to 20% 3M NH₃/MeOH in DCM) to obtain the title compound as white solid (17% yield). ¹H NMR (400 MHz, DMSO-d6) δ 10.42 (s, 1H), 7.98 (t, J=6.0 Hz, 1H), 7.92 (d, J=8.6 Hz, 2H), 7.81 (d, J=8.6 Hz, 2H), 7.68 (dd, J=8.0, 8.0 Hz, 1H), 7.12 (dd, J=11.6, 2.4 Hz, 1H), 6.90 (ddd, J=8.2, 8.2, 2.2 Hz, 1H), 4.11 (t, J=6.4 Hz, 2H), 3.31-3.24 (m, 6H), 3.19 (m, 2H), 3.12 (m, 2H), 1.75 (m, 2H), 1.56 (m, 2H), 1.42-1.16 (m, 16H), 0.93 (t, J=7.2 Hz, 3H), 0.80 (t, J=6.8 Hz, 3H); LCMS (m/z) 564.5 (M); RT (Method B, std LCMS method), 0.76 min.

Example 87

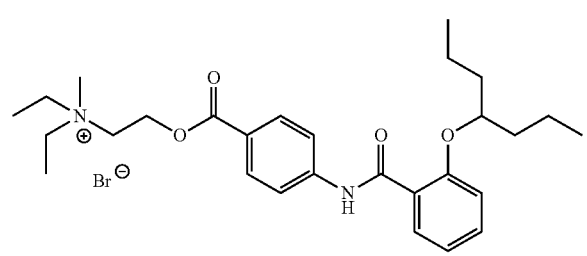 [SMILES: CCCC(CCC)Oc1ccccc1C(=O)Nc1ccc(C(=O)OCC[N+](C)(CC)CC)cc1 ; [Br-]]

N,N-Diethyl-2-((4-(2-(heptan-4-yloxy)benzamido)benzoyl)oxy)-N-methylethan-1-aminium bromide (96). According to general procedure step F; the crude material was purified by Biotage flash chromatography (gradient elution, 0 to 15% 3M NH₃/MeOH in DCM) to obtain the title compound as white solid (86% yield). ¹H NMR (400 MHz, DMSO-d6) δ 10.48 (s, 1H), 7.98 (d, J=8.6 Hz, 2H), 7.86 (d, J=8.6 Hz, 2H), 7.66 (d, J=7.6 Hz, 1H), 7.50 (dd, J=7.6, 7.6 Hz, 1H), 7.20 (d, J=8.4 Hz, 1H), 7.06 (dd, J=7.4, 7.4 Hz, 1H), 4.67 (m, 2H), 4.54 (p, J=5.4 Hz, 1H), 3.74 (m, 2H), 3.45 (q, J=7.2 Hz, 4H), 3.06 (s, 3H), 1.62 (m, 4H), 1.38 (m, 4H), 1.27 (t, J=7.2 Hz, 6H), 0.85 (t, J=7.2 Hz, 6H); LCMS (m/z) 469.6 (M); RT (Method B, std LCMS method), 0.77 min.

Example 88

N,N-Diethyl-N-methyl-2-((4-(2-((5-methylhexyl)oxy)benzamido)benzoyl)oxy)-ethan-1-aminium bromide (97). According to general procedure step F; the title compound was obtained as white powder through filtration (58% yield). ¹H NMR (400 MHz, DMSO-d6) δ 10.45 (s, 1H), 7.97 (d, J=8.2 Hz, 2H), 7.88 (d, J=8.6 Hz, 2H), 7.63 (d, J=7.7 Hz, 1H), 7.51 (dd, J=8.2, 8.2 Hz, 1H), 7.18 (d, J=8.4 Hz, 1H), 7.07 (dd, J=7.4, 7.4 Hz, 1H), 4.67 (m, 2H), 4.11 (t, J=6.2 Hz, 2H), 3.74 (m, 2H), 3.45 (q, J=7.2 Hz, 4H), 3.06 (s, 3H), 1.73 (m, 2H), 1.39 (m, 3H), 1.27 (t, J=7.2 Hz, 6H), 1.14 (m, 2H), 0.75 (d, J=6.6 Hz, 6H); LCMS (m/z) 469.6 (M); RT (Method B, std LCMS method), 0.77 min.

Example 89

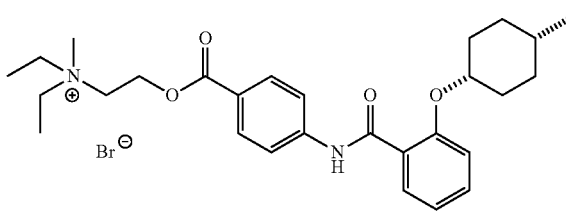

N,N-Diethyl-N-methyl-2-((4-(2-(((1s,4s)-4-methylcyclohexyl)oxy)benzamido)-benzoyl)oxy)ethan-1-aminium bromide (98). According to general procedure step F; the title compound was obtained as white powder through filtration (81% yield). $^1$H NMR (400 MHz, DMSO-d6) δ 10.42 (s, 1H), 7.97 (d, J=8.8 Hz, 2H), 7.89 (d, J=8.6 Hz, 2H), 7.56 (dd, J=7.6, 1.8 Hz, 1H), 7.47 (ddd, J=7.8, 7.8, 1.8 Hz, 1H), 7.20 (d, J=8.4 Hz, 1H), 7.04 (dd, J=7.4, 7.4 Hz, 1H), 4.75 (m, 1H), 4.66 (m, 2H), 3.74 (m, 2H), 3.45 (q, J=7.2 Hz, 4H), 3.06 (s, 3H), 1.92 (m, 2H), 1.54 (m, 3H), 1.37 (m, 2H), 1.27 (t, J=7.2 Hz, 6H), 1.17 (m, 2H), 0.64 (d, J=6.2 Hz, 3H); LCMS (m/z) 467.5 (M); RT (Method B, std LCMS method), 0.75 min.

Example 90

The antibacterial efficacy of the ammonium compounds was assessed. Minimum inhibitory concentrations (MICs) were determined by broth dilution method. Dilutions of each compound, ranging from 1 μg/mL to 256 μg/mL (final concentrations) were prepared in Mueller-Hinton broth. Compound dilutions were added to wells of a 96-well plate, with the concentration of the compound increasing 2-fold by row. Each well contained 5×10$^5$ CFU/ml of target bacterium in a total volume of 100 μl. Plates were incubated overnight at 37° C. The following day, plates were evaluated for a visual change in growth to determine the MIC. The concentration value corresponding to the first row that no longer had visible bacterial growth, as evaluated by turbidity in the wells, was recorded as the MIC. MIC values were representative of at least biological duplicates, each made up of technical triplicates.

TABLE 1

Antibacterial Activity of Ammonium Compounds

| Compound No. | MIC (μg/mL) S. aureus | MIC (μg/mL) A. baumannii |
| --- | --- | --- |
| 10 | ++ | ++ |
| 11 | ++ | ++ |
| 12 | ++ | + |
| 13 | ++ | + |
| 14 | + | + |
| 15 | + | + |
| 16 | + | + |
| 17 | ++ | + |
| 18 | + | + |
| 19 | + | + |
| 20 | + | + |
| 21 | ++ | + |
| 22 | ++ | + |
| 23 | ++ | ++ |
| 24 | ++ | + |
| 25 | ++ | + |
| 26 | ++ | + |
| 27 | +++ | + |
| 28 | ++ | + |
| 29 | ++ | + |
| 30 | ++ | + |
| 31 | + | + |
| 32 | ++ | + |
| 33 | +++ | ++ |
| 34 | +++ | ++ |
| 35 | +++ | ++ |
| 36 | +++ | ++ |
| 37 | +++ | ++ |
| 38 | +++ | + |
| 39 | ++ | + |
| 40 | +++ | + |
| 41 | +++ | + |
| 42 | +++ | ++ |
| 43 | +++ | ++ |
| 44 | +++ | ++ |
| 45 | ++ | ++ |
| 46 | ++ | + |
| 47 | +++ | ++ |
| 48 | +++ | + |
| 49 | +++ | + |
| 50 | +++ | ++ |
| 51 | +++ | + |
| 52 | ++ | + |
| 53 | ++ | + |
| 54 | + | + |
| 55 | + | + |
| 56 | +++ | ++ |
| 57 | ++ | ++ |
| 58 | + | + |
| 59 | ++ | + |
| 60 | ++ | ++ |
| 61 | +++ | ++ |
| 62 | +++ | ++ |
| 63 | +++ | ++ |
| 64 | ++ | + |
| 65 | ++ | + |
| 66 | ++ | + |
| 67 | ++ | + |
| 68 | +++ | ++ |
| 69 | ++ | + |
| 70 | +++ | ++ |
| 71 | +++ | ++ |
| 72 | ++ | + |
| 73 | ++ | + |
| 74 | ++ | + |
| 75 | ++ | + |
| 76 | ++ | + |
| 77 | ++ | + |
| 78 | ++ | ++ |
| 79 | ++ | + |
| 80 | ++ | + |
| 81 | + | + |
| 82 | ++ | ++ |
| 83 | ++ | + |
| 84 | ++ | + |
| 85 | ++ | + |
| 86 | +++ | ++ |
| 87 | ++ | + |
| 88 | ++ | + |
| 89 | ++ | + |
| 90 | ++ | ++ |
| 91 | ++ | + |
| 92 | ++ | + |
| 93 | ++ | + |
| 94 | ++ | ++ |
| 95 | ++ | ++ |

TABLE 1-continued

Antibacterial Activity of Ammonium Compounds

| Compound No. | MIC (μg/mL) S. aureus | MIC (μg/mL) A. baumannii |
|---|---|---|
| 96 | ++ | + |
| 97 | ++ | + |
| 98 | + | + |

+++ MIC < 3 μg/mL
++ 3 μg/mL ≤ MIC ≤ 30 μg/mL
+ 30 μg/mL < MIC

Example 91

The antibacterial efficacy of ammonium compounds in the presence of human plasma was assessed. Minimum inhibitory concentrations (MICs) were determined by broth dilution method. Dilutions of each compound, ranging from 1 μg/mL to 256 μg/mL (final concentrations) were prepared in Mueller-Hinton broth. For the plasma containing samples, compound dilutions were made in Mueller-Hinton broth and supplemented with 5% (final %) human plasma (esterases). Compound dilutions were added to wells of a 96-well plate, with the concentration of the compound increasing 2-fold by row. Each well contained 5×10$^5$ CFU/mL of target bacterium in a total volume of 100 μL. Plates were incubated overnight at 37° C. The following day, plates were evaluated for a visual change in growth to determine the MIC. The concentration value corresponding to the first row that no longer had visible bacterial growth, as evaluated by turbidity in the wells, was recorded as the MIC. MIC values were representative of at least biological duplicates, each made up of technical triplicates.

Compounds according to the present disclosure (e.g., compounds 17, 68, and 95, as summarized in Table 2) were found to provide better stability than otilonium bromide (11) in the presence of enzymes that are found in the gut. Compound 95, in particular, demonstrated a four- to eight-fold increase in stability. The antimicrobial activity of compounds 17, 68, and 95 again Gram positive S. aureus was comparable or better than the activity of otilonium bromide. Compound 68 was found to provide improved selective for Gram positive microbes over Gram negative microbes, and compound 17 was found to provide virtually complete selectivity for Gram positive microbes.

TABLE 2

Antibacterial Activity of Ammonium Compounds in Presence or Absence of Human Blood Plasma

| Compound No. | MIC (μg/ml) S. aureus | MIC (μg/ml) A. baumannii | Δ MIC A. baumannii + human plasma |
|---|---|---|---|
| 11 | ++ | ++ | 8X |
| 17 | +++ | + | N.D. |
| 68 | +++ | ++ | 8X |
| 95 | ++ | ++ | 2X |

+++ MIC < 3 μg/mL
++ 3 μg/mL ≤ MIC ≤ 30 μg/mL
+ 30 μg/mL < MIC

Example 92

The hemolytic potential of ammonium compounds were assessed in vitro. A human red blood cell solution (RBC) was prepared by washing 400 μL of fresh RBCs twice with 7 mL of 1×PBS (pH 7.4) by centrifugation at 4° C., 2500 rpm for 10 minutes. The precipitates were then resuspended in 4 mL of 1×PBS. Hemolysis testing was performed by mixing 500 μL of freshly prepared test compound solutions at a final concentration of both 16 μg/mL and 32 μg/mL in 1×PBS with 400 μL of the washed human RBCs. Two control samples were prepared by separately mixing 400 μL of washed RBCs with 500 μL of 1×PBS (negative control) and 1% Triton X-100 (w/v). After incubation in a water bath at 37° C. for 1 hour, the samples were centrifuged at 2500 rpm for 10 minutes. 300 μL of the supernatant were collected for measurement in a 96-well plate. The release of hemoglobin was assessed by measuring the absorbance of the samples at 540 nm using 1×PBS as the blank. Hemolysis percent was calculated using Equation 1:

$$\% \text{ hemolysis} = \left(absorbance_{sample} - \frac{absorbance_{negative}}{absorbance_{positive}}\right) \times 100. \quad \text{(Eq. 1)}$$

Compounds according to the present disclosure (e.g., compounds 17, 68, and 95, as summarized in Table 3) were found to result in reduced hemolysis as compared to otilonium bromide (11). Compounds 68 and 95, in particular, demonstrated a 94% reduction and an 85% reduction in hemolysis at 32 μg/mL, respectively.

TABLE 3

In Vitro Hemolysis Assay of Ammonium Compounds

| Compound No. | % hemolysis at 16 μg/ml | % hemolysis at 32 μg/ml |
|---|---|---|
| 11 | 7 | 92 |
| 17 | 59 | 90 |
| 68 | 2 | 5 |
| 95 | 3 | 14 |

Example 93

Figure 2A:
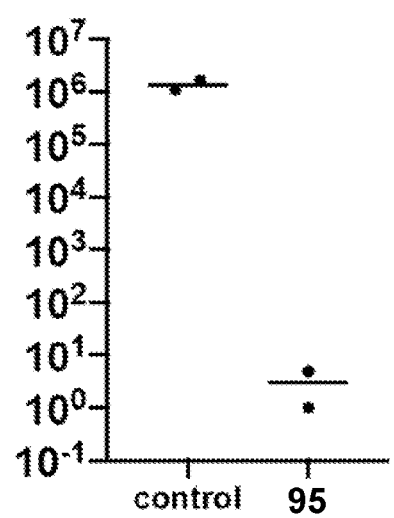
FIG. 2A shows bacterial counts determined exposure of mice to enterotoxigenic *Escherichia coli* with or without administration of compound 95.
Figure 2B:
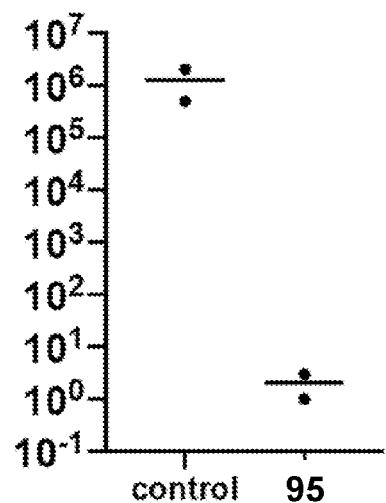
FIG. 2B shows bacterial counts determined after exposure of mice to vancomycin-resistant *enterococcus* with or without administration of compound 95.

Mouse assays were used to evaluate the in vivo activity of compound 95. Male and female neonate CD-1 mice were orally innoculated with 10$^7$ colony forming units of enterotoxigenic *Escherichia coli* (ETEC) (FIG. 2A) or vancomycin-resistant *enterococcus* (VRE) (FIG. 2B) and co-administered compound 95 at 1 mg/kg. Intestines were harvested after 4 hours and plated to determine viable bacteria. As shown in FIG. 2, compound 95 significantly decreased viablity and colonization of both bacteria in the mouse model.

VI. EXEMPLARY EMBODIMENTS

Exemplary embodiments provided in accordance with the presently disclosed subject matter include, but are not limited to, the claims and the following embodiments:

1. A compound according to Formula I:

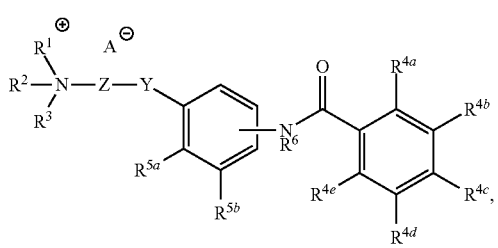

wherein
A is a pharmaceutically acceptable anion;
Y is selected from the group consisting of —OC(O)—, —NR$^7$C(O)—, and —NR$^7$SO$_2$—;
Z is C$_{1-6}$ alkylene;
R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;
L$^1$ is C$_{1-6}$ alkylene;
R$^{1a}$ is selected from the group consisting of C$_{3-8}$ cycloalkyl, C$_{6-10}$ aryl, 3- to 10-membered heterocyclyl, and 5- to 10-membered heteroaryl;
R$^2$ and R$^3$ are independently selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;
L$^2$ is C$_{1-6}$ alkylene;
R$^{2a}$ is selected from the group consisting of C$_{3-8}$ cycloalkyl, C$_{6-10}$ aryl, 3- to 10-membered heterocyclyl, and 5- to 10-membered heteroaryl;
R$^2$ and R$^3$ are optionally taken together with the nitrogen to which they are attached to form 3- to 10-membered heterocyclyl;
one of R$^2$ and R$^3$ is optionally taken together with the nitrogen to which it is attached and Y or Z to form 3- to 10-membered heterocyclyl;
R$^{4a}$, R$^{4b}$, R$^{4c}$, R$^{4d}$, and R$^{4e}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^4$-R$^{4x}$—;
L$^4$ is selected from the group consisting of C$_{1-6}$ alkylene, 2- to 6-membered heteroalkylene, and —O—;
R$^{4x}$ is selected from the group consisting of C$_{3-8}$ cycloalkyl, C$_{6-10}$ aryl, 3- to 10-membered heterocyclyl, and 5- to 10-membered heteroaryl;
R$^{5a}$ and R$^{5b}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^5$-R$^{5x}$;
L$^5$ is selected from the group consisting of C$_{1-6}$ alkylene, 2- to 6-membered heteroalkylene, and —O—;
R$^{5x}$ is selected from the group consisting of C$_{3-8}$ cycloalkyl, C$_{6-10}$ aryl, 3- to 10-membered heterocyclyl, and 5- to 10-membered heteroaryl;
R$^6$ is selected from the group consisting of H, C$_{1-6}$ alkyl, and C$_{2-7}$ acyl;
R$^6$ is optionally taken together with R$^{4a}$ or R$^{4e}$ to form a 5- to -8-membered ring;
each R$^7$ is independently selected from the group consisting of H, C$_{1-6}$ alkyl, and C$_{2-7}$ acyl;
each C$_{3-8}$ cycloalkyl, C$_{6-10}$ aryl, 3- to 10-membered heterocyclyl, and 5- to 10-membered heteroaryl is optionally and independently substituted with one or more substituents selected from the group consisting of C$_{1-18}$ alkyl, C$_{1-18}$ haloalkyl, C$_{1-18}$ alkenyl, C$_{1-18}$ alkoxy, halogen, —OH, —C(O)R$^8$, —C(O)N(R$^7$)$_2$, —N(R$^7$)$_2$, —NO$_2$, —SO$_3$, and —SO$_2$N(R$^7$)$_2$; and
each R$^8$ is independently selected from the group consisting of C$_{1-6}$ alkyl, C$_{1-6}$ alkoxy, and —OH;
provided that at least one of R$^{4a}$, R$^{4b}$, R$^{4c}$, R$^{4d}$, and R$^{4e}$ is C$_{4-18}$ alkoxy; and
provided that if Y is —OC(O)—, Z is ethylene, R$^1$ is methyl, R$^2$ and R$^3$ are ethyl, then at least two of R$^{4a}$, R$^{4b}$, R$^{4c}$, R$^{4d}$, and R$^{4e}$ are other than H; and
provided that the compound is other than:
 an N,N-diethyl-N-methyl-2-(4-(2-(octyloxy)benzamido)benzamido)ethan-1-aminium species,
 an N,N,N-trimethyl-2-((4-(2-(octyloxy)benzamido)benzoyl)oxy)ethan-1-aminium species,
 an N,N,N-trimethyl-2-((4-(4-(isopentyloxy)benzamido)benzoyl)oxy)ethan-1-aminium species,
 an N,N,N-trimethyl-2-((4-(4-(isopentyloxy)benzamido)benzoyl)oxy)propan-1-aminium species,
 an 1-methyl-1-(2-((4-(2-(octyloxy)benzamido)benzoyl)oxy)ethyl)piperidin-1-ium species, or
 4-methyl-4-(2-((4-(2-(octyloxy)benzamido)benzoyl)oxy)ethyl)morpholin-4-ium bromide.

2. The compound of embodiment 1, wherein at least one of R$^{4a}$ and R$^{4e}$ is C$_{4-18}$ alkoxy.

3. The compound of embodiment 1 or embodiment 2, wherein at least two of R$^{4a}$, R$^{4b}$, R$^{4c}$, R$^{4d}$, and R$^{4e}$ are C$_{4-18}$ alkoxy.

4. The compound of any one of embodiments 1-3, wherein one or two of R$^{4a}$, R$^{4b}$, R$^{4c}$, R$^{4d}$, and R$^{4e}$ are C$_{4-13}$ alkoxy.

5. The compound of any one of embodiments 1-4, wherein at least one of R$^{4a}$, R$^{4b}$, R$^{4c}$, R$^{4d}$, and R$^{4e}$ is halogen.

6. The compound of any one of embodiments 1-5, wherein R$^{5a}$ and R$^{5b}$ are independently selected from the group consisting of H and halogen.

7. The compound of any one of embodiments 1-6, which is a compound according to Formula Ia:

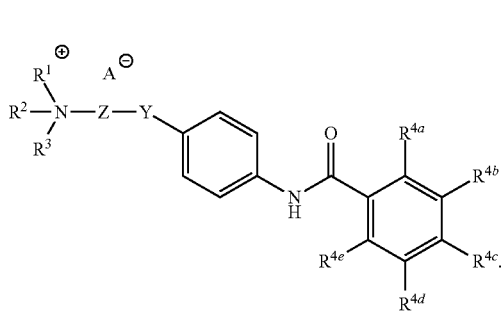

8. The compound of any one of embodiments 1-7, wherein R$^1$ is selected from the group consisting of C$_{3-18}$ alkyl and -L$^1$-R$^{1a}$.

9. The compound of embodiment 8, wherein R$^1$ is C$_4$-1 alkyl.

10. The compound of embodiment 8, wherein R$^1$ is -L$^1$-R$^{1a}$.

11. The compound of embodiment 9, wherein R$^{1a}$ is selected from the group consisting of C$_{3-4}$ cycloalkyl and C$_{6-10}$ aryl.

12. The compound of any one of embodiments 1-11, wherein $R^2$ and $R^3$ are each $C_{1-6}$ alkyl.
13. The compound of any one of embodiments 1-7, wherein $R^2$ and $R^3$ are taken together with the nitrogen to which they are attached to form 3- to 10-membered heterocyclyl.
14. The compound of any one of embodiments 1-7, wherein $R^2$ is taken together with the nitrogen to which it is attached and Z to form 3- to 10-membered heterocyclyl.
15. The compound of embodiment 13 or embodiment 14, wherein $R^1$ is $C_{1-6}$ alkyl.
16. The compound of any one of embodiments 1-15, wherein Y is selected from the group consisting of —OC(O)— and —NR$^7$C(O)—.
17. The compound of any one of embodiments 1-15, wherein Y is -NR$^7$SO$_2$—.
18. The compound of any one of embodiments 1-17, wherein A is bromide.
19-22. A species of ammonium compound as set forth in the specification.
23. A pharmaceutical composition comprising a compound according to any one of embodiments 1-22 and a pharmaceutically acceptable excipient.
24. A method for treating a bacterial infection, the method comprising administering to a subject in need thereof a therapeutically effective amount of a compound according to Formula II:

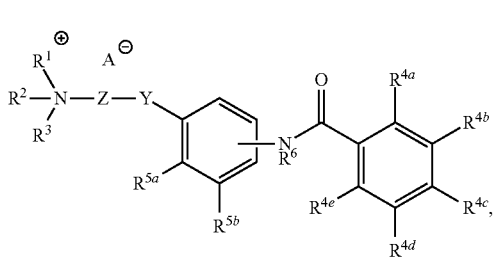

(II)

wherein
A is a pharmaceutically acceptable anion;
Y is selected from the group consisting of —OC(O)—, —NR$^7$C(O)—, and —NR$^7$SO$_2$—;
Z is $C_{1-4}$ alkylene;
$R^1$ is selected from the group consisting of $C_{1-18}$ alkyl, $C_{3-8}$ cycloalkyl, $C_{6-10}$ aryl, 3- to 10-membered heterocyclyl, 5- to 10-membered heteroaryl, and -L$^1$-R$^{1a}$;
L$^1$ is $C_{1-6}$ alkylene;
$R^{1a}$ is selected from the group consisting of $C_{3-8}$ cycloalkyl, $C_{6-10}$ aryl, 3- to 10-membered heterocyclyl, and 5- to 10-membered heteroaryl;
$R^2$ and $R^3$ are independently selected from the group consisting of H, $C_{1-18}$ alkyl, $C_{3-8}$ cycloalkyl, $C_{6-10}$ aryl, 3- to 10-membered heterocyclyl, 5- to 10-membered heteroaryl, and -L$^2$-R$^{2a}$;
L$^2$ is $C_{1-6}$ alkylene;
$R^{2a}$ is selected from the group consisting of $C_{3-8}$ cycloalkyl, $C_{6-10}$ aryl, 3- to 10-membered heterocyclyl, and 5- to 10-membered heteroaryl;
$R^2$ and $R^3$ are optionally taken together with the nitrogen to which they are attached to form 3- to 10-membered heterocyclyl;
one of $R^2$ and $R^3$ is optionally taken together with the nitrogen to which it is attached and Y or Z to form 3- to 10-membered heterocyclyl;

$R^{4a}$, $R^{4b}$, $R^{4c}$, $R^{4d}$, and $R^{4e}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N(R$^7$)$_2$, —NO$_2$, —SO$_3$, —SO$_2$N(R$^7$)$_2$, and -L$^4$-R$^{4x}$;
L$^4$ is selected from the group consisting of $C_{1-6}$ alkylene, 2- to 6-membered heteroalkylene, and —O—;
$R^{4x}$ is selected from the group consisting of $C_{3-9}$ cycloalkyl, $C_{6-10}$ aryl, 3- to 10-membered heterocyclyl, and 5- to 10-membered heteroaryl;
$R^{5a}$ and $R^{5b}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N(R$^7$)$_2$, —NO$_2$, —SO$_3$, —SO$_2$N(R$^7$)$_2$, and -L$^5$-R$^{5x}$;
L$^5$ is selected from the group consisting of $C_{1-6}$ alkylene, 2- to 6-membered heteroalkylene, and —O—;
$R^{5x}$ is selected from the group consisting of $C_{3-8}$ cycloalkyl, $C_{6-10}$ aryl, 3- to 10-membered heterocyclyl, and 5- to 10-membered heteroaryl;
$R^6$ is selected from the group consisting of H, $C_{1-6}$ alkyl, and $C_{2-7}$ acyl;
$R^6$ is optionally taken together with $R^{4a}$ or $R^{4e}$ to form a 5- to -8-membered ring;
each $R^7$ is independently selected from the group consisting of H, $C_{1-6}$ alkyl, and $C_{2-7}$ acyl;
each $C_{3-8}$ cycloalkyl, $C_{6-10}$ aryl, 3- to 10-membered heterocyclyl, and 5- to 10-membered heteroaryl is optionally and independently substituted with one or more substituents selected from the group consisting of $C_{1-18}$ alkyl, $C_{1-18}$ haloalkyl, $C_{1-18}$ alkenyl, $C_{1-18}$ alkoxy, halogen, —OH, —C(O)R$^8$, —C(O)N(R$^7$)$_2$, —N(R$^7$)$_2$, —NO$_2$, —SO$_3$, and —SO$_2$N(R$^7$)$_2$; and
each $R^8$ is independently selected from the group consisting of $C_{1-6}$ alkyl, $C_{1-6}$ alkoxy, and —OH,
provided that the compound is other than otilonium bromide.
25. The method of embodiment 24, wherein at least one of $R^{4a}$, $R^{4b}$, $R^{4c}$, $R^{4d}$, and $R^{4e}$ is $C_{4-18}$ alkoxy.
26. The method of embodiment 24 or embodiment 25, wherein one or two of $R^{4a}$, $R^{4b}$, $R^{4c}$, $R^{4d}$, and $R^{4e}$ are $C_{4-13}$ alkoxy.
27. The method of any one of embodiments 24-26, wherein $R^1$ is selected from the group consisting of $C_{3-18}$ alkyl and -L$^1$-R$^{1a}$.
28. The method of any one of embodiments 24-27, wherein $R^1$ is $C_{4-18}$ alkyl.
29. The method of any one of embodiments 24-28, wherein $R^2$ and $R^3$ are each $C_{1-4}$ alkyl.
30. The method of any one of embodiments 24-29, wherein Y is —OC(O)—.
31-34. The method of embodiment 24, wherein the compound is a species of ammonium compound as set forth in the specification.
35. The method of any one of embodiments 24-34, wherein the bacterial infection is caused by Gram-positive bacteria.
36. The method of embodiment 35, wherein the Gram-positive bacteria are selected from the group consisting of *C. difficile, S. aureus, Streptococcus* spp., *Enterococcus* spp., *C. diphtheriae, L monocytheriae*, and combinations thereof.
37. The method of any one of embodiments 24-36, wherein the infection is an oral infection, a gastrointestinal infection, or a skin infection.
38. A method for altering the microbiome of a subject, the method comprising administering to a subject in need thereof a compound according to Formula II:

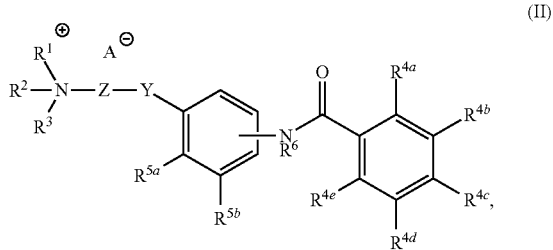

in an amount sufficient to alter the microbiome of the subject, wherein:

A is a pharmaceutically acceptable anion;

Y is selected from the group consisting of —OC(O)—, —NR$^7$C(O)—, and —NR$^7$SO$_2$—;

Z is C$_{1-6}$ alkylene;

R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;

L$^1$ is C$_{1-6}$ alkylene;

R$^{1a}$ is selected from the group consisting of C$_{3-8}$ cycloalkyl, C$_{6-10}$ aryl, 3- to 10-membered heterocyclyl, and 5- to 10-membered heteroaryl;

R$^2$ and R$^3$ are independently selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;

L$^2$ is C$_{1-6}$ alkylene;

R$^{2a}$ is selected from the group consisting of C$_{3-8}$ cycloalkyl, C$_{6-10}$ aryl, 3- to 10-membered heterocyclyl, and 5- to 10-membered heteroaryl;

R$^2$ and R$^3$ are optionally taken together with the nitrogen to which they are attached to form 3- to 10-membered heterocyclyl;

one of R$^2$ and R$^3$ is optionally taken together with the nitrogen to which it is attached and Y or Z to form 3- to 10-membered heterocyclyl;

R$^{4a}$, R$^{4b}$, R$^{4c}$, R$^d$, and R$^{4e}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^4$-R$^{4a}$;

L$^4$ is C$_{1-6}$ alkylene;

R$^{4a}$ is selected from the group consisting of C$_{3-8}$ cycloalkyl, C$_{6-10}$ aryl, 3- to 10-membered heterocyclyl, and 5- to 10-membered heteroaryl;

R$^{5a}$ and R$^{5b}$ are independently selected from the group consisting of H, C$_{1-18}$ alkoxy, C$_{1-18}$ alkyl, C$_{1-18}$ haloalkyl, C$_{1-18}$ alkenyl, halogen, —OH, —COOH, —N(R$^7$)$_2$, —NO$_2$, —SO$_3$, —SO$_2$N(R$^7$)$_2$, and -L$^5$-R$^{5x}$;

L$^5$ is selected from the group consisting of C$_{1-6}$ alkylene, 2- to 6-membered heteroalkylene, and —O—;

R$^{5x}$ is selected from the group consisting of C$_{3-8}$ cycloalkyl, C$_{6-10}$ aryl, 3- to 10-membered heterocyclyl, and 5- to 10-membered heteroaryl;

R$^6$ is selected from the group consisting of H, C$_{1-6}$ alkyl, and C$_{2-7}$ acyl;

R$^6$ is optionally taken together with R$^{4a}$ or R$^{4e}$ to form a 5- to -8-membered ring;

each R$^7$ is independently selected from the group consisting of H, C$_{1-6}$ alkyl, and C$_{2-7}$ acyl;

each C$_{3-8}$ cycloalkyl, C$_{6-10}$ aryl, 3- to 10-membered heterocyclyl, and 5- to 10-membered heteroaryl is optionally and independently substituted with one or more substituents selected from the group consisting of C$_{1-18}$ alkyl, C$_{1-18}$ haloalkyl, C$_{1-18}$ alkenyl, C$_{1-18}$ alkoxy, halogen, —OH, —C(O)R$^8$, —C(O)N(R$^7$)$_2$, —N(R$^7$)$_2$, —NO$_2$, —SO$_3$, and —SO$_2$N(R$^7$)$_2$; and each R$^8$ is independently selected from the group consisting of C$_{1-6}$ alkyl, C$_{1-6}$ alkoxy, and —OH;

provided that the compound is other than otilonium bromide.

39. The method of embodiment 38, wherein at least one of R$^{4a}$, R$^{4b}$, R$^{4c}$, R$^{4d}$, and R$^{4e}$ is C$_{4-18}$ alkoxy.

40. The method of embodiment 38 or embodiment 39, wherein one or two of R$^{4a}$, R$^{4b}$, R$^{4c}$, R$^{4d}$, and R$^{4e}$ are C$_{4-13}$ alkoxy.

41. The method of any one of embodiments 38-40, wherein altering the microbiome includes altering the growth of Gram-positive bacteria in the subject.

42. The method of any one of embodiments 38-41, wherein the Gram-positive bacteria are selected from the group consisting of *C. difficile*, *S. aureus*, *Streptococcus* spp., *Enterococcus* spp., *C. diphtheriae*, *L. monocytogenes*, and combinations thereof.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound according to Formula I:

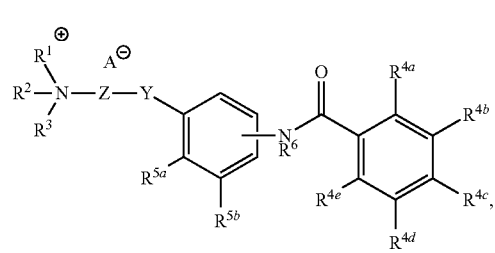

wherein

A is a pharmaceutically acceptable anion;

Y is selected from the group consisting of —NR$^7$SO$_2$—, —OC(O)—, and —NR$^7$C(O)—;

Z is C$_{1-6}$ alkylene;

R$^1$ is selected from the group consisting of C$_{1-18}$ alkyl, C$_{3-8}$ cycloalkyl, C$_{6-10}$ aryl, 3- to 10-membered heterocyclyl, 5- to 10-membered heteroaryl, and -L$^1$-R$^{1a}$;

L$^1$ is C$_{1-6}$ alkylene;

R$^{1a}$ is selected from the group consisting of C$_{3-8}$ cycloalkyl, C$_{6-10}$ aryl, 3- to 10-membered heterocyclyl, and 5- to 10-membered heteroaryl;

R$^2$ is selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;

R$^3$ is selected from the group consisting of H, C$_{1-18}$ alkyl, C$_{3-8}$ cycloalkyl, C$_{6-10}$ aryl, 3- to 10-membered heterocyclyl, 5- to 10-membered heteroaryl, and -L$^2$-R$^{2a}$;

L$^2$ is C$_{1-6}$ alkylene;

R$^{2a}$ is selected from the group consisting of C$_{3-8}$ cycloalkyl, C$_{6-10}$ aryl, 3- to 10-membered heterocyclyl, and 5- to 10-membered heteroaryl;

$R^2$ and $R^3$ are optionally taken together with the nitrogen to which they are attached to form 3- to 10-membered heterocyclyl;

one of $R^2$ and $R^3$ is optionally taken together with the nitrogen to which it is attached and Y or Z to form 3- to 10-membered heterocyclyl;

$R^{4a}$ is selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -$L^4$-$R^{4x}$;

$R^{4c}$ is selected from the group consisting of halogen, H, $C_{1-18}$ alkoxy, $C_{1-18}$ alkyl, $C_{1-18}$ haloalkyl, $C_{1-18}$ alkenyl, —OH, —COOH, —N($R^7$)$_2$, —NO$_2$, —SO$_3$, —SO$_2$N($R^7$)$_2$, and -$L^4$-$R^{4x}$;

$R^{4b}$, $R^{4d}$, and $R^{4e}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -$L^4$-$R^{4x}$;

$L^4$ is selected from the group consisting of $C_{1-6}$ alkylene, 2- to 6-membered heteroalkylene, and —O—;

$R^{4x}$ is selected from the group consisting of $C_{3-8}$ cycloalkyl, $C_{6-10}$ aryl, 3- to 10-membered heterocyclyl, and 5- to 10-membered heteroaryl;

$R^{5a}$ and $R^{5b}$ are independently selected from the group consisting of H, $C_{1-18}$ alkoxy, $C_{1-18}$ alkyl, $C_{1-18}$ haloalkyl, $C_{1-18}$ alkenyl, halogen, —OH, —COOH, —N($R^7$)$_2$, —NO$_2$, —SO$_3$, —SO$_2$N($R^7$)$_2$, and -$L^5$-$R^{5x}$;

$L^5$ is selected from the group consisting of $C_{1-6}$ alkylene, 2- to 6-membered heteroalkylene, and —O—;

$R^{5x}$ is selected from the group consisting of $C_{3-8}$ cycloalkyl, $C_{6-10}$ aryl, 3- to 10-membered heterocyclyl, and 5- to 10-membered heteroaryl;

$R^6$ is selected from the group consisting of H, $C_{1-6}$ alkyl, and $C_{2-7}$ acyl;

$R^6$ is optionally taken together with $R^{4a}$ or $R^{4c}$ to form a 5- to 8-membered ring;

each $R^7$ is independently selected from the group consisting of H, $C_{1-6}$ alkyl, and $C_{2-7}$ acyl;

each $C_{3-8}$ cycloalkyl, $C_{6-10}$ aryl, 3- to 10-membered heterocyclyl, and 5- to 10-membered heteroaryl is optionally and independently substituted with one or more substituents selected from the group consisting of $C_{1-18}$ alkyl, $C_{1-18}$ haloalkyl, $C_{1-18}$ alkenyl, $C_{1-18}$ alkoxy, halogen, —OH, —C(O)$R^8$, —C(O)N($R^7$)$_2$, —N($R^7$)$_2$, —NO$_2$, —SO$_3$, and —SO$_2$N($R^7$)$_2$; and each $R^8$ is independently selected from the group consisting of $C_{1-6}$ alkyl, $C_{1-6}$ alkoxy, and —OH;

provided that at least one of $R^{4a}$, $R^{4b}$, $R^{4c}$, $R^{4d}$, and $R^{4e}$ is $C_{7-18}$ alkoxy or $C_{4-6}$ alkoxy;

provided that if Y is —OC(O)—, Z is ethylene (—(CH$_2$)$_2$—), $R^1$ is methyl, and $R^2$ and $R^3$ are ethyl, then at least two of $R^{4a}$, $R^{4b}$, $R^{4c}$, $R^{4d}$, and $R^{4e}$ are other than H; and provided that the compound is other than:
an N,N-diethyl-N-methyl-2-(4-(2-(octyloxy)benzamido)benzamido)ethan-1-aminium species,
an N,N,N-trimethyl-2-((4-(2-(octyloxy)benzamido)benzoyl)oxy)ethan-1-aminium species,
an N,N,N-trimethyl-2-((4-(4-(isopentyloxy)benzamido)benzoyl)oxy)ethan-1-aminium species,
an N,N,N-trimethyl-2-((4-(4-(isopentyloxy)benzamido)benzoyl)oxy)propan-1-aminium species,
an 1-methyl-1-(2-4-(2-(octyloxy)benzamido)benzoyl)oxy)ethyl)piperidin-1-ium species, or
4-methyl-4-(2-((4-(2-(octyloxy)benzamido)benzoyl)oxy)ethyl)morpholin-4-ium bromide.

2. The compound of claim 1, wherein at least one of $R^{4a}$ and $R^{4c}$ is $C_{4-18}$ alkoxy.

3. The compound of claim 1, wherein at least one of $R^{4a}$, $R^{4b}$, $R^{4c}$, $R^{4d}$, and $R^{4e}$ is halogen.

4. The compound of claim 1, wherein $R^{5a}$ and $R^{5b}$ are independently selected from the group consisting of H and halogen.

5. The compound of claim 1, which is a compound according to Formula Ia:

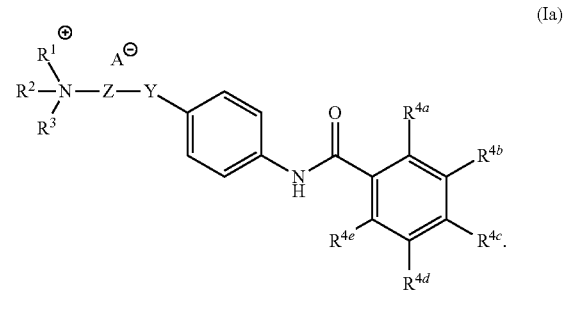

(Ia)

6. The compound of claim 1, wherein $R^1$ is selected from the group consisting of $C_{3-8}$ alkyl and -$L^1$-$R^{1a}$.

7. The compound of claim 6, wherein $R^{1a}$ is selected from the group consisting of $C_{3-8}$ cycloalkyl and $C_{6-10}$ aryl.

8. The compound of claim 1, wherein:
$R^2$ and $R^3$ re each $C_{1-6}$ alkyl;
$R^2$ and $R^3$ are taken together with the nitrogen to which they are attached to form 3- to 10-membered heterocyclyl; or
$R^2$ is taken together with the nitrogen to which it is attached and Z to form 3- to 10-membered heterocyclyl.

9. The compound of claim 8, wherein $R^1$ is $C_{1-6}$ alkyl.

10. The compound of claim 1, wherein Y is —NR$^7$SO$_2$—.

11. The compound of claim 1, wherein Y is selected from the group consisting of —OC(O)— and —NR$^7$C(O)—.

12. The compound of claim 1, wherein A is bromide.

13. The compound of claim 1, which is selected from the group consisting of:

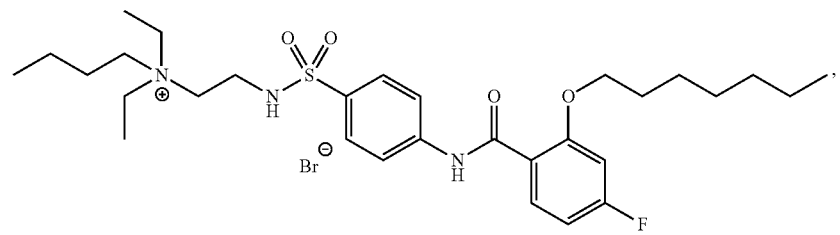

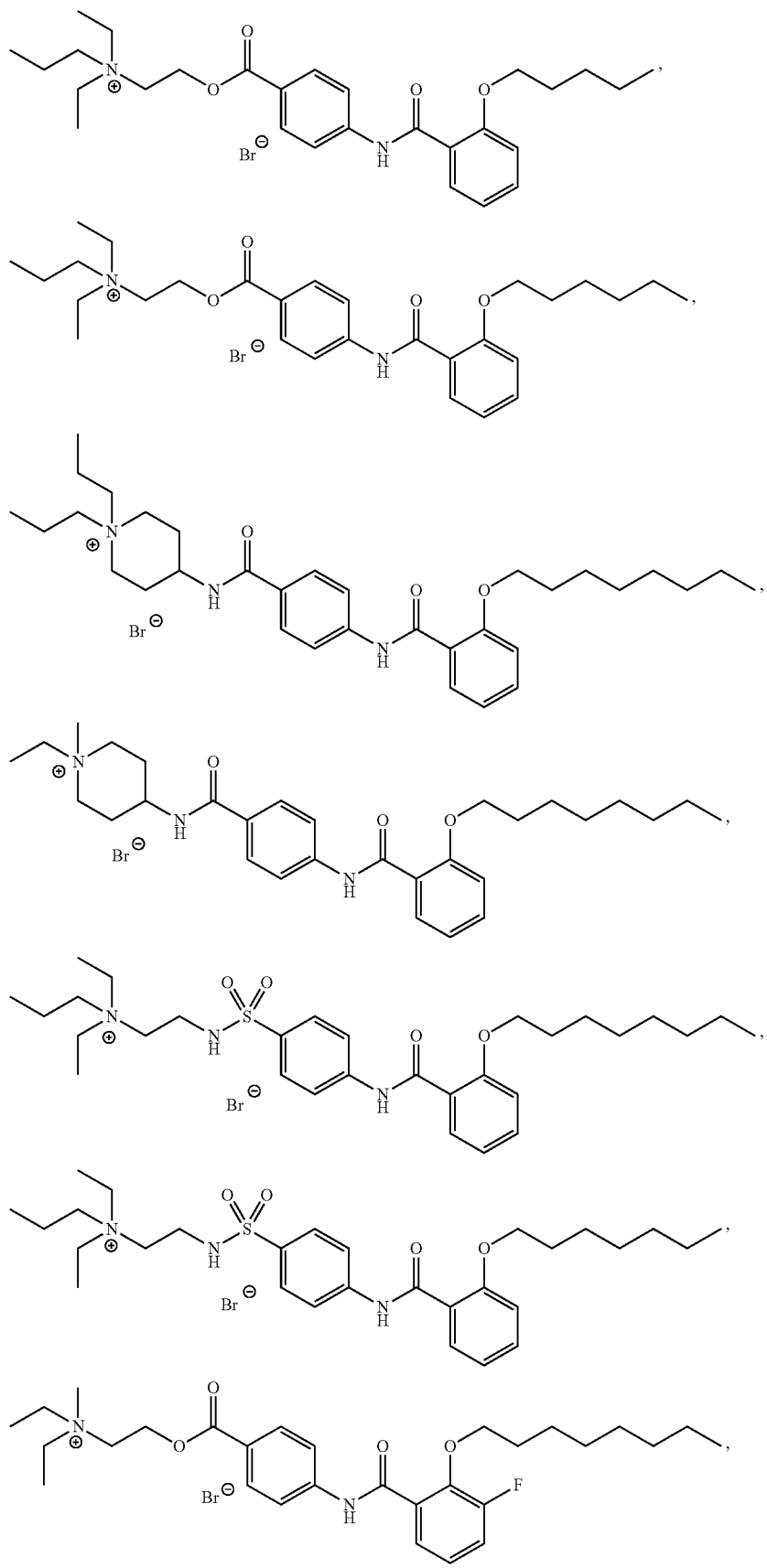

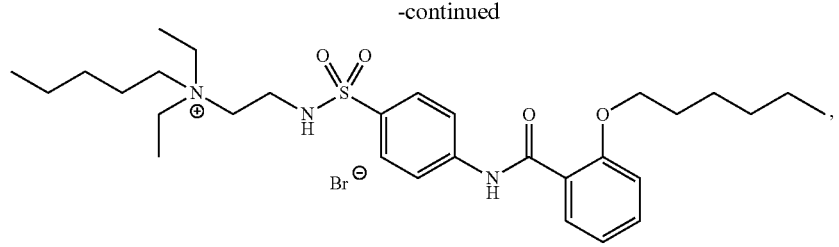
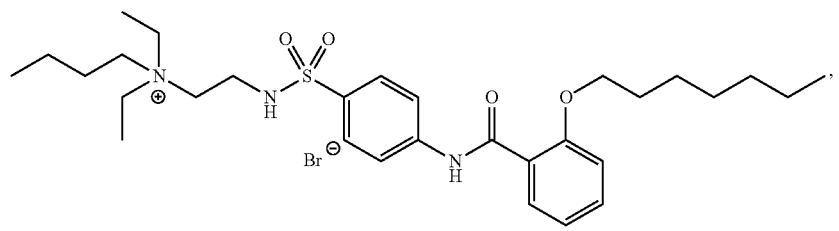
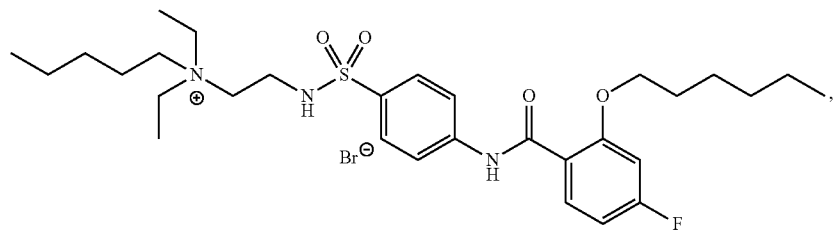
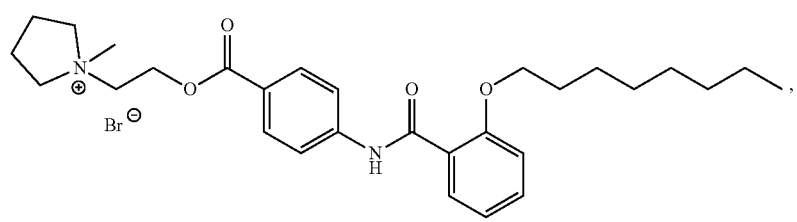
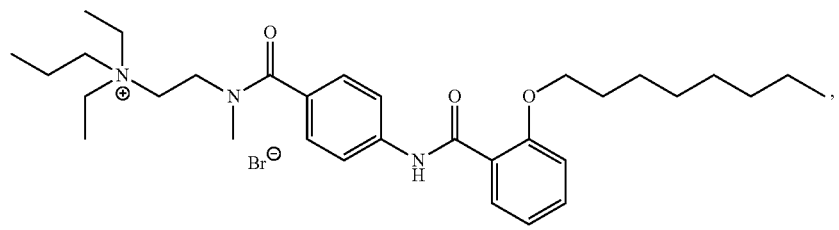
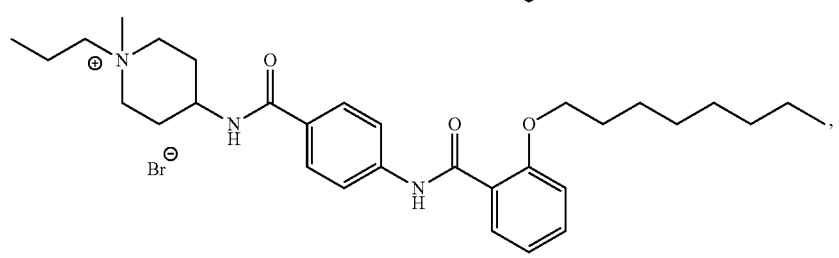
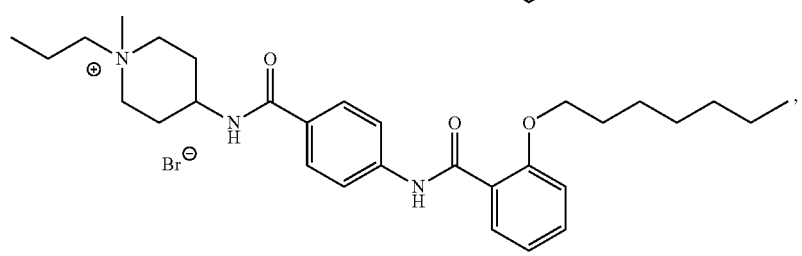

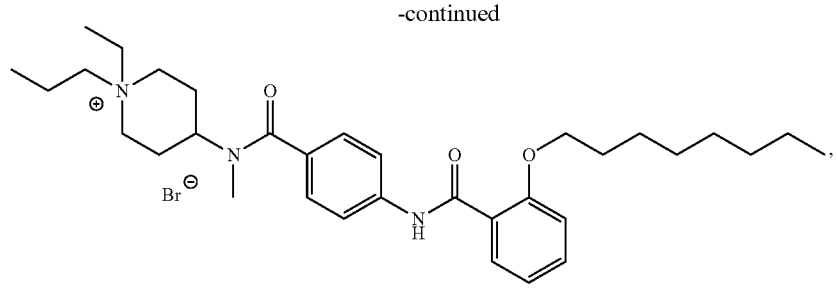
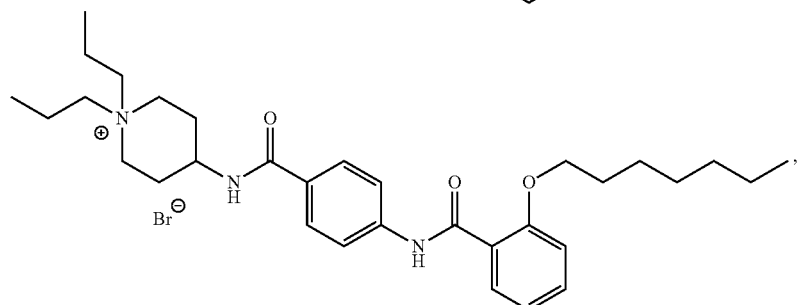
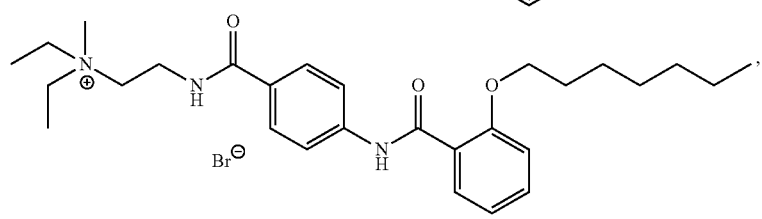
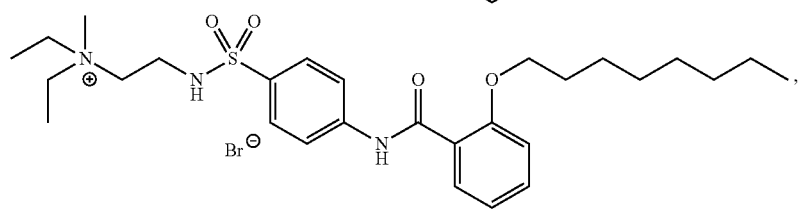
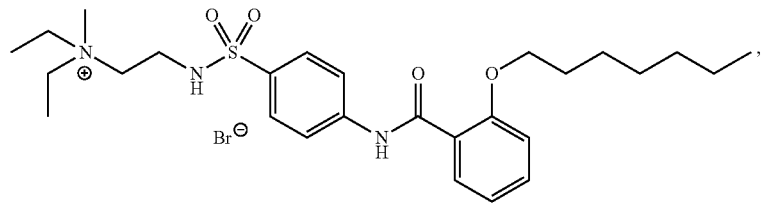
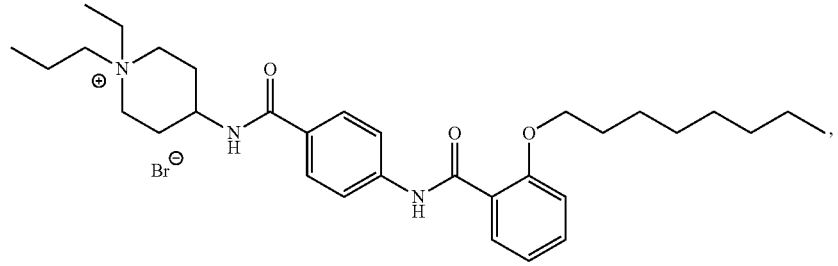
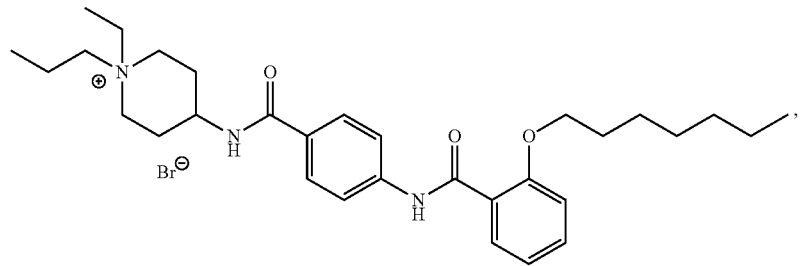

-continued
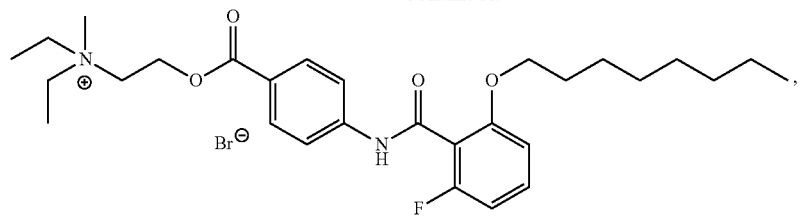
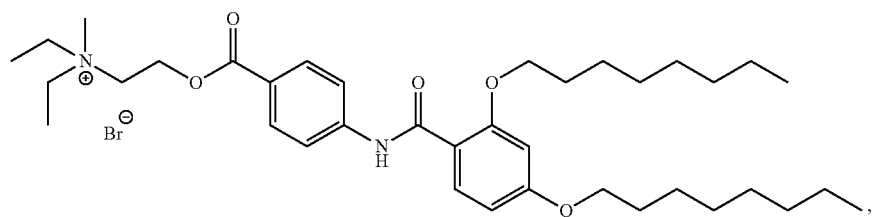
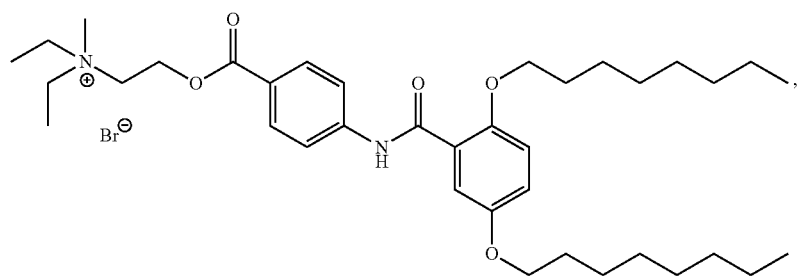
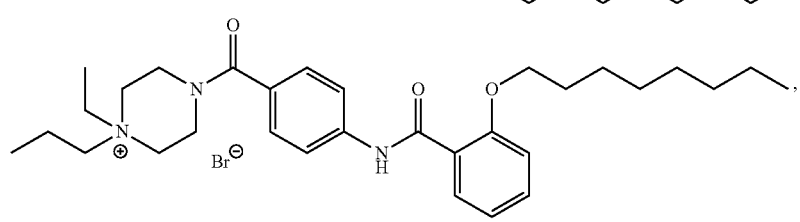
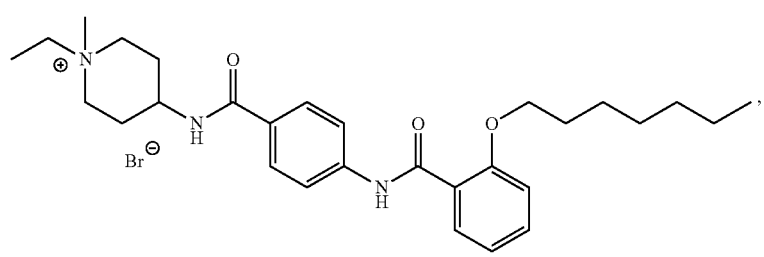
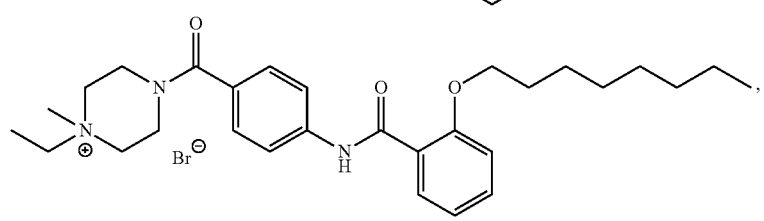
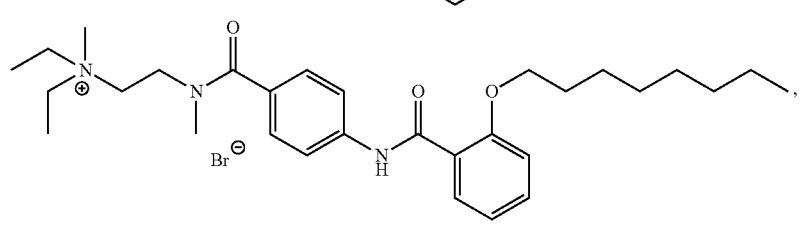

-continued
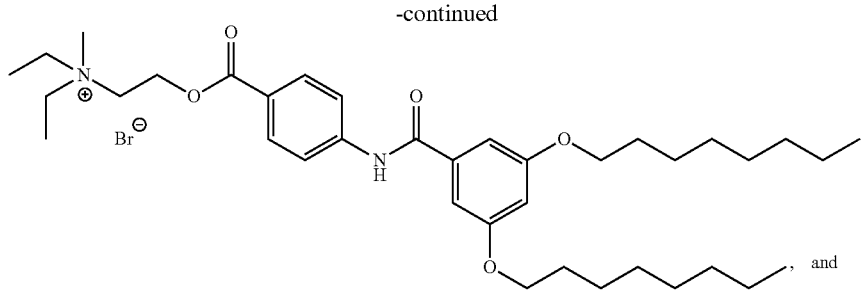, and
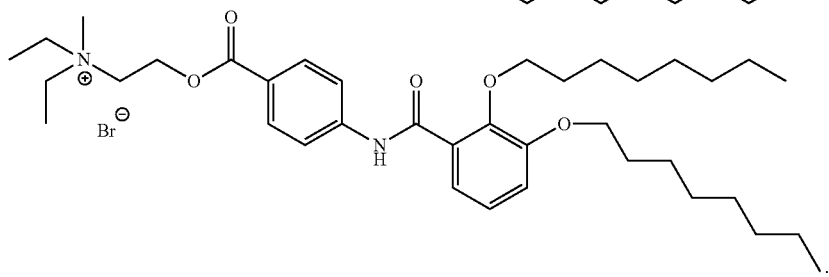.
14. The compound of claim 1, which is selected from the group consisting of:
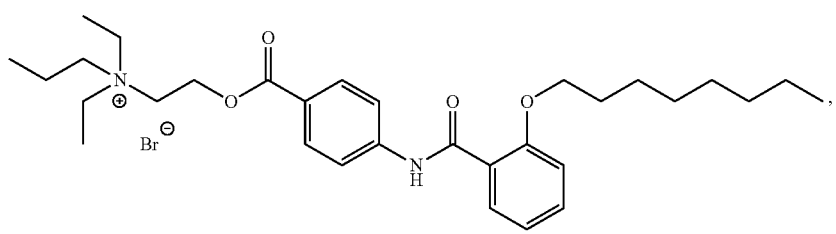,
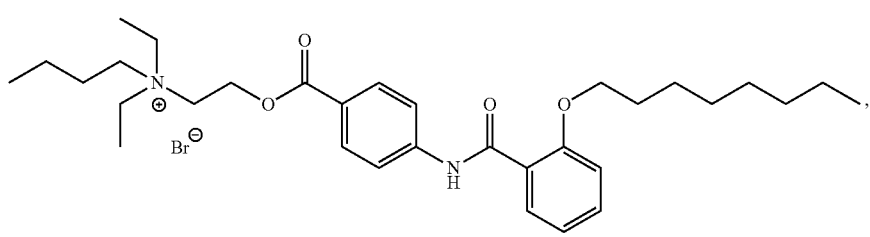,
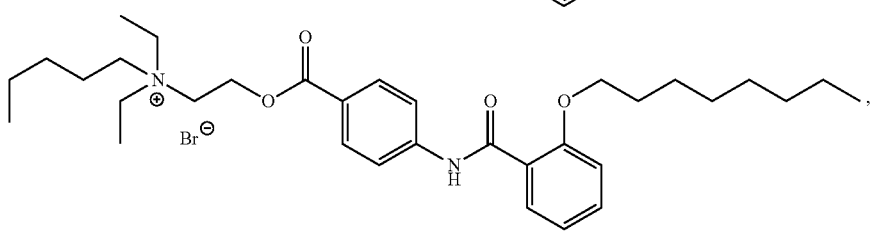,
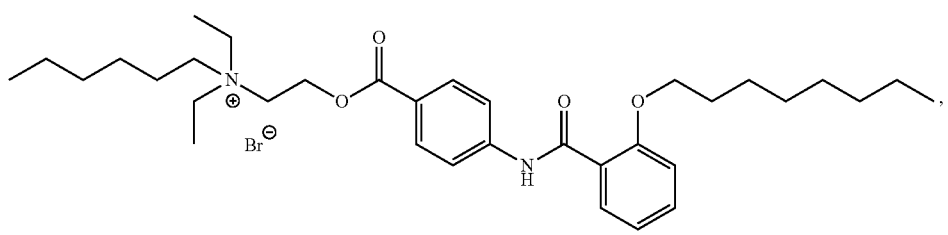, -continued
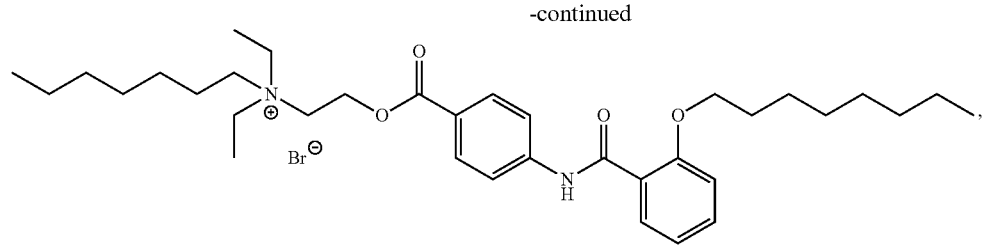
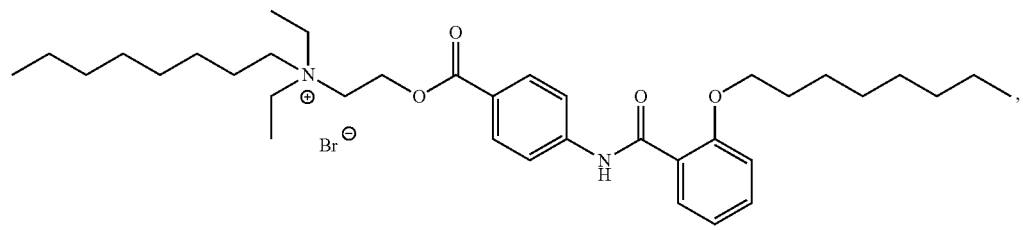
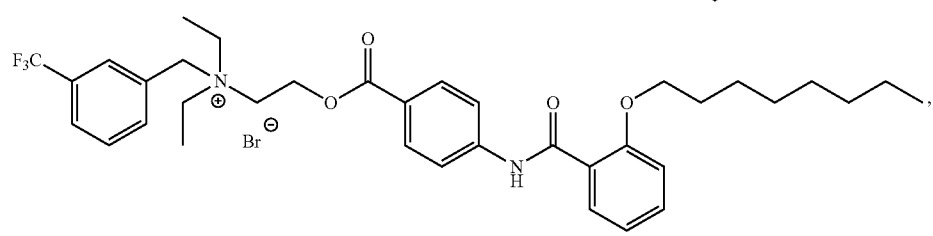
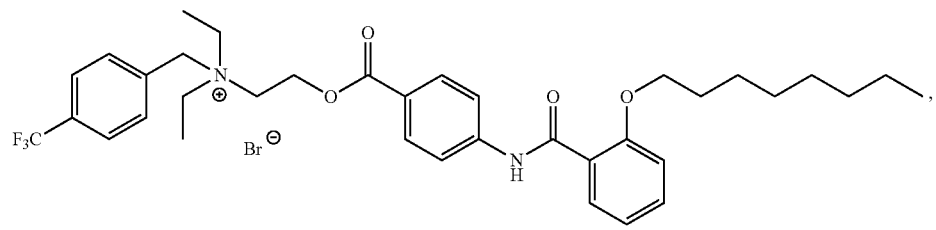
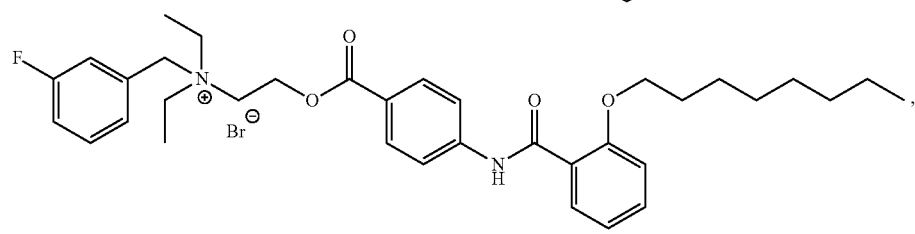
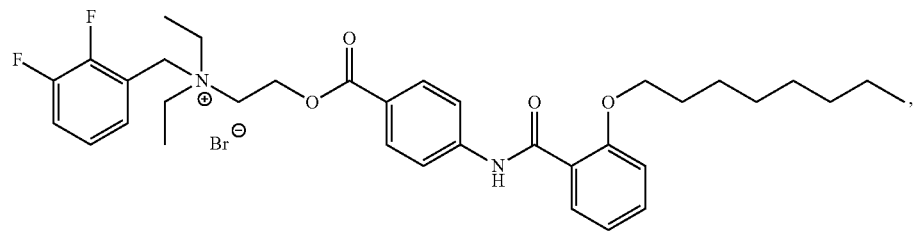
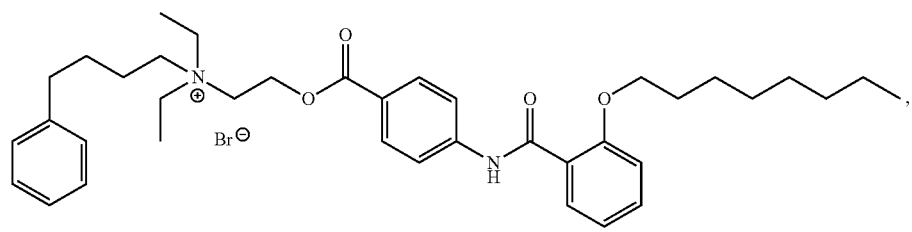

-continued
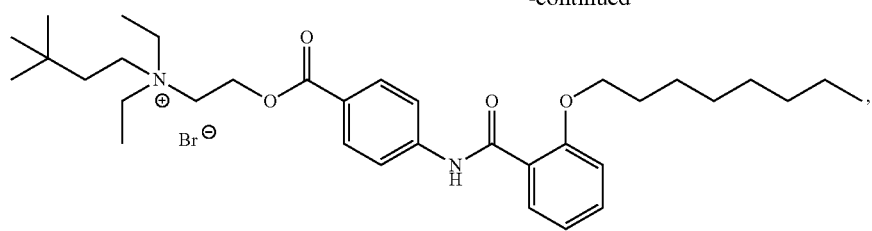
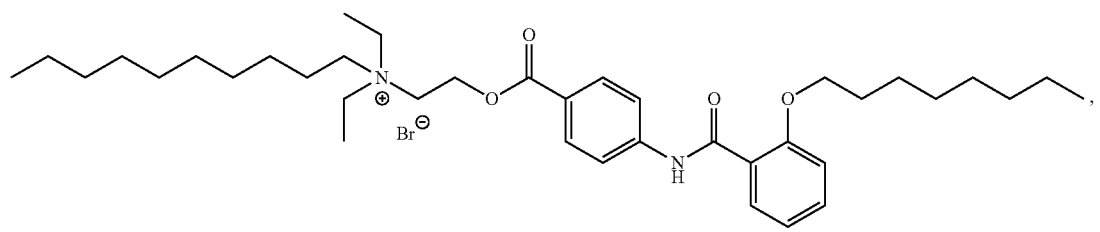
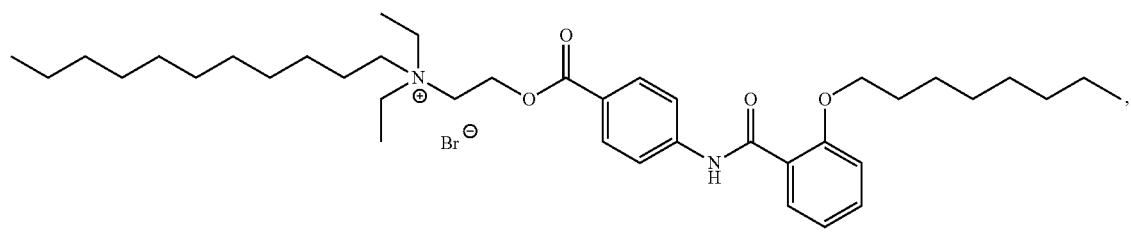
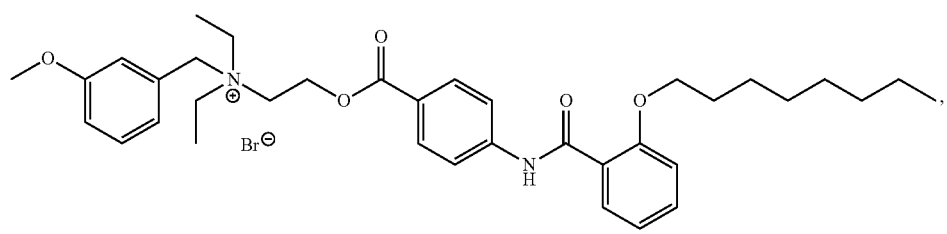
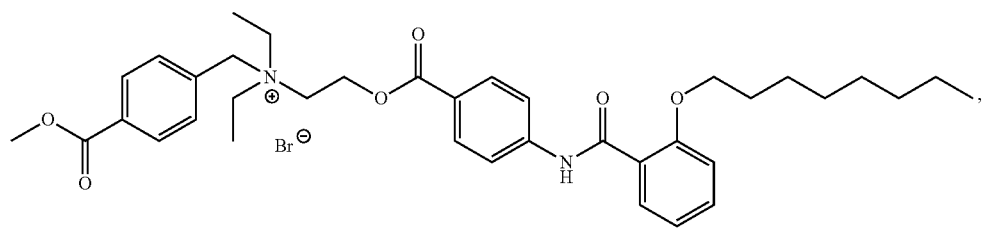
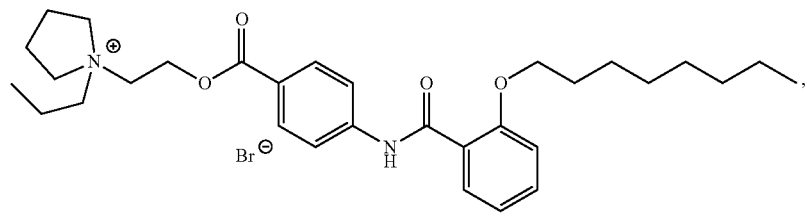
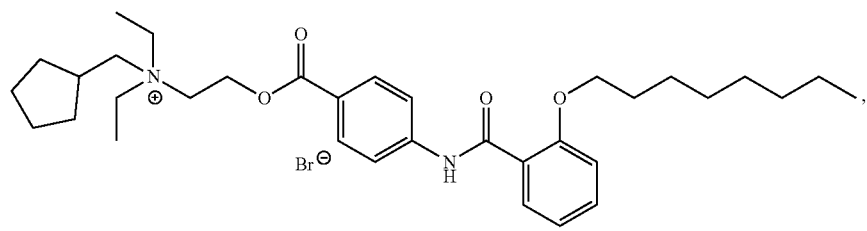

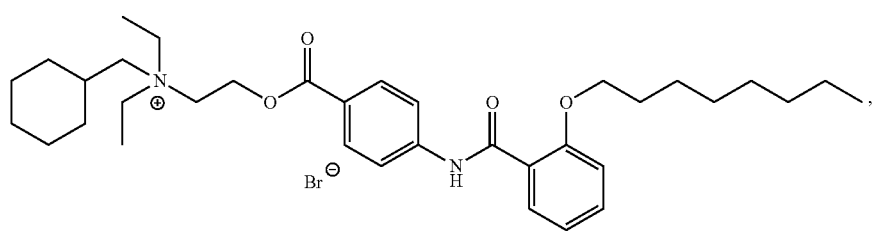
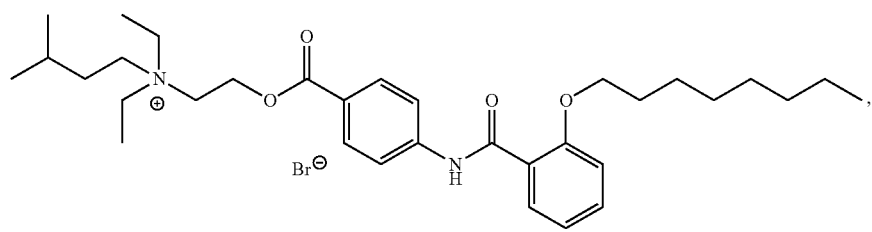
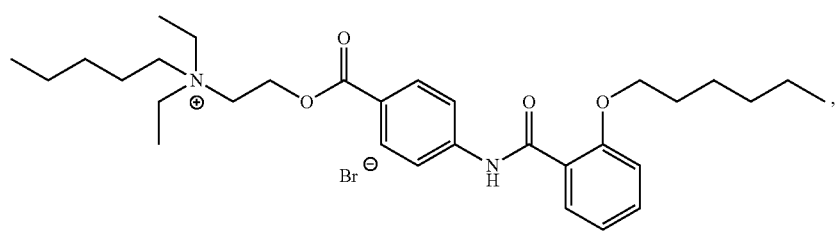
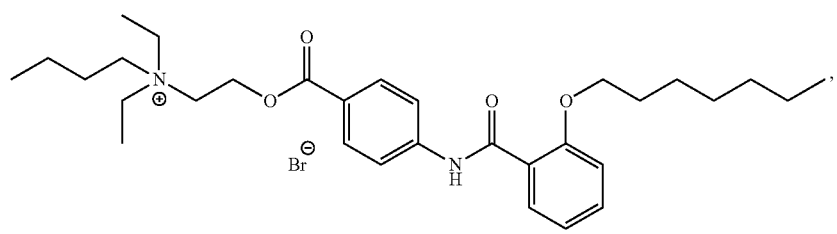
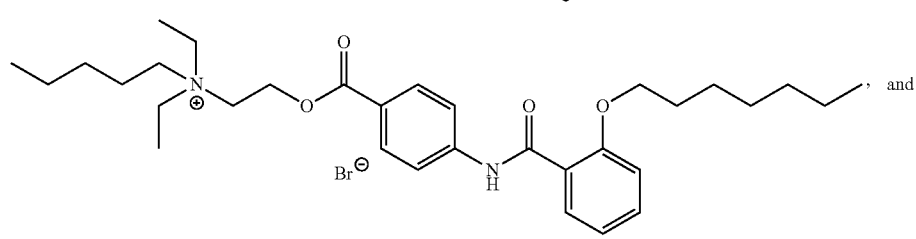, and
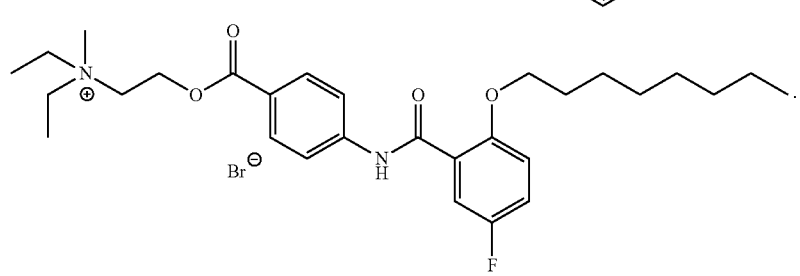

15. The compound of claim 1, which is selected from the group consisting of:
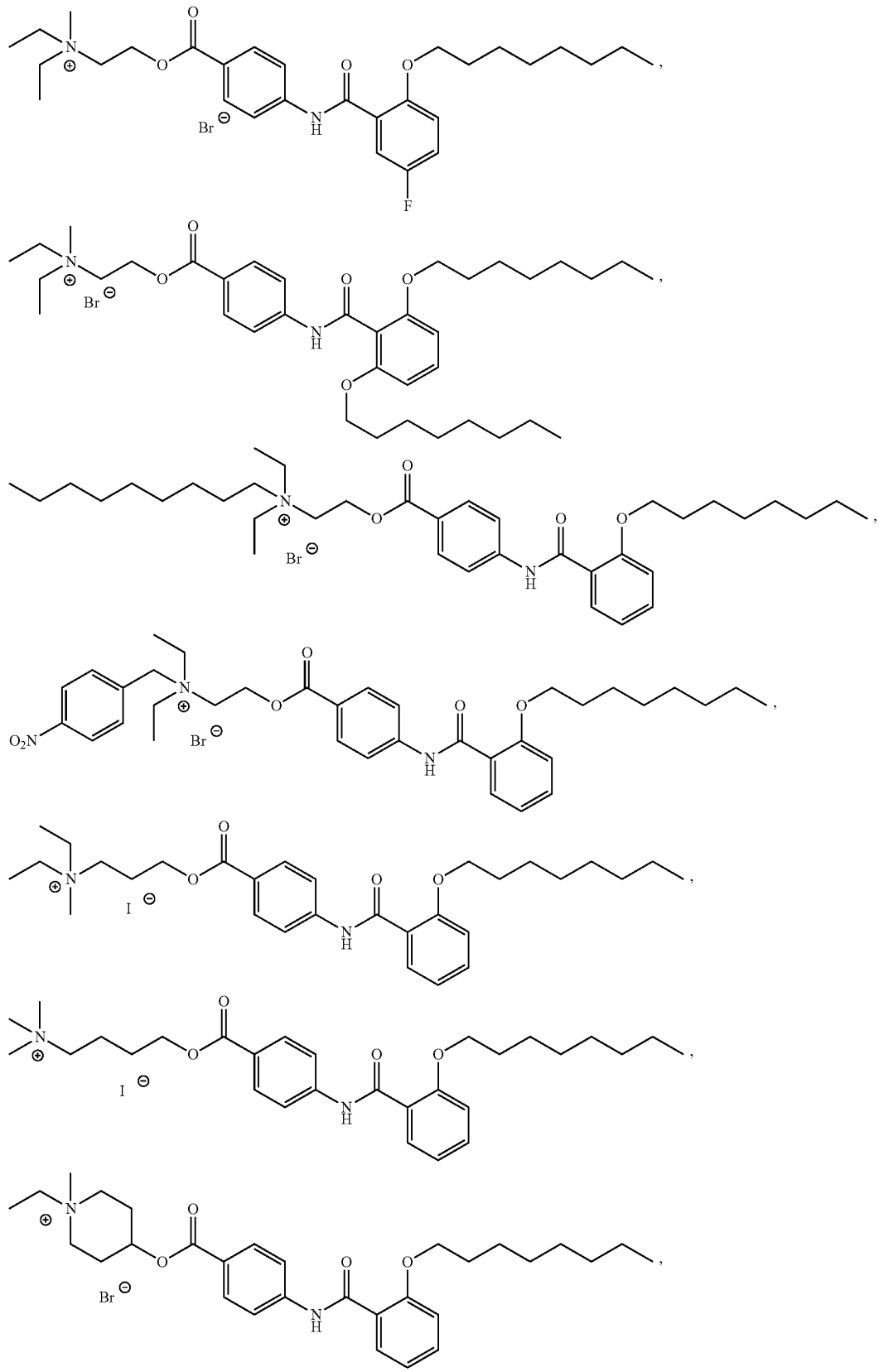

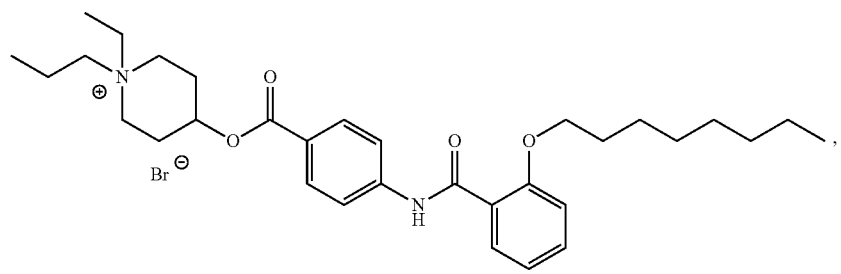
,
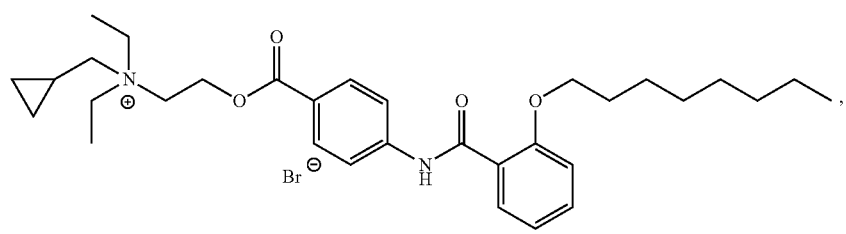
,
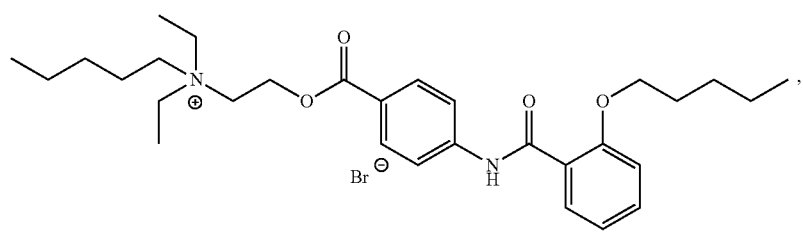
,
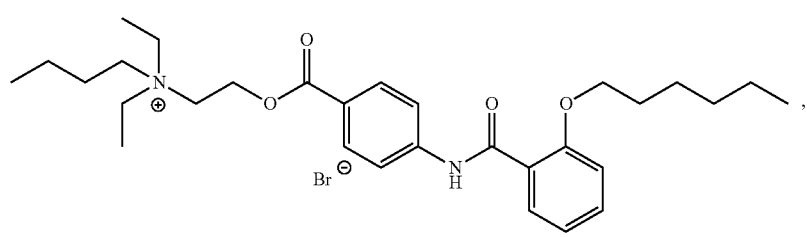
,
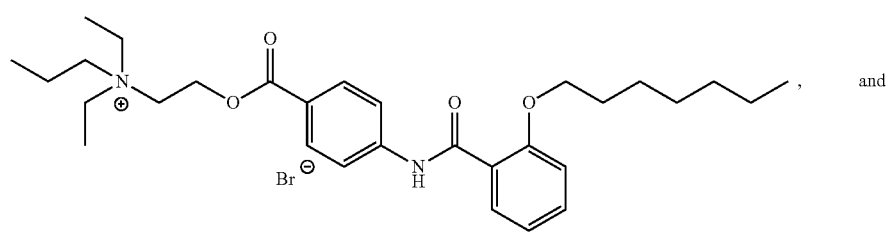
, and
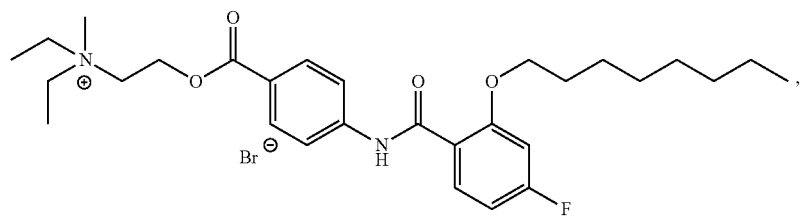
, 16. A compound selected from the group consisting of:
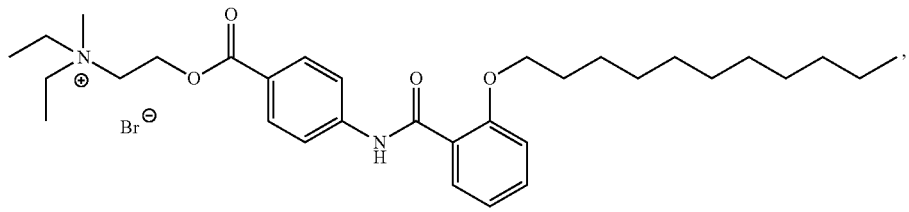
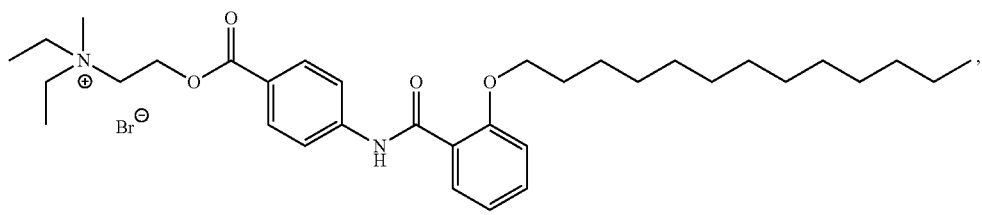
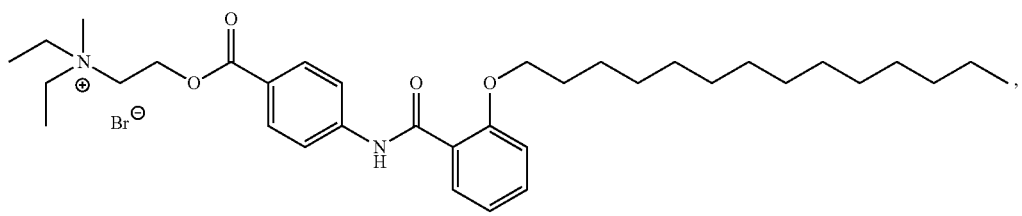
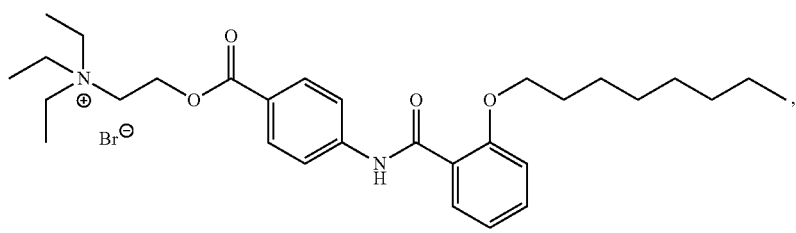
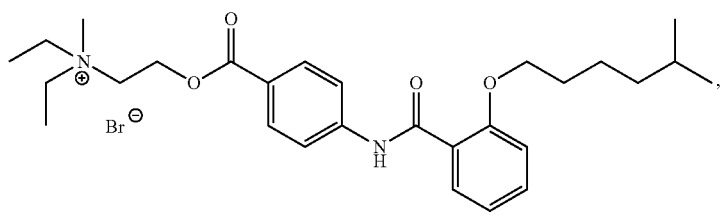
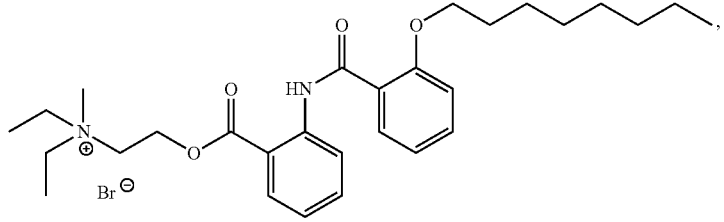

-continued
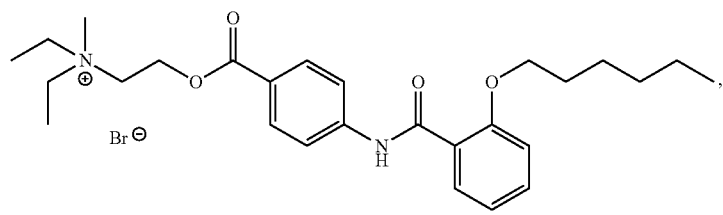
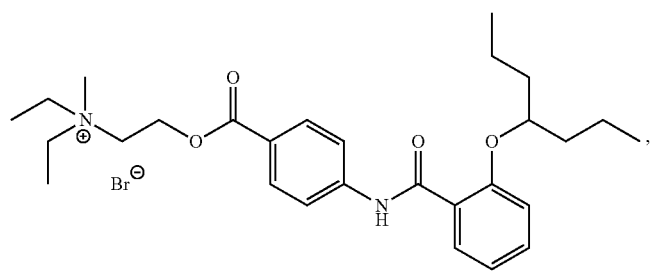
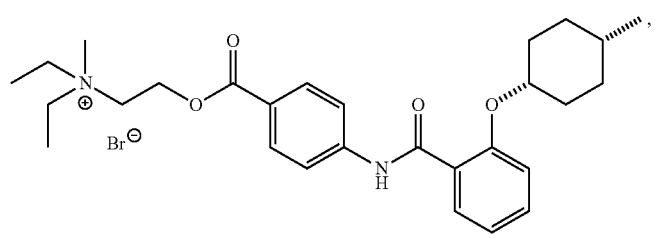
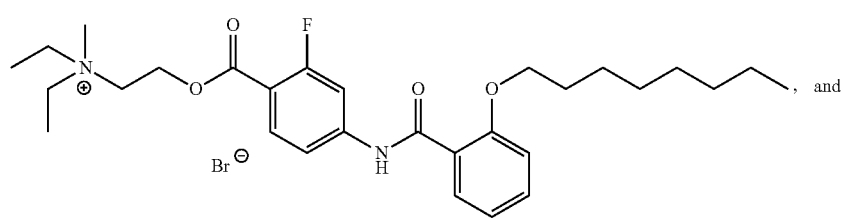, and
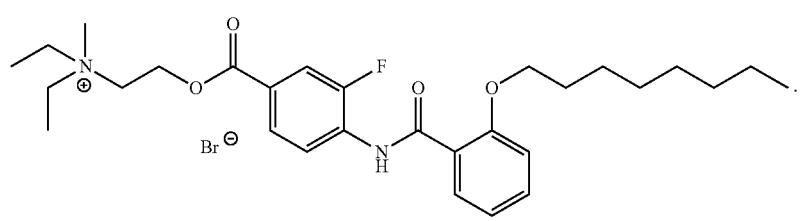.

17. A pharmaceutical composition comprising a compound according to claim 1 and a pharmaceutically acceptable excipient.

\* \* \* \* \*